US010857209B2

(12) United States Patent
Yan et al.

(10) Patent No.: US 10,857,209 B2
(45) Date of Patent: Dec. 8, 2020

(54) LYSOSOMAL ACID LIPASE AND PPAR GAMMA LIGANDS AS IMMUNE THERAPIES FOR CANCER TREATMENT

(71) Applicant: Indiana University Research and Technology Corporation, Indianapolis, IN (US)

(72) Inventors: Cong Yan, Carmel, IN (US); Hong Du, Carmel, IN (US)

(73) Assignee: Indiana University Research and Technology Corporation, Indianapolis, IN (US)

( * ) Notice: Subject to any disclaimer, the term of this patent is extended or adjusted under 35 U.S.C. 154(b) by 143 days.

(21) Appl. No.: 16/077,161

(22) PCT Filed: Feb. 10, 2017

(86) PCT No.: PCT/US2017/017387
§ 371 (c)(1),
(2) Date: Aug. 10, 2018

(87) PCT Pub. No.: WO2017/139588
PCT Pub. Date: Aug. 17, 2017

(65) Prior Publication Data
US 2019/0076508 A1   Mar. 14, 2019

Related U.S. Application Data

(60) Provisional application No. 62/294,533, filed on Feb. 12, 2016, provisional application No. 62/294,540, filed on Feb. 12, 2016.

(51) Int. Cl.
| | |
|---|---|
| *A61K 38/43* | (2006.01) |
| *A61P 35/00* | (2006.01) |
| *A61K 9/00* | (2006.01) |
| *G01N 33/50* | (2006.01) |
| *C12N 9/20* | (2006.01) |
| *G01N 33/574* | (2006.01) |
| *A61K 38/17* | (2006.01) |
| *A61K 31/427* | (2006.01) |
| *A61K 31/47* | (2006.01) |
| *A61K 31/5575* | (2006.01) |
| *A61K 38/46* | (2006.01) |
| *A61K 45/06* | (2006.01) |
| *A61K 31/4439* | (2006.01) |
| *A61K 31/426* | (2006.01) |
| *A61K 31/201* | (2006.01) |
| *A61K 31/428* | (2006.01) |
| *A61K 31/421* | (2006.01) |

(52) U.S. Cl.
CPC ............ *A61K 38/43* (2013.01); *A61K 9/0019* (2013.01); *A61K 31/201* (2013.01); *A61K 31/421* (2013.01); *A61K 31/426* (2013.01); *A61K 31/427* (2013.01); *A61K 31/428* (2013.01); *A61K 31/4439* (2013.01); *A61K 31/47* (2013.01); *A61K 31/5575* (2013.01); *A61K 38/1774* (2013.01); *A61K 38/465* (2013.01); *A61K 45/06* (2013.01); *A61P 35/00* (2018.01); *C12N 9/20* (2013.01); *C12Y 301/01013* (2013.01); *G01N 33/5044* (2013.01); *G01N 33/5743* (2013.01); *G01N 33/57423* (2013.01); *C12Y 301/01* (2013.01); *G01N 2333/92* (2013.01)

(58) Field of Classification Search
CPC .................................................. A61K 9/0019
See application file for complete search history.

(56) References Cited

U.S. PATENT DOCUMENTS

| | | |
|---|---|---|
| 2004/0038365 A1 | 2/2004 | Xiao et al. |
| 2015/0157565 A1 | 6/2015 | Heartlein et al. |

OTHER PUBLICATIONS

Ding et al., Establishment of lal-/-myeloid lineage cell line that resembles Myeloid-Derived Suppressive Cells; PLOA/ONE, Mar. 25, 2015, pp. 1-20.
Du et al., Lysosmal acid lipase-deficient mice: depletion of white and brown fat, severe hepatosplenomegaly, and shortened life span; ASBMB, Journal of Lipid Research, vol. 42, 2001, pp. 489-500.
Du et al., Hepatocyte-Specific Expression of Human Lysome Acid Lipase Corrects Liver Inflammation and Tumor Metastasis in lal-/- Mice; The American Journal of Pathology, vol. 185, No. 9, 2015, pp. 2379-2389.
Folch et al., A Simple Method for the Isolation and Purification of Total Lipides From Animal Tissues; 1957, J. Biol. Chem, vol. 226, pp. 497-509.
Qu et al, Critical Roles of Lysosomal Acid Lipase in T Cell Development and Function; The American Journal of Pathology, vol. 174, No. 3, 2009, pp. 944-956.
Qu eQU et al., Critical Roles of Lysosomal Acid Lipase in Myelopoiesis; The American Journal of Pathology, vol. 176, No. 5, 2010, pp. 2394-2404.
Qu et al., Myeloid-Specific Expression of Api6/AIM/Spa Induces Systemic Inflamation and Adenocarcinoma in the Lung; The Journal of Immunology; 2009, pp. 1648-1659.
Wu et al., Inhibition of PPARγ in myeloid-linage cells induces systemic inflammation, immunosuppression, and tumorigenesis; Blood, 2012, vol. 119, No. 1; pp. 115-126.
Yan et al., Lysosomal acid lipase in cancer; Oncoscience 2015, vol. 2, No. 9,. pp. 727-728.
Zhao et al., Critical role of PPARy in myeloid-derived suppressor cell-stimulated cancer cell proliferation and metastasis; Oncotarget, Advance Publication 2015; pp. 1-15.

(Continued)

*Primary Examiner* — Bin Shen
(74) *Attorney, Agent, or Firm* — Stinson LLP

(57) ABSTRACT

Methods of cancer treatment are disclosed. Particularly, disclosed herein are methods of administering LAL and PPARγ ligands for treating various cancer patients to promote anti-cancer immunity (suppress MDSC), use for inhibiting tumor progression, and use for inhibiting tumor metastasis.

15 Claims, 90 Drawing Sheets
Specification includes a Sequence Listing.

(56) References Cited

OTHER PUBLICATIONS

Zhao et al., Activation of mTOR pathway in myeloid-derived suppressor cells stimulates cancer cell proliferation and metastasis in lal-/- mice; Oncogene, 2015, vol. 34, pp. 1938-1948.
Qu et al., Matrix Metalloproteinase 12 Overexpression in Lung Epithelial Cells Plays a Key Role in Emphysema to Lung Bronchioalveolar Adenocarcinoma Transition; Cancer Res, 2009, vol. 18, pp. 7252-7261.

LYSOSOMAL ACID LIPASE AND PPAR GAMMA LIGANDS AS IMMUNE THERAPIES FOR CANCER TREATMENT

CROSS REFERENCE TO RELATED APPLICATIONS

This application claims priority to International Publication Number WO 2017/139588, filed on Feb. 10, 2017, which claims priority to U.S. Provisional Patent Application Ser. No. 62/294,533, filed Feb. 12, 2016, and U.S. Provisional Patent Application Ser. No. 62/294,540, filed Feb. 12, 2016, the disclosure of which are hereby incorporated by reference in their entireties.

STATEMENT OF GOVERNMENT SUPPORT

This invention was made with government support under CA138759 and CA152099 awarded by the National Institutes of Health. The government has certain rights in the invention.

INCORPORATION OF SEQUENCE LISTING

A paper copy of the Sequence Listing and a computer readable form of the Sequence Listing containing the file named "IURTC_2016-066-05_ST25.txt", which is 1,493 bytes in size (as measured in MICROSOFT WINDOWS® EXPLORER), are provided herein and are herein incorporated by reference. This Sequence Listing consists of SEQ ID NOs:1-6.

BACKGROUND OF THE DISCLOSURE

The present disclosure relates generally to the use of lysosomal acid lipase (LAL) and peroxisome proliferator-activated receptors gamma (PPARγ) ligands as a cancer treatments. Particularly, administration of LAL and PPARγ ligands has been identified to suppress MDSCs expansion and function for treating various cancers by promoting anti-cancer immunity. In some particular embodiments, administration of LAL is shown to block cancer proliferation, migration, and metastasis into the lung and liver.

Inflammation plays crucial roles at all stages of tumor development, from tumor initiation to metastatic progression, and requires close collaboration between cancer cells and inflammatory cells. One such inflammatory cell type are myeloid-derived suppressor cells (MDSCs) that possess a strong immune suppressive function and directly stimulate cancer proliferation in tumor microenvironment. An immunosuppressive state of MDSCs favors tumor development. MDSCs are known to suppress immune surveillance (anti-tumor T cell, NK cell functions) to promote tumorigenesis.

LAL, hydrolyzing cholesteryl esters and triglycerides in the lysosome of cells to generate free fatty acids and cholesterol, is a key enzyme in the metabolic pathway of neutral lipids. LAL has a close connection with inflammation and tumor progression. Genetic ablation of the lal gene in mice has resulted in systemic inflammation, including pulmonary inflammation. In the lung, the high inflammatory state causes remodeling of the alveolar structure, pulmonary emphysema, and Clara cell hypertrophy and hyperplasia. One of the most important manifestations associated with these pathogeneses is the increased pro-inflammatory cytokines/chemokines and infiltration of MDSCs into the lung.

PPARγ, a member of the nuclear receptor superfamily, serves as the receptor of free fatty acid derived compounds which arise downstream of LAL enzymatic action. After binding to these ligands, PPARγ plays an important role in limiting inflammation in various tissues by suppressing the expression of inflammatory cytokines. Overexpression of pro-inflammatory molecules (e.g., apoptosis inhibitor 6 and matrix metalloproteinase 12) that are negatively regulated by PPARγ has been reported to induce chronic inflammation and spontaneous tumor formation.

Accordingly, it would be advantageous to better understand the physiological and pathological role of LAL and PPARγ in cancer cells. As found in the present disclosure, LAL in lung epithelial cells plays an important role in controlling lung pro-inflammatory cytokines/chemokines production, infiltration of MDSCs into the lung, and tumor metastasis. Particularly, as described more fully herein, human LAL (hLAL) expression in CCSP-Tg/KO mice corrected pulmonary damage, inhibited tumor cell proliferation and migration in vitro, and tumor metastasis to the lung in vivo. LAL in liver hepatocytes plays an important role in controlling liver pro-inflammatory cytokines/chemokines production, infiltration of MDSCs into the liver, and tumor metastasis. Particularly, as described more fully herein, human LAL (hLAL) expression in LAP-Tg/KO mice corrected liver damage, inhibited tumor cell proliferation and migration in vitro, and tumor metastasis to the lung in vivo. Further, since LAL downstream metabolic derivatives serve as hormonal ligands for PPARγ, it would be beneficial to examine the role PPARγ plays in LAL mediated functions in MDSCs.

BRIEF DESCRIPTION OF THE DISCLOSURE

The present disclosure is generally related to methods of suppressing MDSCs expansion and function for treating various cancer patients by promoting anti-cancer immunity. Particularly, the methods of the present disclosure are directed to the administration of lysosomal acid lipase (LAL) and peroxisome proliferator-activated receptors gamma (PPARγ) ligands as cancer treatments. In some particular embodiments, administration of LAL is shown to block cancer proliferation, migration, and metastasis into the lung. In some particular embodiments, administration of PPARγ ligands is shown to block cancer proliferation, migration, and metastasis via affecting the mammalian target of rapamycin (mTOR) pathway and by inhibiting overproduction of reactive oxygen species (ROS).

Additionally, the present disclosure relates to the use of LAL deficiency myeloid cell line models for cancer immunity research. Particularly, HD1B cells demonstrated many characteristics similar to $lal^{-/-}$ MDSCs; for example, HD1B cells exhibited increased lysosomes around perinuclear areas, dysfunction of mitochondria skewing toward fission structure, damaged membrane potential, and increased reactive oxidative species (ROS) production. HD1B cells further showed increased glycolytic metabolism during blockage of fatty acid metabolism to fuel the energy need Similar to $lal^{-/-}$ MDSCs, the mTOR signal pathway in HD1B cells is overly activated. As such, the present disclosure has developed screening assays using HD1B to examine anti-cancer efficacy and mechanisms.

The present disclosure is further related to methods of suppressing MSCs' ability to stimulate tumor growth and metastasis. Particularly, the methods of the present disclosure are directed to the administration of lysosomal acid lipase (LAL) as a therapeutic for reducing cancer metastasis.

In one aspect, the present disclosure is directed to a method for treating cancer in an individual in need thereof, the method comprising administering lysosomal acid lipase (LAL) to the individual. This aspect of the disclosure also provides LAL for use in the treatment of cancer.

In another aspect, the present disclosure is directed to a method of inhibiting tumor progression in an individual need thereof, the method comprising administering lysosomal acid lipase (LAL) to the individual. This aspect of the disclosure also provides LAL for use in inhibiting tumor progression.

In another aspect, the present disclosure is directed to a method of inhibiting tumor metastasis in an individual in need thereof, the method comprising administering lysosomal acid lipase (LAL) to the individual. This aspect of the disclosure also provides LAL for use in inhibiting tumor metastasis.

In another aspect, the present disclosure is directed to a method for treating lung cancer in an individual in need thereof, the method comprising administering lysosomal acid lipase (LAL) to the individual. This aspect of the disclosure also provides LAL for use in the treatment of lung cancer.

In another aspect, the present disclosure is directed to a method for screening a candidate compound for treating cancer, the method comprising: contacting the compound with a HD1B cell; and analyzing the HD1B cell.

In another aspect, the present disclosure is directed to a method for treating cancer in an individual in need thereof, the method comprising administering a peroxisome proliferator-activated receptor gamma (PPARγ) ligand to the individual. This aspect of the disclosure also provides a PPARγ ligand for use in the treatment of cancer.

In another aspect, the present disclosure is directed to a method of inhibiting tumor progression in an individual need thereof, the method comprising administering a peroxisome proliferator-activated receptor gamma (PPARγ) ligand to the individual. This aspect of the disclosure also provides a PPARγ ligand for use in inhibiting tumor progression.

In another aspect, the present disclosure is directed to a method of inhibiting tumor metastasis in an individual in need thereof, the method comprising administering a peroxisome proliferator-activated receptor gamma (PPARγ) ligand to the individual. This aspect of the disclosure also provides a PPARγ ligand for use in inhibiting tumor metastasis.

In another aspect, the present disclosure is directed to a method for treating cancer in an individual in need thereof, the method comprising administering lysosomal acid lipase (LAL) in combination with a check point inhibitor (e.g., PD-L1 or PD-1 inhibitor) to the individual. This aspect of the disclosure also provides lysosomal acid lipase (LAL) in combination with a check point inhibitor for use in the treatment of cancer.

In another aspect, the present disclosure is directed to a method for reducing cancer tumor growth in an individual in need thereof, the method comprising administering lysosomal acid lipase (LAL) in combination with a check point inhibitor (e.g., PD-L1 or PD-1 inhibitor) to the individual. This aspect of the disclosure also provides lysosomal acid lipase (LAL) in combination with a check point inhibitor for use in reducing cancer tumor growth.

BRIEF DESCRIPTION OF THE DRAWINGS

The disclosure will be better understood, and features, aspects and advantages other than those set forth above will become apparent when consideration is given to the following detailed description thereof. Such detailed description makes reference to the following drawings, wherein:

FIG. 1A depicts Western blot analysis of lysosome marker LAMP1 expression in wild type (HD1A) and lal$^{-/-}$ (HD1B) cells. FIG. 1B depicts immunofluorescence staining of LAMP1 in wild type (HD1A) and lal$^{-/-}$ (HD1B) cells. Bars=20 μm. FIG. 1C depicts LYSOTRACKER® Red DND-99 staining of live wild type (HD1A) and lal$^{-/-}$ (HD1B) cells. Bar=25 μm. FIG. 1D depicts expression of CD36, FOXO3, SIRT1, CPT1, CPT2, CPT3 with the housekeeping gene β-Actin as internal control by Real-time PCR. The results are means±SD from three independent experiments (n=3), *, p<0.05, **, p<0.001.

FIG. 2A depicts the glucose and pyruvate concentrations, and aconitase activity in wild type (HD1A) and lal$^{-/-}$ (HD1B) cells. The results are means±SD from three independent experiments (n=3), *, p<0.05, **, p<0.001. FIG. 2B depicts expression of Glut1 to Glut13 with the housekeeping gene β-Actin as internal control by Real-time PCR. The results are means±SD from three independent experiments (n=3), *, p<0.05, ** , p<0.001.

FIG. 3A depicts MITOTRACKER® Green FM staining of live wild type (HD1A) and lal$^{-/-}$ (HD1B) cells. Bar=25 μm. FIG. 3B depicts cell proliferation of wild type (HD1A) and lal$^{-/-}$ (HD1B) cells in vitro. FIG. 3C depicts Western blot analyses of protein expression of Opa1 and phosphorylation at Ser616 of DRP1 in wild type (HD1A) and lal$^{-/-}$ (HD1B) cells.

FIG. 4A depicts live wild type (HD1A) and lal$^{-/-}$ (HD1B) cells stained with JC1 to measure the mitochondria membrane potential. JC1 red fluorescent staining represents a healthy membrane potential state, while JC1 green fluorescent staining represents a damaged membrane potential state. FIG. 4B depicts the ROS levels in wild type (HD1A) and lal$^{-/-}$ (HD1B) cells by flow cytometry analysis. Results are mean±SD from three independent experiments (n=3), , p<0.001. FIG. 4C depicts the arginase activity measured in HD1A and HD1B. The result is mean±SD from three independent experiments (n=3), , p<0.001. FIG. 4D depicts the IDO1 and IDO2 expression levels measured by Real-Time. The results are means±SD from three independent experiments (n=3), **, p<0.001.

FIG. 5A depicts Western blot analyses of the phosphorylation level of mTOR downstream effector pS6 in wild type (HD1A) and lal$^{-/-}$ (HD1B) cells. Both cells were treated with solvent (S) or with mTOR inhibitor rapamycin (R) or PP242 (P). FIG. 5B depicts flow cytometry analyses of the ROS levels of rapamycin or PP242 treated or untreated wild type (HD1A) and lal$^{-/-}$ (HD1B) cells. Results are mean±SD from three independent experiments (n=3), p<0.001. FIG. 5C depicts mitochondria membrane potential analyzed in rapamycin or PP242 treated or untreated wild type (HD1A) and lal$^{-/-}$ (HD1B) cells by JC1 staining. Treatment of mTOR inhibitors restored the mitochondria membrane potential in lal$^{-/-}$ (HD1B) cells. FIG. 5D depicts antioxidant reagent NAC or Tempol treated or untreated wild type (HD1A) and lal$^{-/-}$ (HD1B) cells stained with JC1 to measure the mitochondria membrane potential. Treatment of antioxidants restored the mitochondria membrane potential in lal$^{-/-}$ (HD1B) cells.

FIG. 6A depicts CFSE labeled wild type CD4$^+$ T cells stimulated with anti-CD3 and anti-CD28 antibodies, and co-cultured with wild type (HD1A) or (HD1B) cells (1:30). CD3 and CD28 antibody unstimulated CD4$^+$ T cells served as a negative control. Results are mean±SD from three independent experiments (n=3), *, p<0.05; **, p<0.01. FIG. 6B depicts secretion of T cell releasing IL-2, IL-4 and INF-γ in the above co-culture experiment measured to assess the CD4$^+$ T cell function. Results are mean±SD from three independent experiments (n=3), *, p<0.05; **, p<0.01.

FIG. 7A depicts that Western blot analyses showed the mTOR protein expression level, phosphorylated mTOR, and phosphorylated S6 levels reduced in wild type (HD1A) and lal$^{-/-}$ (HD1B) cells by mTOR siRNA knockdown. FIG. 7B depicts T cell suppressive activity of HD1B reduced upon mTOR knockdown by siRNA transfection. Wild type (HD1A) or lal$^{-/-}$ (HD1B) cells were pretreated with control (C) siRNA or mTOR (mTOR) siRNA. Treated cells were incubated with CFSE labeled wild type CD4$^+$ T cells and stimulated with anti-CD3 and anti-CD28 antibodies. Results are mean±SD from three independent experiments (n=3), p<0.05; FIG. 7C depicts secretion of T cell releasing IL-4 in the above co-culture experiment measured to assess the CD4$^+$ T cell function. Results are mean±SD from three independent experiments (n=3), p<0.05.

FIG. 8A depicts wild type (HD1A) and lal$^{-/-}$ (HD1B) cells co-cultured with CFSE labeled LLC or B16 melanoma cells (5:1) for 3 days. The results are presented as percentage of CFSE positive cells increased from none co-culture base line. The results are mean±SD from three independent experiments (n=3), , p<0.01. FIG. 8B depicts that mTOR siRNA knockdown in lal$^{-/-}$ (HD1B) cells inhibited the stimulatory activity of cancer cell growth (LLC and B16 melanoma cells). The same cell ratio was used. The results are mean±SD from three independent experiments (n=3), , p<0.01. FIG. 8C depicts B16 melanoma cells (2×10$^5$) that were mixed with the same amount of wild type (HD1A) or lal$^{-/-}$ (HD1B) cells were left-side and right-side pair-injected subcutaneously into C57BL/6 or FVB/N mice. After 14 days, tumor volumes were measured using the formula: (length X width$^2$)/2. The results are mean±SD from 11-12 independent experiments (n=11-12), p values are listed in comparison of tumor sizes between co-injection of wild type (HD1A) and lal$^{-/-}$ (HD1B) cells.

FIG. 9A depicts Ly6G$^+$ cells from lal$^{+/+}$ or lal$^{-/-}$ FVB/N mice pre-treated with ethanol (E) or 20 μmol/L 9-HODE (H) or without treatment (C) for 24 hours. Pre-treated Ly6G$^+$ cells (6×10$^5$) and B16 melanoma cells (2×10$^5$, without any treatment) were mixed, and co-injected subcutaneously into the flank region of 3-month old lar$^{+/+}$ FVB/N mice. n=8~10. FIG. 9B depicts pre-treated C57BL/6 Ly6G$^+$ cells (6×10$^5$) and B16 melanoma cells (2×10$^5$) co-injected subcutaneously into the flank region of 3-month old lal$^{+/+}$ C57BL/6 mice. n=4. Tumor volume (in cubic millimeters) were measured and statistically analyzed at 7, 14, and 21 days post-injection. For statistical analyses, data were expressed as mean±SD. **P<0.01, * P<0.05. FIG. 9C depicts pre-treated Ly6G$^+$ cells (2×10$^6$) and B16 melanoma cells (5×10$^5$, without any treatment) intravenously co-injected into lal$^{+/+}$ mice for 2 weeks. Representative lungs and quantitative analysis of the melanoma colony numbers in the lungs are shown. Data were expressed as mean±SD; n=9~10. **P<0.01. FIG. 9D depicts representative H&E staining and IHC staining with Ki67 antibody of the lungs with metastasized melanoma are shown. Original magnification, ×400.

FIG. 10A depicts pre-treated Ly6G$^+$ cells (5×10$^5$) co-cultured with B16 melanoma cells (5×10$^3$) in vitro for 72 hours, and numbers of B16 melanoma cells were counted. n=4~5. FIG. 10B depicts pre-treated Ly6G$^+$ cells (5×10$^5$) co-cultured with LLC cells (1×10$^4$) in vitro for 72 hours, and numbers of LLC cells were counted. n=4-5. FIG. 10C depicts the effect of Ly6G$^+$ cell-secreted cytokines on B16 melanoma cell proliferation. Pre-treated Ly6G$^+$ cells (1×10$^6$) were seeded into the upper chamber of transwells, in which B16 melanoma cells (2×10$^4$) were seeded in the lower chamber. After 72 hours, the number of B16 melanoma cells was counted. n=5. FIG. 10D (left) depicts in vitro migration of B16 melanoma cells with pre-treated Ly6G$^+$ cells at 24 hours after co-culture in the presence of mitomycin C. The dotted lines define the areas lacking cells. FIG. 10D (right) depicts the quantification of distance from one end of the wound area to the other end. Data were normalized to B16 melanoma cells co-cultured with control lal$^{+/+}$ Ly6G+ cells at 0 hour. Original magnification, ×40. n=5. For statistical analyses, data were expressed as mean±SD; **P<0.01, *P<0.05.

FIG. 11A shows a transwell assay performed to determine MDSCs transmigration across the endothelial monolayer. Ly6G$^+$ cells from lal$^{+/+}$ or lal$^{-/-}$ mice were pre-treated with ethanol (EtOH) or 20 μmol/L 9-HODE for 48 hours, and then labeled with CMFDA and seeded onto the endothelial monolayer at a density of 2×10$^4$ cells/well. Four hours after seeding Ly6G$^+$ cells on the EC monolayer, the number of Ly6G$^+$ cells that have migrated to the lower chamber was counted. FIG. 11B shows the statistical analysis of Ly6G$^+$CD11b$^+$ cells from Lin-cells treated with ethanol (EtOH) or 10 μmol/L 9-HODE for 5 days by flow cytometry. Data were expressed as mean SD; n=3-4. **P<0.01, *P<0.05.

FIG. 12A depicts 9-HODE decreased phosphorylation of mTOR in gated lal$^{-/-}$ Ly6G$^+$CD11b$^+$ cells. FIG. 12B depicts 9-HODE decreased phosphorylation of S6 in gated lal$^{-/-}$ Ly6G$^+$CD11b$^+$ cells. Statistical analysis of mean fluorescent intensity (MFI) by flow cytometry is shown. Data were expressed as mean±SD; n=7. *P<0.05.

FIG. 13A depicts 9-HODE increased the mitochondrial membrane potential in gated lal$^{-/-}$ Ly6G$^+$CD11b$^+$ cells. FIG. 13A (left) shows a representative dot plot analysis of the JC-1 red and JC-1 green profiles by flow cytometry. FIG. 13A (right) shows the statistical analysis of the mitochondrial membrane potential in Ly6G$^+$CD11b$^+$ cells. FIG. 13B shows that 9-HODE decreased ROS production in lal$^{-/-}$ Ly6G$^+$CD11b$^+$ cells. FIG. 13B (left) shows a representative analysis of MFI by flow cytometry. FIG. 13B (right) shows the statistical analysis of MFI in Ly6G$^+$CD11b$^+$ cells. Data were expressed as mean±SD; n=5~6. **P<0.01, *P<0.05.

FIG. 14A shows the statistical analysis of tumor volume (in cubic millimeters) at 4 weeks after B16 melanoma cells (2×10$^5$) were subcutaneously injected into doxycycline-treated or untreated c-fmsrtTA/(tetO)$_7$-dnPPARγ bi-transgenic mice. n=5. *P<0.05. FIG. 14B shows the quantitative analysis of metastasized B16 melanoma colonies in the lungs of doxycycline-treated or untreated bi-transgenic mice with intravenous injection of 5×10$^5$ B16 melanoma cells for 2 weeks. n=11~12. P<0.01. FIG. 14C shows the number of B16 melanoma cells (5×10$^3$) co-cultured with Ly6G$^+$ cells (5×10$^5$) from doxycycline-treated or untreated bi-transgenic mice in vitro for 72 hours. FIG. 14D depicts the numbers of LLC cells (1×10$^4$) co-cultured with doxycycline-treated or untreated Ly6G$^+$ cells (5×10$^5$) in vitro for 72 hours. FIG. 13E shows the in vitro migration of B16 melanoma cells with doxycycline-treated or untreated Ly6G$^+$ cells at 24 hours after co-culture in the presence of mitomycin C. Data were normalized to B16 melanoma cells co-cultured with untreated Ly6G$^+$ cells at 0 hour. FIG. 14F depicts Ly6G$^+$ cell transendothelial migration. Data are normalized to untreated Ly6G$^+$ cells. In the above experiments (FIGS. 14C-14F), data were expressed as mean±SD; n=4. P<0.01.

FIG. 15A depicts that the mTOR pathway was overactivated in doxycycline-treated bone marrow Ly6G$^+$CD11b$^+$ cells. Statistical analysis of MFI by flow cytometry is shown. Data were expressed as mean±SD; n=4~5. **P<0.01, *P<0.05. FIG. 15B shows that the mitochondrial membrane potential was impaired in doxycycline-treated bone marrow Ly6G$^+$CD11b$^+$ cells. FIG. 15B (left) is a representative dot plot analysis of the JC-1 red and JC-1 green profiles by flow cytometry. FIG. 15B (right) shows the statistical analysis of the mitochondrial membrane potential in Ly6G$^+$CD11b$^+$ cells. FIG. 15C depicts that ROS production was increased in doxycycline-treated Ly6G$^+$CD11b$^+$ cells. FIG. 15C (left) shows a representative analysis of MFI by flow cytometry. FIG. 15C (right) shows the statistical analysis of MFI in Ly6G$^+$CD11b$^+$ cells. For statistical analyses, data were expressed as mean±SD; n=5. **P<0.01, *P<0.05.

FIG. 16A depicts RT-PCR for hLAL mRNA expression in the liver, lung, spleen, and bone marrow (BM) of WT, KO, and LAP-Tg/KO triple mice treated with or without doxycycline (DOX). The housekeeping gene β-actin was used as an internal control. FIG. 16B depicts RT-PCR for hLAL mRNA expression in isolated primary hepatocytes and Ly6G$^+$ cells from WT and LAP-Tg/KO triple mouse liver without DOX. The housekeeping gene β-actin was used as an internal control. FIG. 16C is a Western blot analysis of LAL protein in the liver, lung, spleen, and bone marrow of WT, lal$^{-/-}$ (KO), and LAP-Tg/KO triple mice, treated or untreated with DOX. FIG. 16D shows immunohistochemical staining of hLAL and F4/80 in the livers of DOX-treated (+DOX) or DOX-untreated (−DOX) LAP-Tg/KO triple mice. White arrows indicate representative hepatocytes that express hLAL. Black arrows indicate the F4/80$^+$ Kupffer cells that are also positive for hLAL. Without hLAL expression, there is accumulation of enlarged F4/80-positive storage cells in DOX-treated LAP-Tg/KO triple mice. Original magnification: ×200. Hepa, hepatocyte, Ly6G$^+$, Ly6G$^+$ cells from the liver (FIG. 16B).

FIG. 17A is a gross view of the liver and spleen of lal$^{-/-}$[wild-type (WT)], lal$^{-/-}$ (KO), and doxycycline-untreated (DOX-Off) and doxycycline-treated (DOX-On) LAP-Tg/KO mice. FIGS. 17B-17M depict hematoxylin and eosin staining of the liver, spleen, and small intestine paraffin sections from WT (FIGS. 17B, 17F, and 17J), lal$^{-/-}$ (KO) (FIGS. 17C, 17G, and 17K), DOX-ON (FIGS. 17D, 17H, and 17L), and DOX-OFF (FIGS. 17E, 17I, and 17M) LAP-Tg/KO mice. Original magnification: ×200 (FIGS. 17B-17M).

FIG. 20A depicts B16 melanoma cells (5×10$^5$) intravenously injected into doxycycline-treated (+DOX) or doxycycline-untreated (−DOX) LAP-Tg/KO triple mice for 2 weeks. Metastasized B16 melanoma colonies in the liver and lung are shown. FIG. 20B depicts quantitative analysis of B16 melanoma colonies in the livers of doxycycline-treated or doxycycline-untreated LAP-Tg/KO triple mice. FIG. 20C shows representative hematoxylin and eosin staining of liver and lung sections. FIG. 20D shows representative immunohistochemical staining of metastasized livers and lungs using anti-Ki67 antibody. n=10 to 16 (FIGS. 20A and 20B). **P<0.01. Original magnification: ×200 (FIGS. 20C and 20D).

FIG. 23A shows the concentrations of IL-6, granulocyte-macrophage colony-stimulating factor (GM-CSF), monocyte chemotactic protein-1 (MCP-1), and chemokine ligand (CCL)-5 in the plasma of doxycycline-treated (+DOX) or doxycycline-untreated (−DOX) lal$^{+/+}$[wild type (WT)], lal$^{-/-}$ (KO), and LAP-Tg/KO mice were determined by enzyme-linked immunosorbent assay. FIG. 23B depicts quantitative real-time PCR analyses of mRNA expression levels of cytokines and chemokines in the liver of lal$^{+/+}$ (WT), lal$^{-/-}$ (KO), and +DOX or −DOX LAP-Tg/KO mice. The relative gene expression was normalized to glyceraldehyde-3-phosphate dehydrogenase mRNA, and analysis was performed by the $2^{-\Delta\Delta CT}$ method. Data are expressed as means±SD. n=5 to 6 (FIG. 23A); n=4 (FIG. 23B). *P<0.05, **P<0.01. IFNγ, interferon-γ; TNFα, tumor necrosis factor-α.

FIG. 24A shows the concentrations of IL-6, granulocyte-macrophage colony-stimulating factor (GM-CSF), monocyte chemotactic protein-1 (MCP-1), and chemokine ligand (CCL)-5 in the culture medium were determined by enzyme-linked immunosorbent assay. FIG. 24B depicts quantitative real-time PCR analyses of mRNA expression levels of cytokines and chemokines in the isolated hepatocytes of lal$^{+/+}$ (WT) and LAP-Tg/KO mice treated with or without doxycycline. The relative gene expression was normalized to glyceralde-hyde-3-phosphate dehydrogenase mRNA, and analyses were performed by the $2^{-\Delta\Delta CT}$ method. Data are expressed as means±SD. n=4. *P<0.05, **P<0.01. IFNγ, interferon-γ; TNFα, tumor necrosis factor-α.

FIG. 25A shows representative and statistical analyses of hLAL-Flag fusion protein expression in lung SP-C$^+$ cells or spleen cells of lal$^{-/-}$ doxycycline-treated (+DOX) or untreated (−DOX) CCSP-Tg/KO mice by flow cytometry analyses. Data are expressed as means±s.d.; n=3. P<0.01. FIG. 25B depicts hematoxylin and eosin (H&E) and immunohistochemical staining with anti-Mac-2 antibody of lung sections of lal$^{+/+}$, lal$^{-/-}$, doxycycline-treated (+DOX) or untreated (−DOX) CCSP-Tg/KO (Tg/KO) mice. Original magnification: 400×. FIG. 25C depicts quantitative measurements of alveolar area, diameter and perimeter in lal$^{+/+}$, lal$^{-/-}$ doxycycline-treated or untreated CCSP-Tg/KO (Tg/KO) mice, determined by Nikon NIS Elements imaging software. Data are expressed as means±s.d.; n=10. P<0.01.

FIG. 26A show representative lungs with metastasized B16 melanoma colonies. B16 melanoma cells (5×10$^5$) were intravenously injected into doxycycline-treated (+DOX) or untreated (−DOX) CCSP-Tg/KO (Tg/KO) mice for 2 weeks. FIG. 26B depict quantitative analysis of B16 melanoma colonies in the lungs of doxycycline-treated or untreated CCSP-Tg/KO mice. n=11-13. P<0.01. FIG. 26C shows representative immunohistochemical staining of lung sections from studies in (FIG. 26A) using anti-Ki67-antibody and statistical analysis of relative tumor areas. Original magnification, ×400. Data are expressed as means±s.d.; n=10. P<0.01.

FIG. 27A shows the percentages of Ly6G$^+$CD11b$^+$ cells in the lung, blood, bone marrow (BM) and spleen of lar$^{+/+}$, lal$^{-/-}$, doxycycline-treated or untreated CCSP-Tg/KO mice. Data are expressed as means±s.d.; n=4. **P<0.01, *P<0.05. FIG. 27B depicts Kwik-Diff staining of cells in the same amount of BALF from lal$^{+/+}$, lal$^{-/-}$, doxycycline-treated or untreated CCSP-Tg/KO mice. Original magnification, ×400. FIG. 27C shows proliferation of CFSE-labeled CD4$^+$ T cells in the presence of BALF cells from lal$^{+/+}$, lal$^{-/-}$, doxycycline-treated or untreated CCSP-Tg/KO mice was analyzed by flow cytometry. The ratio between CD4$^+$ T cells and BALF cells was 5:1. Peaks represent cell division cycles. n=4. **P<0.01.

FIG. 30A shows that doxycycline-treated CCSP-Tg/KO BALF decreased tumor cell proliferation in in vitro culture study. LLC or B16 melanoma cells (5×10$^3$) were cultured with BALF from lal$^{+/+}$, lal$^{-/-}$ and CCSP-Tg/KO mice in vitro for 72 hours, and the number of LLC or B16 melanoma cells were counted. Data are expressed as means±s.d.; n=4. **P<0.01, *P<0.05. FIG. 30B shows that doxycycline-treated CCSP-Tg/KO BALF decreased tumor cell migration. Tumor cell migration was assessed by the in vitro wound healing assay in the presence of mitomycin C after cultured with BALF from lal$^{+/+}$, lal$^{-/-}$ and CCSP-Tg/KO mice. Data are expressed as means±s.d.; n=4. *P<0.05.

FIG. 31A shows that doxycycline-treated CCSP-Tg/KO BALF decreased bone marrow cell transendothelial migration by transwell assay. Neutralizing antibodies against IL-6, MCP-1, or TNFα were individually or in combination added to the BALF before seeding bone marrow cells. FIG. 31B shows that doxycycline-treated CCSP-Tg/KO BALF decreased EC proliferation. ECs were co-cultured with BALF from lal$^{+/+}$, lal$^{-/-}$ CCSP-Tg/KO mice in vitro for 72 hours, and the number of ECs was counted. FIG. 31C shows that doxycycline-treated CCSP-Tg/KO BALF decreased EC migration by the in vitro wound healing assay in the presence of mitomycin C. Data are expressed as means±s.d.; n=4. **P<0.01, *P<0.05.

FIG. 32A depicts B16 melanoma cells ($1\times10^5$) subcutaneously injected into lal$^{+/+}$ or lal$^{-/-}$ mice for 3 weeks. A representative picture of tumor is shown. FIG. 32B depicts the statistical analysis of tumor volume (in cubic millimeters). Data were expressed as mean±s.d.; n=10. *P<0.0001 at weeks 2 and 3. FIG. 32C depicts B16 melanoma cells ($5\times10^5$) intravenously injected into lal$^{+/+}$ or lal$^{-/-}$ mice for 2 weeks. Metastasized B16 melanoma colonies in the lungs and livers are shown (n=10). FIG. 32D depicts representative H&E staining of lung sections and statistical analysis of relative tumor areas. Original magnification, ×200. Data were expressed as mean±s.d.; n=10. *P<0.0001. FIG. 32E depicts the quantitative analysis of B16 melanoma colonies in the lungs of doxycycline-treated or untreated Tg/KO triple mice with intravenous injection of $5\times10^5$ B16 melanoma cells for 2 weeks. n=8-10. *P<0.05. FIG. 32F depicts the statistical analysis of relative tumor volume after B16 melanoma cells ($1\times10^5$) were subcutaneously injected into doxycycline-treated or untreated Tg/KO triple mice for 2 weeks. Data were expressed as mean±s.d.; n=8. *P<0.05.

FIG. 33A depicts the number of B16 melanoma cells ($5\times10^3$) co-cultured with Ly6G$^+$ cells ($5\times10^5$) from lal$^{+/+}$ or lal$^{-/-}$ mice or doxycycline-treated or untreated Tg/KO triple mice in vitro for 72 hours. Data were expressed as mean±s.d.; n=3-4. **P<0.01, *P<0.05. FIG. 33B depicts MATRIGEL® mixed with B16 melanoma cells ($1\times10^5$) and Ly6G$^+$ cells ($1\times10^6$) implanted subcutaneously into lal$^{+/+}$ mice for 10 days. Representative H&E staining of MATRIGEL® plug sections is shown. Original magnification, ×400. (n=10 for Ly6G$^+$ cells from lal$^{+/+}$ or lal$^{-/-}$ mice and n=4 for Ly6G$^+$ cells from doxycycline-treated or untreated Tg/KO triple mice). FIG. 33C shows real-time PCR analysis of mRNA expression levels of cytokines in lal$^{-/-}$ vs lal$^{+/+}$ Ly6G$^+$ cells. The relative gene expression was normalized to GAPDH mRNA, and analysis was performed by the $2^{\Delta\Delta CT}$ method. Data were expressed as means±s.d.; n=4. *P<0.05. FIG. 33D shows that to block cytokines, Ly6G$^+$ cells ($2\times10^6$) in 200 µl media were seeded into the upper chamber of 0.4-µm pore 6.5-mm diameter transwells, while B16 melanoma cells ($2\times10^4$) in 600 µl media were placed in the lower chamber. For the neutralization study, Ly6G$^+$ cells were treated with 10 µg/ml neutralizing antibody against IL-6, IL-1β, TNF-α individually or in combination or control immunoglobulin G. After 72 hours, the number of B16 melanoma cells was counted. Data were expressed as mean±s.d.; n=4. *P<0.001, P<0.01, *P<0.05.

FIG. 34A depicts B16 melanoma cells ($5\times10^5$) and Ly6G$^+$ cells ($2\times10^6$) from lar$^{+/+}$ or lal$^{-/-}$ mice intravenously injected into lal$^{+/+}$ mice for 2 weeks. Representative lungs are shown. n=10. FIG. 34B depicts the quantitative analysis of the melanoma colony numbers in the lungs. Data were expressed as mean±s.d.; n=8. P<0.01. FIG. 34C depicts representative H&E staining and IHC staining with Ki67 antibody of the metastasized lungs, including statistical analysis of relative tumor areas. Original magnification, ×400. Data were expressed as mean±s.d.; n=10. *P<0.0001.

FIG. 35A depicts Western blotting analysis of the mTOR downstream proteins in lar$^{+/+}$ or lal$^{-/-}$ Ly6G$^+$ cells. Representative blots are shown. (n=4). FIG. 35B depicts Ly6G$^+$ cells transfected with mTOR siRNA SMARTpool (containing a mixture of siRNAs targeting mTOR) or control (C) siRNA for 24 hours. $5\times10^5$ cells were co-cultured with B16 melanoma cells ($5\times10^3$) in vitro. The numbers of B16 melanoma cells were counted after 72 hours. Data were expressed as mean±s.d.; n=5. *P<0.05, **P<0.01. FIG. 35C depicts Ly6G$^+$ cells ($1\times10^6$) after transfection mixed with B16 melanoma cells ($1\times10^5$) in MATRIGEL® and implanted subcutaneously into lal$^{+/+}$ mice for 10 days. Representative H&E staining of MATRIGEL® plug sections is shown. Original magnification, ×200 (n=10). FIG. 35D depicts representative IHC staining of the MATRIGEL® plug sections using antibodies against Ki67, CD31, F4/80 and CD3. Original magnification, ×400.

FIG. 36A depicts Ly6G$^+$ cells ($2\times10^6$) after siRNA transfection co-injected with B16 melanoma cells ($5\times10^5$) into lal$^{+/+}$ mice via tail vein for 2 weeks. Representative lungs are shown (n=5). FIG. 36B depict representative H&E staining of the metastasized lungs and statistical analysis of relative tumor areas. Original magnification, ×400. Data were expressed as mean±s.d.; n=5. *P<0.001, P<0.01. FIG. 36C depict representative IHC staining of the metastasized lungs using anti-Ki67-antibody is shown. Original magnification, ×400.

FIG. 37A depict Ly6G$^+$ cells transfected with Raptor, Rictor siRNA SMARTpool (containing a mixture of siRNAs targeting Raptor or Rictor) or control (C) siRNA for 24 hours and then co-cultured with B16 melanoma cells in vitro. The numbers of B16 melanoma cells were counted after 72 hours. Data were expressed as mean±s.d.; n=4. *P<0.05, P<0.01. FIG. 37B depict Ly6G$^+$ cells after transfection mixed with B16 melanoma cells in MATRIGEL® and implanted subcutaneously into lal$^{+/+}$ mice for 10 days. Representative H&E staining of MATRIGEL® plug sections is shown. Original magnification, ×200 (n=6). FIG. 37C depict Ly6G$^+$ cells after transfection co-injected with B16 melanoma cells intravenously into lal$^{+/+}$ mice for 2 weeks. Representative H&E staining of the metastasized lungs and statistical analysis of relative tumor areas are shown. Original magnification, ×400. Data were expressed as mean±s.d.; n=7-8. *P<0.001.

FIG. 38A depicts LLC cells or Tramp-C2 cells (1×10$^4$) co-cultured in vitro with lal$^{+/+}$ or lal$^{-/-}$ Ly6G$^+$ cells (5×10$^5$) for 72 hours. The numbers of LLC or Tramp-C2 cells were counted. Data were expressed as mean±s.d.; n=4. *P<0.05, P<0.01. FIG. 38B depicts LLC or Tramp-C2 cells (1×10$^5$) and Ly6G$^+$ cells (1×10$^6$) mixed in MATRIGEL® and implanted subcutaneously into lal$^{+/+}$ mice for 10 days. Representative pictures of MATRIGEL® plugs are shown (n=4). FIG. 38C depicts representative IHC staining with anti-Ki67 antibody of MATRIGEL® plug sections. Original magnification, ×400. FIG. 38**D depicts Ly6G$^+$ cells transfected with mTOR siRNA or control (C) siRNA for 24 hours, followed by co-culture with cancer cells in vitro. The numbers of LLC or Tramp-C2 cells were counted after 72 hours. Data were expressed as mean±s.d.; n=4. *P<0.05, **P<0.01.

FIG. 39A depicts subcutaneous flank injection of A549 cells (1×10$^6$) or MDA-MB-231 cells (5×10$^6$) into wild type (WT) or lal$^{-/-}$ (KO) FVB/N mice. Tumor burden was measured by the maximal length and width of tumor (L×W2/2). n=10. FIG. 39B depicts the cytotoxicity of lymph node cells from wild type or lal$^{-/-}$ mice. The lymph node cell attacking to A549 cells was estimated by fluorescent tracking. The CMTPX labeled lymph node cells were added to the CFSE labeled A549 cells in 2:1 ratio. A representative image and the statistical analysis of the inclusion rate from five fields were shown. FIG. 39C depicts the viability of lymph node cells from wild type and lal mice. The lymph node cells were isolated and cultured overnight and the percentage of cell survival was determined by flow cytometry using 7-AAD/Annexin V staining n=5. FIG. 39D depicts the colony morphology of wild type and lal$^{-/-}$ lymph node cells stimulated by anti-CD3/anti-CD28 antibodies for 2 days. Magnification: upper panel, 40× and lower panel 200×. FIGS. 39E and 39F depicts secretion of IFNγ and IL-10 in lymph node cells from wild type and lal$^{-/-}$ mice after culturing for 2 days with stimulation of the A549 tumor lysate. The culture supernatant was determined by ELISA. n=5 for IFNγ and n=4 for IL-10. FIG. 39G depicts the percentage of GZB positive cells was determined by flow cytometry. n=5. Data shown as mean±SD. *, p<0.05. **, p<0.01.

FIG. 40A depicts the total numbers of lymph node cells. FIG. 40B depicts the total numbers of lymphocytes. FIG. 40C depicts the total numbers of activated lymphocytes. FIG. 40D depicts the percentage numbers of Treg cells. FIG. 40E depicts the total numbers of myeloid cells. FIG. 40F depicts the total numbers of APC myeloid cells. The means±SD were presented, n=5. *, p<0.05. **, p<0.01.

FIG. 41A depicts profiling B cell subsets Fo, T2-MZP and MZ cells. FIG. 41B depicts the percentage and numbers of Fo, T2-MZP, MZ cells and the T2-MZP/Fo ratio. FIG. 41C depicts the percentage numbers of IL-10 or IL-35 positive B220+, Fo and T2-MZP cells. Statistical analysis was performed by Student's t-test, n=6 for IL-10, n=4 for IL-35. *, p<0.05. **, p<0.01.

FIG. 43A depicts PD-L1 co-staining with Breg cell surface markers. FIG. 43B depicts PD-L1 co-staining with Treg cell surface markers. FIG. 43C depicts PD-L1 co-staining with myeloid cell surface markers. FIG. 43D depicts PD-L1 co-staining with APC myeloid cell surface markers. Statistical analysis was performed by Student's t-test, n=6. *, p<0.05. **, p<0.01.

DETAILED DESCRIPTION

Figure 1A:
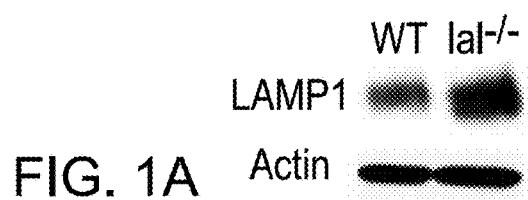
FIGS. 1A-1D depict an increase of lysosome genesis and metabolic disorder in HD1B cells.

Unless defined otherwise, all technical and scientific terms used herein have the same meaning as commonly understood by one of ordinary skill in the art to which the disclosure belongs. Although any methods and materials similar to or equivalent to those described herein can be used in the practice or testing of the present disclosure, the preferred methods and materials are described below.

The lung not only provides an interface for gas exchange between the air and blood to supply oxygen and remove carbon dioxide, but also actively participates in inflammatory responses against pathogens and various diseases. The lung is a highly lipophilic organ and covered with pulmonary surfactant. The round secretory alveolar type II (AT II) epithelial cells scattered around alveolar type I epithelial cells, usually in the corner of the alveoli, are a critical cell type involved in many lung functions. AT II epithelial cells serve as local stem cells to differentiate into AT I epithelial cells during repair of lung injury. They synthesize and secrete surfactant through lamellar bodies rich in phospholipids, which spread out to form a membrane on the surface of the interalveolar walls to prevent the lung from collapsing during respiratory cycles. AT II epithelial cells are able to transform into cancer cells when triggered by overexpression of oncogenic molecules which are downstream genes or effectors of lysosomal acid lipase (LAL) (e.g. Stat3, MMP12, Api6 etc.). In a separate function, AT II epithelial cells serve as local immune cells, which secrete proinflammatory cytokines and chemokines to actively participate in the regional pulmonary microenvironment to form niches for tumor growth and metastasis in the lung.

As shown in the Examples herein, it was found that LAL production in various cell types (myeloid, liver, lung, and the like) by tissue/cell specific expression in transgenic and knock-out mice inhibited tumor initiation, progression and metastasis in the lung, liver, and other organs. Based on these results, the present disclosure is generally directed to methods of administering LAL as a cancer treatment. The present disclosure also provides medical use of LAL in the treatment of cancer. Particularly, the methods and medical uses of the present disclosure are directed to the administration of LAL for suppressing MDSCs homeostasis and function as a means for treating various cancer patients by promoting anti-cancer immunity.

One particularly suitable LAL source is the commercially available soluble LAL source, KANUMA™ (Alexion, New Haven, Conn.), which is currently approved by the US FDA and European Commission for market production to treat Wolman's disease and cholesteryl ester storage disease (CESD). It should be recognized by one skilled in the art, however, that any LAL source as known in the art can suitably be used in the methods and medical uses of the present disclosure.

In one aspect, the methods of the present disclosure generally include methods of treating cancer in an individual in need thereof by administering lysosomal acid lipase (LAL) to the individual. The same aspect provides the use of LAL in the treatment of cancer. As used herein, "treating cancer" and "the treatment of cancer" refers to inhibiting tumor initiation, inhibiting tumor progression and/or inhibiting metastasis. In some particular embodiments, the methods of the present disclosure include methods of treating lung cancer in an individual in need thereof, the methods include administering LAL to the individual. Corresponding medical uses are also provided.

Suitable dosage of LAL for use in the methods and medical uses of the present disclosure will depend upon a number of factors including, for example, age and weight of an individual, at least one precise cancer requiring treatment, severity of a cancer, nature of a composition, route of administration and combinations thereof. Ultimately, a suitable dosage can be readily determined by one skilled in the art such as, for example, a physician, a veterinarian, a scientist, and other medical and research professionals. For example, one skilled in the art can begin with a low dosage that can be increased until reaching the desired treatment outcome or result. Alternatively, one skilled in the art can begin with a high dosage that can be decreased until reaching a minimum dosage needed to achieve the desired treatment outcome or result.

In another aspect, the present disclosure is directed to using LAL deficiency myeloid cell line models for cancer immunity research. Particularly, cell lines, similar to myeloid-derived suppressor cells (MDSCs), have been developed to screen anti-cancer efficacy and mechanisms.

Fatty acid metabolism supports both the biosynthetic and bioenergetic requirements of cell proliferation and survival. Lipids are essential components of plasma and organelle membranes, and can function as secondary messengers for signal pathways. In addition to glycolytic metabolic pathway, free fatty acids oxidation (FAO) also serves as an important metabolic fuel for energy production (e.g., ATP) on the mitochondrial electron transportation chain. Lysosomal acid lipase (LAL) is an essential enzyme that hydrolyzes cholesteryl esters (CE) and tri-glycerides (TG) to generate free fatty acid (FA) and cholesterol in lysosomes. Previously, it was found that lack of LAL in genetically ablated knockout mice ($lal^{-/-}$) shows systemic expansion of MDSCs, which influenced the tissue microenvironment and contributed to local pathogenesis. $Lal^{-/-}$ MDSCs directly stimulated cancer cell proliferation, and suppressed T cell proliferation and impaired T cell function.

Further, mitochondria fission (fragment or dot shape) and fusion (filamentous) play critical roles in maintaining functional mitochondria when cells are under metabolic or environmental stress. Studies have reported that mitochondria fission and fusion respond to cellular triglyceride accumulation. Since the mTOR pathway is highly activated, mitochondria membrane potential is damaged, and the reactive oxygen species (ROS) level is elevated in $lal^{-/-}$ MDSCs.

As shown in the Examples, immortalized wild type $lal^{+/+}$ HD1A and $lal^{-/+}$ HD1B myeloid lineage cell lines were established from wild type and $lal^{-/-}$ mice that were crossbred with Immortomouse expressing a temperature-sensitive version of simian virus 40 large T antigen. The key characters of MDSCs were analyzed in HD1A and HD1B cell lines. HD cells showed higher proliferation than that of HD cells. This is accomplished by high consumption of glucose oxidation in the mitochondria to compensate the deficiency of FAO. Similar to its primary precursor $lal^{-/-}$ MDSCs, $lal^{-/-}$ HD1B myeloid cells in vitro showed stronger immunosuppression on T cells, and stronger stimulation on cancer cell proliferation compared with its wild type counterpart HD1A cells. At the cellular level, HD1B cells showed characteristics of $lal^{-/-}$ MDSCs, including over-activation of the mTOR signaling pathway, increased production of ROS, arginase activity, and damaged membrane potential. At the sub-cellular level, the mitochondrial organization of HD1B cells morphologically showed more fission structure in association with down-regulation of pro-fusion protein Opa1 and phosphorylated activation of pro-fission protein Drp1, while the mitochondrial organization of wild tune HD1A cells showed more fusion structure.

Based on the foregoing, in some aspects, the present disclosure is generally directed to methods for screening candidate compounds for treating cancer. The methods generally include contacting the compound with a HD1B cell; and analyzing the HD1B cell. In one particular aspect, the HD1B cell is analyzed for reactive oxygen species (ROS) production. In another particular aspect, the HD1B cell is analyzed for mitochondrial membrane potential.

In some aspects, the candidate compound can be further contacted with the wild type HD1A cell line and analyzed for ROS production and/or mitochondrial membrane potential.

As shown in the Examples herein, it was found that administration of a peroxisome proliferator-activated receptor gamma (PPARγ) ligand inhibited $lal^{-/-}$ MDSCs stimulation of tumor cell growth and metastasis in vivo, and tumor cell proliferation and migration in vitro. In addition, PPARγ ligand treatment impaired $lal^{-/-}$ MDSCs transendothelial migration, and differentiation from lineage-negative cells. Accordingly, the present disclosure is generally directed to administering a PPAR gamma ligand for cancer treatment. The disclosure also provides the use of a PPAR gamma ligand for the treatment of cancer.

Particularly suitable PPARγ ligands include, for example, 9-hydroxyoctadecadienoic acid (9-HODE), 13-hydroxyoctadecadienoic acid (13-HODE), 15-deoxy-Delta12-14-pro staglandin (J2) (15d-PGD2), prostaglandin A1 (PGA1), prostaglandin A2 (PGA2), and combination thereof. Synthetic PPAR gamma ligands include, for example, rosiglitazone (BRL49653), ciglitazone, pioglitazone, troglitazone, farglitazar, and selective peroxisome proliferator-activated receptor gamma modulator (SPPARM) (i.e., [[4-[2-(6-Benzoyl-2-oxo-3(2H)-benzothiazoly)ethoxy]phenyl]methyl]-1, 3-propanedioic acid dimethyl ester (S26948), T0903131 (INT131)), and the like, and combinations thereof.

In one aspect, the methods of the present disclosure generally include methods of treating MDSCs in cancer in an individual in need thereof by administering a PPARγ ligand to the individual. Corresponding medical uses of PPARγ ligands are also provided. As used herein, "treating cancer" and "the treatment of cancer" refer to inhibiting tumor initiation, inhibiting tumor progression and/or inhibiting metastasis.

Suitable dosages of the PPARγ ligand for use in the methods and medical uses of the present disclosure will depend upon a number of factors including, for example, age and weight of an individual, at least one precise cancer requiring treatment, severity of a cancer, specific PPARγ ligand to be used, nature of a composition, route of administration and combinations thereof. Ultimately, a suitable dosage can be readily determined by one skilled in the art such as, for example, a physician, a veterinarian, a scientist, and other medical and research professionals. For example, one skilled in the art can begin with a low dosage that can be increased until reaching the desired treatment outcome or result. Alternatively, one skilled in the art can begin with a high dosage that can be decreased until reaching a minimum dosage needed to achieve the desired treatment outcome or result.

LAL and PPARγ ligand can be administered as a pharmaceutical composition comprising the LAL and PPARγ ligand source in combination with one or more pharmaceutically acceptable carriers. As used herein, the phrase "pharmaceutically acceptable" refers to those ligands, materials, formulations, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. The phrase "pharmaceutically acceptable carrier", as used herein, refers to a pharmaceutically acceptable material, formulation or vehicle, such as a liquid or solid filler, diluent, excipient, solvent or encapsulating material, involved in carrying or transporting LAL and PPARγ ligand from one organ or portion of the body, to another organ or portion of the body. Each carrier must be "acceptable" in the sense of being compatible with the other components of the composition (e.g., LAL and PPARγ ligand) and not injurious to the individual. Lyophilized compositions, which may be reconstituted and administered, are also within the scope of the present disclosure.

Pharmaceutically acceptable carriers may be, for example, excipients, vehicles, diluents, and combinations thereof. For example, where the compositions are to be administered orally, they may be formulated as tablets, capsules, granules, powders, or syrups; or for parenteral administration, they may be formulated as injections (intramuscular, subcutaneous, intramedullary, intrathecal, intraventricular, intravenous, intravitreal), drop infusion preparations, or suppositories. These compositions can be prepared by conventional means, and, if desired, the active compound (i.e., LAL and PPARγ ligand) may be mixed with any conventional additive, such as an excipient, a binder, a disintegrating agent, a lubricant, a corrigent, a solubilizing agent, a suspension aid, an emulsifying agent, a coating agent, or combinations thereof.

It should be understood that the pharmaceutical compositions of the present disclosure can further include additional known therapeutic agents, drugs, modifications of the synthetic compounds into prodrugs, and the like for alleviating, mediating, preventing, and treating the diseases, disorders, and conditions described herein. For example, in one embodiment, the PPARγ ligand can be administered with lysosomal acid lipase (LAL). One particularly suitable LAL source is the commercially available soluble LAL source, KANUMA™ (Alexion, New Haven, Conn.), which is currently approved by the US FDA and European Commission for market production to treat Wolman's disease and cholesteryl ester storage disease (CESD). It should be recognized by one skilled in the art, however, that any LAL source as known in the art can suitable be used in the methods and medical uses of the present disclosure.

The pharmaceutical compositions including the LAL and PPARγ ligand source and/or pharmaceutical carriers used in the methods and medical uses of the present disclosure can be administered to a subset of individuals in need. As used herein, an "individual in need" refers to an individual at risk for or having cancer, and in particular, lung cancer, liver cancer, prostate cancer, breast cancer, and/or melanoma. Additionally, an "individual in need" is also used herein to refer to an individual at risk for or diagnosed by a medical professional as having cancer. As such, in some embodiments, the methods and medical uses disclosed herein are directed to a subset of the general population such that, in these embodiments, not all of the general population may benefit from the methods and uses. Based on the foregoing, because some of the method and use embodiments of the present disclosure are directed to specific subsets or subclasses of identified individuals (that is, the subset or subclass of individuals "in need" of assistance in addressing one or more specific conditions noted herein), not all individuals will fall within the subset or subclass of individuals as described herein. In particular, the individual in need is a human. The individual in need can also be, for example, a research animal such as, for example, a non-human primate, a mouse, a rat, a rabbit, a cow, a pig, and other types of research animals known to those skilled in the art.

Various functions and advantages of these and other embodiments of the present disclosure will be more fully understood from the examples shown below. The examples are intended to illustrate the benefits of the present disclosure, but do not exemplify the full scope of the disclosure.

EXAMPLES

Example 1

Materials & Methods

All scientific protocols involving the use of animals have been approved by the Institutional Animal Care and Use Committee of Indiana University School of Medicine and followed guidelines established by the Panel on Euthanasia of the American Veterinary Medical Association. Animals were housed under Institutional Animal Care and Use Committee-approved conditions in a secured animal facility at Indiana University School of Medicine.

HD1A and HD1B myeloid cell line establishment from isolation of immortalized mouse myeloid lineage cells Peritoneal macrophages were collected from wild type and lal$^{-/-}$ male mice that had been cross-bred with Immortomouse (Charles River Laboratories) expressing a temperature-sensitive version of simian virus 40 large T antigen from an IFN-γ inducible promoter. Cell suspensions were obtained by peritoneal lavage with 8 ml of PBS, washed, and cells were cultured at 33° C. in RPMI medium 1640 supplemented with 10% FBS, antibiotics, and 5 units/ml IFN-γ. After 10 passages, IFN-γ was omitted from the medium.

Living Cell Lysosome Staining

HD1A and HD1B cells were grown in 24-well plates to the desired confluence. The medium were replaced with pre-warmed (37° C.) LysoTracker Red DND-99 probe (50 nM, Molecular Probes)-containing medium for 1 hour. Cells were replaced with fresh medium, and fluorescent signals were examined under the Nikon ECLIPSE Ti inverted fluorescence microscope.

Glucose and Pyruvate Measurement

The concentration of glucose and pyruvate was measured by the glucose assay kit and pyruvate assay kit (Sigma) respectively according the manufacturer's instruction. Briefly, HD1A or HD1B cells were washed with PBS before being harvested. The cell pellets were added with pre-warmed water and headed in the 70° C. water bath for 10 minutes. After spinning down the cell lysates, for glucose measurement the supernatants were incubated with glucose assay reagent for 15 minutes at room temperature and measured absorbance at the 340 nm. For pyruvate measurement, the supernatants were incubated with pyruvate assay buffer, pyruvate probe solution and pyruvate enzyme mixture for 30 minutes at room temperature and measured absorbance at the 570 nm.

Aconitase Activity Assay

The aconitase activity was measured by the aconitase activity assay kit (Sigma) according the manufacturer's instruction. Briefly, HD1A or HD1B cells were washed with PBS before being harvested. Cells were lysed in the ice-cold assay buffer. After centrifugation, the aconitase activation buffer was added into supernatant and incubated on ice for 1 hour, followed by adding Enzyme Mix, assay buffer and the substrate at 25° C. for 30 minutes. After addition of developer to the incubation mixture at 25° C. for 10 minutes, the reactions were measured at the 450 nm absorbance. One unit of the aconitase activity is the amount of enzyme that isomerizes 1.0 μmole of citrate to isocitrate per minute at pH 7.4 at 25° C.

Living Cell Mitochondrial Staining

HD1A and HD1B cells were grown in 24-well plates to the desired confluence. The medium were replaced with pre-warmed (37° C.) MitoTracker Green FM (100 nM, Molecular Probes)-containing medium for 1 hour. Cells were replaced with fresh medium, and fluorescent signals were examined under the Nikon ECLIPSE Ti inverted fluorescence microscope.

Immunofluorescence

HD1A and HD1B cells were fixed for 15 minutes in 4% paraformaldehyde, and permeabilized for 10 minutes in 0.02% Triton X 100. After washing, cells were blocked with 5% normal goat serum in 1×PBS for 1 hour followed by incubation of primary goat anti-LAMP1 antibody (1:200, Santa Cruz) overnight. Cells were then incubated with secondary donkey anti-goat antibody conjugated with Cy3 (1:1000, Jackson ImmunoResearch) for 1 hour, and co-stained with DAPI. Fluorescent signals were examined under the Nikon fluorescence microscope.

Western Blot

HD1A and HD1B cells were lysed in the Cell Lytic M mammalian cell lysis/extraction buffer (Sigma-Aldrich) according to the manufacturer's instruction. Protein samples were fractionated on a Novex 4-20% Tris-Glycine Mini Gel (Invitrogen). After transferring to the polyvinylidene difluoride membrane (Bio-Rad), the membrane was blotted with 5% nonfat dry milk in 1×PBS, and incubated with rabbit anti-p-S6 (Ser235/236), anti-S6, anti-p-Drp1 (Ser616), anti-Drp1, and anti-actin primary antibodies (from Cell Signaling), or rat anti-LAMP1, rabbit anti-Opa1 antibodies (from Santa Cruz). Following incubation with the secondary antibody that conjugated with horse radish peroxidase, proteins were visualized with chemiluminescent substrate (Thermo Scientific) under ChemiDox MP Image System.

ROS Measurement

HD1A and HD1B cells were treated with solvent, rapamycin (40 nM), or PP242 (40 nM) for 60 minutes. Cells were washed and stained with 2 μM of 2',7'-dichlorodihydrofluorescein diacetate stained (DCFDA, Invitrogen) which is nonfluorescent until the acetate group is removed by intracellular esterases and oxidation occurs within the cell (Invitrogen). The incubation was at 37° C. for 20 minutes, followed by washing with cold PBS. The ROS level was measured by flow cytometry.

Arginase Activity Measurement

HD1A or HD1B cells were lysed for 30 minutes at room temperature with 50 μl 0.1% Triton X-100 PBS containing 5 μg pepstatin, 5 μg aprotinin, and 5 μg antipain protease inhibitors per ml. Subsequently, 50 μl 10 mM $MnCl_2$ and 50 μl 50 mM Tris-HCl (pH 7.5) were added, and the enzyme was activated by heating at 56° C. for 10 minutes. Arginine hydrolysis was conducted by incubating the lysate (100 μl) with 100 μl 0.5 M L-arginine (pH 9.7) at 37° C. for 60-120 minutes. The reaction was stopped with 400 μl $H_2SO_4$ (96%)/$H_3PO_4$ (85%)/$H_2O$ (1:3:7, v/v/v). The urea concentration was measured at 540 nm after addition of 25 ml 9% α-isonitrosopropiophenone (dissolved in 100% ethanol), followed by heating at 95° C. for 45 minutes and 10 minutes at room temperature in the dark. One unit of enzyme activity is defined as the amount of enzyme that catalyzes the formation of 1 μmol urea per minute.

T Cell Proliferation and Lymphokine Release Assays in Vitro

Freshly isolated wild type $CD4^+$ T cells from the spleen were labeled with carboxyfluorescein diacetate succinimidyl diester (CFSE, Molecular Probes) (1 μM in PBS) at room temperature for 5 minutes, and resuspended in complete medium for 20 minutes. $CD4^+$ T cells were spun down and cultured in 96-well flat-bottom plates coated with anti-CD3 mAb (2 μg/ml) and anti-CD28 mAb (5 μg/ml) for 4 days in the presence or absence of HD1A or HD1B cells at 37° C. The ratio between HD1A or HD1B cells and $CD4^+$ T cells was 1:30. Cells were harvested and stained with APC-labeled anti-CD4 mAb (eBiosciences). Proliferation of $CD4^+$ T cells was evaluated as CFSE dilution by FACS. To measure T cell secreting lymphokines, OptEIA ELISA kits for IL-2, IL-4 and IFNγ were used according to the manufacturer's instruction (BD BioScience).

HD1A and HD1B Cell Surface Marker Staining

HD1A and HD1B cells were harvested and stained with anti-CD11b-PEcy7 and anti-Ly6G-Apccy7 for flow cytometry analysis.

mTOR Knockdown by siRNAs

HD1A and HD1B cells were transfected with mTOR-specific or scrambled control siRNAs (final concentration 25 nM) according to the manufacturer's protocol (Dharmacon, Lafayette, Colo.). After 48 hours incubation, cells were washed and co-cultured in wells with CFSE-labeled wild type $CD4^+$ T cells (1:30) for T cell proliferation (96 hours) and lymphokine release study (48 hours), or lysed to test mTOR signaling pathway protein expression, or co-cultured with B16 or LLC cancer cells, or labeled for BrdU incorporation study.

Mitochondrial Membrane Potential Assay

HD1A and HD1B cells were grown in 24-well plates to the desired confluence. Cells were treated with solvent (DMSO, 0.1%), rapamycin (40 nM), or PP242 (40 nM) for 1 hour, or NAC (100 μM, Sigma-Aldrich), or Tempol (10 μM, Sigma-Aldrich) overnight. Treated cells were replaced with the pre-warmed (37° C.) medium containing JC1 (5 μM, Molecular Probes) for 1 hour. Labeled cells were replaced with fresh medium and examined under the Nikon inverted fluorescence microscope.

BrdU Incorporation

For cell proliferation analysis, HD1A and HD1B cells were grown in 24-well plate to the desired confluence. BrdU (BD Biosciences) was added at a final concentration of 10 µM in cell culture medium for 1 hour. Cells were harvested and washed twice with PBS. Cells were fixed and permeabilized with BD Cytofix/Cytoperm buffer, then incubated with DNase I and washed again followed by staining with fluorescent anti-BrdU antibody before analysis by flow cytometry.

Cancer Cell Proliferation in Vitro

B16 melanoma or LLC cancer cells were harvested and labeled with CFSE (1 µM in PBS) at room temperature for 5 minutes. Labeled cancer cells were resuspended in complete medium for 20 minutes, spun down, and co-cultured with HD1A or HD1B cells (1:5, $3 \times 10^4$ cells per well of 24-well plate). After culture for 3 days, the cells were harvested and analyzed on the LSR II to determine cancer cell proliferation by gating CFSE labeled cells.

Cancer Cell Growth in Vivo

B16 melanoma cells ($2 \times 10^5$) were mixed with HD1A or HD1B cells ($2 \times 10^5$) and injected subcutaneously at left or right flank sites of C57BL/6 or FVB/N mice. The tumor sizes were measured 14 days post-injection with calipers. The tumor volumes were determined using the formula: (length X width$^2$)/2. At the end of the experiment, the animals were euthanized.

Real-Time PCR

Total RNAs from HD1A or HD1B cells were purified using the Qiagen total RNA purification kit (Qiagen). cDNAs were generated by SuperScript III (Invitrogen). Real-Time PCR for CD36, CPT1a, CPT1b, CPT1c, Foxo3, Glut1-13, ID01, ID02, SIRT1 and the housekeeping gene β-Actin was performed on a StepOnePlusReal-Time PCR System (Applied Biosystems) using Power SYBR Green PCR Master Mix (Applied Biosystems) according to the manufacturer's protocol. The ($2^{-\Delta\Delta CT}$) algorithm was used to determine the relative gene expression.

Results

Lysosome Accumulation in lal$^{-/-}$ Macrophage Cell Lines

Figure 1B:
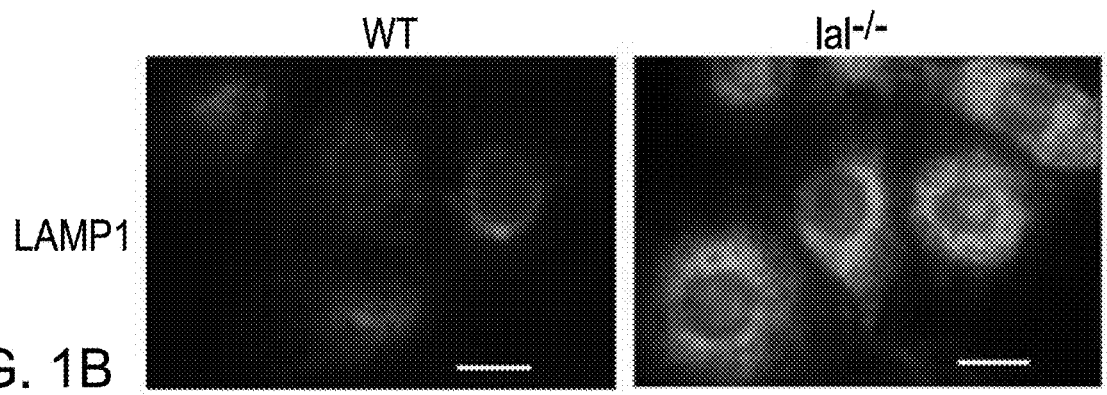
Figure 1C:
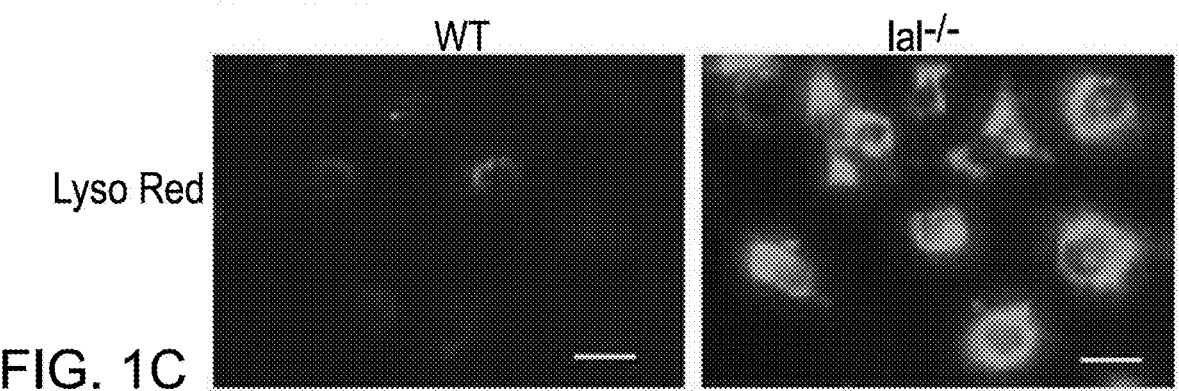
Figure 1D:
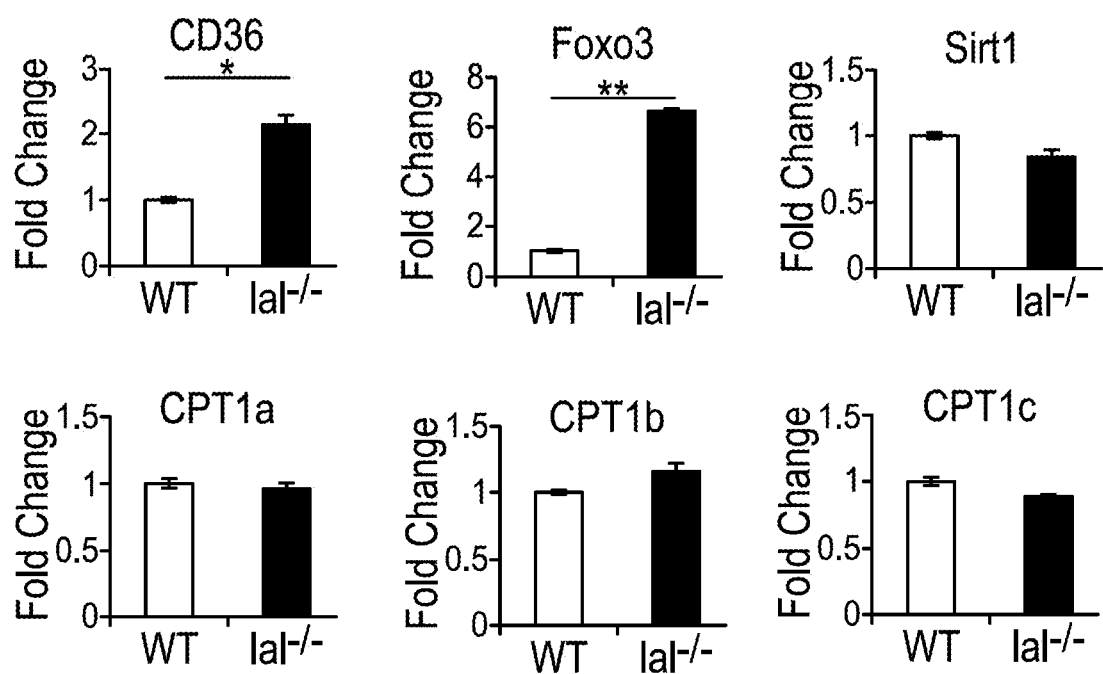

To generate HD1A and HD1B cells, wild type and lal$^{-/-}$ mice were crossbred with Immortomouse (Charles River laboratory), which express a temperature-sensitive simian virus 40 T antigen under an INF-γ inducible promoter. HD1A and HD1B cell lines were established and passaged as described above. As LAL is a lysosome localized enzyme, the lysosome numbers and localization were examined in HD1A and HD1B cells. Western blot analysis showed an increased LAMP1 (a marker for lysosome) expression level in HD1B cells compared with that ofHD1A (FIG. 1A) Immunofluorescent staining of LAMP1 showed increased lysosomal numbers in HD1B cells around the perinuclear area (FIG. 1B). This was confirmed by another lysosome specific dye LYSOTRACKER® Red DND-99 staining (FIG. 1C). The malfunction of HD1B was assessed by several molecules that are involved in fatty acid uptake and function, including CD36, forkhead box O (FOXO3), and SIRT1. CD36 or FOXO3 expression was increased in HD1B cells compared with HD1A cells, while SIRT1 had no change (FIG. 1D). Another group of fatty acid (FA) transporters were investigated, carnitine palmitoyl transferase (CPT1a, CPT1b and CPT1c) that transports long-chain FA into the mitochondria and are a rate limiting step of mitochondrial fatty-acid oxidation (FAO). None of these transporters showed expression changes in HD1B cells compared with those in HD1A cells (FIG. 1D), suggesting no increased activity of this pathway for FA transportation into the mitochondria during LAL dysfunction. Taken together, these results indicate that LAL deficiency increases lysosome genesis and the abnormal activities of fatty acid metabolism in HD1B myeloid cells.

Figure 2A:
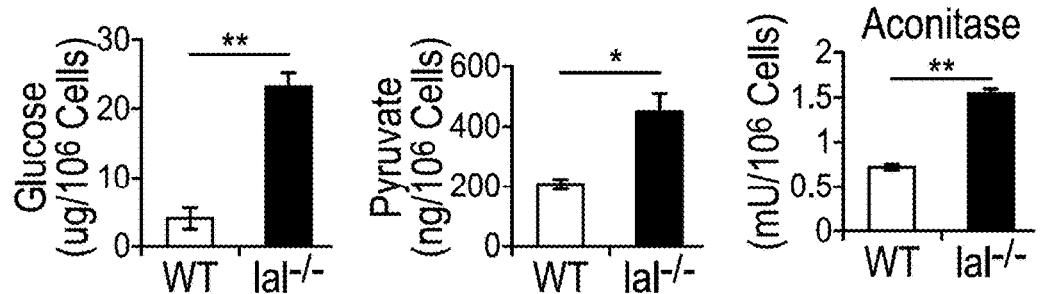
FIGS. 2A & 2B depict glucose transportation, glycolysis and TCA in HD1A and HD1B cells.
Figure 2B:
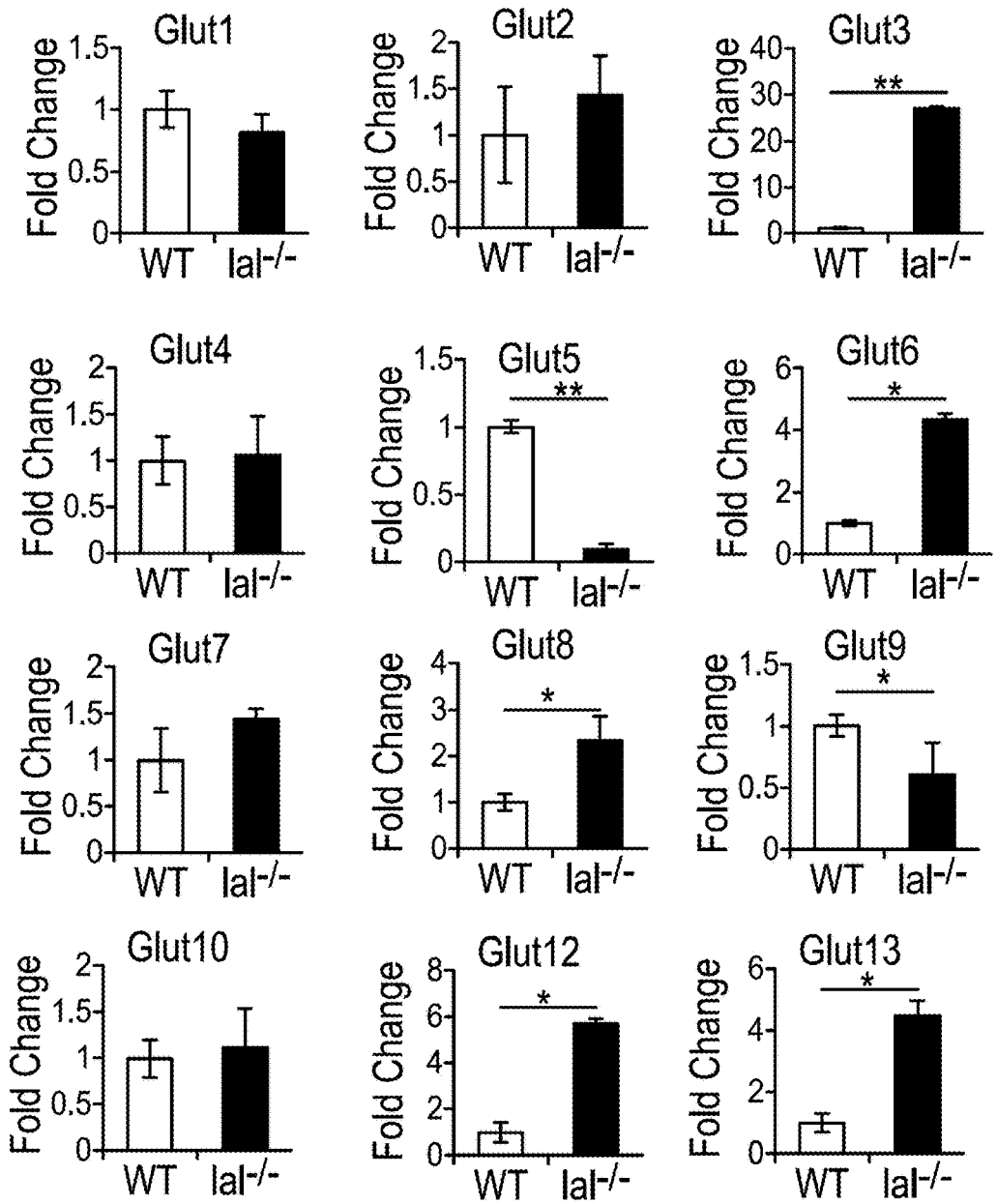

Glucose level, pyruvate level, aconitase activity, and GLUT expression in HD1A and HD1B cells Compared with HD1A cells, HD1B cells showed increased glucose concentration (FIG. 2A), suggesting the enhanced glycolysis metabolic pathway, in which glucose converts into pyruvate. Indeed, the pyruvate concentration was increased in HD1B cells compared with that in HD1A cells (FIG. 2A). Glycolysis occurs in the cytosol of the cell. Pyruvic acid supplies energy to living cells through the citric acid cycle (TCA) in the mitochondria, which generates NADH for the oxidative phosphorylation (OXPHOS, electron transport pathway) to produce ATP. Aconitase is the rate-limiting enzyme in the TCA cycle. Its activity was doubled in HD1B cells compared with HD1A cells (FIG. 2A). The high glycolysis metabolic rate and TCA turnover lead to the investigation of GLUT (SLC2) family members. These are the major membrane transporters. Among them, GLUT 1-5 have been well characterized as glucose and/or fructose transporters in various tissues and cell types. Thirteen GLUT proteins have been reported to be expressed in mice (14 in humans). Using the Real-time PCR method, expression of all GLUT members was assessed in HD1A and HD1B cells, in which GLUT3, GLUT6, GLUTS, GLUT12 and GLUT13 were upregulated, while GLUT 5 and GLUT 9 were downregulated in HD cells (FIG. 2B). This supports a concept that the neutral lipid metabolic pathway controls the balance of glucose transportation to fuel the energy need in myeloid cells.

Mitochondrial Morphology Change in HD1B Cells

Figure 3A:
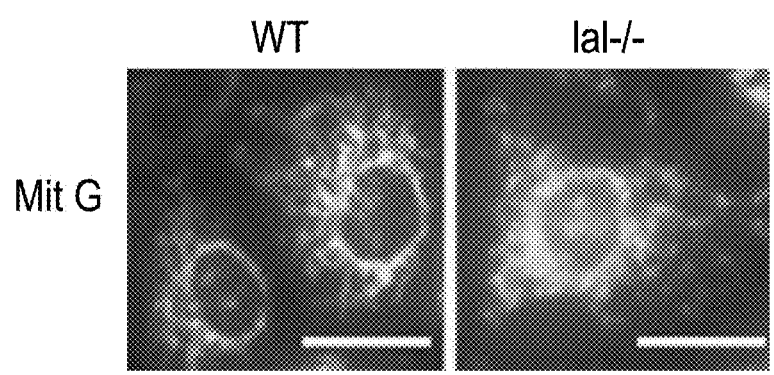
FIGS. 3A-3C depict the morphological change of mitochondria in wild type (HD1A) and lal$^{-/-}$ (HD1B) cells.
Figure 3B:
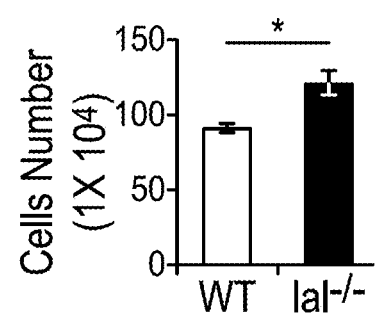
Figure 3C:
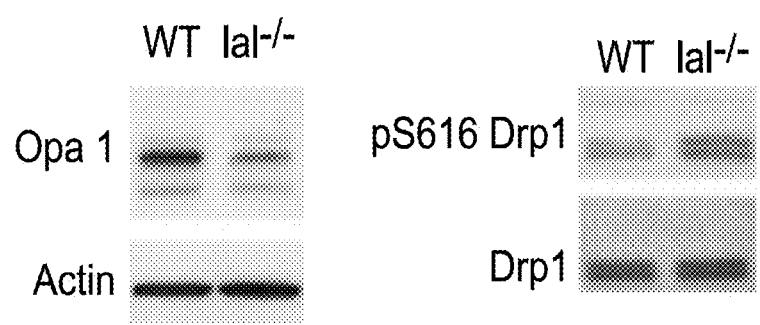

As demonstrated above, compared to HD1A cells the glycolytic pathway in HD1B cells are enhanced and utilized to fuel the energy need for this transition. Mitochondria are central organelles in carbohydrate, lipid and amino acid metabolisms in cells. Glycolytic metabolic influx into mitochondria and enter the TCA cycle to enhance mitochondrial respiration on the mitochondrial electron transport chain (ETC). Mitochondria are double-membrane-bound subcellular organelles of eukaryotic cells with various functions, including oxidative-phosphorylation, apoptosis, and ROS production. In order to fully understand pathogenic malformation and malfunction in HD1B cells, it is necessary to characterize and compare mitochondrial structures in HD1A and HD1B cells for comparison. It has been well documented that the mitochondrial fission and fusion processes play critical roles in governing these mitochondrial functions. Using mitochondria-specific labeling dye Mit G, mitochondria in HD1B cells showed more fission shaped structure (dots) when compared with more fusion shaped structure in HD1A cells (FIG. 3A). The fission process of mitochondria is engaged in a more proliferative state. Indeed, HD1B cells are more proliferative than HD1A cells (FIG. 3B). This observation is also in consistence with higher transportation and consumption of glucose as outlined in FIGS. 1A-1D. Opa1 is a key mediator controlling mitochondrial fusion. Western blot analysis showed a decreased level of Opa1 expression in HD1B cells compared with that of HD1A cells (FIG. 3C, left panel). On the other hand, Drp1 is a key mediator controlling mitochondrial fission. Phosphorylation on Ser616 activates Drp1 to stimulate mitochondrial fission. In HD1B cells, phosphorylation on Ser616 of Drip1 was increased significantly (FIG. 3C, right panel). Therefore, LAL deficiency in HD1B cells leads to mitochondrial fusion to fission conversion, a more proliferative state.

Mitochondrial Dysfunction in HD1B Cells

Figure 4A:
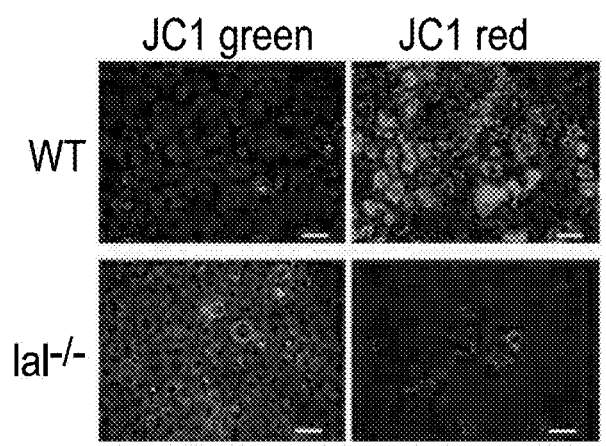
FIGS. 4A-4D depict mitochondrial membrane potential, ROS production, arginase, and IDOs in wild type (HD1A) and lal$^{-/-}$ (HD1B) cells.
Figure 4B:
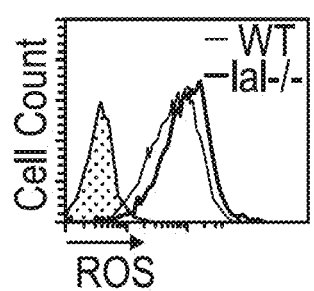
Figure 4B:
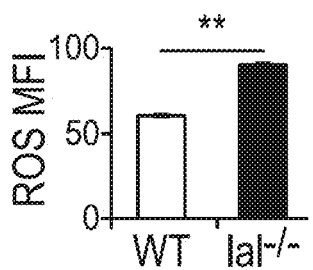
Figure 4C:
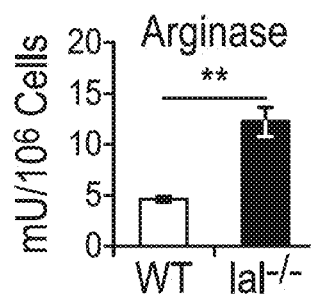
Figure 4D:
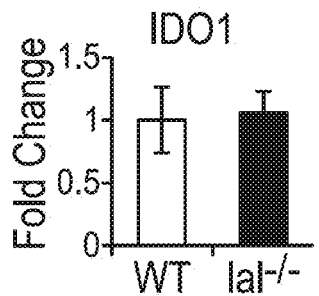
Figure 4D:
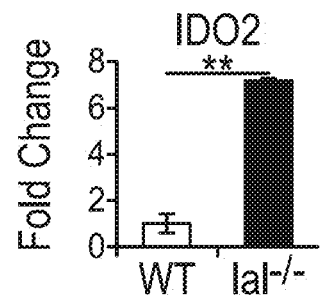

To see if the structural change leads to functional changes, the mitochondrial membrane potential and ROS production, which are coupled with OXPHOS, were measured in HD1A and HD1B cells. The mitochondrial membrane potential was analyzed by JC1 staining. While most HD1A cells were stained with red fluorescence staining (representing healthy mitochondria), HD1B cells were stained with less red fluorescence and more green fluorescence (representing damaged mitochondria) (FIG. 4A). A damaged mitochondrial membrane potential restricts electron flow and increases the leakage of electrons to form ROS through the electron transport chain. Indeed, increased ROS production in HD1B cells was observed (FIG. 4B). Compared with that in HD1A cells, HD1B cells also increased the arginase activity, which is another important characteristic parameter of MDSCs (FIG. 4C). These phenotypes resemble to what were observed in lal$^{-/-}$ MDSCs. Because tryptophan (Trp) metabolizing enzyme indoleamine 2,3-dioxygenase (IDO) plays a pivotal role in MDSCs via suppressing T cell function, expression of both IDO1 and IDO2 were measured in HD1A and HD1B cells. Interestingly, only IDO2 was highly overexpressed in HD1B cells (FIG. 4D). Therefore, there are profound differences between the mitochondrial structures and functions in HD1A and HD1B cells.

mTOR Inhibition or Antioxidant Treatment Rescued Abnormal HD1B Phenotypes

Figure 5A:
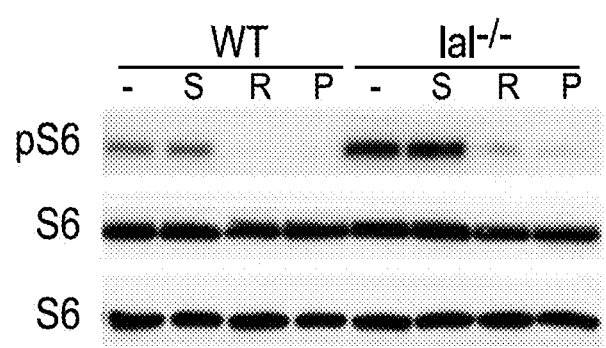
FIGS. 5A-5D depict overactivation of the mTOR signal pathway in wild type (HD1A) and lal$^{-/-}$ (HD1B) cells.
Figure 5B:
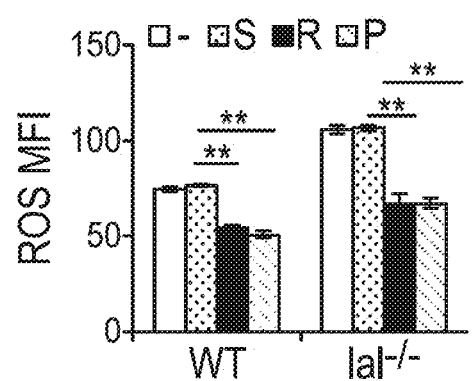
Figure 5C:
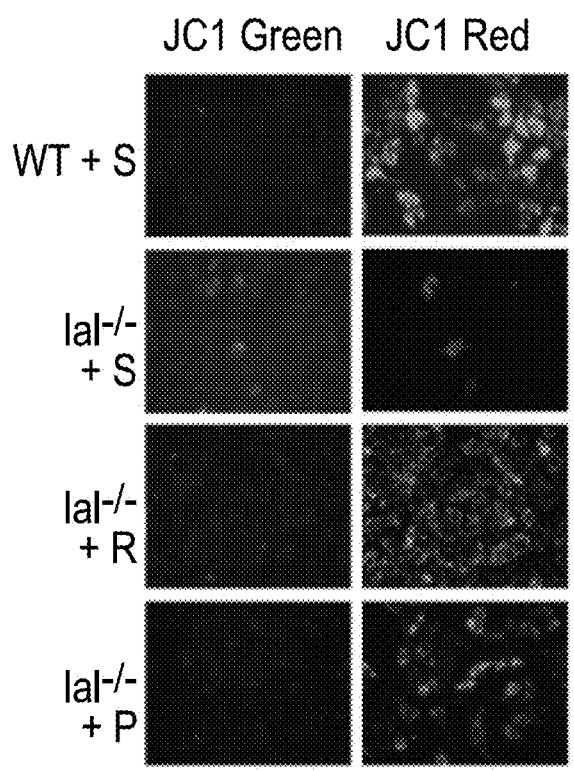
Figure 5D:
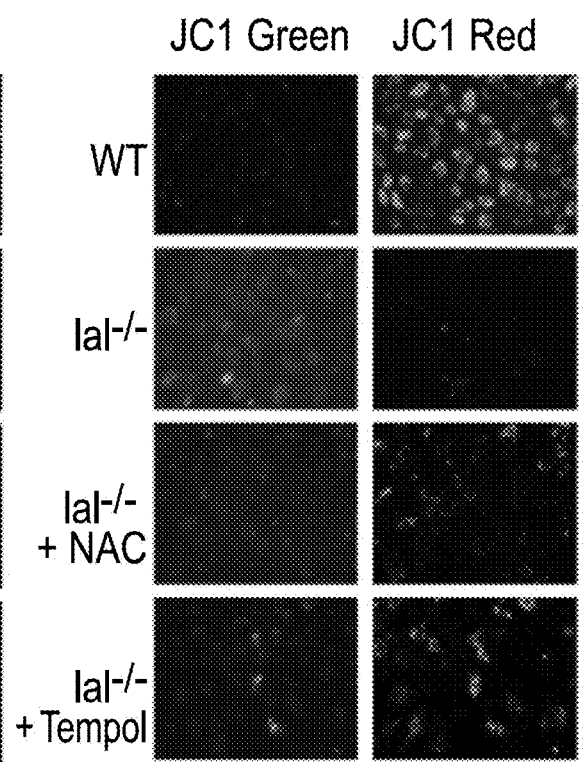

Previously, Affymetrix GeneChip microarray showed over-activation of the mTOR signaling pathway in association with mitochondrial membrane potential damage and ROS over-production in lal$^{-/-}$ MDSCs. To see if mTOR is overly activated in HD1B cells, rapamycin or PP242 were used to suppress the mTOR signaling pathway. As demonstrated by the Western blot result, both inhibitors blocked mTOR downstream effector S6 phosphorylation in HD1A and HD1B cells (FIG. 5A). The treatment also decreased ROS production (FIG. 5B) and reversed the damaged mitochondrial membrane potential in HD1B cells (FIG. 5C). To confirm that ROS over-production is responsible for the damage of the mitochondrial membrane potential in HD1B cells, antioxidant NAC or TEMPOL was used to diminish ROS. This treatment partially improved the condition of the mitochondrial membrane potential as shown with more red JC-1 fluorescence staining in HD1B cells (FIG. 5D).

Immunosuppressive Function of HD1B Cells

Figure 6A:
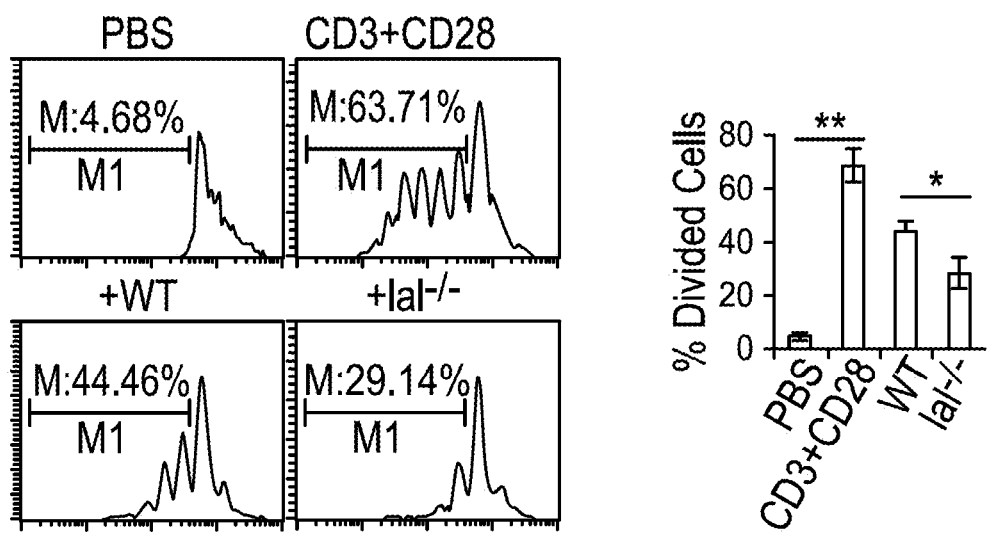
FIGS. 6A & 6B depict immunosuppression on T cell proliferation and function by wild type (HD1A) and lal$^{-/-}$ (HD1B) cells.
Figure 6B:
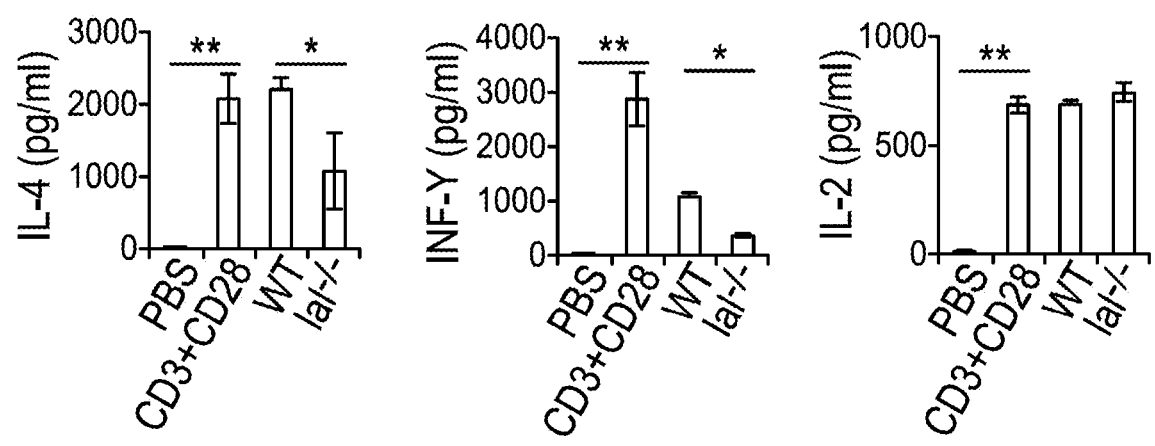
Figure 7A:
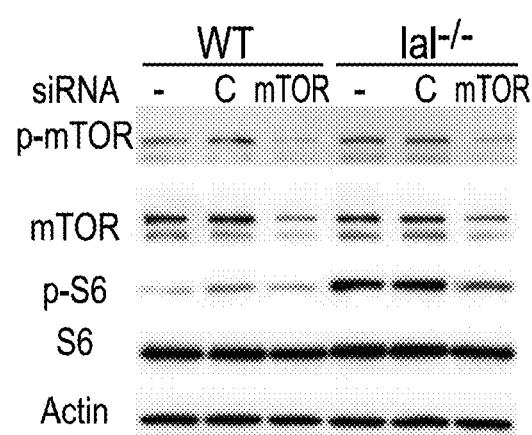
FIGS. 7A-7C depict that siRNA knockdown of mTOR inhibited immunosuppression on T cell proliferation and function of lal$^{-/-}$ (HD1B) cells.
Figure 7B:
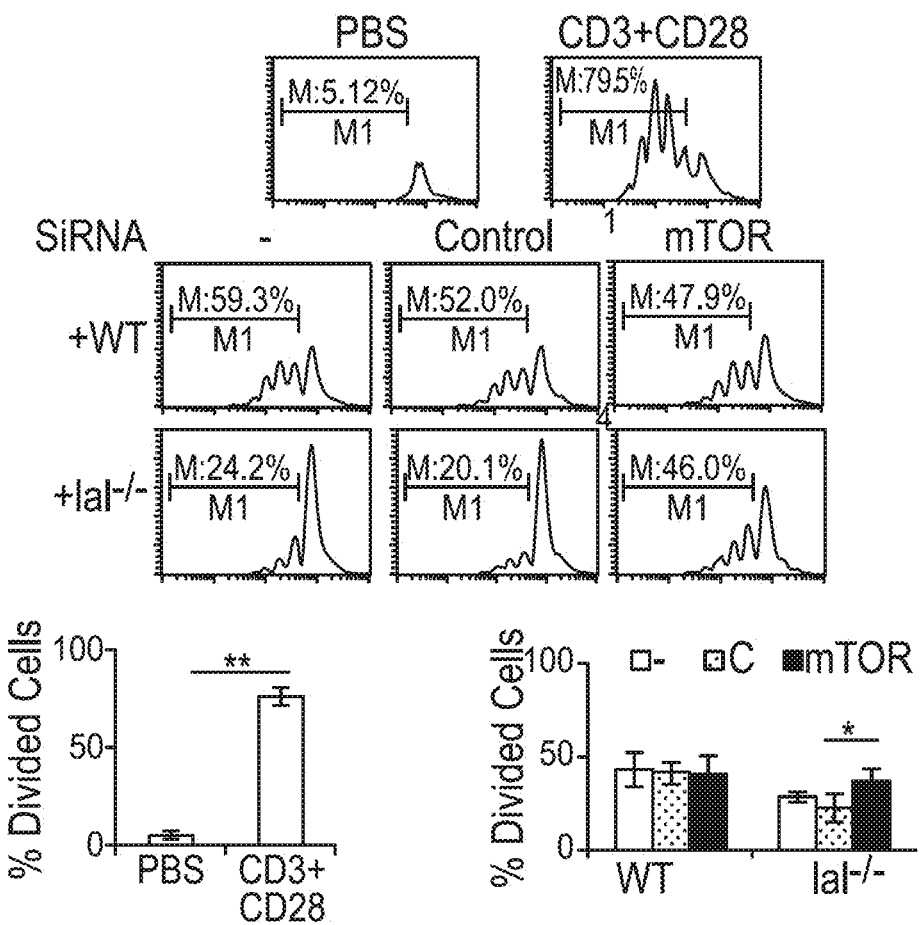
Figure 7C:
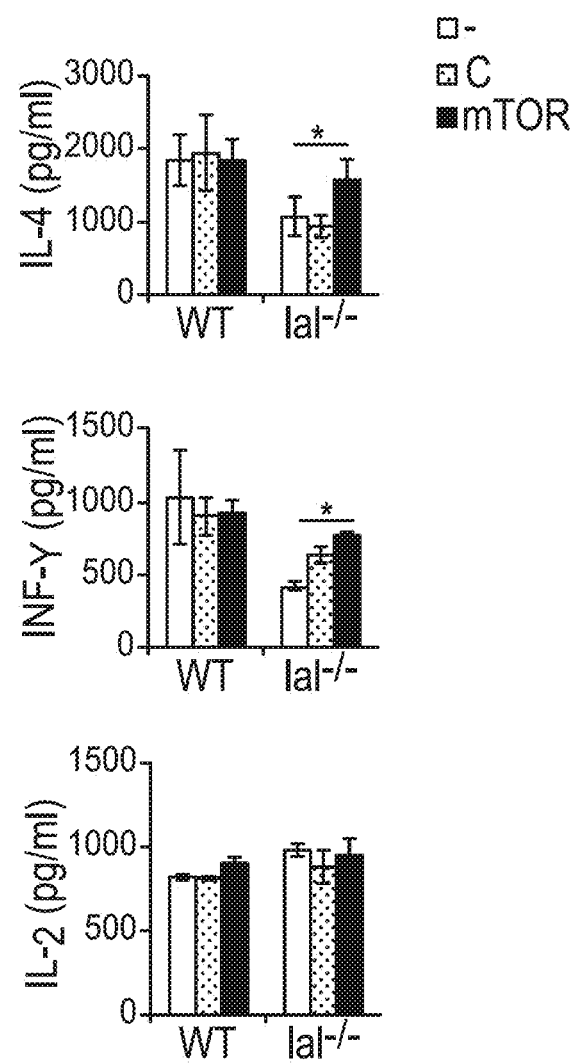

Immunosuppression is the hallmark of MDSCs. To see if HD1B cells possess immunosuppressive function, HD1B cells (or HD1A cells as control) were co-cultured with CFSE-labeled splenocyte CD4$^+$ T cells in the anti-CD3 and anti-CD28 antibody coated plate. After 4 days, CD4$^+$ T cell proliferation was analyzed by flow cytometry. Compared with HD 1A cells, HD1B cells showed a stronger suppressive function on CD4$^+$ T cell proliferation (FIG. 6A). Lymphokine release of INFγ (TH1) and IL-4 (TH2) by CD4$^+$ T cells was also decreased when CD4$^+$ T cells were co-cultured with HD1B cells (FIG. 6B). These results indicate that HD1B cells exhibit a similar immunosuppressive function as lal$^{-/-}$ MDSCs.

mTOR Signal Inhibition Reversed HD1B Cell Immunosuppressive Function mTOR protein expression was knocked down by mTOR siRNA in HD1B cells as confirmed by Western blot analysis, which led to decreased mTOR and S6 phosphorylation (FIG. 7A). After transfection with mTOR siRNAs, HD1B cells showed reduced immunosuppression on splenocyte CD4$^+$ T cell proliferation in the co-culture experiment (FIG. 7B), while control siRNAs showed no reduced effect. Furthermore, lymphokine IL-4 and INFγ secretion was also recovered when CD4$^+$ T cells were co-cultured with HD1B cells that had been knocked down by mTOR siRNA compared with those knocked down by control siRNA (FIG. 7C). Therefore, mTOR overactivation is partially responsible for HD1B cell immunosuppressive function.

HD1B Cells Stimulate Tumor Cell Proliferation

Figure 8A:
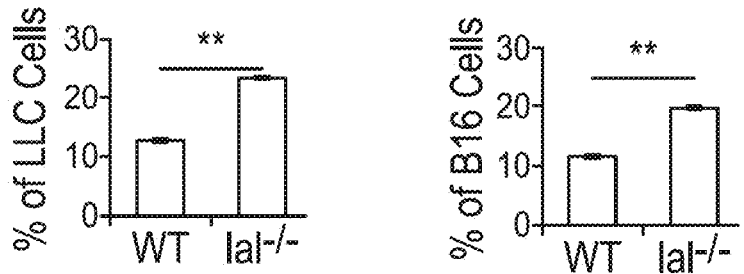
FIGS. 8A-8C depict that lal$^{-/-}$ cells (HD1B) stimulated cancer cells growth.
Figure 8B:
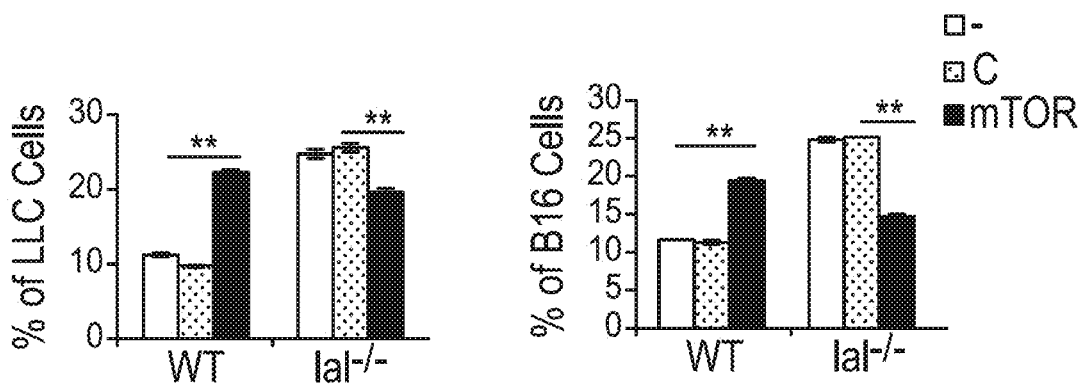
Figure 8C:
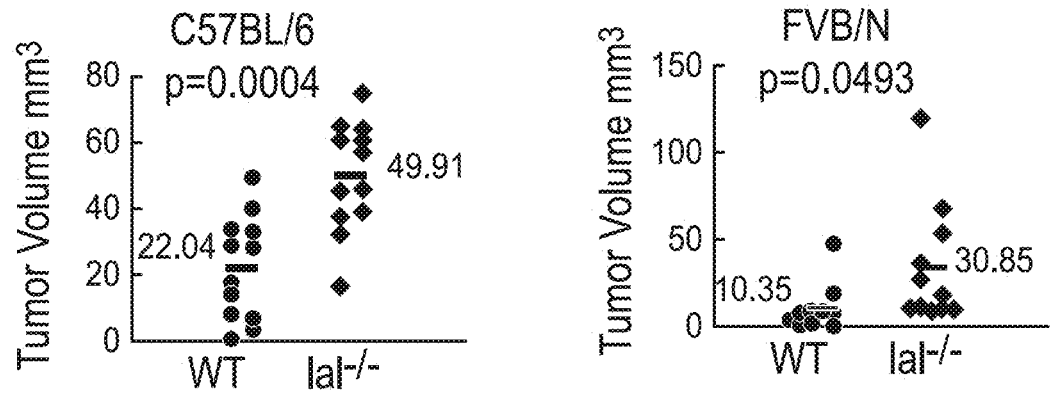

Lal$^{-/-}$ MDSCs have been shown to directly stimulate cancer cell proliferation. To compare the tumor stimulatory effects between HD1A and HD1B cells, both cells were co-cultured with CFSE-labeled B16 melanoma cells or LLC cells in vitro. After 3 days, more tumor cells were observed when co-cultured with HD1B cells compared with those co-cultured with HD1A cells in flow cytometry analysis (FIG. 8A), suggesting that HD1B cells possess a stronger stimulatory effect on both B16 melanoma cells and LLC cells. Knockdown of mTOR in HD1B cells showed a decreased stimulatory effect on cancer cells (FIG. 8B). Surprisingly, knockdown of mTOR in HD1A cells showed an increased stimulatory effect on cancer cells (FIG. 8B). Perhaps the mTOR signaling plays differential roles in HD1A cells and HD1B cells. In an in vivo model, when B16 melanoma cells were co-injected with HD1A or HD1 B cells into syngeneic C57BL/6 or allogeneic FVB/N wild type recipient mice, the tumor size and volume were much larger in the group with HD1B cell co-injection than the group with HD1A cell co-injection in both syngeneic and allogeneic background (FIG. 8C).

Discussion

Lipids have long been recognized not only as the nutrients for cell growth and structural components, but also as the cell signaling molecules that have the capacity to trigger profound physiological responses. Previously, extensive studies showed that LAL is a critical enzyme that controls inflammation, especially MDSCs development and homeostasis.

Deletion of this neutral lipid metabolic controlling enzyme induces massive MDSCs expansion in lal$^{-/-}$ mice, which leads to immunosuppression and multiple pathogenic diseases including cancer formation and metastasis. These studies have firmly established the functional roles of neutral lipid metabolism controlled by LAL in MDSCs development, homeostasis and function. Based on these solid characterizations, lal$^{-/-}$ mouse model is an ideal system to generate "MDSCs-like" cell lines. By crossbreeding wild type or lal$^{-/-}$ mice with Immortomouse expressing a temperature-sensitive version of simian virus 40 large T antigen, two myeloid-derived cell lines were established, HD1A (wild type myeloid cell line) and HD1B (lal$^{-/-}$ myeloid cell line).

In lal$^{-/-}$ HD1B cells, more intensified lysosomal subcellular structures were observed by both LysoTracker and LAMP1 staining studies compared with HD1A cells (FIG. 1B, C), implicating that LAL deficiency increases lysosome genesis. In addition, the lysosomal structures in HD1B cells were located around perinuclear areas, while lysosomal structures in HD1A were spread out in the cytoplasm. This localization change implicates functional changes of lysosomes in HD1B cells. The lysosome functions far beyond the traditional cell component to degrade and recycle cellular waste.

In addition to morphological changes, expression of several functional proteins critical for fatty acid transportation across the plasma membrane or mitochondrial membrane, and metabolic stress protein were investigated. CD36 is a scavenger receptor for modified LDL lipid particles and long-chain fatty acid uptake. To compensate the inability of intracellular fatty acid generation due to LAL deficiency, HD1B cells upregulated CD36 expression perhaps trying to export more extracellular ones (FIG. 1D). On the other hand, due to the reduced intracellular generation of fatty acids in HD1B cells, there is no change in expression of carnitine O-palmitoyltransferase (CPT), the rate-limiting enzyme for long chain fatty acid entry into mitochondria and fatty acid oxidation (FAO) (FIG. 1D). However, under the metabolic stress, mTOR activated forkhead box protein O3 (FOXO3) was upregulated in HD1B cells (FIG. 1D). When high levels of ROS are generated, FOXOs translocate into the nucleus to activate both lysosomal and proteasomal protein degradation. FOXO proteins activate the expression of genes that encode superoxide dismutase and catalase enzymes (required for the detoxification of ROS). It has also been shown that the transcription factor forkhead homeobox type protein O1 (FoxO1) is induced by nutrient restriction in adipocytes and exerts transcriptional control of lipid catabolism via the induction of LAL.

Co-regulators for histone acetyltransferases (HATs), including sirtuins (SIRTs) regulate the levels of FOXO acetylation during oxidative stress. $NAD^+$-dependent SIRTs coordinate a switch from glucose to fatty acid oxidation during the acute inflammatory response. At least SIRT1 expression remains unchanged, suggesting that the switch from glucose to fatty acid oxidation may not be needed in HD1B cells.

In the mitochondria, oxidative phosphorylation (OXPHOS) is the metabolic pathway to reform ATP by the oxidation of nutrients. There are several catabolic biochemical processes that produce energy (in the form of ATP), including glycolysis, the citric acid cycle, and 3-oxidation of free fatty acids. In fat catabolism, triglycerides are hydrolyzed to break into fatty acids and glycerol by LAL. Fatty acids are further broken down through a process known as 3-oxidation and result in acetyl-CoA, which can be used in the citric acid cycle in mitochondria. 3-oxidation of fatty acids with an odd number of methylene bridges produces propionyl CoA, which is converted into succinyl-CoA and fed into the citric acid cycle. In the absence of the regular supply of fatty acids during LAL deficiency, it seems that the energy consumption switches more to the metabolic pathway on extracellular glucose consumption to fuel OXPHOS in HD1B cells. This was first observed by gene microarray analysis, in which the glycolytic metabolic gene profile of bone marrow $lal^{-/-}$ MDSCs was increased. Glycolysis breaks glucose (a six-carbon-molecule) down into pyruvate (a three-carbon molecule). Pyruvate moves into the mitochondria to be converted into acetyl-CoA by decarboxylation and enters the citric acid cycle. As demonstrated in FIG. 2A, both glycolysis (measured by the pyruvate concentration) and TCA in mitochondria (measured by the aconitase activity) were significantly elevated in HD1B cells. This observation was further supported by increased expression of glucose transporters (GLUT3, GLUT6, GLUT8, GLUT12, and GLUT13) in HD1B cells (FIG. 2B). On the other hand, there was no difference between expression levels of CPT1a, CPT1b and CPT1c that are required for transporting long-chain FA into the mitochondria in HD1A cells and HD1B cells (FIG. 1D). There is a report showing that in IL-15 memory T cells, glucose is used to produce FA for OXPHOS, which is dependent on LAL to funnel fatty acids into mitochondria for oxidative phosphorylation. This is unlikely in HD1B cells.

It was previously reported that Affymetrix GeneChip microarray of $lal^{-/-}$ bone marrow $Ly6G^+$ cells (almost all bone marrow $Ly6G^+$ cells are $CD11b^+$ in $lal^{-/-}$ mice) revealed overactivation of the mTOR signaling pathway. Pharmacological inhibition of mTOR blocked $lal^{-/-}CD11b^+Ly6G^+$ cell development and expansion. It has been well documented that the mTOR signaling controls mitochondrial functions, including maintaining proper membrane potential and ROS production. ROS are generated as by-products of aerobic respiration and various other catabolic and anabolic processes. Mitochondria are the major producer of ROS in cells at the electron transport chain Electrons leak from the electron transport chain directly to oxygen, producing short-lived free radicals. A decline in mitochondrial function such as damaged membrane potential leads to enhanced ROS production. Indeed, $lal^{-/-}$ $Ly6G^+$ cells showed damaged mitochondrial membrane potential and increased ROS production. These abnormal mitochondrial functions can be reversed by mTOR pharmacological inhibitors. Similarly, the mTOR downstream gene S6 was hyper-phosphorylated in HD1B cells compared with that in HD1A cells (FIG. 5A), indicating overactivation of mTOR signaling in HD1B cells. Damaged mitochondrial membrane potential and increased ROS production were observed as well in HD1B cells (FIGS. 4A and 4B). Similar to those observed in isolated $lal^{-/-}$ MDSCs, these abnormal mitochondrial activities can be blocked by treatment with mTOR pharmacological inhibitor rapamycin and PP242 (FIGS. 5B and 5C), as well as by anti-ROS chemicals (FIG. 5D). Interestingly, the mitochondrial structure in HD1B cells showed a more fission pattern (dots), whereas HD1A showed a more fusion pattern (linear lines) morphologically by MitG staining (FIG. 3A). Importantly, pro-fusion protein Opa1 was down-regulated, while phosphorylation of pro-fission protein Drp1 was increased in HD1B cells compared with HD1A cells (FIG. 3C). Mitochondria are double-membrane-bound subcellular dynamic organelles that constantly fuse and divide. Mitochondrial fission and fusion processes are essential for mitochondrial functions to meet the cellular activity of proliferation. Since the mitochondrial fission state indicates more cell proliferation, this is in agreement with a higher proliferative rate of isolated $lal^{-/-}$ MDSCs and HD1B cells (FIG. 3B). Compared with that in HD1A cells, HD1B cells also increased the arginase activity, which is another important characteristic parameter for MDSCs (FIG. 4C). Interestingly, IDO2 was highly overexpressed in HD1B cells, whereas IDO1 was not (FIG. 4D).

Functionally, the hallmark feature of MDSCs is to suppress T cell proliferation and function. It was previously shown that $lal^{-/-}$ $CD11b^+Ly6G^+$ MDSCs exhibit strong immunosuppressive function on T cell proliferation and lymphokine secretion. This is partially responsible for the decreased T cell populations in $lal^{-/-}$ mice. Therefore, it is essential to demonstrate that HD1B cells possess immunosuppressive function before claiming it as an "MDSC-like" cell line. When co-cultured with wild type $CD4^+$ T cells in vitro and stimulated with anti-CD3 and anti-CD28 antibodies, HD1B cells showed a strong suppressive activity on $CD4^+$ T cell proliferation (FIG. 6A), and TH1 INFγ, TH2 IL-4 secretion (FIG. 6B). After transfection with mTOR siRNAs, HD1B cells showed a decreased immunosuppressive activity on $CD4^+$ T cell proliferation (FIG. 7B) and lymphokine secretion (FIG. 7C). This is also similar to what has been observed in $lal^{-/-}$ $CD11b^+Ly6G^+$ MDSCs. The second hallmark for $lal^{-/-}$ MDSCs is their ability to directly stimulate cancer cell proliferation in vitro. Interestingly and importantly, HD1B cells also demonstrated stimulatory activity on cancer cells both in in vitro co-culture experiment and in in vivo co-injection experiment, including LLC and B16 melanoma cancer cell models (FIG. 8).

In summary, several parallel studies showed resemblances between $lal^{-/-}$ MDSCs and the newly established MDSC-like HD1B cell line, including but not limited to: 1) both $lal^{-/-}$ MDSCs and HD1B cells showed increased glycolytic metabolic activity; 2) both $lal^{-/-}$ MDSCs and HD1B cells showed overactivation of mTOR signaling; 3) both $lal^{-/-}$ MDSCs and HD1B cells showed the increased mitochondrial membrane potential damage and altered expression of metabolic molecules involved in mitochondrial functions; 4) both $lal^{-/-}$ MDSCs and HD1B cells showed increased ROS production; 5) both $lal^{-/-}$ MDSCs and HD1B cells showed immunosuppressive function on T cell proliferation and lymphokine secretion; 6) all above pathogenic cellular activities were corrected by either mTOR pharmacological inhibitors, or by siRNA knockdown in $lal^{-/-}$ MDSCs and HD1B cells; 7) both $lal^{-/-}$ MDSCs and HD1B cells showed stimulation on cancer cell proliferation and growth. Taken all together, this newly established HD1B cell line shows similar characteristics of MDSCs from $lal^{-/-}$ mice, and supports a concept that LAL supports FAO in myeloid cells and that lysosomal lipolysis contributes to normal function of myeloid cells.

Example 2

In this Example, the role of PPARγ in LAL-mediated functions in MDSCs was examined. Particularly, the corrective effects of the PPARγ ligand 9-hydroxyoctadecadienoic acid (9-HODE) on the neutral lipid metabolic signaling controlled by LAL were examined, including effects on the development and function of MDSCs, MDSCs transendothelial migration, tumor cell proliferation and metastasis.
Materials and Methods
  Animals and Cell Lines
  Wild-type ($lal^{+/+}$) and $lal^{-/-}$ mice of the FVB/N background were bred in house. c-fms-rtTA/(TetO)$_7$-CMV-dnPPARγ bitransgenic mice of the FVB/N background is a previously generated bitransgenic mouse model. All scientific protocols involving the use of animals have been approved by the Institutional Animal Care and Use Committee of Indiana University School of Medicine and followed guidelines established by the Panel on Euthanasia of the American Veterinary Medical Association. Animals were housed under Institutional Animal Care and Use Committee-approved conditions in a secured animal facility at Indiana University School of Medicine.

The murine B16 melanoma cell line, Lewis lung carcinoma (LLC) cell line, and murine endothelial cell (SVEC) line (purchased from ATCC, Manassas, Va., USA) were cultured in DMEM supplemented with 10% FBS (Gibco, Grand Island, N.Y., USA).
  PPARγ Ligand Treatment
  For in vitro PPARγ ligand treatment, 9-HODE (Cayman Chemical Co., Ann Arbor, Mich., USA) was added into the culture medium of MDSCs to a final concentration of 20 µmol/L for 24 or 48 hours. For the study of the effect of PPARγ ligand on the mTOR signaling pathway, bone marrow cells were treated with 9-HODE (20 µmol/L) for 2 hours.
  Isolation of Bone Marrow-Derived MDSCs
  MDSCs were isolated as described in Zhao et al., Oncogene. 2015; 34:1938-48; Yan et al., PLoS ONE. 2012; 7:e30701. Unlike those being classified into monocytic and granulocytic MDSCs, almost all $lal^{-/-}$ MDSCs were Ly6G$^+$Ly6C$^+$, and almost all $lal^{-/-}$ MDSCs were CD11b$^+$Ly6G$^+$ cells. Therefore, to simplify the $lal^{-/-}$ MDSCs isolation procedure, Ly6G antibody-coupled magnetic beads were used and sufficient to isolate $lal^{-/-}$ MDSCs from the lal bone marrow, and equivalent control from the wild type bone marrow. Briefly, bone marrow cells were isolated from the femurs and tibias of mice. Cells were first incubated with biotin-conjugated anti-Ly6G antibody at 4° C. for 15 minutes. After washed with PBS, cells were incubated with anti-biotin microbeads at 4° C. for another 15 minutes. Subsequently, cells were subjected to magnetic bead sorting according to the manufacturer's instructions (Miltenyi Biotec., Auburn, Calif., USA).
  Mouse Tumor Growth and Metastasis Model
  The tumor growth and metastasis model were described in Zhao et al., Oncogene. 2015; 34:1938-48. MDSCs and B16 melanoma cells were collected separately. A pilot study was performed to determine the best ratio between MDSCs and B16 melanoma cells. To test the tumor growth potential, $6 \times 10^5$ pre-treated MDSCs and $2 \times 10^5$ B16 melanoma cells were mixed, centrifuged and re-suspended in 100 µL PBS, and then injected subcutaneously into the flank region of 3-month old recipient $lal^{+/+}$ mice. Tumor volume (length× width$^2 \times \pi/6$) was monitored every week for 4 weeks. To test the metastasis potential, $2 \times 10^6$ pre-treated MDSCs and $5 \times 10^5$ B16 melanoma cells were mixed and incubated at 37° C., 5% $CO_2$ for 30 minutes. After the incubation, cells were centrifuged, re-suspended, and injected intravenously into 3-month old $lal^{+/+}$ mice. Two weeks after the injection, the mice were sacrificed and the lungs were inflated with 4% paraformaldehyde for examination of metastasis.
  Histology and Immunohistochemical Staining
  The harvested lungs were fixed with 4% paraformaldehyde in PBS at 4° C. for overnight. After fixation and embedding in paraffin, tissue sections were cut to 5 µm thick. Hematoxylin and eosin (H&E) staining and immunohistochemical (IHC) staining with anti-Ki67 antibody were performed by the Histological Core Facility, Department of Pathology and Laboratory Medicine, Indiana University. Images were taken by Olympus microscopy image system (Olympus, Tokyo, Japan).
  In Vitro Co-Culture of MDSCs and B16 Melanoma Cells
  Ethanol or 20 µmol/L 9-HODE pre-treated (for 24 hours) MDSCs ($5 \times 10^5$) and B16 melanoma cells ($5 \times 10^3$) were mixed, and seeded into a well of 96-well plates in DMEM supplemented with 10% FBS. Seventy-two hours later, unattached MDSCs were removed by washing with PBS, and the number of attached B16 melanoma cells was counted. Morphologically, MDSCs are much smaller than B16 melanoma cells for exclusion.
  In Vitro Migration Assay
  In vitro wound healing assay was performed to analyze B16 melanoma cell migration. Briefly, B16 melanoma cells were seeded at a density of $1.5 \times 10^5$ cells/well into a 24-well plate and incubated overnight to form a confluent monolayer. Scratch was created by scraping the cell monolayer in a straight line with a p200 pipet tip. After washing 3 times with DMEM, the medium was changed with DMEM containing 10% FBS and 5 µg/mL mitomycin C (Sigma-Aldrich, St. Louis, Mo., USA), and MDSCs pre-treated with 9-HODE or ethanol for 24 hours were added onto B16 melanoma cell monolayer at a density of $1 \times 10^6$ cells/well. Images were taken at 0 and 24 hours after creating the scratch. Migration was estimated by measuring the distances from one side of scratch to the other side using Image Pro-Plus software (Media Cybernetics, Rockville, Md., USA).

Transwell Assay

Transwell assay was used to determine MDSC transendothelial migration. SVECs were added to the upper chamber of 24-well 8.0-μm-pore Transwell plates (Corning, Corning, N.Y., USA), and incubated at 37° C., 5% $CO_2$ for 48 hours to form an EC monolayer. The supernatant was then removed, and CellTracker™ Green 5-Chloromethylfluorescein Diacetate (CMFDA) (Invitrogen, Grand Island, N.Y., USA)-labeled MDSCs ($2\times10^4$ cells in 200 μL media) were added to the upper well. After 4 hours, transendothelial migration of MDSCs was determined by counting their numbers in the lower chamber under 5 random microscopic fields.

To observe the effect of MDSCs-secreted cytokines on melanoma cell proliferation, transwell assay was performed with 0.4-μm-pore 6.5-mm diameter Transwell plates (Corning) to separate MDSCs and B16 melanoma cells. One million pre-treated MDSCs in 200 μL media were seeded into the upper chamber of the plates, while $2\times10^4$ melanoma cells in 500 μL media were placed in the lower chamber. After 72 hours' culture, the transwells were removed, and the number of B16 melanoma cells in the lower chamber was counted.

Isolation of Bone Marrow Lineage-Negative Cells

Lineage-negative (Lin–) cells were isolated from the bone marrow by removing blood lineage marker-positive cells with an immunomagnetic microbead technique. Briefly, bone marrow cells were first incubated with a cocktail of biotin-conjugated antibodies against lineage specific antigens: CD11b, GR-1, B220, TER-119, and CD3ε (Mouse Lineage Panel Kit, BD Pharmingen, San Diego, Calif., USA) at 4° C. for 15 minutes. After washed with PBS, cells were then incubated with anti-biotin microbeads at 4° C. for another 15 minutes. Subsequently, cells were subjected to magnetic bead sorting according to the manufacturer's instructions (Miltenyi Biotec.). The resulting Lin– cells were cultured in RPMI1640 with 10% FBS. Five days later, $Ly6G^+CD11b^+$ cells derived from Lin– cells were analyzed by flow cytometry analysis.

ROS and Mitochondrial Membrane Potential Measurement

The reactive oxygen species (ROS) level and mitochondrial membrane potential in MDSCs was measured by flow cytometry. Briefly, bone marrow cells were first treated with or without 20 μmol/L 9-HODE or ethanol for 2 days. For ROS level detection, cells were harvested, washed, and stained with 2',7'-dichlorofluorescein diacetate (2 μmol/L, Invitrogen), allophycocyanin cy7-conjugated anti-Ly6G Ab, and phycoerythrin cy7-conjugated anti-CD 11b Ab (eBioscience) at 37° C. for 15 minutes. After PBS wash, the ROS level in $Ly6G^+CD11b^+$ cells was analyzed using a LSRII machine (BD Biosciences).

For mitochondrial membrane potential measurement, cells were stained with the fluorescent dye JC-1 (2 μmol/L, Molecular Probes, Eugene, Oreg., USA), allophycocyanin cy7-conjugated anti-Ly6G antibody, and phycoerythrin cy7-conjugated anti-CD 11b antibody (eBioscience) at 37° C. for 15 minutes, and then analyzed for phycoerythrin (JC-1 red) and fluorescein isothiocyanate (JC-1 green) fluorescent cells in $Ly6G^+CD11b^+$ cells by flow cytometry. Cells treated with 50 μmol/L carbonyl cyanide 3-chlorophenylhydrazone for 5 minutes were served as a fluorescein isothiocyanate-positive control.

Flow Cytometry Analysis

Single cells from the bone marrow of 5-month-old $lal^{+/+}$ and $lal^{-/-}$ mice were prepared as described in Qu et al., Cancer Res. 2009; 69:7252-7261. After 20 μmol/L 9-HODE treatment for 2 hours, cells were harvested, and labeled with anti-Ly6G and CD11b cell surface antibody (eBioscience) at 4° C. for 15 minutes. Cells were then fixed and permeabilized using BD Cytofix/Cytoperm Fixation/Permeabilization Kit (BD Biosciences) according to the manufacturer's instructions, and incubated with Alexa Fluor 647-conjugated anti-mTOR antibody, Alexa Fluor 488-conjugated anti-S6 antibody, Alexa Fluor 488-conjugated anti-pS6 (Ser235/236) antibody, and rabbit anti-pmTOR (Ser2448) antibody (Cell Signaling Technology, Beverly, Mass., USA) at 4° C. overnight. For anti-pmTOR antibody staining, cells were incubated with Alexa Fluor 647-conjugated anti-rabbit IgG in the following day. Cells were washed and ready for flow cytometry analysis. Mean fluorescence intensities of the proteins in the gated $Ly6G^+CD11b^+$ area were analyzed. For flow cytometry analysis, ≥10,000 cells were acquired and scored using a LSRII machine (BD Biosciences). Data were processed using the CellQuest software program (BD Biosciences).

Statistics

Data were expressed as mean±SD. Differences between two treatment groups were compared by Student's t-test. When more than two groups were compared, one-way ANOVA with post-hoc Newman-Keul's multiple comparison test was used. Results were considered statistically significant when P<0.05. All analyses were performed with GraphPad Prism 5.0 (GraphPad, San Diego, Calif., USA).

Results

Figure 9A:
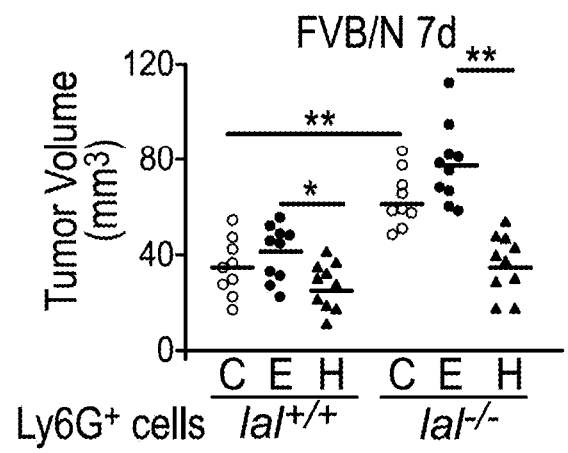
FIGS. 9A-9D show that PPARγ ligand reversed lal$^{-/-}$ MDSCs stimulation on tumor growth and metastasis in vivo.
Figure 9A:
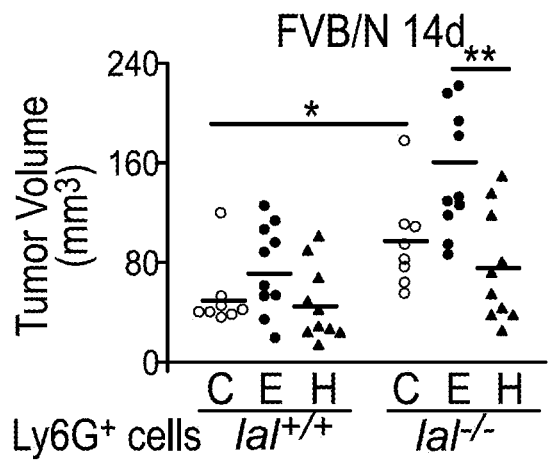
Figure 9A:
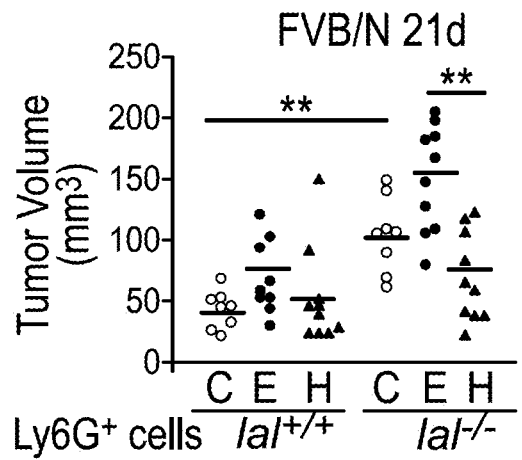
Figure 9B:
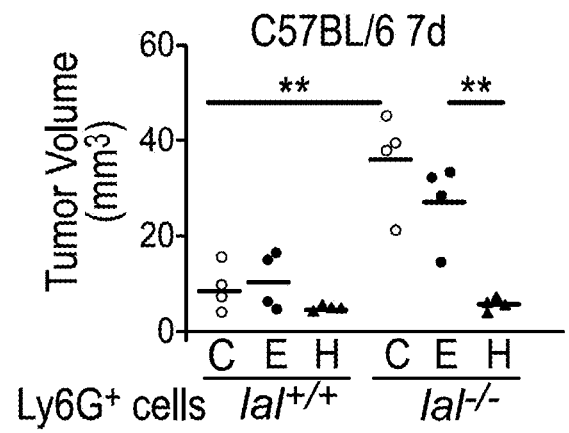
Figure 9B:
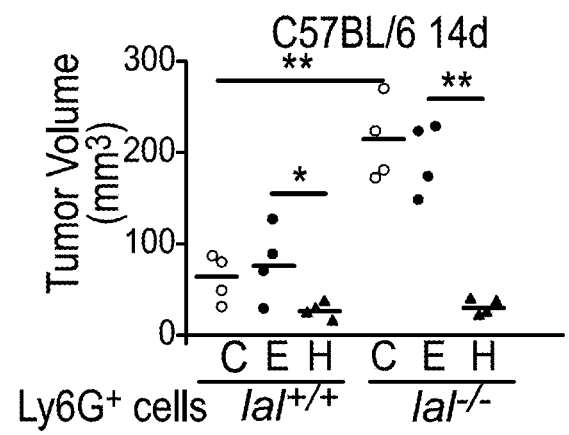
Figure 9B:
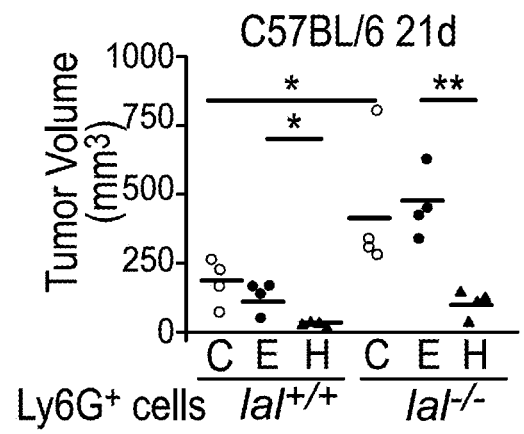

PPARγ ligand impaired $lal^{-/-}$ $Ly6G^+$ cell stimulation of tumor growth and metastasis in vivo PPARγ inactivation has previously been reported to cause inflammation-triggered cell growth and emphysema in lal mice, and treatment with the PPARγ ligand 9-HODE significantly rescued $lal^{-/-}$ pulmonary inflammation and aberrant gene expression. $lal^{-/-}$ $Ly6G^+$ MDSCs have recently been found to play a role in stimulating tumor growth and metastasis. The wild type bone marrow is comprised of ~50% $CD11b^+Ly6G^+$ myeloid precursor cells (with very low immunosuppressive function) and very few $CD11b^+$ or $Ly6G^+$ single cells. On the other hand, the $lal^{-/-}$ bone marrow is comprised of 70% $CD11b^+Ly6G^+$ cells (with very strong immunosuppression and cancer cell stimulation potential). These $lal^{-/-}$ bone marrow cells do not further differentiate into more mature myeloid cells as wild type cells. To see whether PPARγ inactivation within $lal^{-/-}$ $Ly6G^+$ MDSCs contributes to their ability to stimulate tumor cells, freshly isolated bone marrow-derived $lal^{+/+}$ or $lal^{-/-}$ $Ly6G^+$ cells were pretreated with 9-HODE or the vehicle, ethanol for 24 hours. In $lal^{-/-}$ mice, since almost all $Ly6G^+$ cells are positive for CD11b, a Ly6G-specific antibody was used for purification of $Ly6G^+CD11b^+$ cells. To examine tumor growth potential in vivo, pre-treated or untreated $Ly6G^+$ cells were mixed with untreated B16 melanoma cells, and then co-injected subcutaneously into $lal^{+/+}$ mice. One week after the injection, subcutaneous tumors detected in the $lal^{-/-}$ $Ly6G^+$ cell-injected mice were significantly larger (tumor volume=63.2±11.7 $mm^3$) than those tumors in $lal^{+/+}$ $Ly6G^+$ cell-injected mice (tumor volume=34.6±11.9 $mm^3$, p<0.01). However, the tumors from 9-HODE-treated $lal^{-/-}$ $Ly6G^+$ cell-injected mice (tumor volume=36.3±12.4 $mm^3$) were significantly smaller when compared with those developed in ethanol-treated $lal^{-/-}$ $Ly6G^+$ cell-injected mice (tumor volume=77.6±16.4 $mm^3$, p<0.01) (FIG. 9A). The similar effect of 9-HODE treatment on $lal^{-/-}$ $Ly6G^+$ cells to tumor size was also observed at 14 and 21 days post-injection (FIG. 9A). Moreover, when B16 melanoma cells were co-injected with C57BL/6 $Ly6G^+$ cells into C57BL/6 mice, similar results were observed that the tumors from 9-HODE-treated lal$^{-/-}$ Ly6G$^+$ cell-injected mice were significantly smaller than those developed in ethanol-treated lal$^{-/-}$ Ly6G$^+$ cell-injected mice at 7, 14 and 21 days post-injection (FIG. 9B). As predicted, B16 melanoma tumor grew larger in C57BL/6 than that in FVB/N mice at 14 and 21 days post-injection.

Figure 9C:
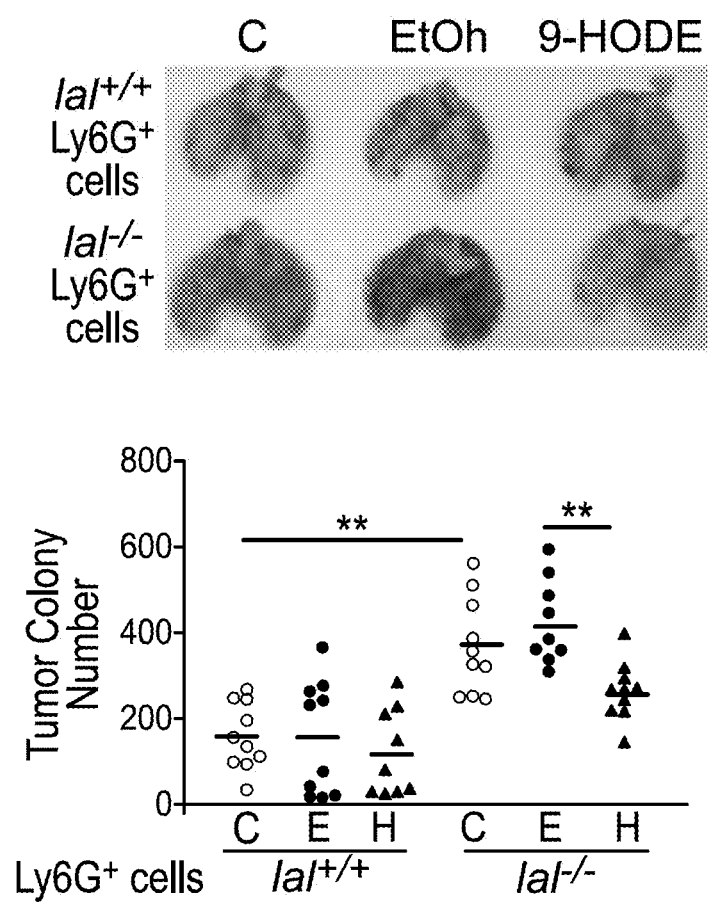
Figure 9D:
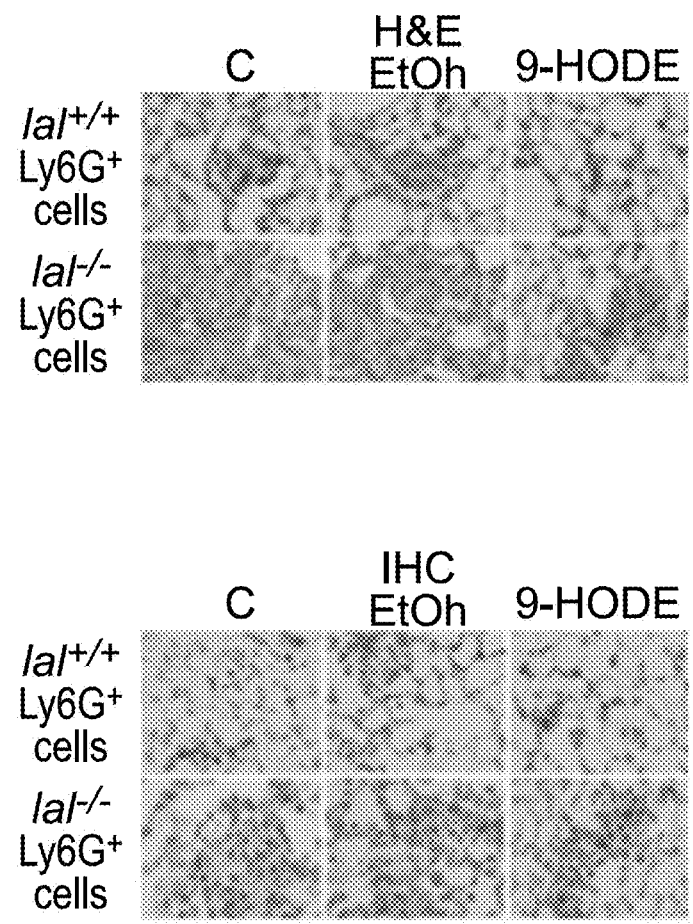

Next, the pre-treated Ly6G$^+$ cells and B16 melanoma cells were injected into the tail veins of lal$^{+/+}$ recipient mice to detect metastatic potential. Two weeks after injection, less B16 melanoma colonies were observed in the lungs of lal$^{+/+}$ mice that received 9-HODE-treated lal$^{-/-}$ Ly6G$^+$ and B16 cell co-injection than those received ethanol-treated lal$^{-/-}$ Ly6G$^+$ and B16 cell co-injection (FIG. 9C). 9-HODE treatment of lal$^{+/+}$ Ly6G$^+$ cells did not affect B16 melanoma colonization in the lung (FIG. 9C). Sections of the lungs showed less neoplastic cells by H&E staining and less Ki67 positive cells by IHC staining (FIG. 9D). These observations suggest that ligand-induced activation of the PPARγ pathway in lal$^{-/-}$ Ly6G$^+$ MDSCs impaired the ability of these myeloid cells to stimulate tumor growth and metastasis.

Figure 10A:
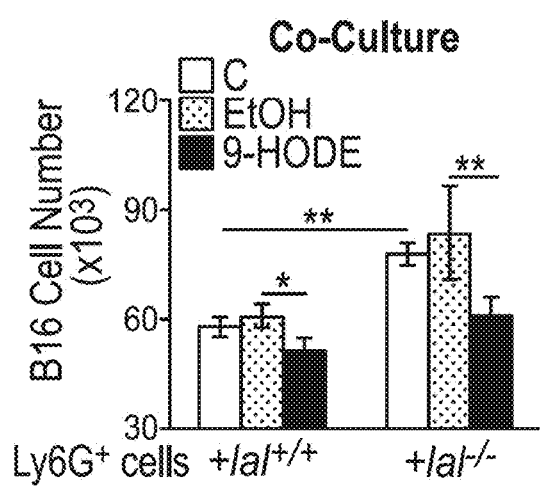
FIGS. 10A-10D show that PPARγ ligand inhibited lal$^{-/-}$ MDSCs stimulation on tumor proliferation and migration in vitro. Ly6G$^+$ cells from lal$^{+/+}$ or lal$^{-/-}$ mice were pre-treated with ethanol (EtOH) or 20 μmol/L 9-HODE for 24 hours.
Figure 10B:
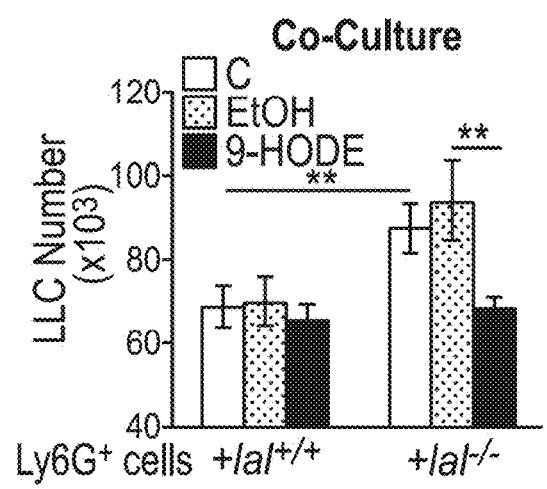

PPARγ ligand inhibited lal$^{-/-}$ Ly6G$^+$ MDSCs stimulation of tumor proliferation and migration in vitro The inhibitory effects of the PPARγ ligand on lal$^{-/-}$ Ly6G$^+$ MDSCs stimulation of tumor growth were further examined by in vitro co-culture experiments. Ligand or vehicle pre-treated lal$^{+/+}$ or lal$^{-/-}$ Ly6G$^+$ cells were co-cultured with B16 melanoma cells for 72 hours. As shown in FIG. 10A, 9-HODE treatment of lal$^{-/-}$ Ly6G$^+$ cells significantly decreased proliferation of B16 melanoma cells upon co-culture, compared with that of ethanol-treated lal$^{-/-}$ Ly6G$^+$ cells. When 9-HODE-treated lal$^{-/-}$ Ly6G$^+$ cells were co-cultured with Lewis lung cancer (LLC) cells, reduced proliferation of LLC cells was also observed (FIG. 10B). Taken together, these results suggest that activation of the PPARγ pathway in lal$^{-/-}$ Ly6G$^+$ cells impaired the capacity of these myeloid cells to stimulate tumor cell proliferation.

Figure 10C:
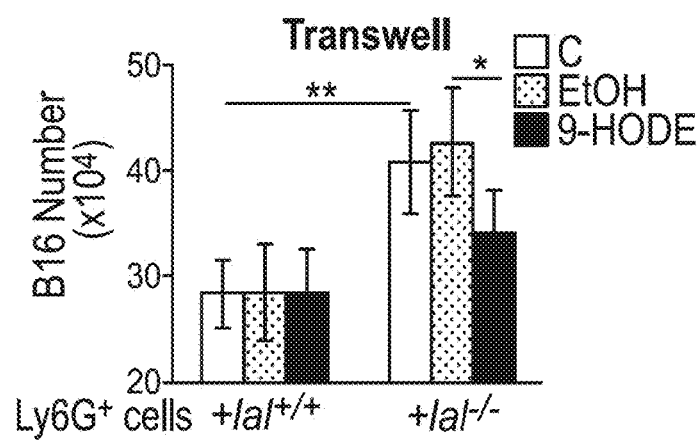

Cytokines secreted by lal$^{-/-}$ Ly6G$^+$ MDSCs have been reported to be responsible for mediating their stimulatory effects on cancer cell proliferation. To examine whether 9-HODE treatment has an effect on cytokine-mediated Ly6G$^+$ MDSCs stimulation on cancer cell proliferation, transwell studies were performed with 9-HODE pre-treated Ly6G$^+$ cells seeded in the upper chamber and melanoma cells seeded in the lower chamber. After 72 hours co-culture, the number of B16 melanoma cells that were co-cultured with 9-HODE pre-treated lal$^{-/-}$ Ly6G$^+$ cells was significantly less (FIG. 10C), suggesting the ability of lal$^{-/-}$ Ly6G$^+$ cells to promote melanoma cell proliferation was impaired by PPARγ ligand treatment.

Figure 10D:
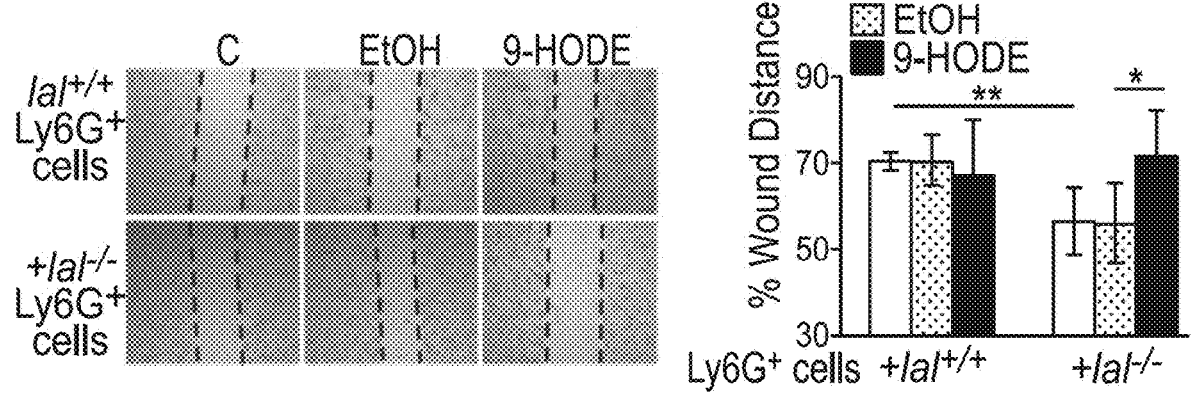

Because cell migration contributes to metastasis, in vitro tumor cell migration assay was analyzed to determine whether PPARγ ligand treatment of lal$^{-/-}$ Ly6G$^+$ cells influences B16 melanoma cell migration. Melanoma cells were treated with mitomycin C to eliminate the potential effects of cell proliferation in these assays. As shown in FIG. 10D, 24 hours after co-culture with lal$^{-/-}$ Ly6G$^+$ cells, B16 melanoma cells migrated more efficiently into the area of an artificial wound area compared with those tumor cells co-cultured with lal$^{+/+}$ Ly6G$^+$ cells. However, delayed migration towards the scratch was observed in 9-HODE pre-treated lal$^{-/-}$ Ly6G$^+$ cells, as revealed by a significant increase in the span of the wounded area. These results also suggest that activation of the PPARγ pathway in lal$^{-/-}$ Ly6G$^+$ cells impaired the stimulatory effects of these MSDCs on B16 melanoma cell migration in vitro.

Figure 11A:
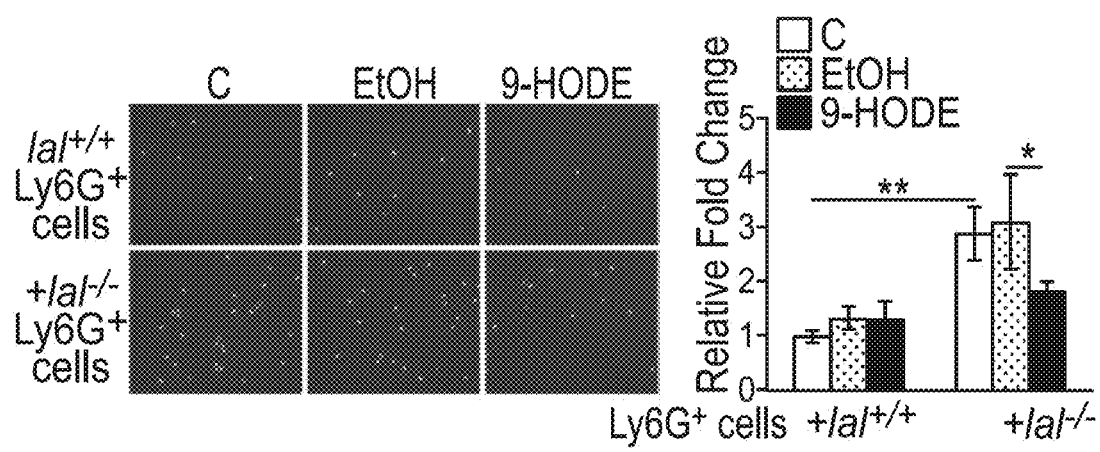
FIGS. 11A & 11B show that PPARγ ligand decreased lal$^{-/-}$ MDSCs transendothelial migration capacity and differentiation from lal$^{-/-}$ Lin-cells.

PPARγ ligand decreased lal$^{-/-}$ MDSC transendothelial migration capability and differentiation from lal$^{-/-}$ Lin– cells Besides effects on tumor growth and metastasis, lal$^{-/-}$ Ly6G$^+$ MDSCs displayed increased transendothelial migration capability, which likely results in the severe infiltration of MDSCs in multiple organs of lal$^{-/-}$ mice. To test whether PPARγ inactivation in lal$^{-/-}$ Ly6G$^+$ cells plays a role in their increased transendothelial migration, transwell assays were performed with 9-HODE pre-treated CMFDA-labeled Ly6G$^+$ cells seeded onto an endothelial monolayer in the upper chamber of the plates. Four hours later, the number of Ly6G$^+$ cells that had migrated through to the lower chamber was determined. As shown in FIG. 11A, there were less Ly6G$^+$ cells in the lower chamber when lal$^{-/-}$ Ly6G$^+$ cells were treated with 9-HODE compared with these cells treated with ethanol, suggesting that the PPARγ pathway is involved in Ly6G$^+$ cell endothelial transmigration capability.

Figure 11B:
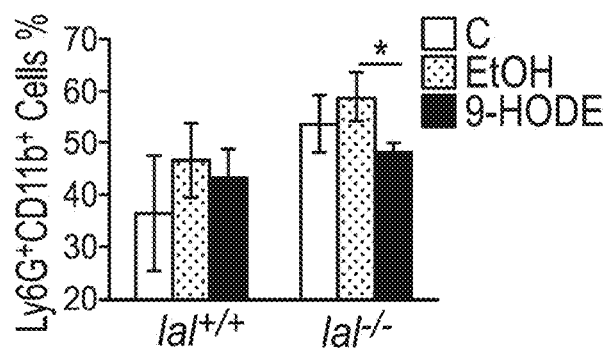

Abnormal expansion of MDSCs was also observed in lal$^{-/-}$ mice, which was due to increased differentiation from Lin-cells. PPARγ is known to be expressed in bone marrow progenitor cells and play a critical role in mesenchymal stem cell differentiation and adipogenesis. To test the role of PPARγ in this process, bone marrow-derived Lin-cells from lal$^{+/+}$ and lal$^{-/-}$ mice were isolated and treated with 9-HODE or ethanol. After 5 days of incubation, fewer Ly6G$^+$CD11b$^+$ cells were derived from 9-HODE-treated lal$^{-/-}$ Lin$^-$ cells compared with those with ethanol treatment (FIG. 11B), suggesting that activation of the PPARγ pathway by 9-HODE prevented these Lin$^-$ cells from differentiating into MDSCs.

Figure 12A:
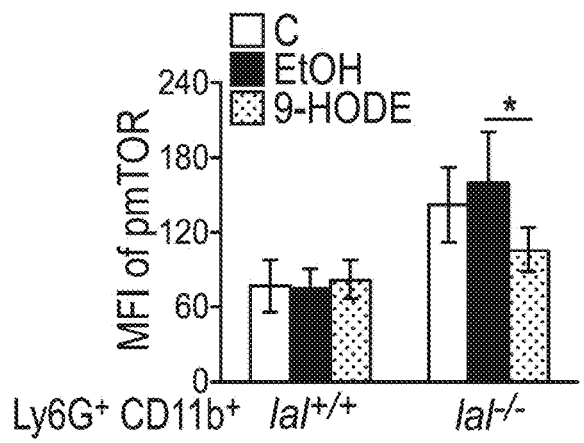
FIGS. 12A & 12B show that PPARγ ligand down-regulated the overactivation of the mTOR pathway in lal$^{-/-}$ MDSCs. Bone marrow cells from lal$^{+/+}$ or lal$^{-/-}$ mice were treated with ethanol (EtOH) or 20 μmol/L 9-HODE for 2 hours.
Figure 12B:
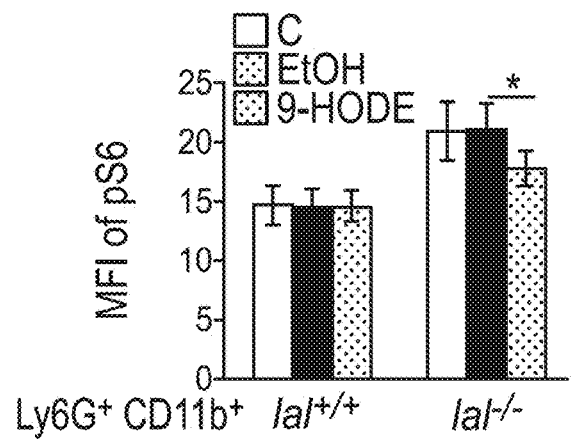

PPARγ Ligand Down-Regulated mTOR Pathway Activation in lal$^{+/+}$ Ly6G$^+$ CD11b$^+$ Cells It was previously reported that the tumor-promoting function of lal$^{-/-}$ MDSCs is mediated, at least in part, through enhanced activation of the mTOR pathway, and that the mTOR pathway is involved in the differentiation of Lin$^-$ cells into Ly6G$^+$CD11b$^+$ cells. To test whether PPARγ has an effect on the mTOR pathway, bone marrow cells from lal$^{+/+}$ and lal$^{-/-}$ mice were treated with 9-HODE or ethanol. After 2 hours of incubation, the expression levels of phosphorylated mTOR (pmTOR) and phosphorylated S6 (pS6) in gated Ly6G$^+$CD11b$^+$ cells were measured by flow cytometry analysis. As shown in FIGS. 12A and 12B, the increased levels of pmTOR and pS6 in lal$^{-/-}$ Ly6G$^+$CD11b$^+$ cells were not observed in cells following PPARγ ligand treatment. These results suggest that ligand-induced activation of the PPARγ pathway in lal$^{-/-}$ Ly6G$^+$CD11b$^+$ cells by 9-HODE downregulated mTOR pathway activation.

Figure 13A:
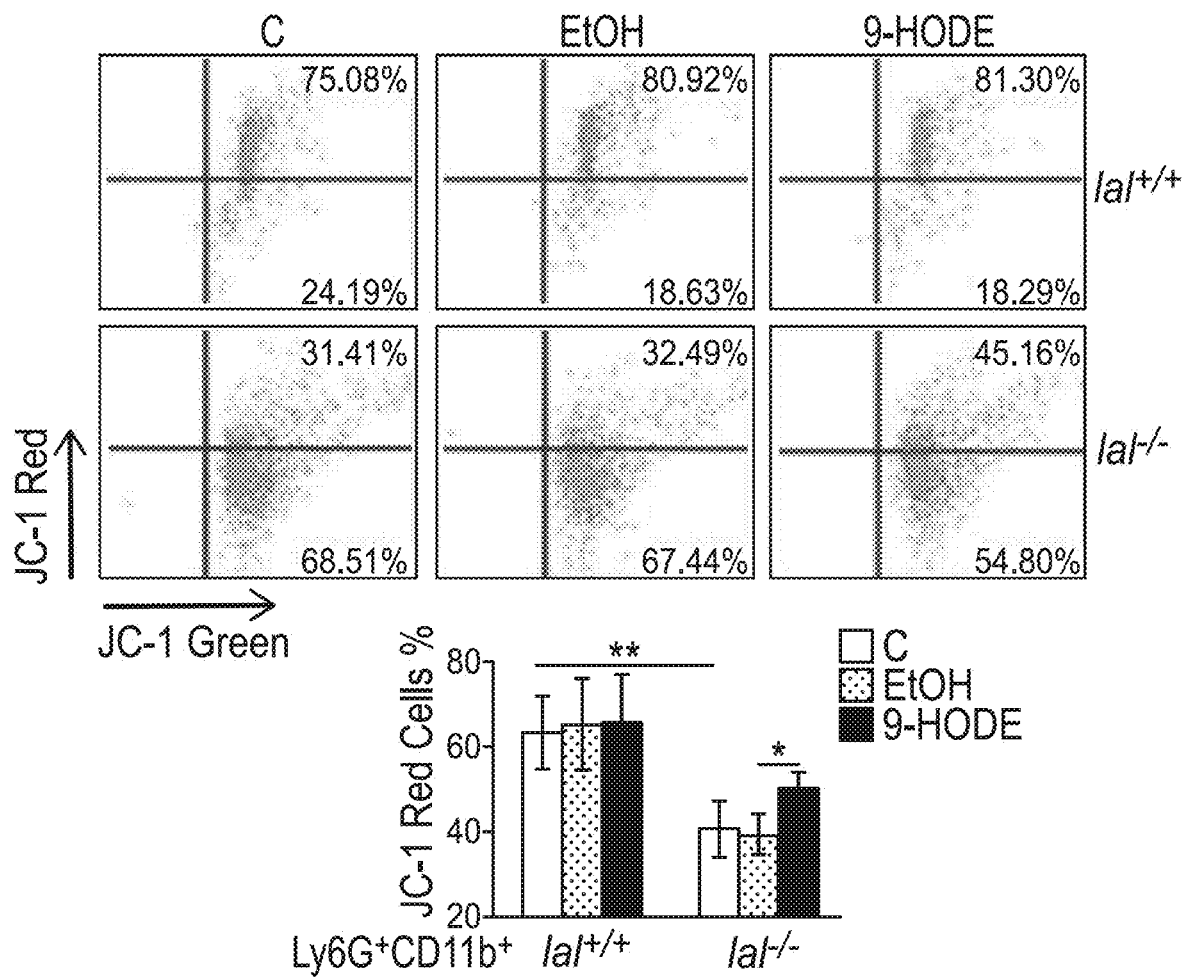
FIGS. 13A & 13B show that PPARγ ligand reversed the damaged mitochondrial membrane potential and suppressed ROS production in lal$^{-/-}$ MDSCs. Bone marrow cells from lal$^{+/+}$ or lal$^{-/-}$ mice were treated with ethanol (EtOH) or 20 μmol/L 9-HODE for 48 hours.

PPARγ ligand reversed damaged mitochondrial membrane potential and suppressed ROS production in lal$^{-/-}$ Ly6G$^+$CD11b$^+$ cells ROS is an important mediator for MDSCs functions, and its increase is often associated with mitochondrial damage. In lal$^{-/-}$ MDSCs, both damaged mitochondrial function and ROS overproduction have been observed, and inhibition of the mTOR pathway decreased the ROS levels and abnormal mitochondrial membrane potential in lal$^{-/-}$ MDSCs. To see whether PPARγ ligand treatment corrects these defects, bone marrow cells were treated with 9-HODE or ethanol, and ROS levels and mitochondrial membrane potentials were measured by flow cytometry analysis. As demonstrated in FIG. 13A, the impaired mitochondrial membrane potential in lal$^{-/-}$ Ly6G$^+$ CD11b$^+$ cells was partially recovered with 9-HODE treatment compared with that in ethanol-treated cells.

Figure 13B:
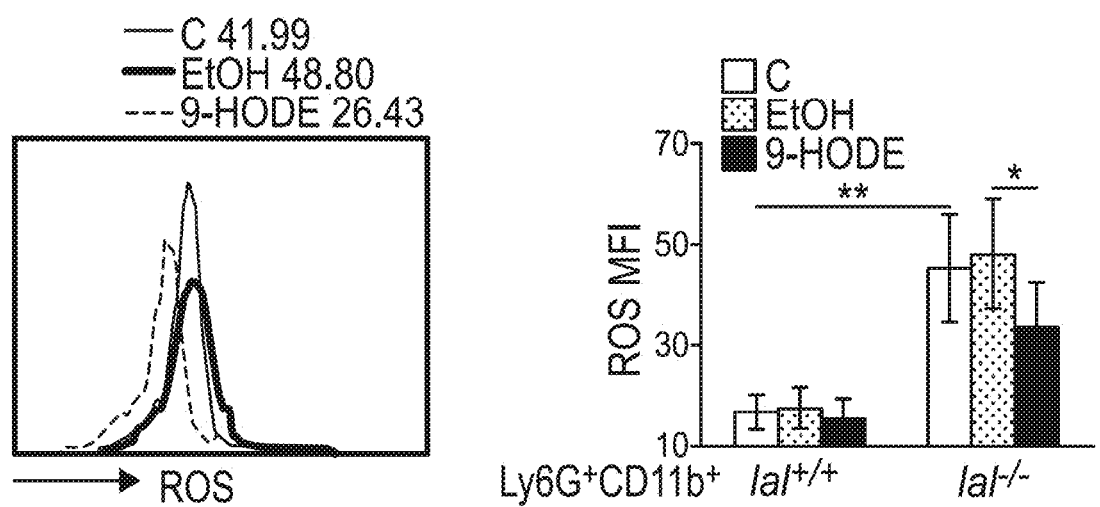

In addition, 9-HODE treatment suppressed the increased ROS production in lal$^{-/-}$ Ly6G$^+$CD11b$^+$ cells (FIG. 13B). These results suggest that ROS overproduction and damaged mitochondrial membrane potential associated with lal$^{-/-}$ MDSCs can be corrected by PPARγ ligand treatment.

Figure 14A:
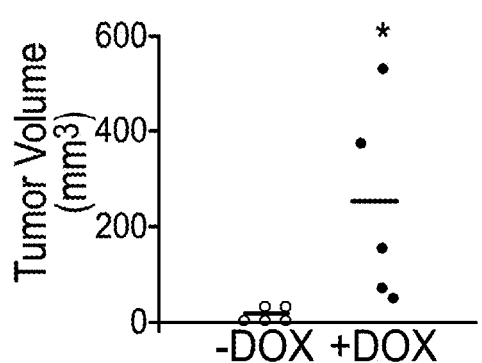
FIGS. 14A-14F depict that overexpression of dnPPARγ in myeloid cells facilitates tumor growth and metastasis in vivo, and tumor proliferation and migration in vitro.
Figure 14B:
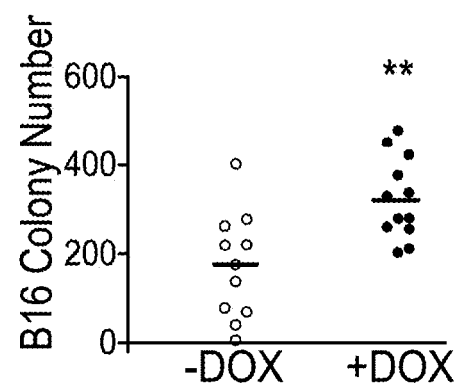

Overexpression of dnPPARγ in myeloid cells facilitated tumor growth and metastasis in vivo, and tumor proliferation and migration in vitro To further confirm the critical role of PPARγ in myeloid-lineage cells, a doxycycline-inducible c-fms-rtTA/(tetO)$_7$-CMV-dnPPARγ bitransgenic mouse model was used, in which a dominant negative PPARγ (dnPPARγ) was overexpressed in myeloid cells under the control of the c-fms promoter. As published before when the endogenous PPARγ signaling pathway was inhibited by overexpression of dnPPARγ in myeloid cells, the MDSCs level increased in bone marrow, spleen, blood and lung. Whether the disruption of PPARγ function by expression of dnPPARγ in myeloid cells has a similar effect on tumor cell growth and metastasis in vivo and tumor cell proliferation and migration in vitro was assessed. In tumor growth assessment, B16 melanoma cells were subcutaneously injected into the flank region of the bi-transgenic mice. FIG. 14A showed that the tumor volume from doxycycline-treated bi-transgenic mice was significantly increased compared with those in untreated mice at 4 weeks post-injection. For the tumor metastasis potential, statistical analysis revealed that two weeks after intravenous injection of B16 melanoma cells, the doxycycline-treated bi-transgenic mice showed increased number of melanoma colonies in the lungs compared with untreated mice (FIG. 14B). These results suggest that PPARγ inactivation in myeloid cells contributed to the increased tumor growth and metastasis.

Figure 14C:
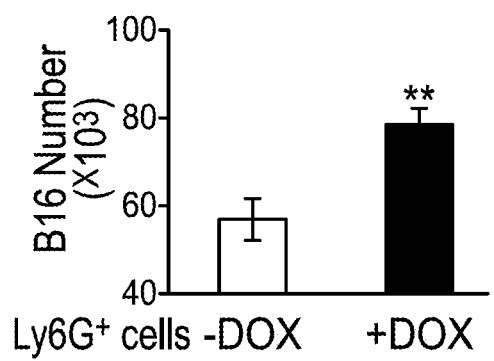
Figure 14D:
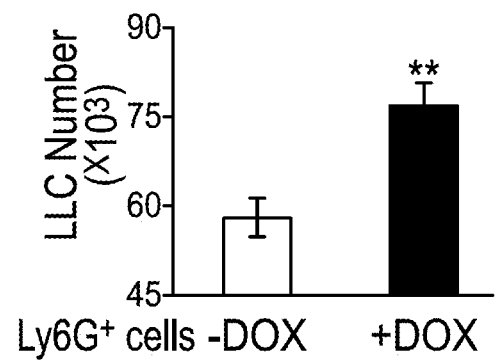
Figure 14E:
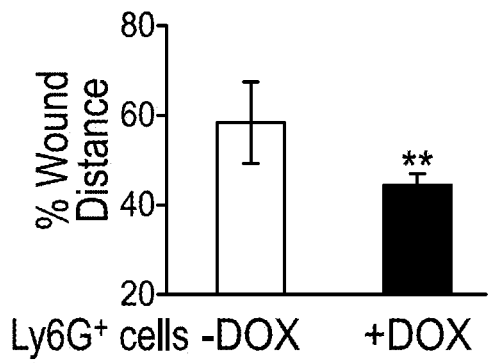
Figure 14F:
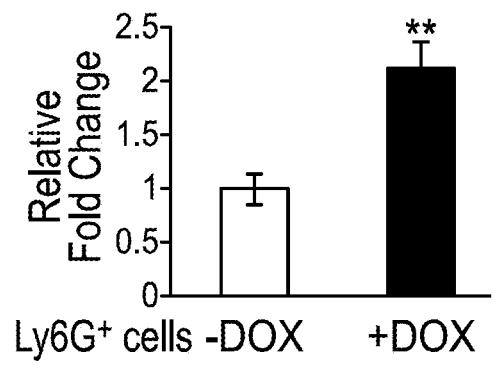

When bone marrow Ly6G$^+$ cells from doxycycline-treated bi-transgenic mice were co-cultured with B16 melanoma cells in vitro, increased proliferation of B16 melanoma cells was observed in comparison with those cells from untreated bi-transgenic mice (FIG. 14C). Similarly, proliferation of LLC was significantly increased after co-cultured with bone marrow Ly6G$^+$ cells from doxycycline-treated bi-transgenic mice (FIG. 14D). Furthermore, the in vitro wound healing assay showed accelerated migration towards the scratch in B16 melanoma cells co-cultured with bone marrow Ly6G$^+$ cells from doxycycline-treated bi-transgenic mice 24 hours after creating the scratch, with a significant decrease of distance in the wounding area (FIG. 14E). In addition, the transendothelial migration capability of Ly6G$^+$ cells from doxycycline-treated bi-transgenic mice was obviously increased as shown in FIG. 14F. Taken together, these results indicate that PPARγ inactivation in Ly6G$^+$ cells facilitated their transendothelial migration, and stimulation of tumor cell proliferation and migration.

Figure 15A:
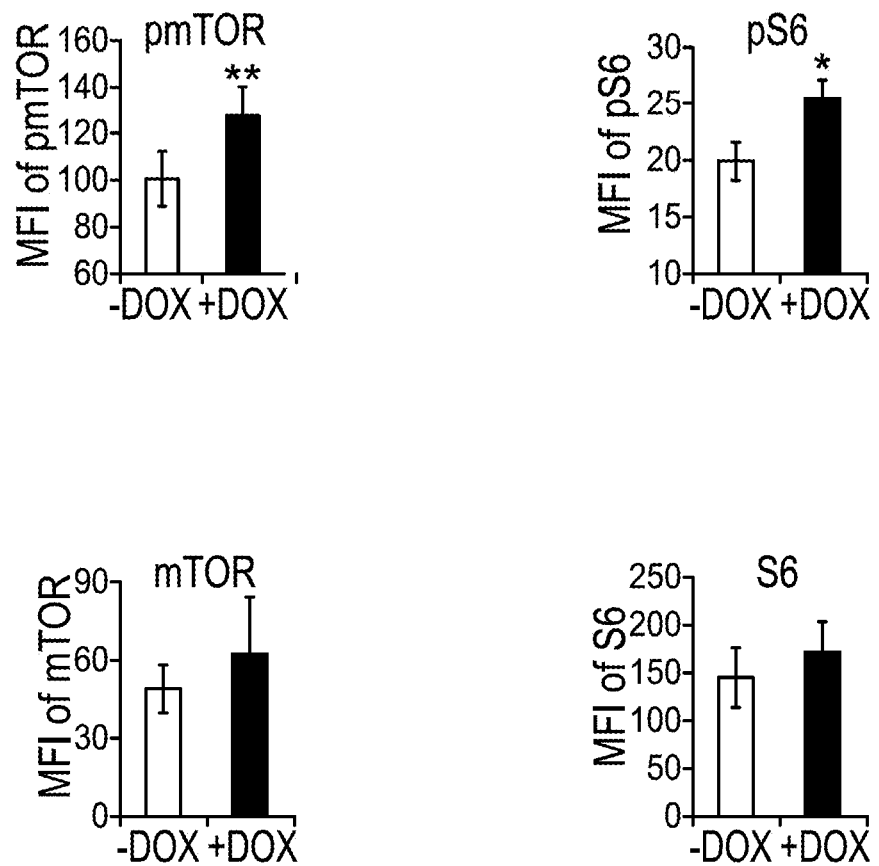
FIGS. 15A-15C show that the overexpression of dnPPARγ in myeloid cells overactivated the mTOR pathway, increased ROS production and impaired mitochondrial membrane potential.
Figure 15B:
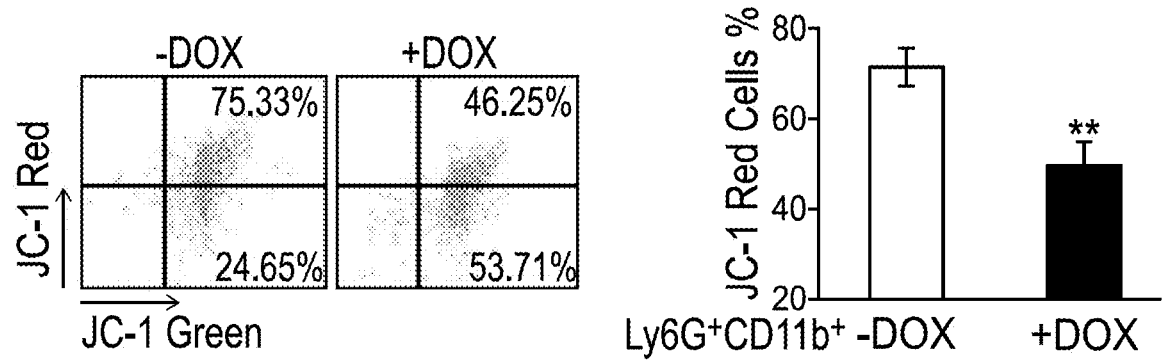
Figure 15C:
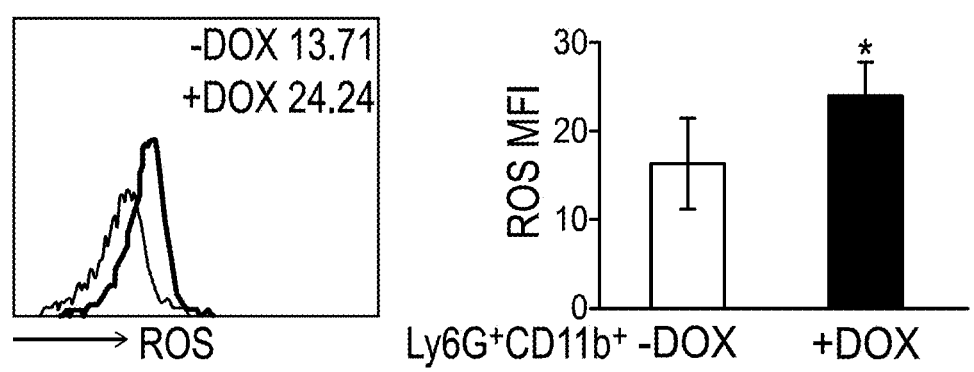

Overexpression of dnPPARγ in myeloid cells overactivated the mTOR pathway, increased ROS production and impaired maintenance of mitochondrial membrane potential To explore the potential mechanisms underlying the dysfunctions of MDSCs from doxycycline-treated dnPPAR-γ bitransgenic mice, changes in the mTOR pathway were explored. As determined above using PPARγ ligands, the pathogenic function of MDSCs could be linked to mTOR activation in lal$^{-/-}$ MDSCs. Results showed that the phosphorylation levels of mTOR and S6 in gated doxycycline-treated Ly6G$^+$CD11b$^+$ cells were increased significantly compared with those of untreated Ly6G$^+$CD11b$^+$ cells, with no statistically significant change of mTOR and S6 protein levels (FIG. 15A). As a consequence, the mitochondrial membrane potential in doxycycline-treated Ly6G$^+$CD11b$^+$ cells was impaired (FIG. 15B). In addition, the ROS production in doxycycline-treated Ly6G$^+$CD11b$^+$ cells was significantly increased compared with untreated Ly6G$^+$CD11b$^+$ cells (FIG. 15C). These results support that the PPAR-γ pathway regulates MDSCs functions by modulating mTOR, ROS production and mitochondrial membrane potential.

Discussion

LAL deficiency causes inactivation of PPARγ by blocking PPARγ ligand synthesis. The PPARγ signaling pathway has recently been reported to play a key role in controlling MDSC expansion and T cell proliferation. In this Example, 9-HODE, a PPARγ ligand, reversed the increased MDSC expansion (FIG. 11B) and decreased T cell numbers in lal$^{-/-}$ mice (data not shown), suggesting that PPARγ signaling is critical in regulating LAL-mediated metabolic pathways central to immune suppression.

In addition to inhibition of the PPARγ pathway, enhanced activation of the mTOR pathway was associated with lal$^{-/-}$ MDSC dysfunction as detected by Affymetrix GeneChip microarray and Ingenuity analyses. Thus, multiple pathways may contribute to regulate MSDCs functions. Studies have shown that the mTOR pathway regulates PPARγ activation during adipogenesis by targeting the transactivation activity of PPARγ. Interaction between mTOR and PPARγ has been reported before in hepatocytes. Deficiency of PPARγ in chondrocytes resulted in aberrant activation of mTOR signaling pathway. The present Example shows that the mTOR pathway in lal$^{-/-}$ MDSCs is regulated by PPARγ. Incubation with 9-HODE not only significantly decreased the phosphorylation levels of mTOR and S6, but also reduced the overall levels of mTOR and S6 in lal$^{-/-}$ MDSCs (FIGS. 12A and 12B). ROS production has been reported to be one mechanism underlying MDSCs function. In previous studies, ROS production was increased in lal$^{-/-}$ MDSCs with impaired mitochondrial function, which mediated the mTOR-regulated lal$^{-/-}$ MDSCs dysfunctions. Activation of the PPARγ pathway in lal$^{-/-}$ bone marrow cells with its ligand 9-HODE effectively improved the mitochondrial function and blocked ROS overproduction in lal$^{-/-}$ Ly6G$^+$CD11b$^+$ MDSCs (FIGS. 13A and 13B), suggesting that ROS overproduction by lal$^{-/-}$ MDSCs is controlled by the PPARγ pathway. Therefore, the mTOR-ROS pathway serves as a potential mechanism to mediate the LAL-PPARγ axis in MDSC dysfunctions. It was recently found that PPARγ inhibits cancer cell proliferation by a metabolic switch, including suppressing pyruvate oxidation and reducing glutathione levels, which results in a marked increase of ROS levels, leading to rapid hypophosphorylation of retinoblastoma protein and cell-cycle rest. Similarly, in a "lal$^{-/-}$ MDSCs-like cell line", it was observed an mTOR-controlled metabolic switch towards increased glycolysis and ROS levels (see Example 1). In the current Example, with PPARγ ligand treatment of lal$^{-/-}$ MDSCs these cells were found to display reduced ROS and were unable to effectively stimulate tumor cell proliferation.

The role of the PPARγ pathway in MDSC functions was further investigated using an established bi-transgenic mouse model, in which dnPPARγ was overexpressed in myeloid-lineage cells, resulting in blockade of endogenous PPARγ function. In this mouse model, the function of the receptor of PPARγ pathway is impaired rather than the ligand expression which is perturbed in lal$^{-/-}$ mouse model. When melanoma cells were injected subcutaneously into these mice, larger tumor developed in the mice with myeloid-specific dnPPARγ overexpression induced by doxycycline than non-induced bi-transgenic mice (FIG. 14A). In addition, after intravenous injection of melanoma cells, more melanoma developed in the lungs of mice with myeloid-specific dnPPARγ overexpression (FIG. 14B). When MDSCs from the mice with myeloid-specific dnPPARγ overexpression were co-cultured with B16 melanoma cells or LLC cells in vitro, cancer cell proliferation was enhanced (FIGS. 14C and 14D). Moreover, these MDSCs facilitated melanoma cell migration (FIG. 14E), possessed increased transmigration through the EC monolayer (FIG. 14F), overactivated the mTOR pathway, and impaired mitochondrial function and ROS overproduction (FIGS. 15A-15C), similar to the characteristics observed in lal$^{-/-}$ MDSCs, which showed inactivation of the PPARγ pathway.

In conclusion, the PPARγ pathway plays a critical role in metabolic signaling controlled by LAL through regulating the function of MDSCs. The PPARγ pathway served as a novel target to modulate the emergence of MDSCs to reduce the risk of cancer progression and metastasis. It has been extensively reported that PPARγ ligands have a direct inhibitory effect on tumor cells. But their effect in MDSCs of the tumor microenviroment is poorly understood, and should be given a special attention. Therefore, PPARγ may impact cancer cell proliferation through both direct and indirect mechanisms including effects on MSDCs. This Example indicates that enhancing PPARγ function in MDSCs should prove to be a highly effective strategy in blocking tumor cell growth and spread even in cases where tumors may not respond directly to PPARγ ligands. Among collection of ligands to PPARγ, those more likely to achieve this therapeutic outcome in MDSCs remain to be tested.

Example 3

Materials & Methods

Animals and Cell Lines

LAP-tTA/(TetO)$_7$-CMV-hLAL; lal$^{-/-}$ (LAP-Tg/KO) triple mice of the FVB/N background was established by cross-breeding of LAP-tTA transgenic mice (Jackson's Laboratory, Bar Harbor, Me.) with a previously generated (tetO)$_7$-CMV-hLAL transgenic mice into lal$^{-/-}$ mice. This triple transgenic mouse model was hepatocyte-specific Tet-off expression of wild-type hLAL in lal$^{-/-}$ mice under the control of the LAP. All scientific protocols that involved the use of animals were approved by the Institutional Animal Care and Use Committee of Indiana University School of Medicine and followed guidelines established by the Panel on Euthanasia of the American Veterinary Medical Association. Animals were housed in a secured animal facility at Indiana University School of Medicine.

The murine B16 melanoma cell line (ATCC, Manassas, Va.) was cultured in Dulbecco's modified Eagle's medium supplemented with 10% fetal bovine serum (Gibco, Grand Island, N.Y.).

Characterization of Tissue Expression of the hLAL Transgene by RT-PCR

Total RNAs from the liver, lung, spleen, and bone marrow cells of wild-type, lal$^{-/-}$, and LAP-Tg/KO triple mice or hepatocytes and Ly6G$^+$ cells isolated from the liver were purified using a total RNA purification kit (Qiagen, Valencia, Calif.). Ly6G$^+$ cells from the liver were isolated by incubation with biotin-labeled anti-Ly6G$^+$ antibody after liver perfusion, followed by incubation with anti-biotin immune-magnetic microbeads and magnetic-activated cell sorting technique according to the manufacturer's instruction (Miltenyi Biotech, Auburn, Calif.). cDNA was generated by a reverse transcription kit (Invitrogen, Grand Island, N.Y.) from isolated total RNA. PCR amplification was used with two different sets of primers for verification of hLAL expression. The first pair of primers covered different exons (exons 8 and 9) unique to the hLAL gene (forward primer, 5'-AGCCAGGCTGTTAAATTCCAAA-3' (SEQ ID NO:1); reverse primer, 5'-GAATGCTCTCATGGAACACCAA-3' (SEQ ID NO:2)). The second pair of primers covered an exon (exon 9) that is unique to the hLAL gene and the Flag epitope coding sequence that is at the 30 end of hLAL cDNA in the (tetO)$_7$-CMV-hLAL vector, which is unique to the hLAL-Flag combination (forward primer, 5'-TGCAG-TCTGGAGCGGGG-3' (SEQ ID NO:3); reverse primer, 5'-TGTCATCGTCGTCCTTGTAGTCC-3' (SEQ ID NO:4)). The house-keeping gene β-actin (forward primer, 5'-ACCGTGAAAA-GATGACCCAGAT-3' (SEQ ID NO:5); reverse primer, 5'-GCCTGGATG-GCTACGTA-CATG-3' (SEQ ID NO:6)) was used as an internal control. PCR were performed on Mastercycler (Eppendorf, Hamburg, Germany).

Western Blot Analysis of hLAL Protein Expression

Protein samples from the liver, lung, spleen, and bone marrow cells of wild-type, lal$^{-/-}$, and LAP-Tg/KO mice were prepared in the Cell Lytic M mammalian cell lysis/extraction buffer (Sigma-Aldrich, St Louis, Mo.) according to the manufacturer's instruction. Protein samples were fractionated on a Novex 4% to 20% Tris-Glycine Mini Gel (Invitrogen). After protein transferred to the polyvinylidene difluoride membrane (Bio-Rad, Hercules, Calif.), the membrane was blotted with 5% nonfat dry milk in 1× phosphate-buffered saline with 0.05% Tween 80 and incubated with rabbit anti-LAL and anti-actin primary antibodies (Cell Signaling, Danvers, Mass.). After incubation with the secondary antibody that conjugated with horseradish peroxidase, proteins were visualized with chemiluminescent substrate under the ChemiDoc™ MP Image System (Thermo Fisher Scientific, Waltham, Mass.).

Tissue Lipid Extraction and Determination of CE and TG Concentrations

Total tissue lipids were extracted from the liver and small intestine by the Folch method (Folch et al., J Biol. Chem 1957, 125:497-509). Concentrations of CEs and TGs were determined as described in Due et al., J Lipid Res 2001, 42:489-500 and Du et al., J Immunol 2009, 182:1648-1659).

Oil Red-O Staining

Frozen tissue sections were prepared from the liver and intestine after a standard cryostat procedure. Tissue section slides were stained with Oil Red-O solution (0.5% in propylene glycol) in a 60° C. oven for 10 minutes and placed in 85% propylene glycol for 1 minute; slides were counterstained in hematoxylin.

IHC Staining

Tissues from the liver, intestine, and lung were collected after mice were anesthetized. All tissues were washed with phosphate-buffered saline and dehydrated by a series of increasing ethanol concentrations, followed by paraffin embedding. Sections were stained with anti-Ki67 antibody, anti-LAL antibody, and anti-F4/80 antibody by the histologic core.

Flow Cytometry Analysis

Single-cell suspensions from the bone marrow, spleen, blood, liver, and lung were prepared and analyzed as described in Qu et al., Am J Pathol 2009, 174:944-956; Qu et al., Am J Pathol 2010, 176:2394-2404; Qu et al., J Immunol 2009, 182:1648-1659). Approximately 1×10$^6$ cells from various organs were blocked with FcR blocking antibodies in flow cytometry buffer (BD Biosciences, San Jose, Calif.) followed by incubation with isotype control or surface specific primary antibodies. Anti-CD11b (M1/70) PE-Cyanine7, anti-Ly6G (RB6-8c5) allophycocyanin-eFluor 780, anti-CD4 fluorescein isothiocyanate, anti-CD8 phosphatidylethanolamine, and anti-B220 allophycocyanin were purchased from e-Biosciences (San Diego, Calif.). Cells were analyzed on a LSRII machine (BD Biosciences). Data were analyzed using the BD FACStation software (Cell-Quest Pro version 2.2.1, BD Bio-sciences). The total gated number of positive cells (approximately 30,000 events) was calculated as the percentage of total gated viable cells. Quadrants were assigned using isotype control monoclonal antibody.

Mouse Metastasis Models

For experimental metastasis, $5 \times 10^5$ B16 melanoma cells in 200 µL of phosphate-buffered saline were injected into the mice via tail vein. Two weeks after the injection, the mice were sacrificed, and the livers and lungs were harvested for examination of metastasis.

qPCR

Total RNAs were purified from livers or isolated hepatocytes using RNeasy Mini Kits according to the manufacturer's instruction (Qiagen). Quantitative real-time RT-PCR (qPCR) was performed as described in Wu et al., Blood 2012, 119:115-126). Relative gene expression levels were analyzed using the $2^{-\Delta\Delta CT}$ method. Primers of mouse IL-6, mouse granulocyte-macrophage colony-stimulating factor (GM-CSF), mouse macrophage colony-stimulating factor, mouse tumor necrosis factor (TNF)-α, mouse IL-2, mouse IL-4, mouse IL-17, mouse interferon (IFN)-γ, mouse monocyte chemotactic protein-1 (MCP-1), mouse chemokine ligand (CCL)-3, mouse CCL4, mouse CCL5, mouse CXCL10, and glyceraldehyde-3-phosphate dehydrogenase for qPCR were described in Qu et al. Cancer Res 2009, 69:7252-7261; Zhao et al., Oncogene 2014, 34:1938-1948.

Cytokine Measurement by ELISA

The expression levels of IL-6, GM-CSF, MCP-1 (BD Bio-sciences), and CCL5 (R&D Systems, Minneapolis, Minn.) in the plasma and hepatocyte culture medium were measured using enzyme-linked immunosorbent assay (ELISA) kits according to the manufacturer's instructions.

Mouse Hepatocyte Isolation

Hepatocytes were isolated from the mouse using a two-step perfusion and digestion technique. Briefly, the hepatic portal perfusion of the mouse liver with 37° C. pre-warmed solution A (0.5 mmol/L EGTA and 5 mmol/L HEPES in Hanks) was followed by digestion with 37° C. pre-warmed solution B (3.75 mmol/L $CaCl_2$ and 0.05 mg/mL of collagenase H in L15) perfusion. The digested liver tissues were gently dispersed with tweezers, and hepatocytes were spun down and washed with 1×HEPES buffer. The cell pellets were resuspended in phosphate-buffered saline for flow cytometry. For tissue culture, isolated hepatocytes were resuspended in William's Medium E with 10% fetal bovine serum and cultured in 37° C. After 2 hours, cells were replaced with new medium and prepared for cytokine and chemokine analyses of mRNA and protein expression.

Statistical Analysis

Data were expressed as means±SD. Differences between the two treatment groups were compared with the t-test. When more than two groups were compared, one-way analysis of variance with post hoc Newman-Keul's multiple comparison test was used. Results were considered statistically significant when $P<0.05$. All analyses were performed with GraphPad Prism software version 5.0 (GraphPad, La Jolla, Calif.).

Results

Hepatocyte-Specific Expression of hLAL in $lal^{-/-}$ Mice

Figure 16A:
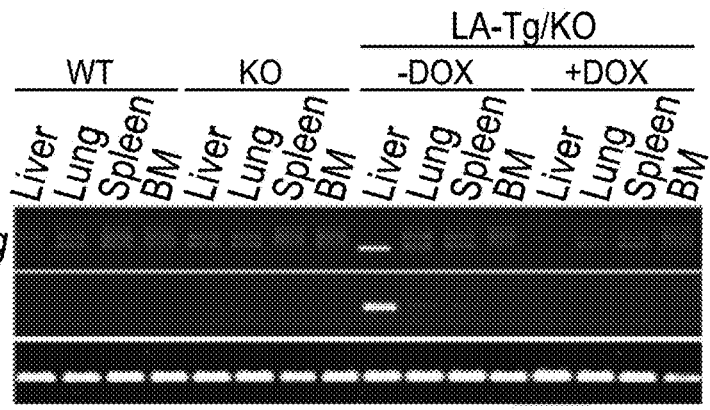
FIGS. 16A-16D depict human LAL (hLAL) expression in wild-type (WT), lal$^{-/-}$ (KO), and liver-activated promoter (LAP)-driven tTA transgene and (tetO)$_7$-CMV-hLAL transgene with lal$^{-/-}$ (LAP-Tg/KO) triple mice.
Figure 16B:
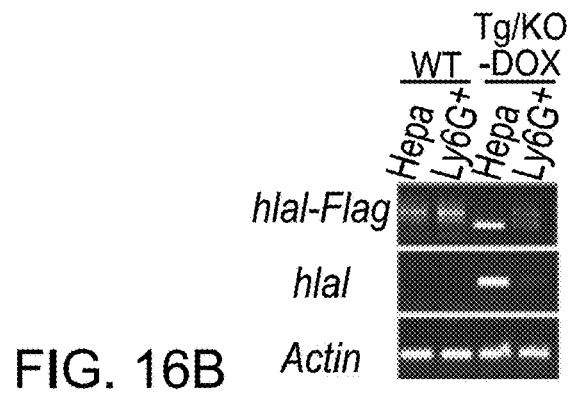

Specific expression of hLAL mRNA in the liver of doxycycline-untreated LAP-Tg/KO triple mice was confirmed by RT-PCR. Two sets of hLAL primers covering different ranges of hLAL cDNA were used to distinguish hLAL expression from endogenous murine LAL expression. One pair of primers covered exons 8 to 9 of hLAL (FIGS. 1A and 1B), whereas another pair of primers covered exon 9 of hLAL and the Flag epitope coding sequence at the 3' end of hLAL cDNA in the $(tetO)_7$-CMV-hLAL vector, which is unique to the hLAL-Flag combination (FIGS. 1A and 1B). As predicted, no hLAL mRNA expression was detected in the liver, lung, spleen, and bone marrow cells of wild-type, $lal^{-/-}$, and doxycycline-treated (turned off) LAP-Tg/KO triple mice. When doxycycline was removed from this Tet-off system, hLAL mRNA expression was induced primarily in the liver of LAP-Tg/KO triple mice (FIG. 16A). To further confirm hLAL mRNA expression in hepatocytes of the liver, hepatocyte and Ly6G$^+$ myeloid cells were isolated from the liver of wild-type and doxycycline-untreated LAP-Tg/KO mice. Indeed, hLAL mRNA expression was detected in hepatocytes, but not in Ly6G$^+$ cells of LAP-Tg/KO triple mice. No detection was observed in hepatocyte and Ly6G$^+$ cells of wild-type mice (FIG. 16B).

Figure 16C:
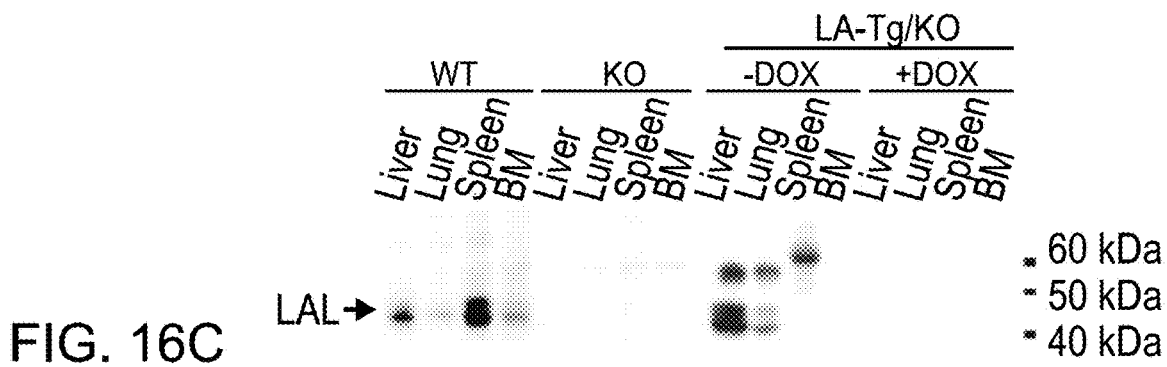

Next, LAL protein expression was also evaluated. Because hLAL and murine LAL share 75% identity and 95% similarity at the peptide sequence level, the anti-LAL antibody recognized both of them. In wild-type mice, expression of the LAL protein was detected in the liver, lung, spleen and bone marrow, but was undetectable in KO mice (FIG. 16C). In LAP-Tg/KO triple mice, expression of the hLAL protein was detected strongly in the liver and weakly in the lung and spleen of doxycycline-untreated LAP-Tg/KO triple mice, but not in doxycycline-treated LAP-Tg/KO triple mice (FIG. 16C).

Figure 16D:
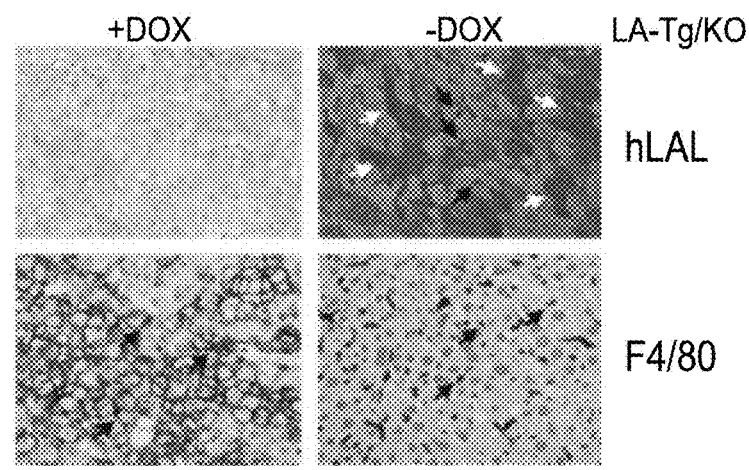

To further clarify the cellular specificity of hLAL protein in the liver, immunohistochemical (IHC) staining of the liver sections with anti-LAL antibody and anti-F4/80 antibody were performed. The results revealed that approximately 50% of hepatocytes were positive for LAL antibody staining, and F4/80$^+$ Kupffer cells were also positive for LAL staining (FIG. 16D) in doxycycline-untreated LAP-Tg/KO mice. Because LAL is a secreted protein, the lack of hLAL mRNA expression for the detection of LAL protein in the lung and spleen of doxycycline-untreated LAP-Tg/KO triple mice is likely due to the uptake of LAL from the circulation system that is secreted from the liver. However, the possibility of uptake of LAL from circulation that is secreted from the liver needs to be further confirmed. The multiple forms of LAL protein were due to differential glycosylation.

Figure 17A:
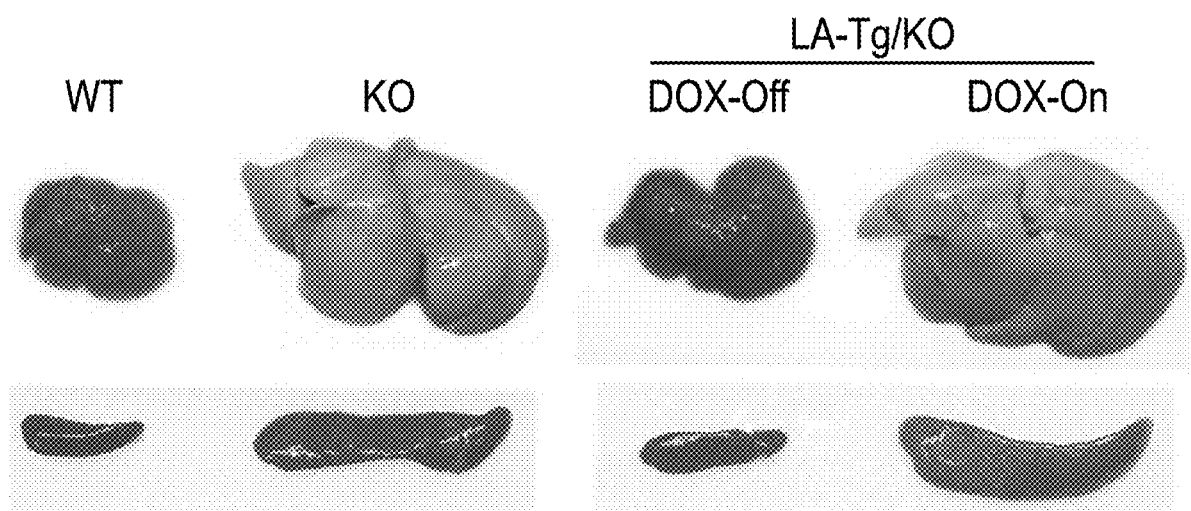
FIGS. 17A-17M show that hepatic expression of hLAL in liver-activated promoter (LAP)-driven tTA transgene and (tetO)$_7$-CMV-hLAL transgene with lal$^{-/-}$ (LAP-Tg/KO) mice corrected abnormality in the liver, spleen, and small intestine.
Figure 17B:
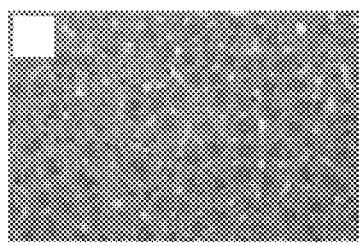
Figure 17C:
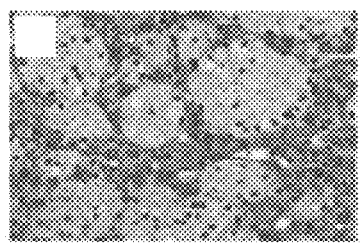
Figure 17D:
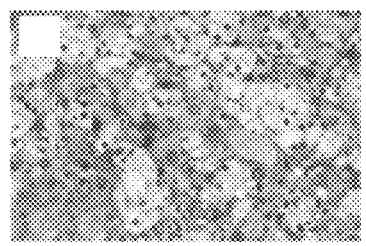
Figure 17E:
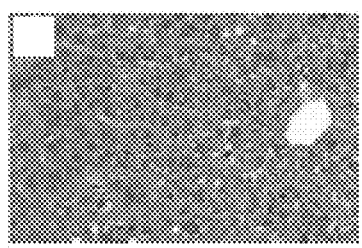
Figure 17F:
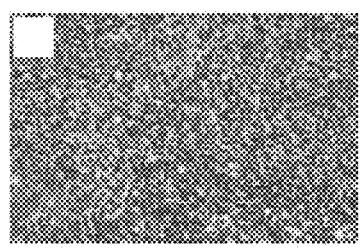
Figure 17G:
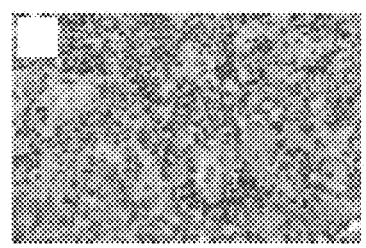
Figure 17H:
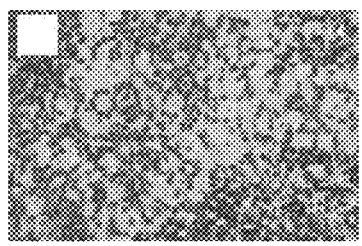
Figure 17I:
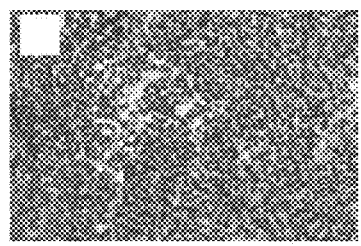
Figure 17J:
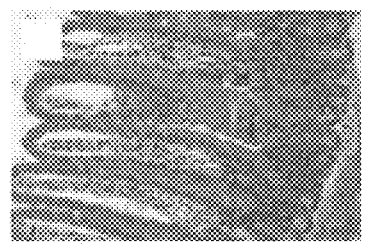
Figure 17K:
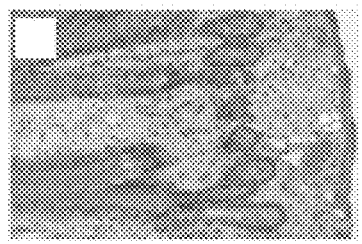
Figure 17L:
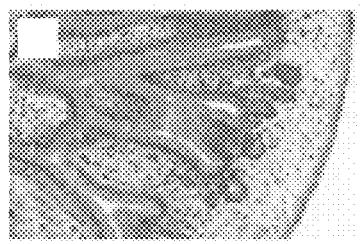
Figure 17M:
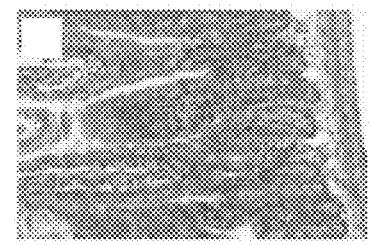
Figure 18A:
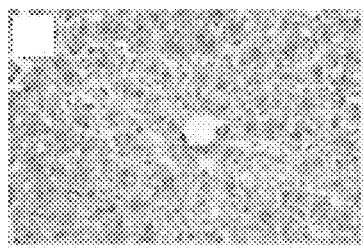
FIGS. 18A-18L depict that hepatic expression of human lysosomal acid lipase (hLAL) in liver-activated promoter (LAP)-driven tTA transgene and (tetO)$_7$-CMV-hLAL transgene with lal$^{-/-}$ (LAP-Tg/KO) mice corrected neutral lipid storage in the liver, spleen, and small intestine. Oil Red-O staining of liver, spleen, and small intestine frozen sections from wild-type (WT) (FIGS. 18A, 18E, and 18I), lal$^{-/-}$ (KO) (FIGS. 18B, 18F, and 18J), doxycycline-treated (DOX-On) (FIGS. 18C, 18G, and 18K), and doxycycline-untreated (DOX-Off) (FIGS. 18D, 18H, and 18L) LAP-Tg/KO mice. Original magnification: ×200 (FIGS. 18A-18L).
Figure 18B:
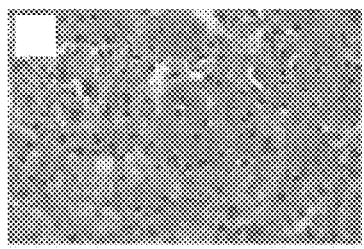
Figure 18C:
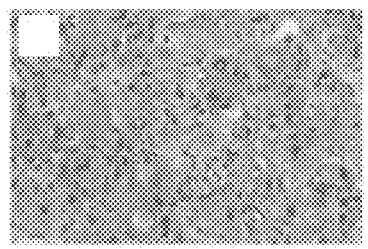
Figure 18D:
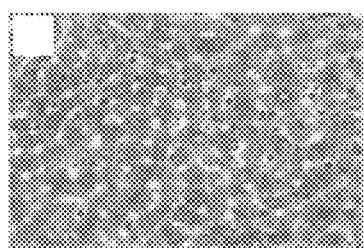
Figure 18E:
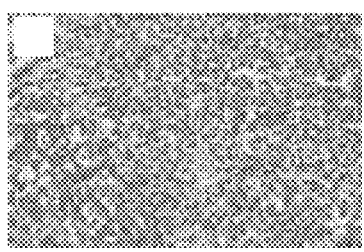
Figure 18F:
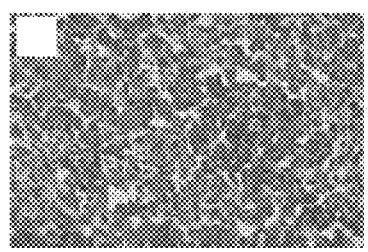
Figure 18G:
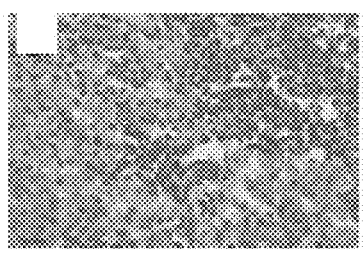
Figure 18H:
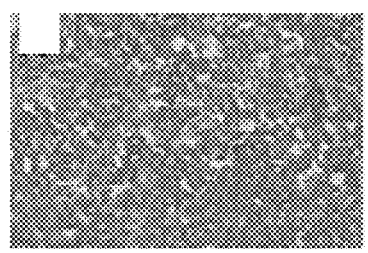
Figure 18I:
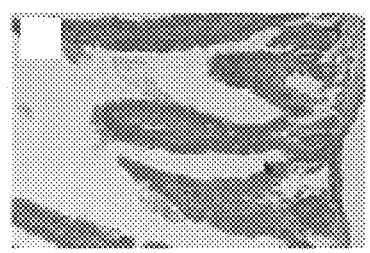
Figure 18J:
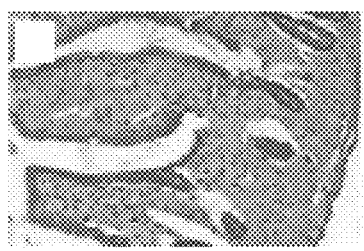
Figure 18K:
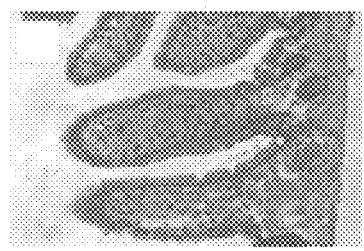
Figure 18L:
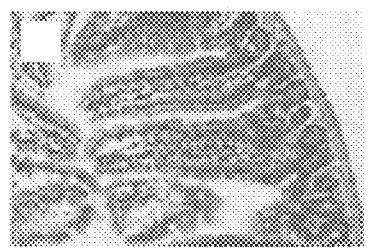

Hepatocyte-Specific Expression of hLAL in $lal^{-/-}$ Mice Reduces Lipid Storage in Multiple Organs Hepatomegaly is the major symptom in patients with Wolman disease (WD) and cholesteryl esters storage disease (CESD). Characterization of $lal^{-/-}$ mice revealed neutral lipid storage in both hepatocytes and Kupffer cells in the liver. In the tet-off LAP-Tg/KO system, both gross view and the histologic phenotypes of the liver, spleen, and small intestine in doxycycline-treated LAP-Tg/KO triple mice (for 7 months) were essentially similar to those in $lal^{-/-}$ mice (FIGS. 17A, 17C, 17D, 17G, 17H, 17K, and 17L). Doxycycline-untreated LAP-Tg/KO triple mice, in which hLAL expression was induced, lacked lipid storage not only in hepatocytes, but also in Kupffer cells (FIG. 17E) similar to the wild-type liver (FIG. 17B). The same observations were found in the spleen and small intestine (FIGS. 17I and 17M), resembling those of wild-type mice (FIGS. 17F and 17J).

Figure 19:
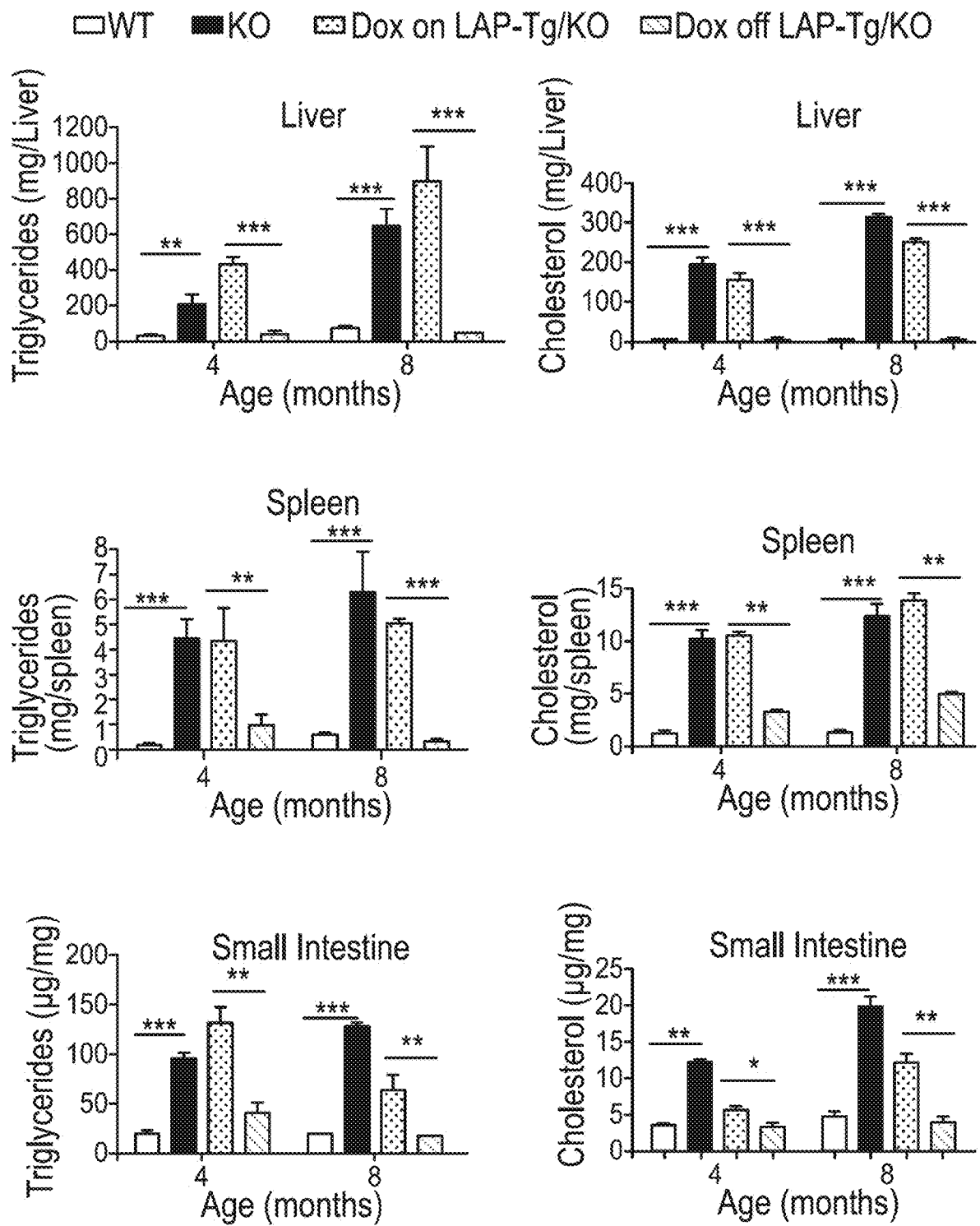
FIG. 19 depicts quantitative analyses of cholesterol and triglycerides in the liver, spleen, and small intestine of human lysosomal acid lipase (hLAL) in liver-activated promoter (LAP)-driven tTA transgene and (tetO)$_7$-CMV-hLAL transgene with lal$^{-/-}$ (LAP-Tg/KO) mice. Concentrations of cholesterol and triglycerides in the liver, spleen, and small intestine of hLAL in LAP-Tg/KO mice were determined as described in Example 3. Data are expressed as means±SEM from five mice in each group. *P<0.05, P<0.01, and *P<0.001. WT, wild type.

Neutral lipid staining by Oil Red-O revealed that doxycycline-treated LAP-Tg/KO triple mice have the similar level of neutral lipid storage in the liver, spleen, and small intestine compared with those of lal$^{-/-}$ mice (FIGS. 18B, 18C, 18F, 18G, 18J, and 18K). Doxycycline-untreated LAP-Tg/KO triple mice had no lipid storage in the liver, spleen, or small intestine similar to those of wild-type mice (FIGS. 18A, 18D, 18E, 18H, 18I, and 18L). Quantitative analyses of cholesterol and triglyceride tissue lipids in the liver, spleen, and small intestine further confirmed that lipid storage in lal mice was completely cleaned up by hepatocyte expression of hLAL (FIG. 19).

Figure 20A:
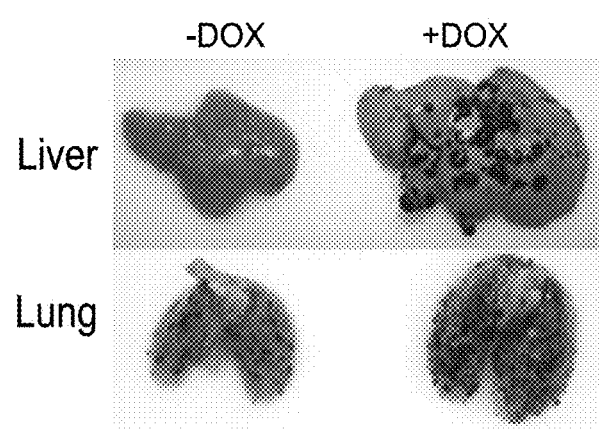
FIGS. 20A-20D depict that hepatic expression of human lysosomal acid lipase (hLAL) in liver-activated promoter (LAP)-driven tTA transgene and (tetO)$_7$-CMV-hLAL transgene with lal$^{-/-}$ (LAP-Tg/KO) mice reduced B16 melanoma metastasis.
Figure 20B:
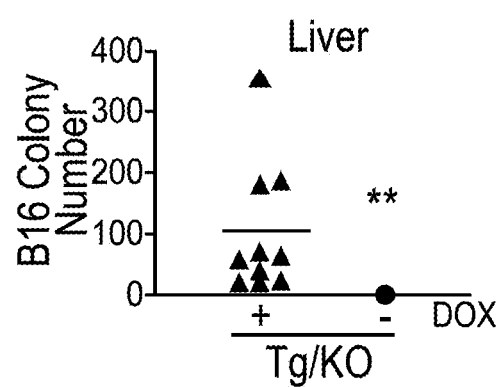
Figure 20C:
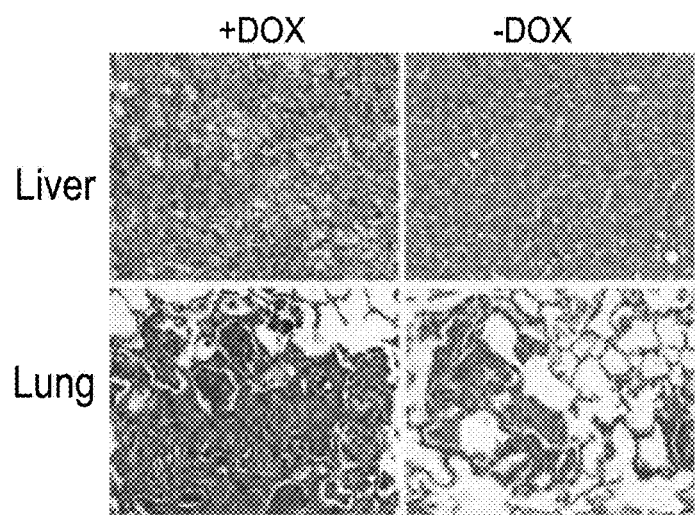
Figure 20D:
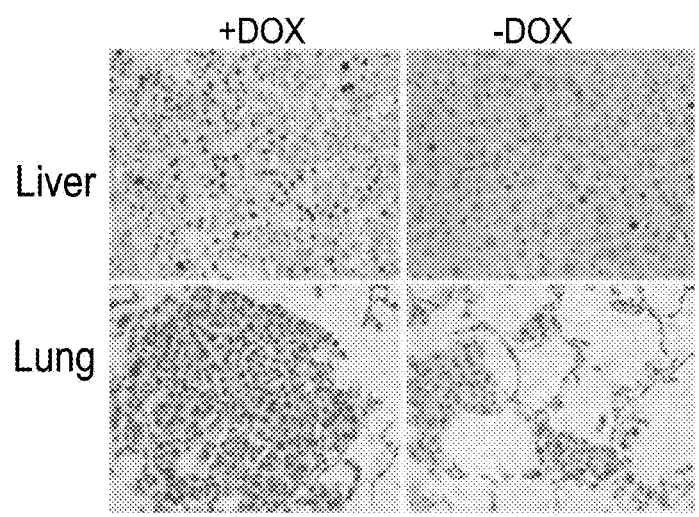

Hepatocyte-Specific Expression of hLAL in lal$^{-/-}$ Triple Mice Reduces B16 Melanoma Cell Metastasis It was recently reported that LAL deficiency facilitates inflammation-induced tumor progression and metastasis in the liver and lung. To evaluate the effects of hLAL in hepatocytes on tumor metastasis, B16 melanoma cells were injected into the tail veins of LAP-Tg/KO triple mice to assess the metastatic potential. Two weeks after injection, more B16 melanoma colonies were observed in the livers and lungs of doxycycline-treated LAP-Tg/KO triple mice compared with those in untreated mice with statistical significance (FIGS. 20A and 20B). Hematoxylin and eosin (H&E) and IHC staining of liver and lung sections revealed more neoplastic melanoma cells and Ki-67 positive proliferative cells in doxycycline-treated LAP-Tg/KO triple mice than those from untreated mice (FIGS. 20C and 20D). Taken together, these observations suggest that hepatocyte-specific expression of hLAL in lal$^{-/-}$ mice reduced B16 melanoma cell metastasis.

Figure 21A:
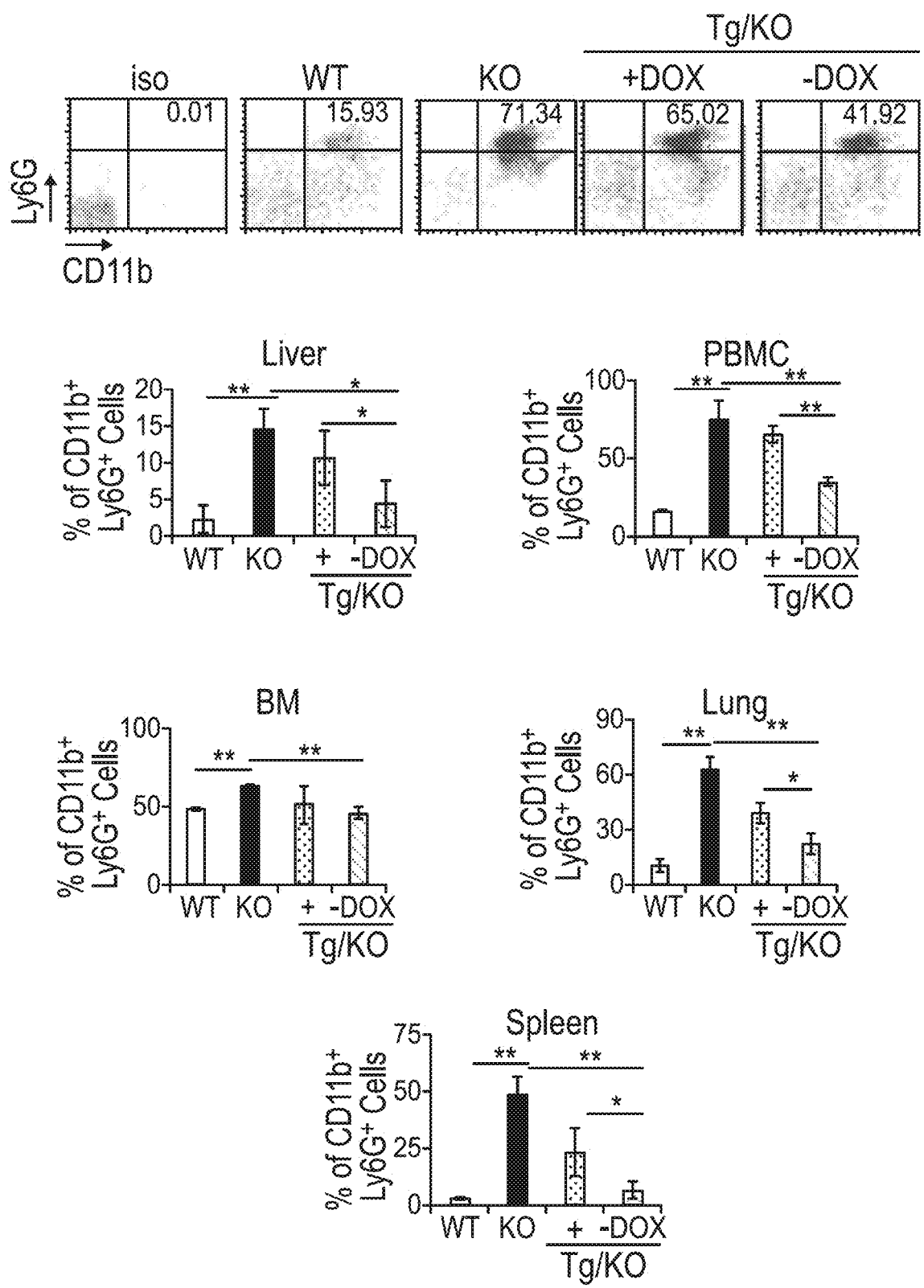
FIGS. 21A & 21B depict that hepatic expression of human lysosomal acid lipase (hLAL) in liver-activated promoter (LAP)-driven tTA transgene and (tetO)$_7$-CMV-hLAL transgene with lal$^{-/-}$ (LAP-Tg/KO) mice reduced CD11b$^+$Ly6G$^+$ cell expansion. The percentages (FIG. 21A) and total cell numbers (FIG. 21B) of CD11b$^+$Ly6G$^+$ cells in the wild-type (WT), lal$^{-/-}$ (KO), doxycycline-treated (+DOX), or doxycycline-untreated (−DOX) LAP-Tg/KO liver, bone marrow (BM), blood [peripheral blood mononuclear cells (PBMCs)], lung, and spleen (3×10$^4$). A representative dot plot of CD11b$^+$Ly6G$^+$ cells in the blood is shown. Data are expressed as means±SD from four mice in each group. n=4. *P<0.05, **P<0.01.
Figure 21B:
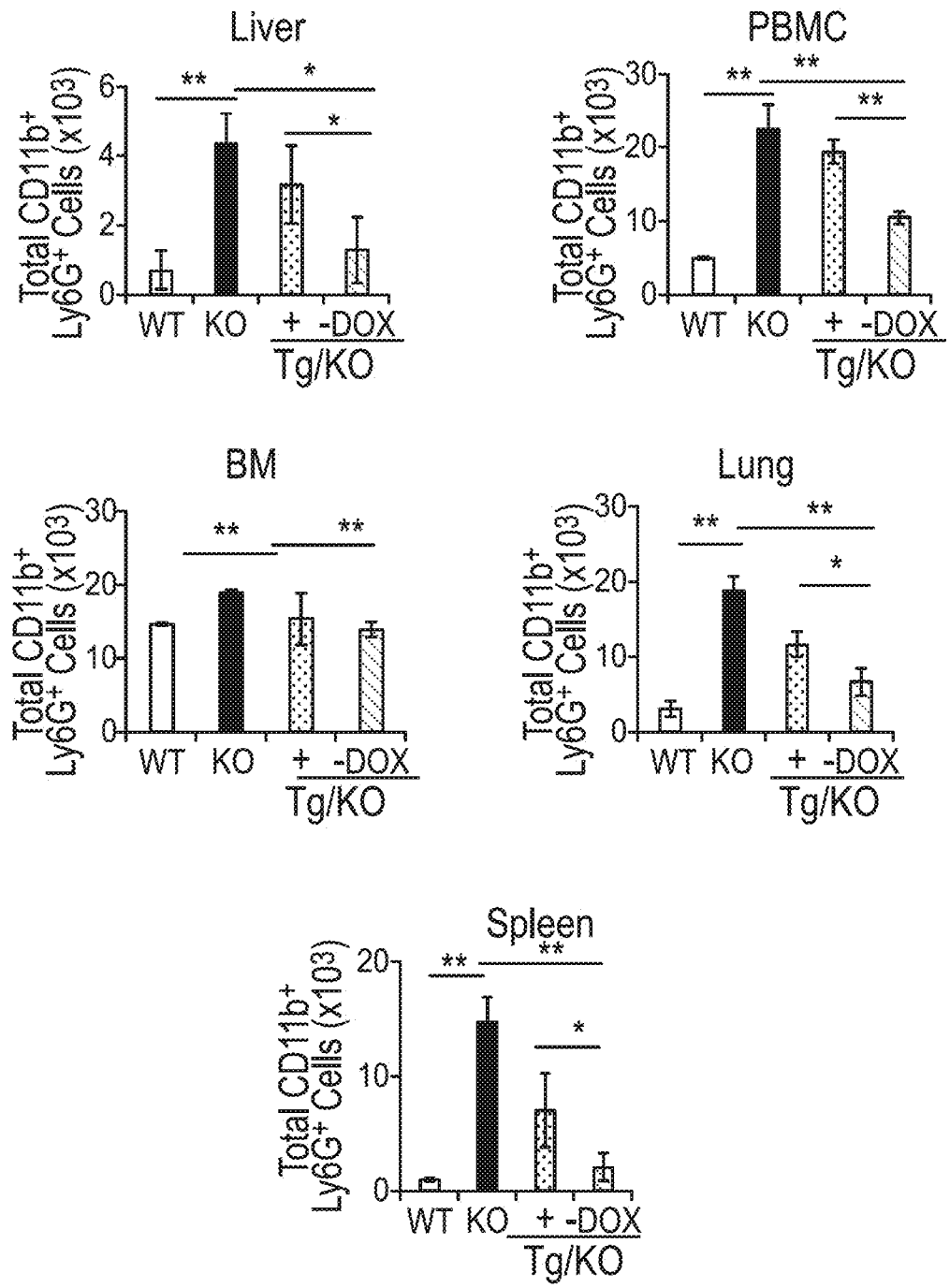

Hepatocyte-Specific Expression of hLAL in lal$^{-/-}$ Triple Mice Decreases Abnormal Expansion of CD11b$^+$ Ly6G$^+$ Cells Previous studies have found that loss of LAL causes significant expansion of CD11b$^+$Ly6G$^+$ immature myeloid cells in multiple organs. When tested in the liver, this cell population was also markedly increased in lal$^{-/-}$ mice (FIGS. 21A and 21B). To test whether hLAL expression in hepatocyte reversed this phenotype, the LAP-Tg/KO triple mice were treated with or without doxycycline for 6 to 7 months. Age-matched wild-type and lal$^{-/-}$ mice were used as controls. Cells from the bone marrow, blood, spleen, lung, and liver of four groups were isolated and stained with anti-CD 11b and anti-Ly6G antibodies for flow cytometry analysis. In the liver, the percentage and total number of CD11b$^+$Ly6G$^+$ cells in doxycycline-untreated LAP-Tg/KO triple mice were decreased to the levels of wild-type mice (FIGS. 21A and 21B). With doxycycline treatment, hLAL expression was shut down in LAP-Tg/KO hepatocytes, which led to CD11b$^+$Ly6G$^+$ cell expansion to the level observed in lal$^{-/-}$ mice. Because hLAL is a secretory enzyme, reduction of CD11b$^+$Ly6G$^+$ cell expansion was also observed in the blood, spleen, and lung, but not in the bone marrow of doxycycline-untreated LAP-Tg/KO triple mice (FIGS. 21A and 21B).

Figure 22A:
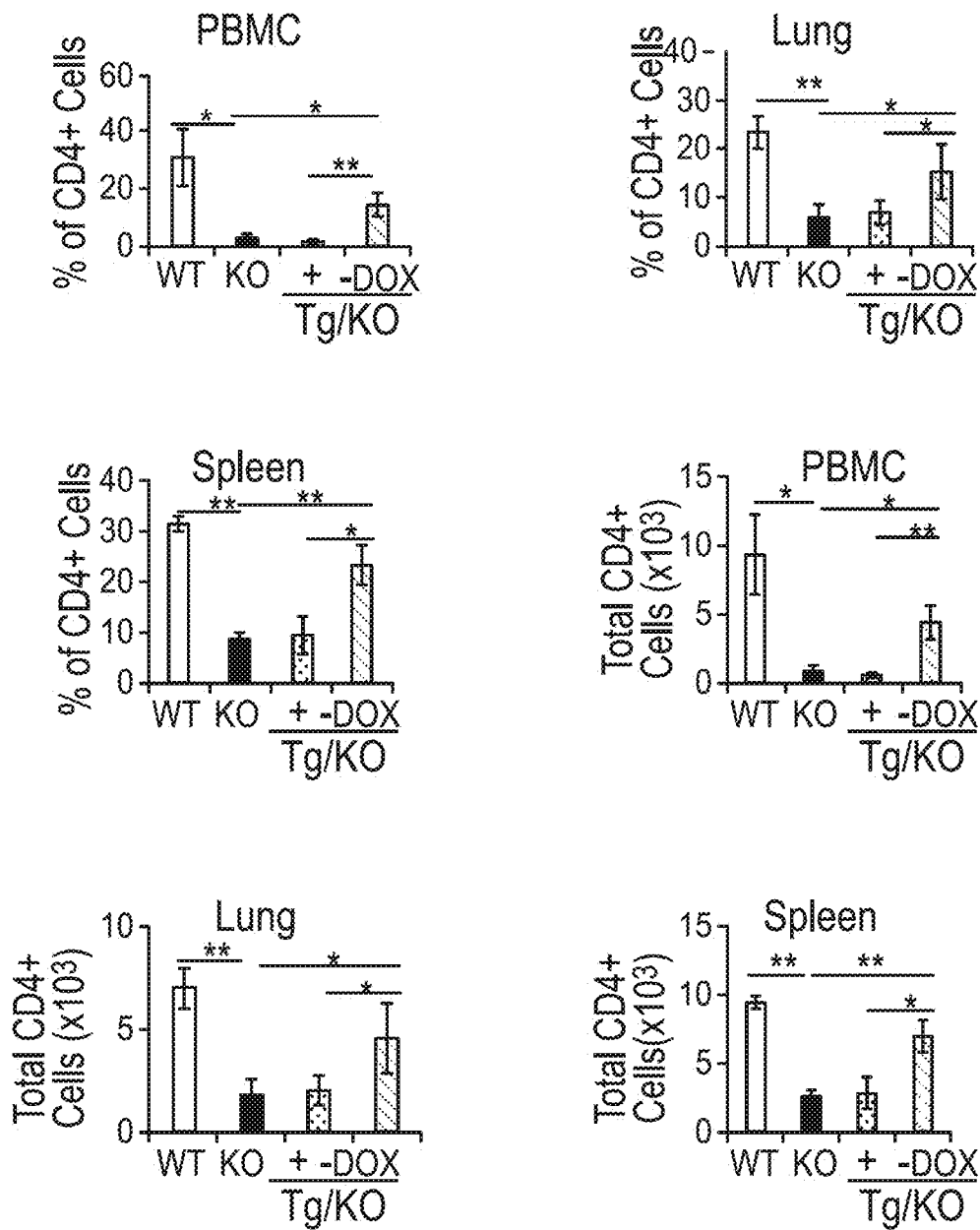
FIGS. 22A-22C depict that hepatic expression of human lysosomal acid lipase (hLAL) in liver-activated promoter (LAP)-driven tTA transgene and (tetO)$_7$-CMV-hLAL transgene with lal$^{-/-}$ (LAP-Tg/KO) mice increased CD4$^+$, CD8$^+$, and B220$^+$ cells. The percentages and total cell numbers of CD4$^+$ T cells (FIG. 22A), CD8$^+$ T cells (FIG. 22B), and B220$^+$ B cells (FIG. 22C) in the wild-type (WT), lal$^{-/-}$ (KO), doxycycline-treated (+DOX), or doxycycline-untreated (−DOX) LAP-Tg/KO bone marrow (BM), blood [peripheral blood mononuclear cells (PBMCs)], lung, and spleen. Representative dot plots or histograms of CD4$^+$, CD8$^+$, and B220$^+$ cells in the blood (PBMCs) are shown, respectively. Data are expressed as means±SD from four mice in each group. n=4. *P<0.05, **P<0.01.
Figure 22B:
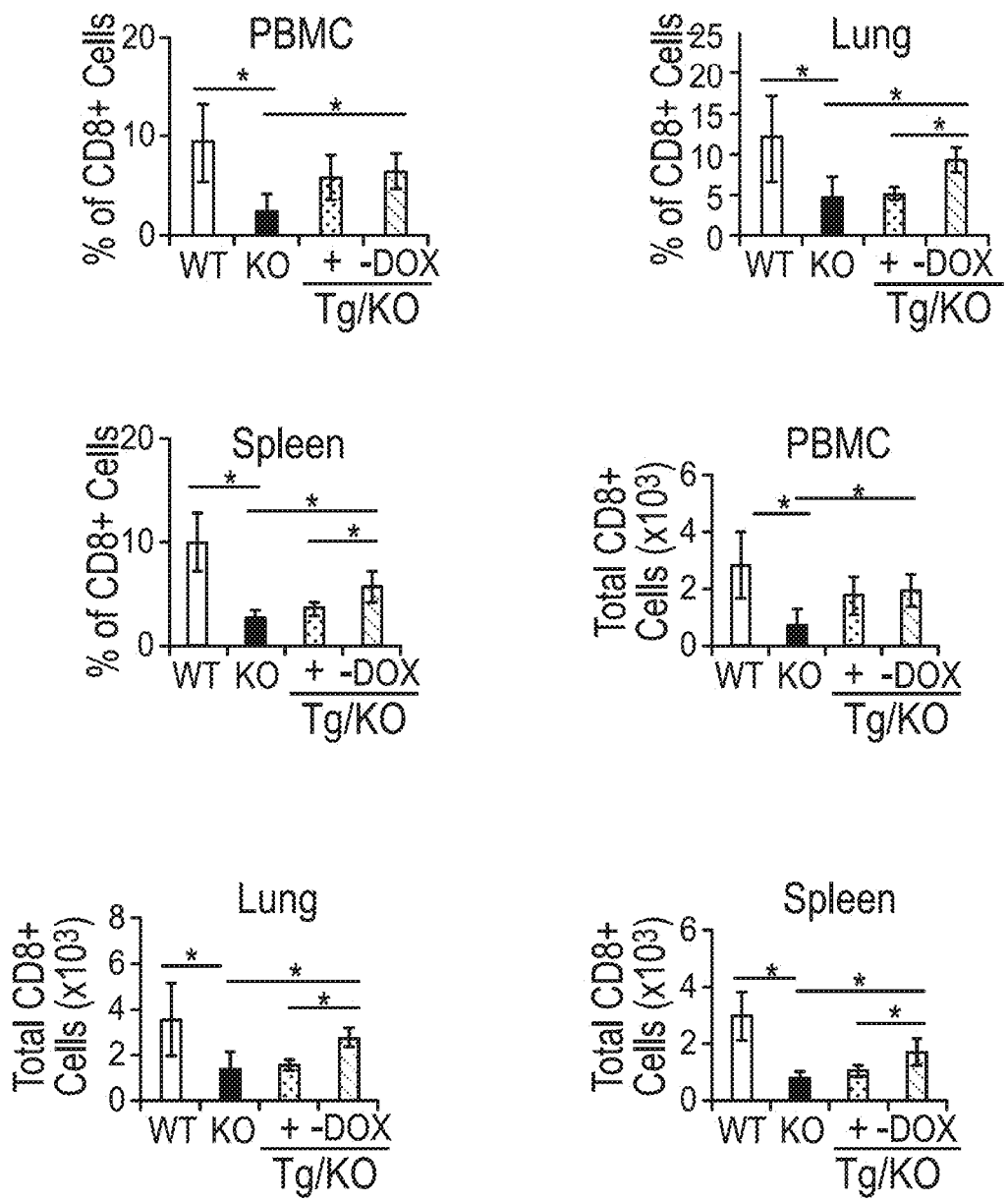
Figure 22C:
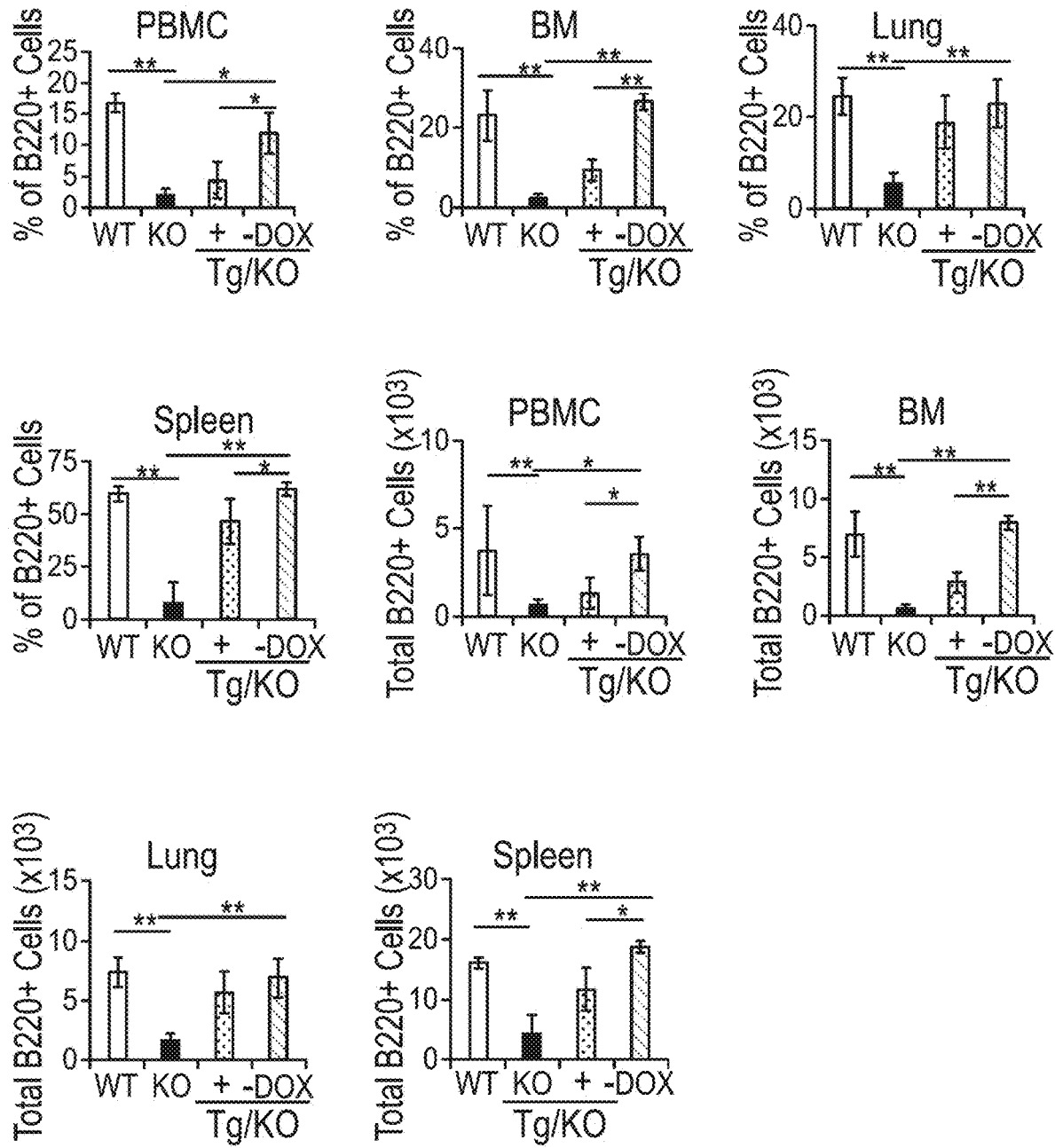

Hepatocyte-Specific Expression of hLAL in lal$^{-/-}$ Triple Mice Increases CD4$^+$, CD8$^+$, and B220$^+$ Cells CD11b$^+$Ly6G$^+$ cells are partially responsible for the decrease of CD4$^+$ and CD8$^+$ T cells in lal$^{-/-}$ mice. It was further determined whether a decrease of CD11b$^+$Ly6G$^+$ cells in doxycycline-untreated LAP-Tg/KO triple mice leads to an increase of CD4$^+$ and CD8$^+$ T cells. The CD4$^+$ T-cell level was low in doxycycline-treated LAP-Tg/KO triple mice, which is similar to that of lal mice. However, hLAL hepatocyte-specific expression increased CD4$^+$ T cells in LAP-Tg/KO triple mice in the blood, lung, and spleen (FIG. 22A). CD8$^+$ T cells had a similar outcome in the lung and spleen, but not in the blood (FIG. 22B). The result for the B220$^+$ B-cell population was similar to those observed in T-cell populations (FIG. 22C). Because of the overlap and interference of strong autofluorescence from liver cells of lal$^{-/-}$ mice, the T-cell and B-cell levels in the liver were unable to be determined by flow cytometry.

Figure 23A:
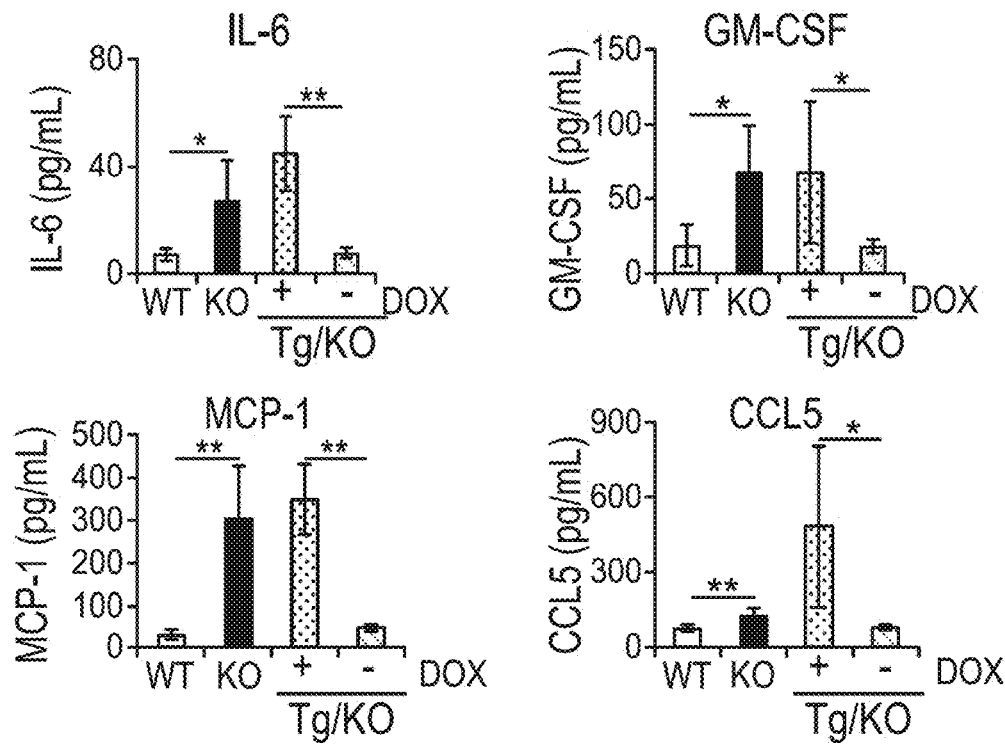
FIGS. 23A & 23B depict that hepatic expression of human lysosomal acid lipase (hLAL) in liver-activated promoter (LAP)-driven tTA transgene and (tetO)$_7$-CMV-hLAL transgene with lal$^{-/-}$ (LAP-Tg/KO) mice reduced synthesis and secretion of cytokines and chemokines.
Figure 23B:
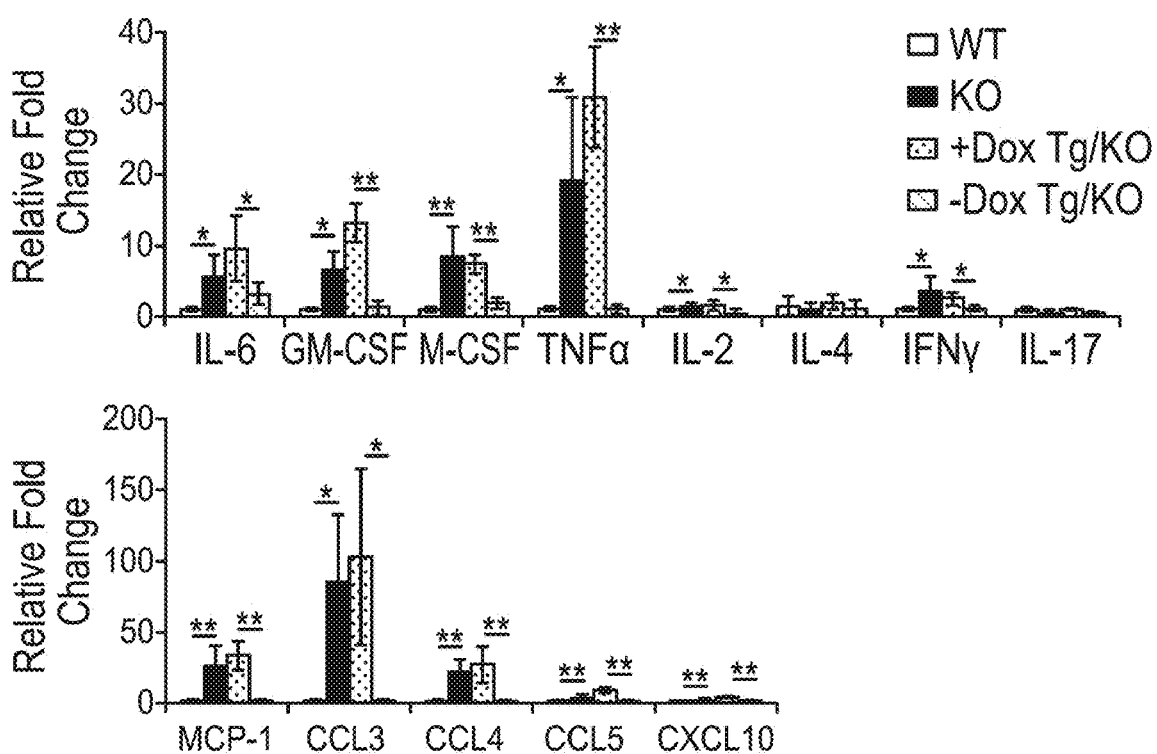

Hepatocyte-Specific Expression of hLAL in lal$^{-/-}$ Triple Mice Reduces Synthesis and Secretion of Tumor-Promoting Cytokines and Chemokines In addition to the changes of immune cells, cytokines and chemokines that are known to promote inflammation and tumorigenesis were measured in the blood plasma by ELISA. The plasma concentrations of IL-6, GM-CSF, MCP-1, and CCL5 were decreased in untreated LAP-Tg/KO triple mice compared with those in doxycycline-treated mice (FIG. 23A). These cytokines and chemokines are important for MDSC accumulation and tumorigenesis. mRNA syntheses of these cytokines and chemokines in the liver were further investigated. mRNA levels of IL-6, GM-CSF, M-CSF, and TNF-α were significantly down-regulated in the liver of doxycycline-untreated LAP-Tg/KO triple mice, accompanied by reduced mRNA levels of T-cell-secreted lymphokines IL-2 and IFN-γ, and unchanged IL-4 and IL-17 levels (FIG. 23B). In addition, mRNA syntheses of chemokines that have been reported to be involved in liver injury were markedly down-regulated in the livers of doxycycline-untreated LAP-Tg/KO triple mice, including MCP-1, CCL3, CCL4, CCL5, and CXCL10. Therefore, reduced synthesis and secretion of cytokines and chemokines were, at least in part, responsible for the decreased metastasis in the lal$^{-/-}$ mice with hepatocyte-specific hLAL expression. These cytokines may or may not be synthesized and secreted by hepatocytes, which were tested below.

Figure 24A:
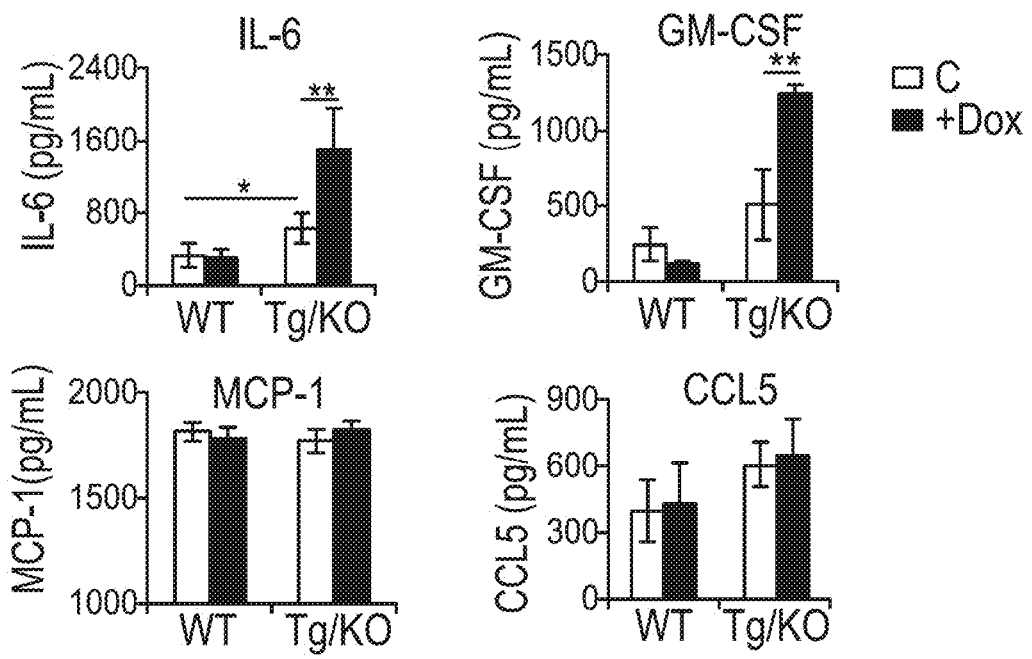
FIGS. 24A & 24B depict that in vitro doxycycline treatment of primary hepatocytes from untreated liver-activated promoter (LAP)-driven tTA transgene and (tetO)$_7$-CMV-hLAL transgene with lal$^{-/-}$ (LAP-Tg/KO) triple mice induced synthesis and secretion of inflammatory cytokines and chemokines. Hepatocytes isolated from lal$^{+/+}$[wild type (WT)] and doxycycline-untreated LAP-Tg/KO triple mice were treated with doxycycline in vitro for 5 days.
Figure 24B:
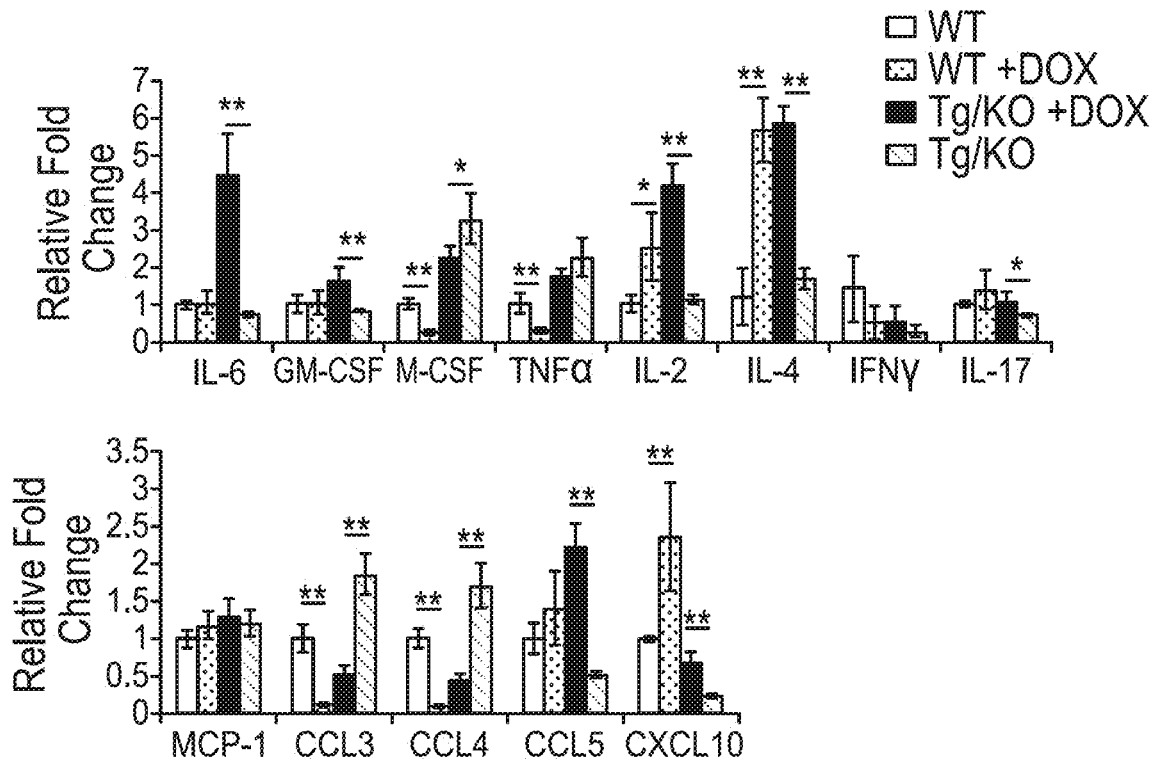

In Vitro Doxycycline Treatment of Hepatocytes from Untreated LAP-Tg/KO Triple Mice Induces Synthesis and Secretion of Inflammatory Cytokines and Chemokines To determine which of these tumor-promoting cytokines are secreted by hepatocytes of LAP-Tg/KO triple mice, hepatocytes were isolated from lal$^{+/+}$ and doxycycline-untreated LAP-Tg/KO triple mice, followed by treatment with doxycycline in vitro for 5 days. The culture medium was harvested and cytokine levels were determined by ELISA. The concentrations of GM-CSF and IL-6 in the culture medium of doxycycline-treated LAP-Tg/KO hepatocytes were significantly increased, whereas MCP-1 and CCL5 did not change, compared with those from untreated hepatocytes (FIG. 24A). This observation suggests that doxycycline-inducible hLAL off-expression in hepatocytes partially contributes to the increased concentrations of GM-CSF and IL-6, but not those of MCP-1 and CCL5. mRNA syntheses of these cytokines/chemokines in the hepatocytes were further investigated. mRNA levels of IL-6, GM-CSF, IL-2, IL-4, IL-17, CCL5, and CXCL10 were significantly up-regulated in the doxycycline-treated LAP-Tg/KO hepatocytes, accompanied by reduced mRNA levels of M-CSF, CCL3, and CCL4, and no change of TNF-α, IFN-γ, and MCP-1 (FIG. 24B). The increased synthesis of IL-6, GM-CSF, IL-2, CCL5, and CXCL10 in doxycycline-treated LAP-Tg/KO hepatocytes was similar to that observed in the whole liver of doxycycline-treated LAP-Tg/KO triple mice, suggesting that the changes of these cytokines and chemokines syntheses were mainly contributed by hepatocytes, whereas the syntheses of other cytokines and chemokines were contributed by other cell types in the liver.

Discussion

This Example found that hLAL-specific expression in the hepatocytes almost completely corrected liver malformation in LAP-Tg/KO mice (FIGS. 17A-17M) and myeloid cell infiltration (FIGS. 18C, 18D, 18G, 18H, 18K, and 18L). Simultaneously, it reduced production of proinflammatory cytokines and chemokines and the MDSC level (FIGS. 21A, 21B, 23A, 23B, 24A and 24B), which resulted in recovery of T-cell and B-cell populations in the liver (FIGS. 22A-22C). Interestingly, hLAL-specific expression in the hepatocytes reduced MDSCs and increased T-cell and B-cell populations in other organs as well (FIGS. 21A, 21B and 22A-22C). This observation indicates that hLAL made in the liver is secreted into the circulation system and affects distant organs. LAL deficiency in both residential hepatocytes and myeloid cells is responsible for liver disease formation. Notably, the mouse version and the human version of LAL are functionally interchangeable in animal models.

In addition to WD and CESD, patients with mutations in the LAL gene have been reported to associate with liver carcinogenesis. When tested in the lal$^{-/-}$ mouse model, it was recently discovered that LAL deficiency-induced inflammation plays crucial roles at all stages of tumor development. In lal$^{-/-}$ mice, B16 melanoma metastasized in the liver and lung of allogeneic lal$^{-/-}$ mice, which was suppressed in allogeneic lal$^{+/+}$ mice due to immune rejection. Importantly, in addition to the immune suppressive function, it was found that MDSCs from lal$^{-/-}$ mice alone directly stimulated B16 melanoma cell in vitro proliferation and in vivo growth and metastasis. Cytokines (i.e., IL-1β, IL-6, and TNF-α) from lal$^{-/-}$ MDSCs are required for B16 melanoma proliferation. In addition to MDSCs, it seems that hepatocytes were also responsible for production of tumor-promoting cytokines as found here. hLAL-specific expression in the hepatocytes reduced expression of tumor-promoting cytokines (FIGS. 23A, 23B, 24A and 24B), as well as MDSCs (FIGS. 21A and 21B). Taken together, both immune cells and tumor-promoting cytokines contribute to tumor growth and metastasis in allogeneic lal$^{-/-}$ mice. As a consequence, B16 melanoma metastasis was almost completely blocked in the liver of allogeneic LAP-Tg/KO mice, an indication of recovery of immune rejection to tumor cells. Reduction of B16 melanoma metastasis in the distant organ lung was also observed by hLAL-specific expression in the hepatocytes (FIGS. 20A-20D).

In summary, LAL in hepatocytes plays critical roles in maintaining liver homeostasis and function. The molecular mechanisms that mediate LAL functions in hepatocytes can be two-fold. First, the derivatives of free fatty acid metabolites serve as hormonal ligands for peroxisome proliferator-activated receptor gamma (PPARγ). Activation of PPARγ by these ligands inhibits proinflammatory molecule (TNF-α, IL-1β, and IL-6) production and induces MDSC expansion. PPARγ ligand treatment improves the pathogenic phenotypes in the lungs of lal$^{-/-}$ mice. Second, Affymetrix GeneChip micro-array analysis and Ingenuity Pathway Analysis identified the mammalian target of rapamycin (mTOR) as a major signaling pathway in mediating lal$^{-/-}$ MDSCs malfunctions, including immunosuppression and tumor stimulation. Membrane trafficking causes mTOR to shuttle to lysosomes and regulate mTOR signaling.

Example 4

Materials & Methods

Animals and Cell Lines

Wild-type (lal$^{+/+}$) and lal$^{-/-}$ mice of the FVB/N background were bred in house. CCSP-rtTA/(TetO)7-CMV-hLAL; lal$^{-/-}$ (CCSP-Tg/KO) triple mice were generated by crossbreeding previously made CCSP-rtTA transgenic mice and (TetO)7-CMV-hLAL transgenic mice into lal$^{-/-}$ mice. This triple transgenic mouse model is lung AT II epithelial cells-specific Tet-on expression of wild-type human LAL (hLAL) in lal$^{-/-}$ mice under the control of the CCSP promoter. All scientific protocols involving the use of animals were approved by the Institutional Animal Care and Use Committee of Indiana University School of Medicine and followed guidelines established by the Panel on Euthanasia of the American Veterinary Medical Association. Animals were housed under Institutional Animal Care and Use Committee-approved conditions in a secured animal facility at Indiana University School of Medicine.

The murine B16 melanoma cell line and Lewis lung carcinoma (LLC) cell line (ATCC, Manassas, Va., USA) were cultured in DMEM supplemented with 10% FBS (Gibco, Grand Island, N.Y., USA).

Flow Cytometry Analysis

For immune cell profile analysis, single cells from the lung, bone marrow, spleen and blood of lal$^{+/+}$, lal$^{-/-}$ and CCSP-Tg/KO triple mice were prepared. Cells were labeled with isotype control or surface-specific primary antibodies at 4° C. for 15 minutes, and then washed and ready for flow cytometry analysis. Anti-CD11b (M1/70) PE-Cyanine7 and anti-Ly6G (RB6-8c5) APC-eFluor® 780 were purchased from eBiosciences (San Diego, Calif., USA). For characterization of tissue-specific expression of the hLAL transgene, single cells from the lungs of lal$^{+/+}$, lal$^{-/-}$ and CCSP-Tg/KO triple mice were prepared and stained. Surfactant protein C (SP-C, AT II epithelial cell marker) Ab and Flag Ab were purchased from Santa Cruz Biotechnology (Dallas, Tex., USA) and Sigma-Aldrich (St. Louis, Mo., USA), respectively. In gated SP-C$^+$ cells, the number of the Flag$^+$ cells were analyzed by flow cytometry and calculated based on M1, which is defined by isotype control. Whole spleen cells were used as a control, in which the number of the Flag$^+$ cells was analyzed. For flow cytometry analysis, ≥30,000 cells were acquired and scored using a LSRII machine (BD Biosciences, San Jose, Calif., USA). Data were processed using the CellQuest software program (BD Biosciences).

Histology and Immunohistochemical Staining

The lungs were harvested and fixed with 4% paraformaldehyde in PBS at 4° C. overnight. After embedding in paraffin, tissue sections were cut to 5 μm thick. Hematoxylin and eosin (H&E) staining was performed by the Histological Core Facility, Department of Pathology and Laboratory Medicine, Indiana University. Images were taken by Nikon microscopy image system (Nikon, Tokyo, Japan). Morphometric analysis was performed on sections taken throughout various lobes of the lungs. Images were analyzed by Nikon NIS Elements imaging software. A threshold was applied to the spaces of the alveoli. Large vessels, smaller arterioles and venules were excluded from the Example. The alveoli were assessed by area, diameter and perimeter using the integrated morphometry analysis tool. All data were exported to Microsoft excel.

Mouse Metastasis Model

For the tumor metastasis model, 5×10$^5$ B16 melanoma cells in 200 μL PBS were injected into the mice via tail vein. Two weeks after the injection, the mice were sacrificed and the lungs were harvested for examination of metastasis.

Kwik-Diff Staining of Bronchoalveolar Lavage Fluid (BALF) Cells

Kwik-Diff staining of BALF cells was performed by collecting BALF cells in 1 mL PBS. Cells were then centrifuged and re-suspended with 0.5 mL PBS. Same volume of cell suspension (125 µL) was cyto-spun on the slide and stained with the Kwik-Diff stain kit according to the manufacturer's instruction (Thermo Shandon, Pittsburgh, Pa., USA) Images were taken by Olympus microscopy image system (Olympus).

Cytokine Measurement by ELISA

BALF was collected by 1 mL PBS. The expression levels of IL-6, GM-CSF, MCP-1 and TNFα in the BALF and plasma were measured using ELISA kits (BD Biosciences, San Jose, Calif.) according to the manufacturer's instructions.

Quantitative Real-Time RT-PCR

Total RNAs were purified from lungs of $lal^{+/+}$, $lal^{-/-}$ and CCSP-Tg/KO triple mice using RNeasy Mini Kits according to the manufacturer's instruction (Qiagen, Valencia, Calif., USA). Quantitative (q)RT-PCR was performed as described previously (Wu et al., Blood. 2012; 119:115-26). Analysis was performed by the $2^{-\Delta\Delta CT}$ method. Primers of mIL-6, mIL-1β, mIL-10, mGM-CSF, mM-CSF, mTNF-α, mMCP-1, mCCL5 and GAPDH were used for real-time PCR.

Isolation and in Vitro Culture of Pulmonary Endothelial Cells (ECs)

ECs were isolated from $lal^{+/+}$ lungs and cultured in vitro. Briefly, the mouse was anesthetized and 1 mL collagenase A (2 mg/mL, Roche, Indianapolis, Ind., USA) was infused into the lung through the trachea. The lung was removed and then incubated with 10 mL collagenase A at 37° C. for 30 minutes. After the incubation, the resulting cell suspension was filtered through a 40 µm strainer and centrifuged for 5 minutes at 1,500 rpm. After removal of the supernatant, the cell pellet was subjected to magnetic bead sorting using anti-CD31 microbeads (Miltenyi Biotec., Auburn, Calif., USA) according to the manufacturer's protocol. The resulting cells were plated onto gelatin-coated (Sigma-Aldrich) 6-well plates and maintained in DMEM supplemented with endothelial cell growth supplement, heparin, L-Glutamine (Sigma-Aldrich), FBS, and Antibiotic-Antimycotic (Gibco).

In Vitro BALF Treatment

BALF was harvested by 1 mL PBS, and cells were removed by centrifugation. To determine the effect of BALF on tumor cell proliferation, B16 melanoma or LLC cells ($5 \times 10^3$) were seeded into a well of 96-well plates in 100 µL DMEM supplemented with 10% FBS, and then treated with 100 µL BALF harvested from $lal^{+/+}$, $lal^{-/-}$ or CCSP-Tg/KO triple mice. Seventy-two hours later, the number of B16 melanoma or LLC cells was counted.

To examine the effect of BALF on EC proliferation, $5 \times 10^4$ ECs were seeded into a well of 24-well plates in 250 µL DMEM supplemented with 10% FBS, and then treated with 250 µL BALF harvested from $lal^{+/+}$, $lal^{-/-}$ or CCSP-Tg/KO triple mice. Seventy-two hours later, the number of ECs was counted.

To analyze the effects of BALF on tumor cell or EC migration, in vitro wound healing assays were performed. Briefly, tumor cells or ECs were seeded at a density of $1.5 \times 10^5$ cells/well into a 24-well plate and incubated overnight to form a confluent monolayer. Scratch was created by scraping the cell monolayer in a straight line with a p200 pipet tip. After washing 3 times with PBS, the medium was changed with 250 µL DMEM containing 10% FBS and 5 µg/mL mitomycin C (Sigma-Aldrich). Then 250 µL BALF from $lal^{+/+}$, $lal^{-/-}$ or CCSP-Tg/KO triple mice were added to the well. Cells were kept on culture at 37° C., 5% $CO_2$. Images were taken at 0 and 15 hours after creating the scratch. Migration was estimated by measuring the distances from one side of the scratch to the other side using Image Pro-Plus software (Media Cybernetics, Rockville, Md., USA).

T Cell Proliferation Assay

To determine the immunosuppressive effects of BALF cells, BALF was harvested by PBS. After the centrifugation, the resulting cell pellets were collected and used. $CD4^+$ T cells were prepared and CFSE labeled as we previously described (15). Labeled $CD4^+$ T cells were co-cultured with BALF cells in 96-well plates pre-coated with anti-CD3 monoclonal antibody (mAb) (2 µg/mL) and anti-CD28 mAb (5 µg/mL) at 37° C., 5% $CO_2$ for 4 days. The ratio of BALF cells:$CD4^+$ T cells was 1:5. Proliferation of $CD4^+$ T cells was evaluated as CFSE dilution by FACS.

Transwell Assay

Transwell assay was used to determine cell transendothelial migration. ECs were added to the upper chamber of 24-well 8.0-µm-pore Transwell plates (Corning, Corning, N.Y., USA), and incubated at 37° C., 5% $CO_2$ for 48 hours to form an EC monolayer. The supernatant was then removed, and CELLTRACKER™ Green 5-Chloromethylfluorescein Diacetate (CMFDA) (Invitrogen, Grand Island, N.Y., USA)-labeled bone marrow cells ($1 \times 10^4$ cells in 200 µL media) were added to the upper well. After 4 hours, transendothelial migration of bone marrow cells was determined by counting their numbers in the lower chamber under 5 random microscopic fields.

Statistics

Data were expressed as mean±SD. Differences between two treatment groups were compared by Student's t-test. When more than two groups were compared, one-way ANOVA with post-hoc Newman-Keul's multiple comparison test was used. Results were considered statistically significant when $P<0.05$. All analyses were performed with GraphPad Prism 5.0 (GraphPad, San Diego, Calif., USA).

Results hLAL Expression Reduces Lung Destruction

Figure 25A:
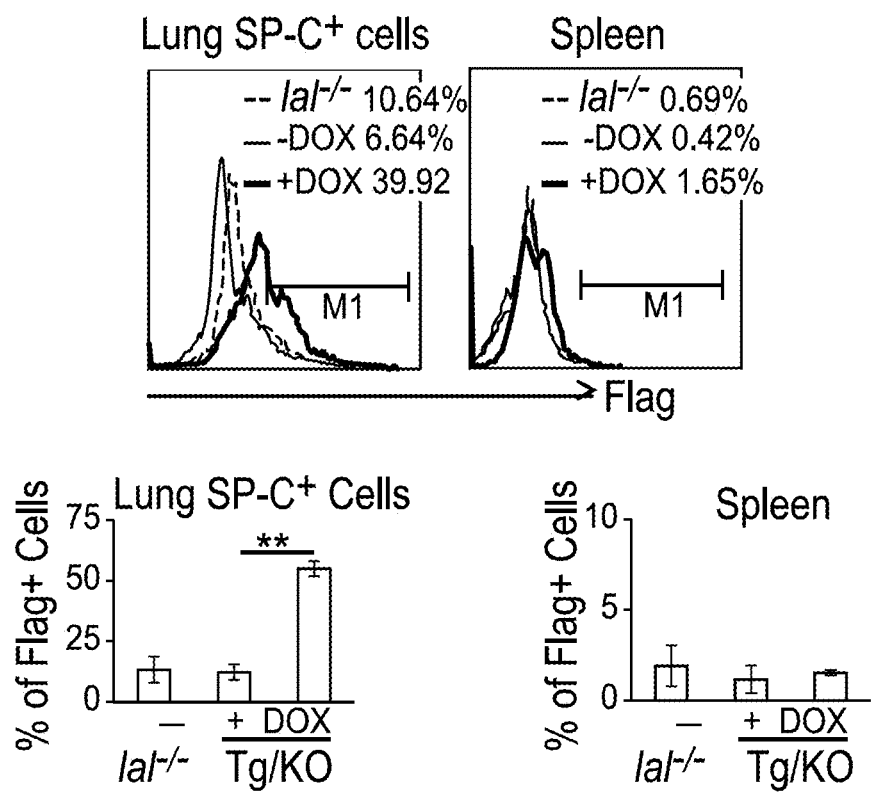
FIGS. 25A-25C depict hLAL expression in lung epithelial cells reduces lung destruction in lal$^{-/-}$ mice.
Figure 25B:
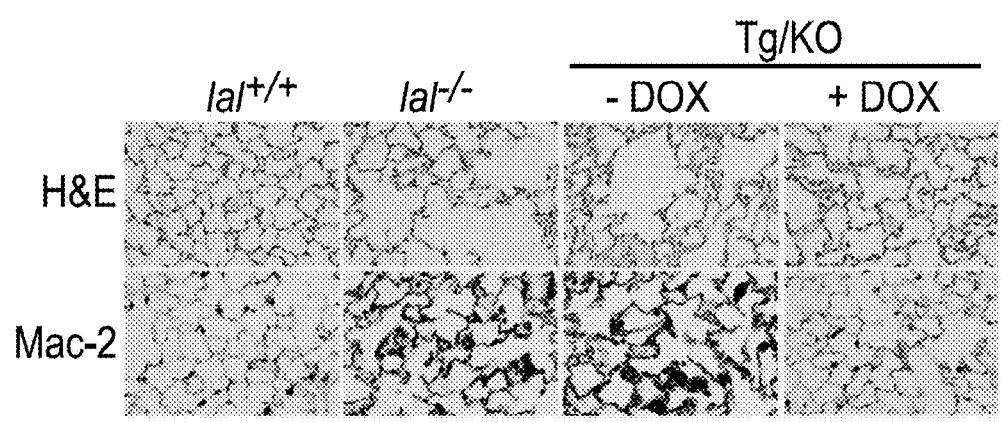
Figure 25C:
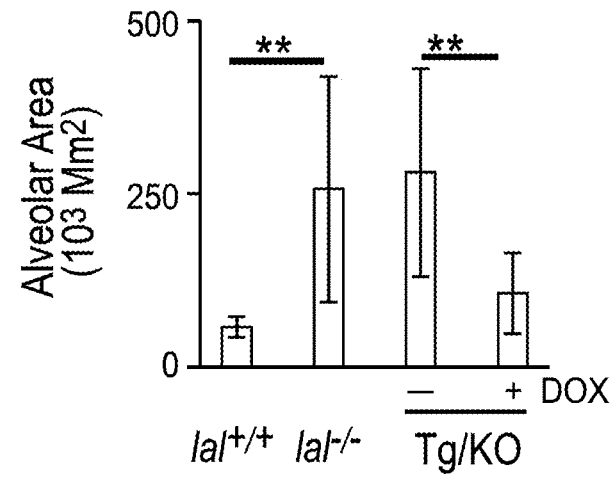
Figure 25C:
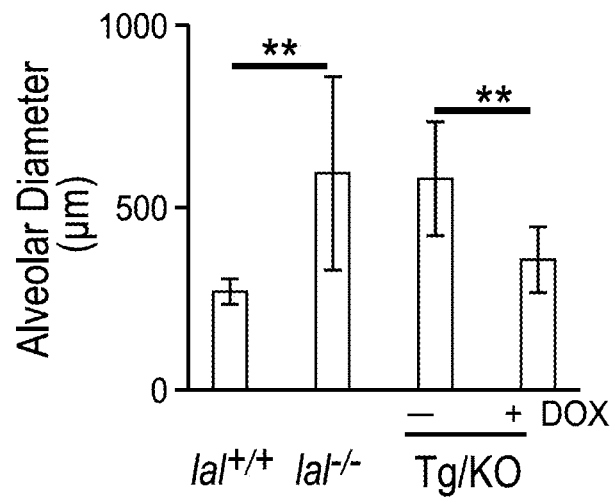
Figure 25C:
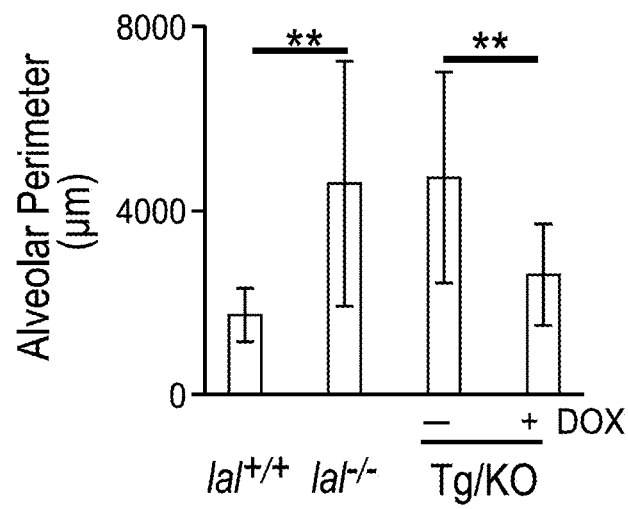

The specific expression of hLAL protein in lung epithelial cells of doxycycline-treated CCSP-Tg/KO mice was confirmed by flow cytometry analysis. Flag antibody was used to detect hLAL-Flag fusion protein to distinguish from the endogenous murine LAL expression. By flow cytometry analysis, expression of the hLAL-Flag fusion protein was significantly induced in SP-$C^+$ (AT II cell marker) lung epithelial cells of CCSP-Tg/KO mice with doxycycline treatment (FIG. 25A). No hLAL-Flag fusion protein was detected in the spleen of CCSP-Tg/KO mice, regardless of doxycycline treatment (FIG. 25A). As a result, the lung damage observed in $lal^{-/-}$ mice was partially restored with hLAL expression in doxycycline-treated CCSP-Tg/KO mice, which was demonstrated by reversed emphysema with smaller alveolar space areas as assessed by H&E staining and morphometric measurements of alveolar area, diameter and perimeter (FIGS. 25B & 25C). However, CCSP-Tg/KO mice with doxycycline-treatment showed no improvement in the liver and spleen compared to doxycycline-untreated mice.

hLAL Expression Reduces Cancer Metastasis

Figure 26A:
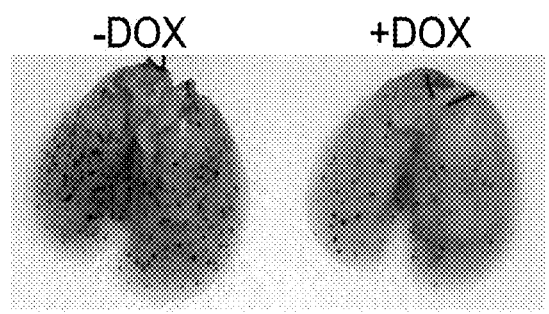
FIGS. 26A-26C depict hLAL expression in lung epithelial cells reduces cancer metastasis in lal$^{-/-}$ mice.
Figure 26B:
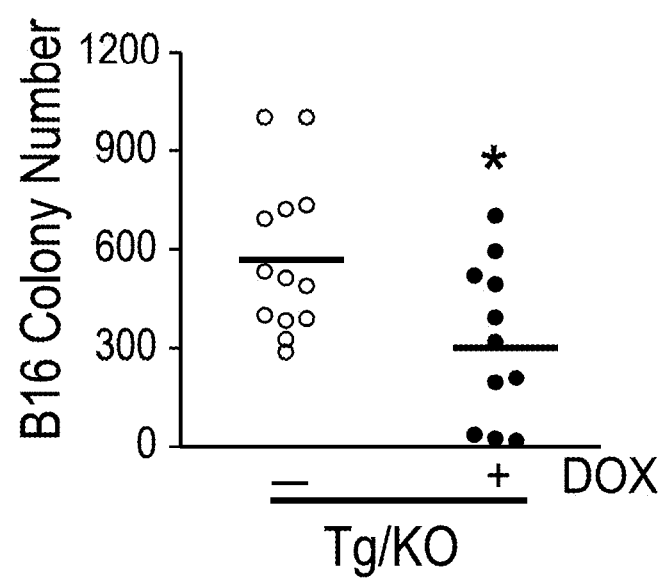
Figure 26C:
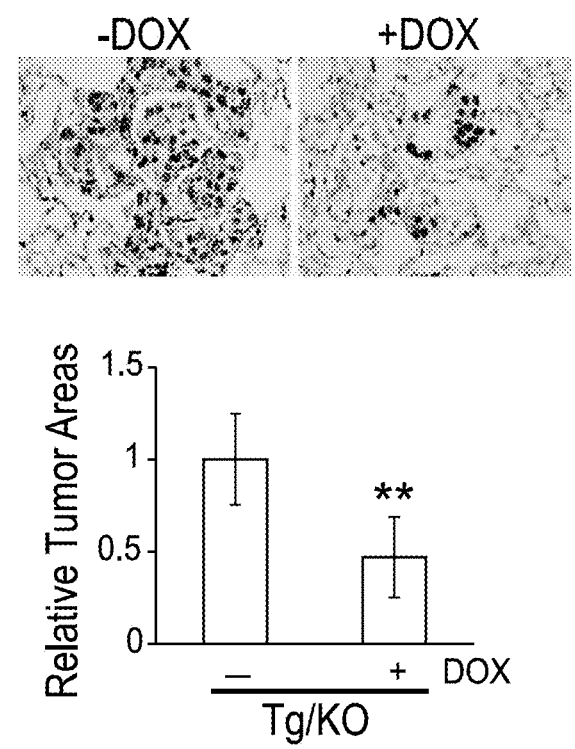

LAL deficiency has been reported to facilitate tumor growth and metastasis. To evaluate the effects of hLAL expression in lung epithelial cells on tumor metastasis, B16 melanoma cells were injected intravenously into CCSP-Tg/KO mice. Two weeks after injection, less B16 melanoma colonies were observed in the lungs of doxycycline-treated CCSP-Tg/KO mice compared to those in untreated mice with statistical significance (FIGS. 26A & 26B). IHC staining of lung sections revealed that there were less neoplastic melanoma cells and Ki-67 positive proliferative cells in the lungs of doxycycline-treated CCSP-Tg/KO mice than those in the lungs of untreated mice (FIG. 26C). These observations suggest that lung epithelial-specific expression of hLAL in lal mice reduced B16 melanoma cell metastasis.

hLAL Expression Decreases Abnormal Expansion of Ly6G$^+$CD11b$^+$ Cells

Figure 27A:
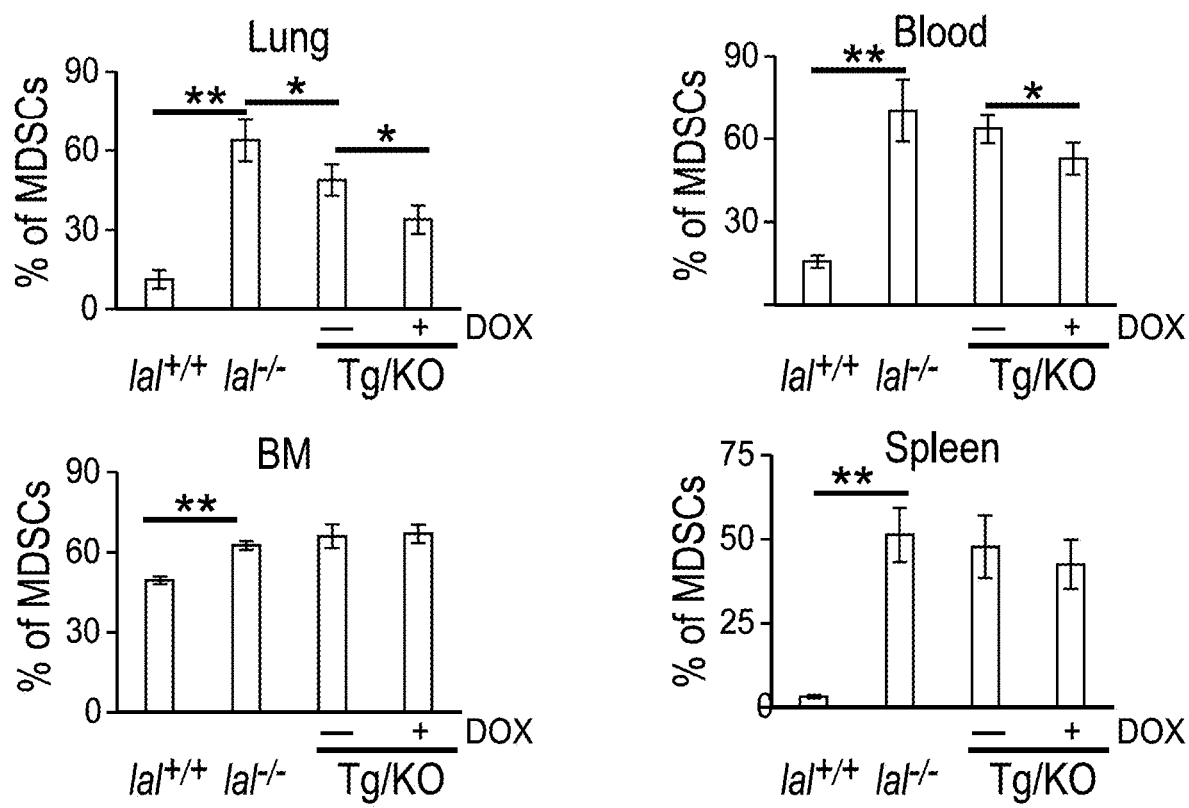
FIGS. 27A-27C depict hLAL expression in lung epithelial cells decreases abnormal expansion of Ly6G$^+$CD11b$^+$ cells in lal$^{-/-}$ mice.
Figure 27B:
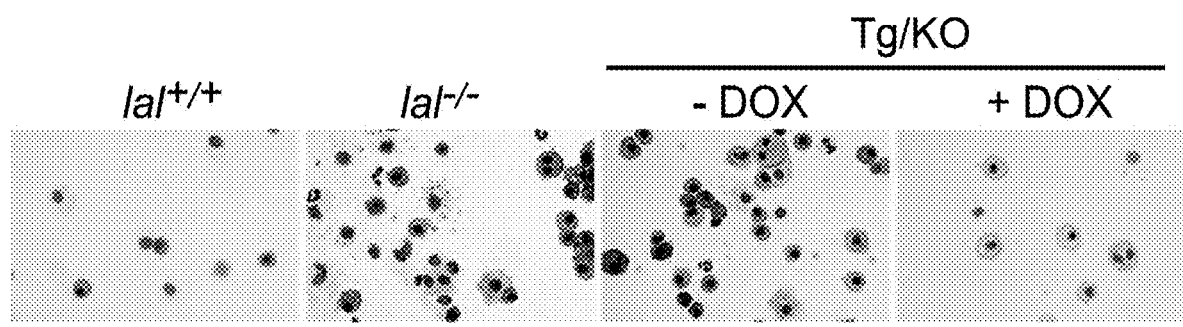
Figure 28A:
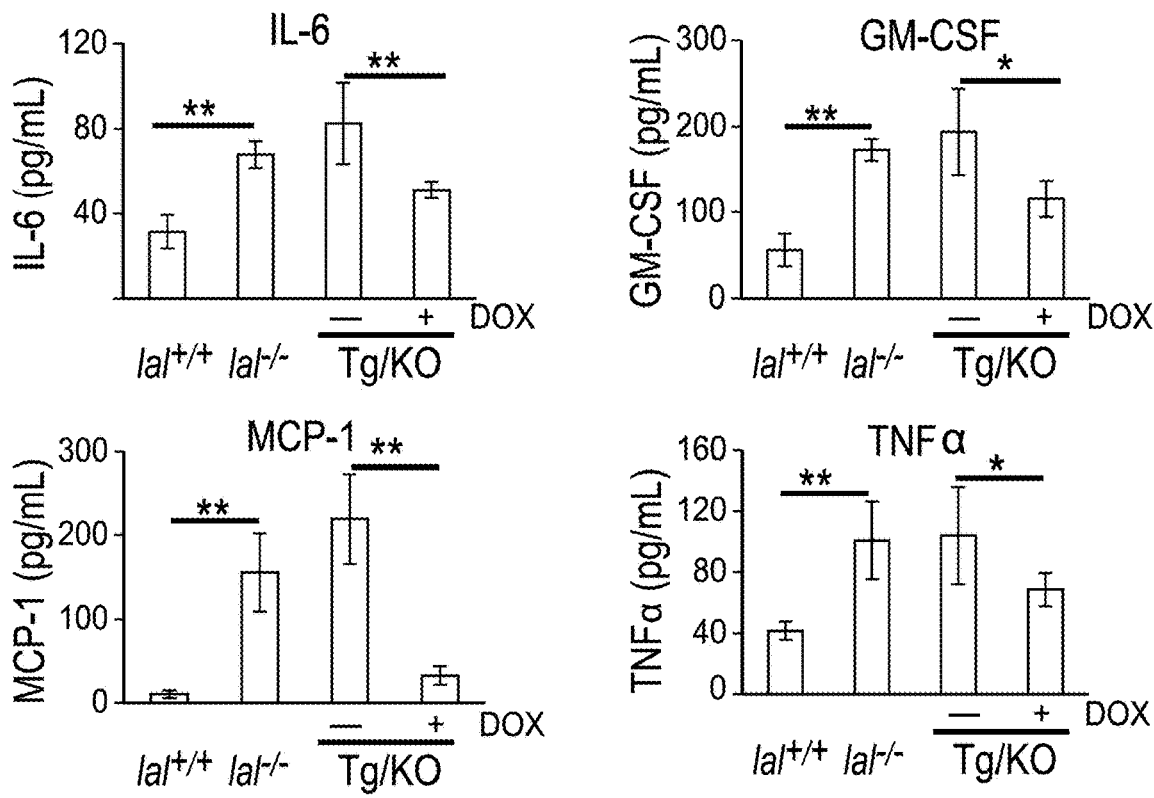
FIGS. 28A & 28B depict hLAL expression in lung epithelial cells reduces secretion of cytokines/chemokines in lal$^{-/-}$ mice. The concentrations of IL-6, GM-CSF, MCP-1 and TNFα in the BALF (FIG. 28A) and plasma (FIG. 28B) of lar$^{+/+}$, lal$^{-/-}$, doxycycline-treated or untreated CCSP-Tg/KO mice were determined by ELISA. Data are expressed as means±s.d.; n=4-5. **P<0.01, *P<0.05.
Figure 28B:
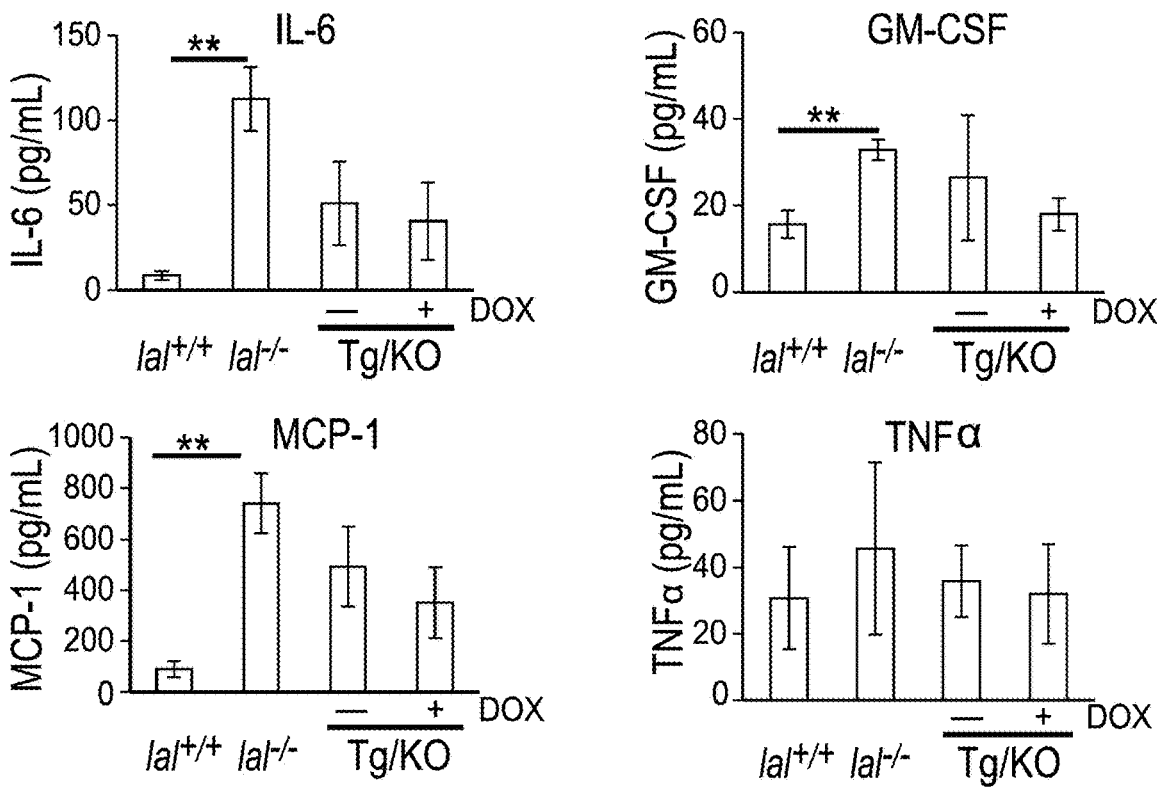
Figure 29:
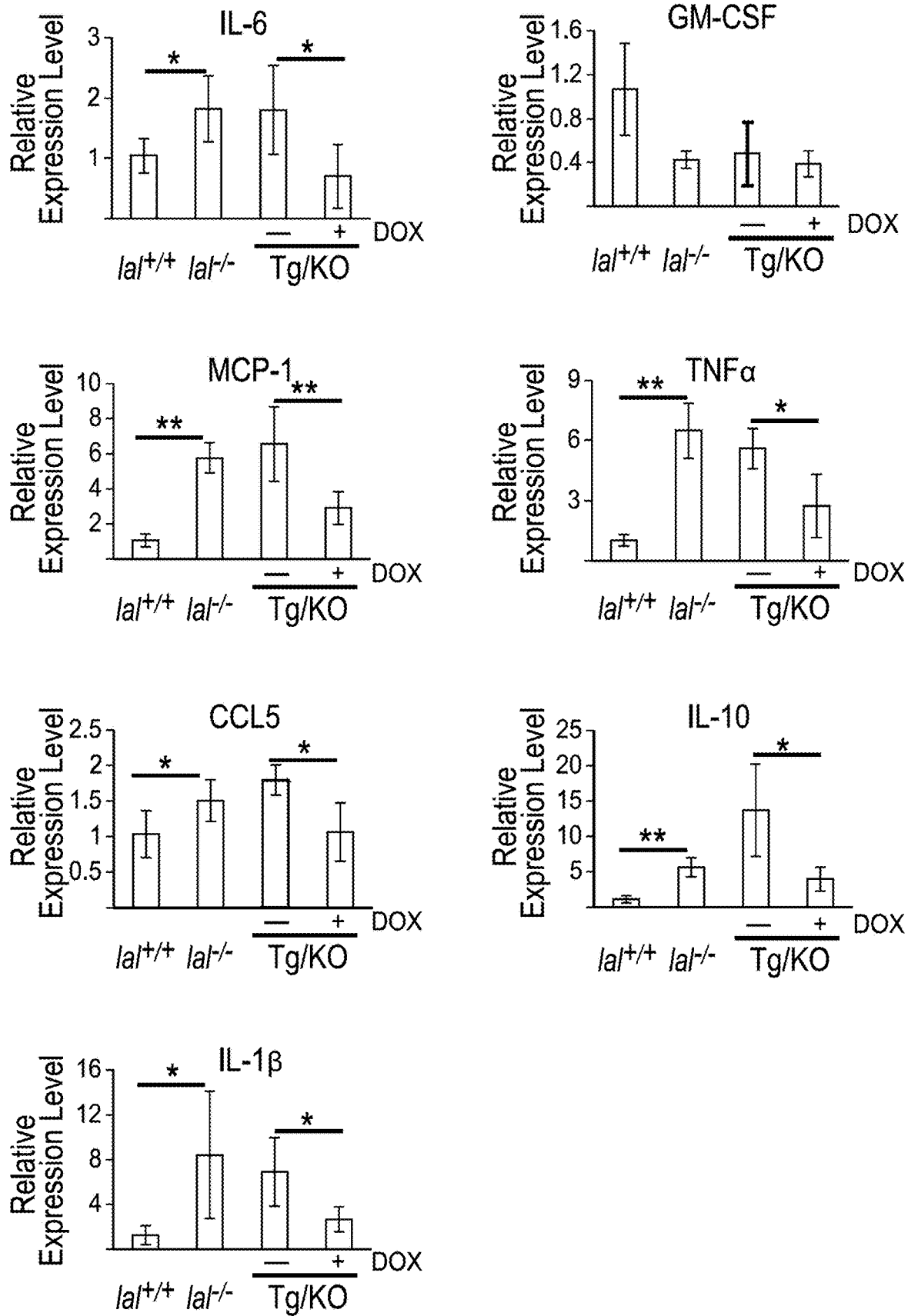
FIG. 29 depicts the effects of hLAL expression in lung epithelial cells on synthesis of cytokines/chemokines in lal$^{-/-}$ mice. Real-time PCR analysis of mRNA expression levels of cytokines/chemokines in the lungs of lal$^{+/+}$, lal$^{-/-}$ doxycycline-treated or untreated CCSP-Tg/KO mice is shown. The relative gene expression was normalized to GAPDH mRNA, and analysis was performed by the $2^{-\Delta\Delta CT}$ method. Data are expressed as means±s.d.; n=4. **P<0.01, *P<0.05.

LAL deficiency has been reported to result in severe infiltration and accumulation of tumor-promoting MDSCs in multiple organs of the mice, including the lung. To test whether lung epithelial expression of hLAL affects the accumulation of Ly6G$^+$CD11b$^+$ MDSCs, whole cells were harvested from the lungs of doxycycline-treated or untreated CCSP-Tg/KO mice for flow cytometry analysis. Age-matched lal$^{+/+}$ and lal$^{-/-}$ mice were used as controls. Cells obtained from the bone marrow, blood and spleen of these mice were also analyzed by flow cytometry analysis. As shown in FIG. 27A, compared with untreated CCSP-Tg/KO mice, the percentage of Ly6G$^+$CD11b$^+$ cells in the lung was significantly decreased in doxycycline-treated CCSP-Tg/KO mice, while there was no reversing effect of Ly6G$^+$CD11b$^+$ cells in the spleen and bone marrow. Ly6G$^+$CD11b$^+$ cell accumulation in the blood was reduced with doxycycline treatment as well (FIG. 27A), which might be explained by hLAL, as a secretory enzyme, was secreted from the lung into circulation. This reduction of Ly6G$^+$CD11b$^+$ cells in the lung was confirmed by Kwik-Diff staining of the BALF, in which myeloid cells were significantly reduced in CCSP-Tg/KO mice with doxycycline-induced hLAL expression (FIG. 27B). Since more than 95% BALF cells are myeloid cells, cells from BALF were harvested to determine their suppressive activity on T cells. As demonstrated in FIG. 3C, BALF cells from untreated CCSP-Tg/KO mice showed inhibition on T cell proliferation, which was similar to BALF cells from lal$^{-/-}$ mice, whereas BALF cells from doxycycline-treated CCSP-Tg/KO mice displayed reduced inhibition on T cell proliferation. The above result indicates that the immunosuppressive functions of lal$^{-/-}$ BALF cells were impaired by lung epithelial expression of LAL.

hLAL expression reduces synthesis and secretion of tumor-promoting cytokines and chemokines Cytokines and chemokines play very important roles in MDSC recruitment and expansion in lung tumorigenesis, and their synthesis and secretion are greatly dependent on the LAL activity. To determine the effects of lung epithelial cell-specific expression of hLAL on the secretion of these cytokines and chemokines, their levels in the BALF were measured by ELISA. As shown in FIG. 28A, the IL-6, GM-CSF, MCP-1, and TNFα concentrations in BALF were significantly decreased in doxycycline-treated CCSP-Tg/KO mice compared with those in untreated CCAP-Tg/KO mice. On the other hand, the levels of these cytokines and chemokines in the plasma were similar in doxycycline-treated CCSP-Tg/KO mice to those in untreated CCSP-Tg/KO mice (FIG. 28B). To confirm this observation, mRNA syntheses of these cytokines and chemokines in the lungs were further investigated. mRNA levels of IL-6, MCP-1, TNFα, CCL5, IL-10 and IL-1β were significantly down-regulated in the lungs of doxycycline-treated CCSP-Tg/KO mice, while the GM-CSF level remained unchanged (FIG. 29).

hLAL Expression Reduces Tumor Cell Proliferation and Migration

Figure 30A:
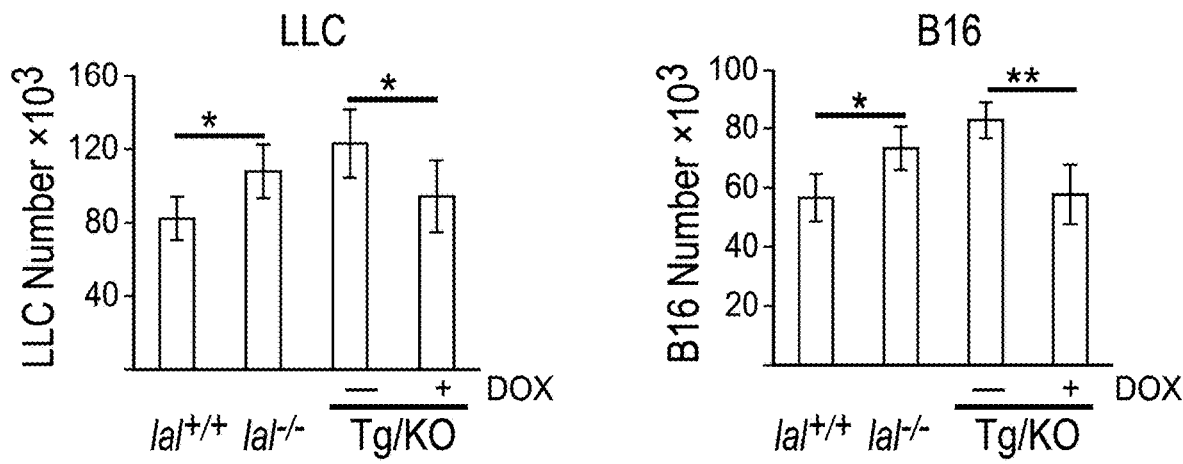
FIGS. 30A & 30B depict the effects of hLAL expression in lung epithelial cells on tumor cell proliferation and migration.

Whether down-regulation of cytokines and chemokines in BALF had an impact on tumor cell in vitro proliferation and migration was further investigated. BALF supernatants from lal$^{+/+}$, lal$^{-/-}$ doxycycline-treated or -untreated CCSP-Tg/KO mice were added into the culture medium of LLC cells for 72 hours. As shown in FIG. 30A, compared with BALF from doxycycline-untreated CCSP-Tg/KO mice, BALF from doxycycline-treated CCSP-Tg/KO mice significantly decreased LLC cell proliferation in vitro. The same observation was also made in B16 melanoma cells (FIG. 30A).

Figure 30B:
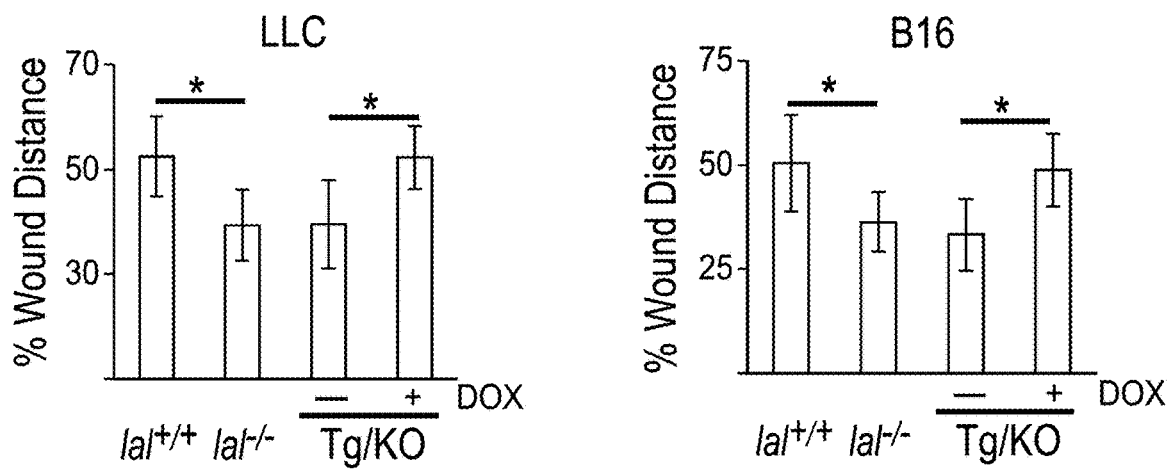
Figure 31A:
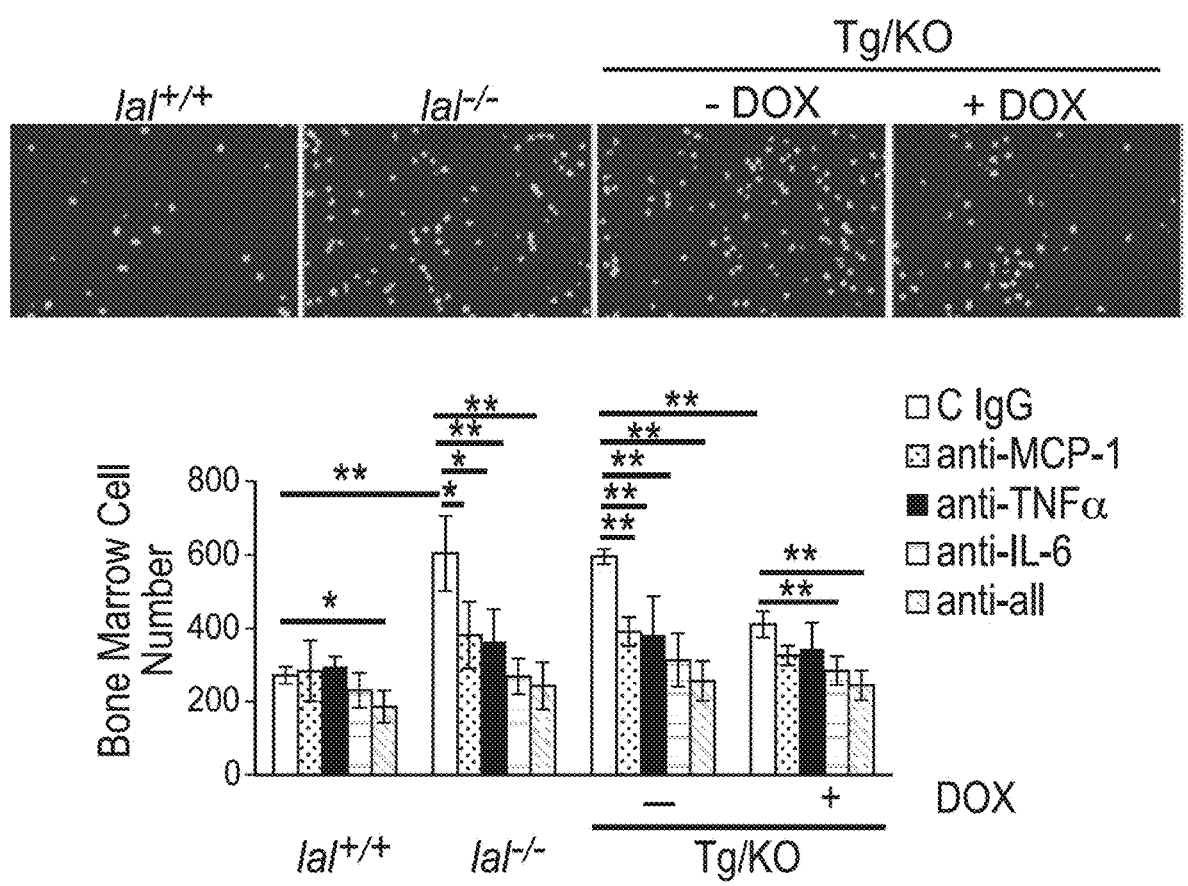
FIGS. 31A-31C depict the effects of hLAL expression in lung epithelial cells on transendothelial migration, endothelial cell proliferation and migration.

Because cell migration contributes to metastasis, in vitro tumor cell migration assay was performed. LLC or B16 melanoma cells were treated with mitomycin C to eliminate the potential effects of cell proliferation in these assays. As shown in FIG. 30B, 15 hours after being cultured with lal$^{-/-}$ BALF, LLC or B16 melanoma cells migrated more efficiently into the area of an artificial wound area compared with those cells cultured with lal$^{+/+}$ BALF. However, delayed migration towards the scratch was observed in LLC or B16 melanoma cells cultured with BALF from doxycycline-treated CCSP-Tg/KO mice. Taken together, these results suggest that lung epithelial hLAL expression reduced tumor cell proliferation and migration in vitro, which may explain why lung epithelial hLAL expression in lal$^{-/-}$ mice reduced B16 melanoma cell metastasis in vivo (FIGS. 26A-26D).

hLAL Expression Reduces Transendothelial Migration, EC Proliferation and Migration Transendothelial migration of leukocytes is a critical step in the inflammatory response. In addition, transendothelial migration plays an important role in cancer metastasis. It was recently reported that LAL deficiency increased MDSC and T cell transendothelial migration. The cytokines and chemokines in the BALF might induce the transendothelial migration of leukocytes. To mimic the in vivo condition, BALF was added into the culture medium of the lower chamber of transwell plates with bone marrow cells seeding on top of the primary lung EC monolayer in the upper chamber. Four hours later, the number of bone marrow cells that had migrated to the lower chamber was counted. As shown in FIG. 31A, there were significantly less bone marrow cells migrating to the lower chamber in which BALF from doxycycline-treated CCSP-Tg/KO mice was added than those migrating to the chamber added with untreated CCSP-Tg/KO BALF. To examine whether the reduced bone marrow cell transmigration was due to the decreased secretion of cytokines into BALF, the transwell study was further performed with BALF pre-treated with anti-IL-6, anti-MCP-1, or anti-TNFα neutralizing antibodies. Results showed that bone marrow cell transmigration was significantly inhibited when doxycycline-untreated CCSP-Tg/KO BALF was treated with anti-IL-6, MCP-1 or TNFα antibodies (FIG. 31A). Combination of these three neutralizing antibodies further blocked the transendothelial migration by doxycycline-untreated CCSP-Tg/KO BALF (FIG. 31A). Therefore, lung epithelial LAL expression-reduced cytokines (especially IL-6) secretion into the BALF is, at least in part, responsible for the decreased accumulation of myeloid cells in the BALF.

The effects of CCSP-Tg/KO BALF on lal$^{+/+}$ EC proliferation and migration were further investigated. When treated with lal$^{-/-}$ BALF, lal$^{+/+}$ ECs showed increased proliferation compared with those treated with lal$^{+/+}$ BALF. However, the increased proliferation of lal$^{+/+}$ ECs was reversed by doxycycline-treated CCSP-Tg/KO BALF (FIG.

31B). Furthermore, the in vitro wound healing assay showed increased migration (reduced wound distance) of lal$^{+/+}$ ECs treated with lal$^{-/-}$ BALF at 15 hours after creating the scratch, whereas the increased EC migration was reduced when doxycycline-treated CCSP-Tg/KO BALF was added (FIG. 31C). Taken together, lung epithelial LAL expression in lal$^{-/-}$ mice decreased the stimulation of BALF on lung EC proliferation and migration.

Discussion

In summary, the Examples herein demonstrated that lipid metabolism controlled by LAL is critical for AT II epithelial cell homeostasis and alveolar genesis. Blockage of the LAL metabolic pathway in AT II epithelial cells results in exuberant inflammation, hyperplasia and emphysema in the lung, which are caused by aberrant inflammatory gene expression in an age-dependent manner. To further identify the roles of LAL in AT II epithelial cells in tumorigenicity and metastasis, hLAL was specifically re-introduced into the lal$^{-/-}$ mice and its expression was driven by AT II epithelial cell-specific promoter. AT II epithelial cell-specific hLAL expression in CCSP-Tg/KO mice was verified at the protein expression level (FIG. 1A). Histological analysis revealed that the hLAL expression in lung AT II epithelial cells reversed alveolar destruction in doxycycline-treated CCSP-Tg/KO mice (FIGS. 1B & 1C). Therefore, LAL in AT II epithelial cells is essential for maintaining normal alveolar structure and functions in the lung.

Figure 27C:
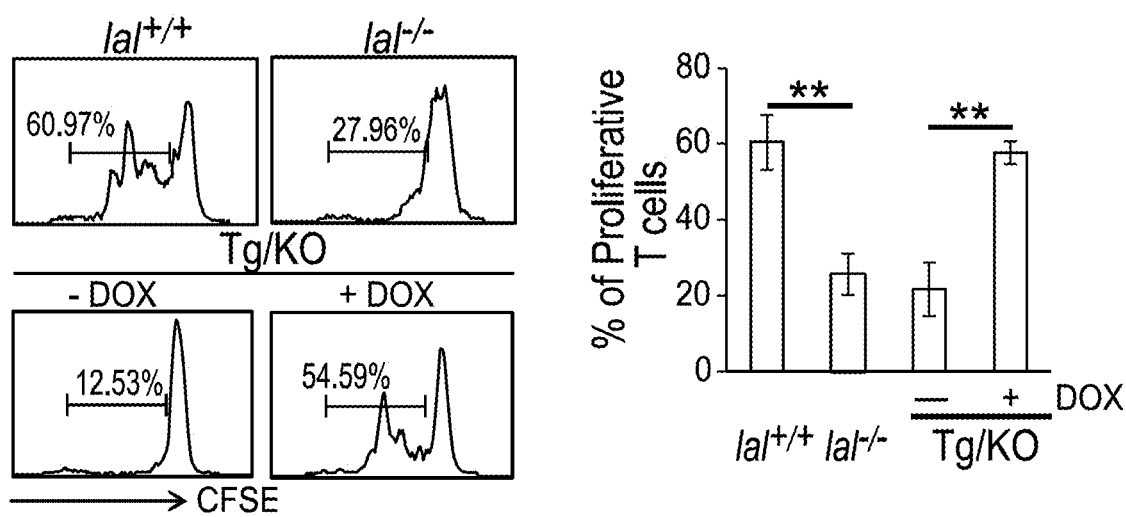

LAL deficiency has been found to facilitate melanoma growth and metastasis in the lung. The functional role of AT II epithelial cells in this pathogenic process is not clear. In this Example, AT II epithelial cell-specific expression of hLAL in CCSP-Tg/KO mice reduced B16 melanoma cell metastasis in the lung (FIGS. 26A-26D), accompanied by a decrease in the number of tumor-promoting MDSCs (FIG. 27A). The reduced MDSCs level was also observed in the peripheral blood of doxycycline-treated CCSP-Tg/KO mice (FIG. 27B). MDSCs that possess immunosuppression on T cells are a critical component in the tumor microenvironment. Indeed, BALF cells, mainly MDSCs, from AT II epithelial cell-specific expression of hLAL reduced T cell suppression (FIG. 27C). Consistent with this observation, it was previously shown that MDSCs from lal$^{-/-}$ mice directly stimulate proliferation of B16 melanoma cells in vitro, as well as growth and metastasis in vivo. Myeloid-specific expression of hLAL in lal$^{-/-}$ mice (the c-fms-Tg/KO mouse model) reduced the systemic MDSCs influx and inflammation-associated pathogenesis in multiple organs, including tumor growth and metastasis. This is mainly by correction of MDSC expansion starting from the early developing stage of granular myeloid progenitor cells in the bone marrow. Myeloid-specific expression of hLAL in lal$^{-/-}$ mice reduced MDSCs' ability to stimulate cancer cell proliferation and overcome immune rejection of cancer metastasis, which switches metabolic reprogramming of MDSCs.

In a separate LAP-Tg/KO mouse model, in which hepatocyte-specific expression of hLAL was driven by the hepatocyte cell-specific LAP promoter, LAL expression reduced MDSC expansion, increased T cell population, reduced tumor metastasis through down-regulation of inflammatory cytokines and chemokines in the liver (Du et al., Am J Pathol. 2015; 185: 2379-89). Similarly, the concentrations of these cytokines (i.e., IL-6, TNFα, GM-CSF and MCP-1) were increased in the BALF of the lal$^{-/-}$ lung, which were reduced in the BALF of the doxycycline-treated CCSP-Tg/KO mice (FIG. 28A). This observation was confirmed by mRNA expression levels (FIG. 29). Importantly, BALF from lal$^{-/-}$ mice facilitated LLC and B16 cell proliferation and migration in vitro, which was corrected by AT II epithelial cell-specific expression of hLAL in CCSP-Tg/KO mice (FIGS. 30A & 30B). Therefore, LAL production in various cells (e.g. AT II epithelial cells, hepatocytes, myeloid cells) is a safe guard to block cancer cell progression and metastasis via controlling MDSCs and tumor-promoting cytokines and chemokines in various organs.

Figure 31B:
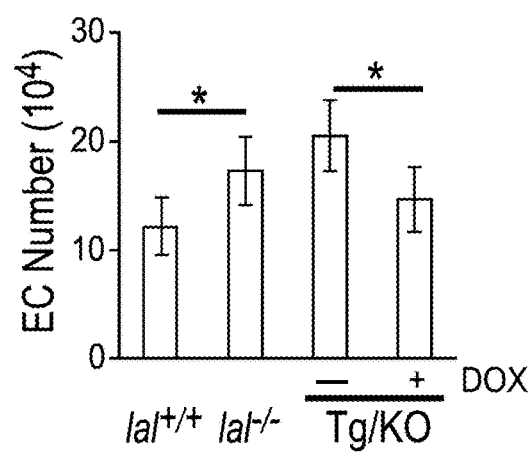
Figure 31C:
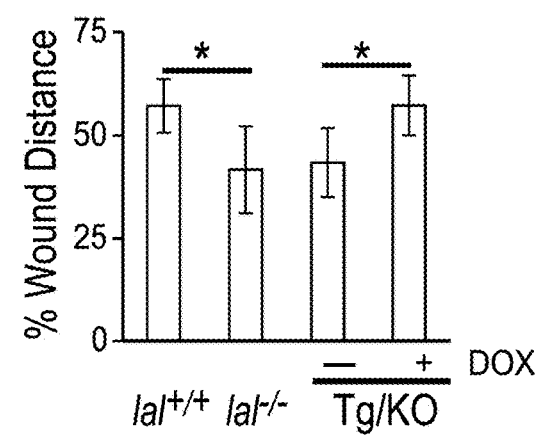

In the present Example, lal$^{-/-}$ BALF significantly increased lung EC proliferation, migration and permeability of bone marrow cells, all of which were reversed by BALF from the doxycycline-treated CCSP-Tg/KO mice (FIGS. 31A-31C). Addition of neutralizing antibodies against IL-6, TNFα, and MCP-1 into the untreated CCSP-Tg/KO BALF inhibited transmigration of bone marrow cells (FIG. 31A), further supporting that proinflammatory cytokines in BALF play pleiotropic roles in mediating LAL functions.

Taken together, AT II epithelial cells play a central role in the lung to control MDSC homeostasis, EC permeability and tumorigenesis. The metabolic pathway controlled by LAL in AT II epithelial cells tightly regulates synthesis and secretion of proinflammatory cytokines and chemokines, and immune cells that actively participate in the regional pulmonary microenvironment to form niches for tumor growth and metastasis in the lung. Therefore, LAL can be used as an effective drug in immuno-therapy to treat various inflammation-induced cancer forms.

Example 5

In this Example, the role of LAL through modulation of the mTOR pathway in regulating MDSCs' ability to directly stimulate cancer cell proliferation and overcome immune rejection of cancer metastasis was analyzed.

Materials & Methods

Animals and Cell Lines lal$^{+/+}$ and lal$^{-/-}$ mice of the FVBN background were bred in house. c-fms-rtTA/(TetO)$_7$-CMV-hLAL; lal$^{-/-}$ (Tg/KO) triple mice of the FVBN background is a previously generated triple transgenic mouse model with myeloid-specific doxycycline-inducible expression of wild-type human LAL (hLAL) in lal$^{-/-}$ mice under the control of the c-fms promoter. All scientific protocols involving the use of animals have been approved by the Institutional Animal Care and Use Committee of Indiana University School of Medicine and followed guidelines established by the Panel on Euthanasia of the American Veterinary Medical Association. Animals were housed under Institutional Animal Care and Use Committee-approved conditions in a secured animal facility at the Indiana University School of Medicine.

The murine B16 melanoma cell line, LLC cell line and transgenic mouse prostate cancer (Tramp-C2) cell line (purchased from ATCC, Manassas, Va., USA) were cultured in Dulbecco's modified Eagle's medium supplemented with 10% fetal bovine serum (Gibco, Grand Island, N.Y., USA).

Isolation of Bone Marrow-Derived MDSCs

Briefly, bone marrow cells were isolated from the femurs and tibias of mice. Cells were first incubated with biotin-conjugated anti-Ly6G antibody at 4° C. for 15 minutes. After washing with phosphate-buffered saline (PBS), cells were then incubated with anti-biotin microbeads at 4° C. for another 15 minutes. Subsequently, cells were subjected to magnetic bead sorting according to the manufacturer's instructions (Miltenyi Biotec, Auburn, Calif., USA).

In Vitro Co-Culture of MDSCs and B16 Melanoma Cells

A pilot study was performed to determine the best ratio between MDSCs and B16 melanoma cells. B16 melanoma cells were harvested, resuspended and adjusted to density at 5×10$^4$ cells/ml. Isolated MDSCs were used immediately, and the cell density was adjusted to 5×10$^6$ cells/ml. One hundred microliter of MDSCs and 100 μl of B16 melanoma cells were mixed and seeded into a well of 96-well plates in Dulbecco's modified Eagle's medium supplemented with 10% fetal bovine serum. Seventy-two hours later, unattached MDSCs were removed by washing with PBS, and the number of attached B16 melanoma cells was counted. Morphologically, MDSCs are much smaller than B16 melanoma cells for exclusion.

In vivo MATRIGEL® plug assay with MDSCs and B16 melanoma cells

This assay was performed according to an established method with minor modifications. MDSCs and B16 melanoma cells were collected separately.

A pilot study was performed to determine the best ratio between MDSCs and B16 melanoma cells. After washing with PBS, 1×10$^6$ MDSCs and 1×10$^5$ B16 melanoma cells were mixed, centrifuged and resuspended in 40 μl PBS and mixed with 500 μl MATRIGEL® Basement Membrane Matrix (BD Biosciences, San Jose, Calif., USA) containing 15 units of heparin (Sigma-Aldrich, St Louis, Mo., USA). The cellMATRIGEL® mixture was then injected subcutaneously into the abdomen of 3-month old lal$^{+/+}$ mice. After 10 days, the mice were killed, and plugs were harvested from underneath the skin.

Mouse Metastasis Models

Four-month-old lal$^{+/+}$ or lal$^{-/-}$ mice were inoculated with 1×10$^5$ B16 melanoma cells subcutaneously into the flank region, and tumor size (length×width$^2$×π/6) was monitored every week for 3 weeks. For intravenous injection of B16 melanoma cells, 5×10$^5$ B16 melanoma cells in 200 μl PBS were injected into 4-month-old lal$^{+/+}$ or lal$^{-/-}$ mice via tail vein. A pilot study was performed to determine the best ratio between MDSCs and B16 melanoma cells. For co-injection of MDSCs and B16 melanoma cells via tail vein, 2×10$^6$ MDSCs and 5×10$^5$ B16 melanoma cells were mixed and incubated at 37° C. and 5% CO$_2$ for 30 minutes. After the incubation, cells were centrifuged, resuspended and injected intravenously into 4-month-old recipient lal$^{+/+}$ mice. Two weeks after the injection, the mice were killed, and the lungs were harvested for examination of metastasis.

Histology and IHC Staining

The harvested plugs and lungs were fixed with 4% paraformaldehyde in PBS at 4° C. for overnight. After fixation and embedding in paraffin, tissue sections were cut to 5-μm thick sections. H&E staining and IHC staining were performed by the Histological Core Facility, Department of Pathology and Laboratory Medicine, Indiana University, Ind., USA. The following antibodies were tested: Ki67, CD31, CD3 and F4/80. Tumor area quantitative analyses were performed by Metamorph 6.02 (Molecular Devices, Sunnyvale, Calif., USA) on images taken by Olympus microscopy image system (Olympus, Tokyo, Japan).

Western Blotting Analysis

Briefly, MDSCs were lysed in Cell Lytic MT lysis buffer (Sigma, St Louis, Mo., USA) with Protease Inhibitor Cocktail (Invitrogen, Grand Island, N.Y., USA) and phosphatase inhibitor 2 and 3 (Sigma) for 15 minutes on a shaker. After centrifugation for 20 minutes at 12000 g (4° C.), the supernatants were saved, and protein concentrations of the samples were determined using the Pierce BCA Protein Assay Kit (Thermo Scientific, Waltham, Mass., USA). Equal amounts of protein (30 μg) were loaded onto sodium dodecyl sulfate-polyacrylamide gels and blotted onto polyvinylidene difluoride membranes (Bio-Rad, Hercules, Calif., USA). Western blotting analysis was performed using antibodies against mTOR, phospho-mTOR, p70S6K, phospho-p70S6K, S6 and phospho-S6 (rabbit monoclonal antibodies, 1:1000, Cell Signaling, Beverly, Mass., USA). Antibody against β-actin (rabbit monoclonal anti-β-actin, 1:2000, Cell Signaling) was used as a loading control. For detection, the membrane was incubated with anti-rabbit immunoglobulin G secondary antibodies conjugated with horseradish peroxidase (1:2000, Cell Signaling). Bands were visualized using the SuperSignal West Pico Chemiluminescent substrate (ThermoScientific Pierce, Rockford, Ill., USA).

SiRNA Transfection

Before transfection, MDSCs were seeded into 96-well plates at a density of 1×10$^6$ cells/well. For siRNA-mediated gene knockdown, 50 nmol/l of mTOR siRNA SMARTpool (containing a mixture of several siRNAs targeting mTOR), Raptor siRNA, Rictor siRNA or control siRNA (Dharmacon, Chicago, Ill., USA) was transfected into MDSCs with DharmaFECT Transfection Reagent I (Dharmacon) according to the manufacturer's protocol. After 24 hours of transfection, cells were harvested for further analysis.

Real-Time Reverse Transcriptase-PCR

Total RNAs from Ly6G$^+$ cells were purified using the Qiagen total RNA purification kit (Qiagen, Valencia, Calif., USA) and subjected to quantitative reverse transcriptase-PCR. Analysis was performed by the $2^{\Delta\Delta CT}$ method. Primers for mIL-6, mIL-1β, mTNF-α and GAPDH (glyceraldehyde 3-phosphate dehydrogenase) for real-time PCR were used.

Transwell Assay

For transwell experiment, 0.4-μm pore size, 6.5-mm diameter transwells were used to separate Ly6G$^+$ cells and B16 melanoma cells (Corning, Corning, N.Y., USA) to observe the effect of Ly6G$^+$ cell-secreted cytokines on melanoma cell proliferation. Freshly isolated 2×10$^6$ Ly6G$^+$ cells in 200 μl media were seeded into the upper chamber of transwells, while 2×10$^4$ melanoma cells in 600 μl media were placed in the lower chamber. For the neutralization study, Ly6G$^+$ cells were treated with 10 μg/ml neutralizing antibody against IL-6, IL-1β, TNF-α or control immunoglobulin G. After 72-hour culture, the transwells were removed, and the number of B16 melanoma cells in the lower chamber was counted.

Statistics

Data were expressed as mean±s.d. Differences between two treatment groups were compared by Student's t-test. When more than two groups were compared, one-way analysis of variance with post-hoc Newman-Keul's multiple comparison test was used. Results were considered statistically significant when P<0.05. All analyses were performed with GraphPad Prism 5.0 (GraphPad, San Diego, Calif., USA).

Results

LAL Deficiency Stimulated B16 Melanoma Cell Growth and Metastasis

Figure 32A:
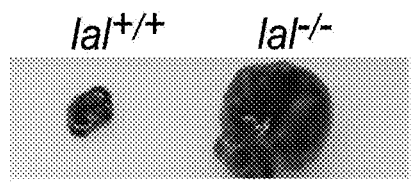
FIGS. 32A-32F depict B16 melanoma cell growth and metastasis in lal mice.
Figure 32C:
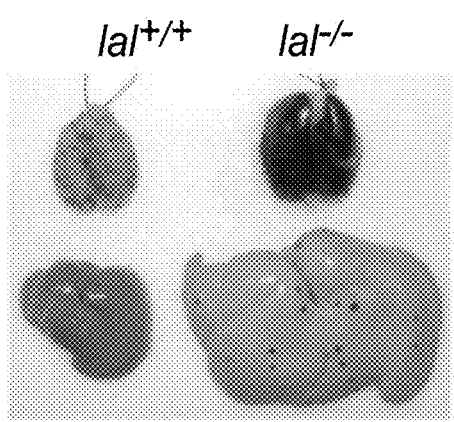
Figure 32D:
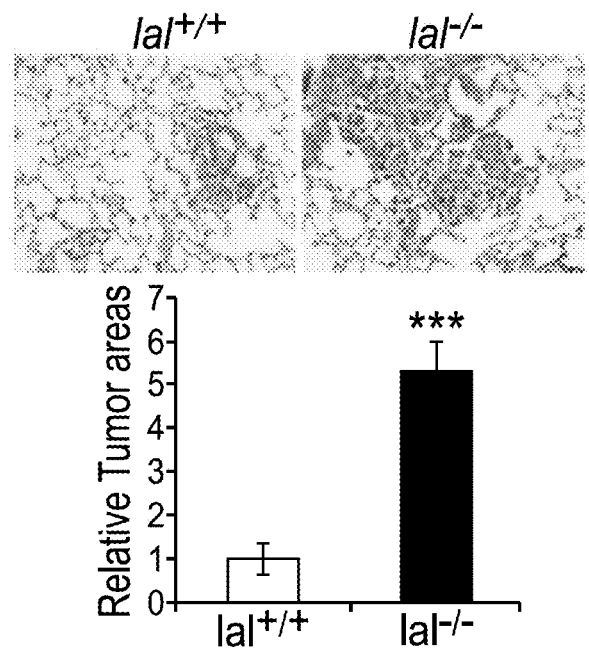
Figure 32B:
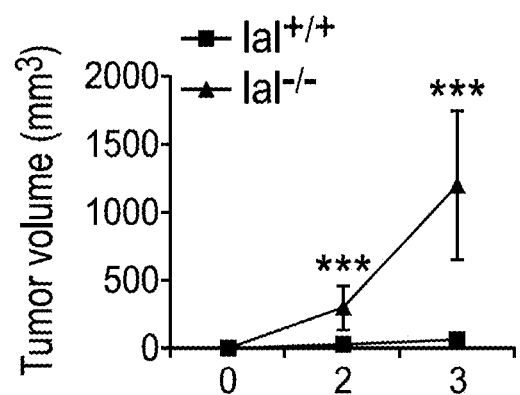
Figure 32E:
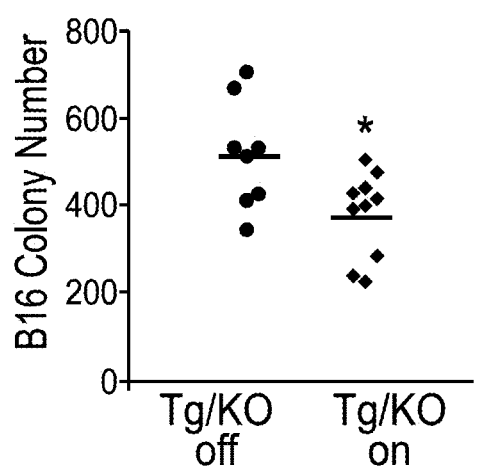
Figure 32F:
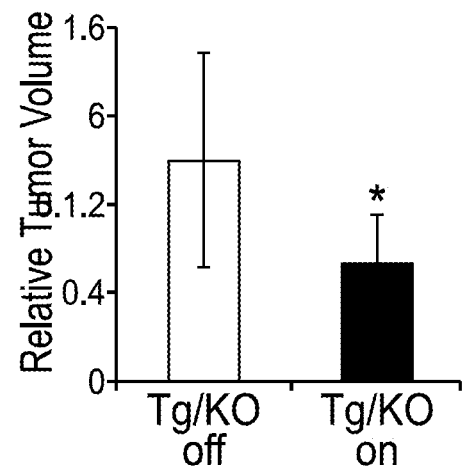

To see whether LAL deficiency-induced inflammation influences tumor progression and metastasis, the B16 melanoma cell model was used for subcutaneous and intravenous injection in allogeneic wild-type (lal$^{+/+}$) and lal$^{-/-}$ FVBN mouse models. To examine growth potential in vivo, B16 melanoma cells were injected subcutaneously into mice. Large subcutaneous tumors were developed in 10 of the 10 lal$^{-/-}$ mice, while only 1 of the 10 lal$^{+/+}$ mice developed tumors. In addition, the tumors from lal$^{-/-}$ mice (tumor volume=1189.8±554.0 mm$^3$) were significantly larger when compared with those developed in lal$^{+/+}$ mice (tumor volume=48.0±31.2 mm$^3$, P<0.0001) at 3 weeks post-tumor cell injection (FIGS. 32A & 32B). Next, B16 melanoma cells were injected into the tail veins of mice to detect metastatic potential. Two weeks after injection, more B16 melanoma colonies were observed in lal$^{-/-}$ mice at the distal lung and liver organs (FIG. 32C). Hematoxylin and eosin (H&E) staining revealed more neoplastic melanoma cells in the lungs of lal$^{-/-}$ mice than in those of lal$^{+/+}$ mice (FIG. 32D). Myeloid cell expansion is a major manifestation in lal$^{-/-}$ mice. To evaluate the effects of LAL in myeloid lineage cells on B16 melanoma cell metastasis, a doxycycline-inducible hLAL myeloid-specific expressing Tg/KO (transgenic/knockout) triple mouse model was used.3,7 Statistical analysis displayed that 2 weeks after intravenous injection of B16 melanoma cells, doxycycline-treated Tg/KO triple mice showed reduced number of melanoma colonies in the lungs compared with untreated mice (FIG. 32E), suggesting that hLAL expression in lal$^{-/-}$ myeloid cells partially restored immune rejection of B16 melanoma cells in the allogeneic mice model. In tumor growth assessment, B16 melanoma cells were subcutaneously injected into the flank region of Tg/KO triple mice. FIG. 32F showed that the volume of tumors from doxycycline-treated Tg/KO triple mice was decreased by 50% compared with those developed in untreated mice at 2 weeks post-injection. Taken together, LAL in myeloid lineage cells has a critical role in rendering immune rejection of cancer cells in the allogeneic mouse model.

LAL Deficiency in Ly6G$^+$ Cells Stimulated B16 Melanoma Cell Proliferation

Figure 33A:
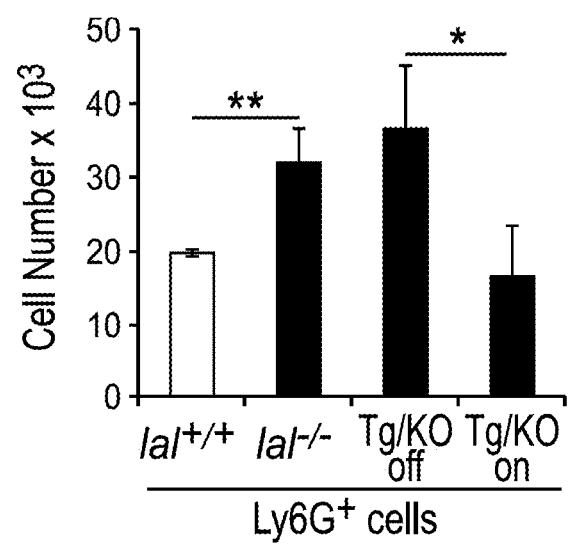
FIGS. 33A-33D depict that lal$^{-/-}$ Ly6G$^+$ cells directly stimulated B16 melanoma cell proliferation and growth.
Figure 33B:
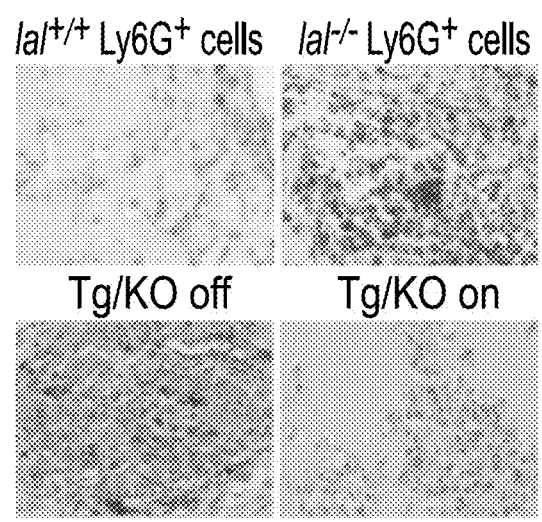

In lal$^{-/-}$ mice, systemic Ly6G$^+$CD11b$^+$ MDSCs' elevation has been observed in multiple organs. To evaluate the influence of lal$^{-/-}$ Ly6G$^+$CD11b$^+$ MDSCs on proliferation of B16 melanoma cells, freshly isolated bone marrow-derived lal$^{+/+}$ or lal$^{-/-}$ Ly6G$^+$ cells were co-cultured with B16 melanoma cells for 72 hours. In lal$^{-/-}$ mice, as almost all Ly6G$^+$ cells are positive for CD11b, Ly6G antibody was used for purification of Ly6G$^+$CD11b$^+$ cells. As shown in FIG. 33A, the number of B16 melanoma cells was significantly increased after co-culture with lal$^{-/-}$ Ly6G$^+$ cells, suggesting that lal$^{-/-}$ Ly6G$^+$ cells exert a directly stimulatory effect on proliferation of B16 melanoma cells in vitro. When Ly6G$^+$ cells from doxycycline-treated Tg/KO triple mice were co-cultured with B16 melanoma cells in vitro, reduced proliferation of B16 melanoma cells was observed, compared with those of untreated Tg/KO triple mice. As in vitro co-culture conditions are not representative of the tumor microenvironment, in vivo co-culture experiment was performed to study the effect of lal$^{-/-}$ Ly6G$^+$ cells on B16 melanoma cell growth. MATRIGEL® mixed with lal$^{+/+}$ or lal$^{-/-}$ Ly6G$^+$ cells and B16 melanoma cells were subcutaneously injected into allogeneic recipient lal$^{+/+}$ mice. Ten days later, the plugs mixed with lal$^{-/-}$ Ly6G$^+$ cells and B16 melanoma cells showed larger size than those mixed with lal$^{+/+}$ Ly6G$^+$ cells and B16 melanoma cells. Consistently, H&E staining revealed robust melanoma cell proliferation in the plugs containing lal$^{-/-}$Ly6G$^+$ cells, whereas Ly6G$^+$ cells from doxycycline-treated Tg/KO triple mice decreased B16 melanoma cell growth (FIG. 33B). Therefore, lal$^{-/-}$ MDSCs possess a direct stimulatory activity on cancer cell proliferation.

Figure 33C:
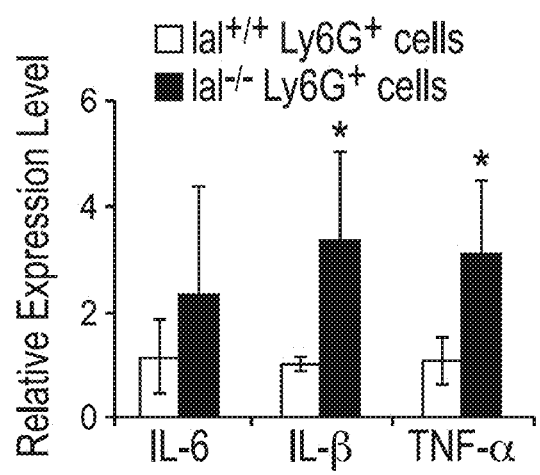
Figure 33D:
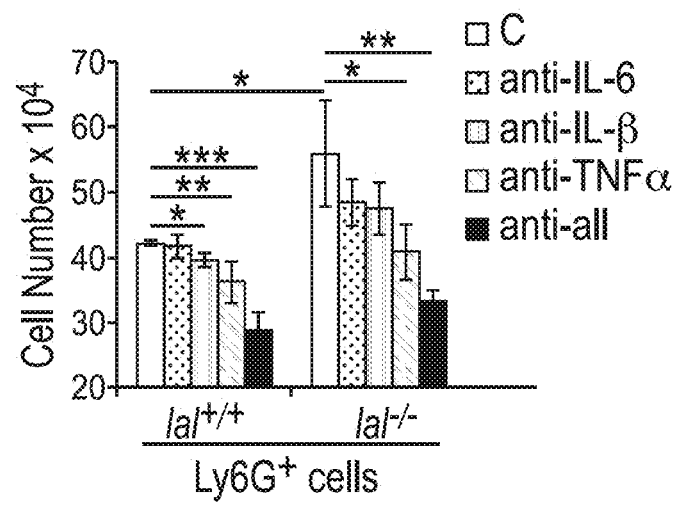

Activated MDSCs secrete cytokines that contribute to tumor cell invasion, proliferation and survival. In lal$^{-/-}$ Ly6G$^+$ cells, mRNA levels of interleukin (IL)-1β and tumor necrosis factor (TNF)-α were upregulated by a real-time PCR analysis, while IL-6 showed no statistical difference (FIG. 33C). To examine whether these cytokines secreted by lal$^{-/-}$ Ly6G$^+$ cells facilitate melanoma cell proliferation, transwell study was performed with Ly6G$^+$ cells seeding in the upper chamber and melanoma cells in the lower chamber. After 72-hour co-culture, the number of B16 melanoma cells that were co-cultured with lal$^{-/-}$ Ly6G$^+$ cells was significantly increased (FIG. 33D). When Ly6G$^+$ cells were treated with anti-IL-6, IL-1β or TNF-α antibodies to neutralize cytokines, the stimulatory effects on melanoma cell proliferation were significantly inhibited in the anti-TNF-α antibody-treated group. Although anti-IL-6 and anti-IL-1β antibodies showed no statistically significant effect, combination of all three cytokine antibodies further blocked the stimulatory effect of melanoma cell proliferation by lal$^{-/-}$ Ly6G$^+$ cells (FIG. 33D). Therefore, cytokines (especially TNF-α) secreted by lal$^{-/-}$ Ly6G$^+$ cells are, at least in part, responsible for mediating stimulatory effects on cancer cells.

LAL deficiency in Ly6G$^+$ cells facilitated B16 melanoma cell metastasis

Figure 34A:
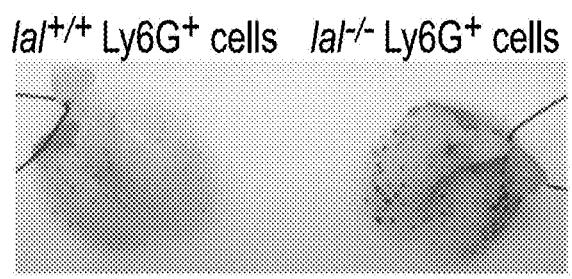
FIGS. 34A-34C show that lal$^{-/-}$ Ly6G$^+$ cells facilitated B16 melanoma cell metastasis.
Figure 34C:
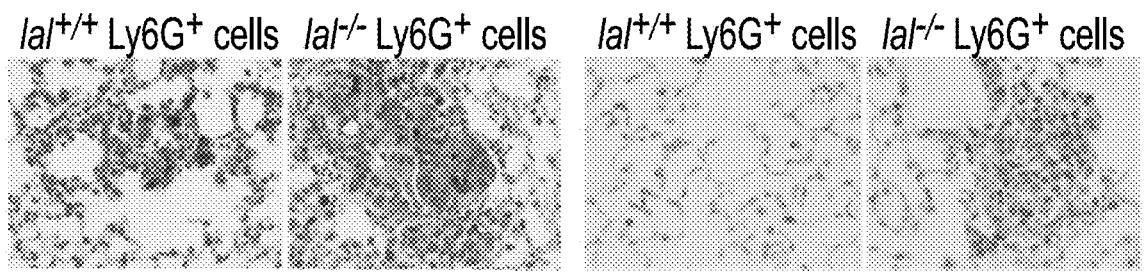
Figure 34C:
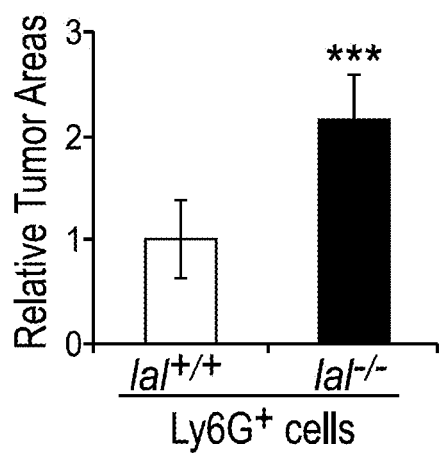
Figure 34B:
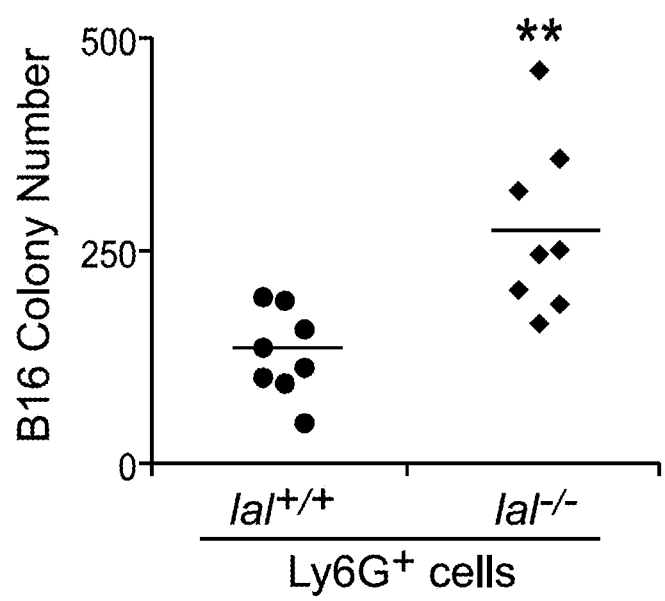
Figure 36A:
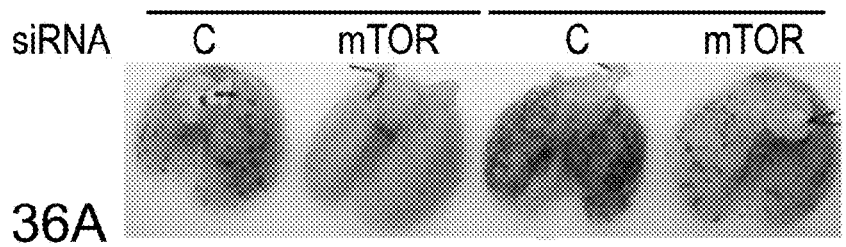
FIGS. 36A-36C show that mTOR inhibition impaired the ability of lal$^{-/-}$ Ly6G$^+$ cells to facilitate B16 melanoma cell metastasis.
Figure 36B:
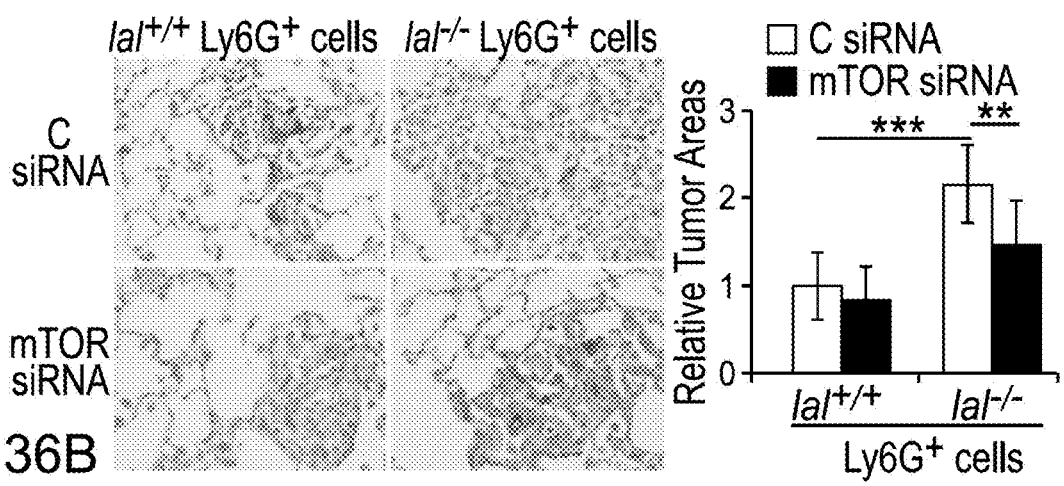
Figure 36C:
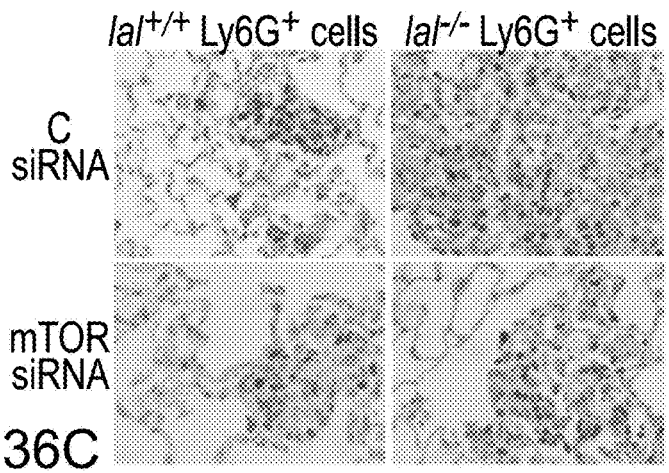

As lal$^{-/-}$ Ly6G$^+$ cells possess both immune suppressive function on T cells and stimulatory function on cancer cells, it is intriguing to investigate whether lal$^{-/-}$ Ly6G$^+$ cells facilitate B16 melanoma cell metastasis. Two weeks after intravenous co-injection, melanoma metastasized more aggressively in allogeneic recipient lal$^{+/+}$ mice with co-injection of lal$^{-/-}$ Ly6G$^+$ cells and B16 melanoma cells than those with lal$^{+/+}$ Ly6G$^+$ cells and B16 melanoma cells (FIGS. 34A & 34B). H&E staining and immunohistochemical (IHC) staining of the lung sections displayed more neoplastic melanoma cells and Ki67-positive proliferative cells in the lungs of lal$^{-/-}$ Ly6G$^+$ cell-injected recipient mice than those from lal$^{+/+}$ Ly6G$^+$ cell-injected recipient mice (FIG. 34C).

mTOR inhibition impaired the ability of lal$^{-/-}$ Ly6G$^+$ cells to enhance B16 melanoma cell proliferation and growth It was recently reported that genes involved in the mTOR signaling pathway were altered in bone marrow-derived lal$^{-/-}$ Ly6G$^+$ cells by Affymetrix GeneChip microarray. This was confirmed by Western blotting assay, in which mTOR downstream effectors p70S6K and S6 were highly phosphorylated in lal$^{-/-}$ Ly6G$^+$ cells (FIG. 35A), indicating over-activation of the mTOR pathway. To see whether over-activation of the mTOR pathway contributes to stimulation of lal$^{-/-}$ Ly6G$^+$ cells on cancer cell proliferation, Ly6G$^+$ cells were transfected with mTOR small interfering RNAs (siRNAs). The knockdown efficiency of several mTOR siRNAs in myeloid cells was confirmed by the mTOR protein level and its downstream effectors in Western blotting assay (data not shown). For the in vitro co-culture study, both lal$^{+/+}$ and lal$^{-/-}$ Ly6G$^+$ cells with mTOR knockdown significantly reduced their abilities to stimulate proliferation of B16 melanoma cells (FIG. 35B) Similar results were observed in in vivo co-culture MATRIGEL® assay, which showed less neoplastic cells in the plugs with mTOR siRNA inhibition in lal$^{-/-}$ Ly6G$^+$ cells (FIG. 35C). This was supported by IHC staining, in which less Ki67-positive cells were monitored after mTOR knockdown in Ly6G$^+$ cells (FIG. 35D). In the tumor areas, positive cells for the endothelial marker CD31, the monocyte/macrophage marker F4/80 or T-cell marker CD3 were all decreased following mTOR knockdown in Ly6G$^+$ cells, especially knockdown in lal$^{-/-}$ Ly6G$^+$ cells, indicating that both tumor-associated angiogenesis and inflammatory cell infiltration were impaired (FIG. 35D). Taken together, these results suggest that over-activation of the mTOR pathway has a very important role in lal$^{-/-}$ Ly6G$^+$ cells to stimulate B16 melanoma cell proliferation and growth.

mTOR inhibition impaired the ability of lal$^{-/-}$ Ly6G$^+$ cells to facilitate B16 melanoma cell metastasis The role of mTOR pathway in lal$^{-/-}$ Ly6G$^+$ cell-facilitated B16 melanoma cell metastasis was further examined lal$^{+/+}$ or lal$^{-/-}$ Ly6G$^+$ cells after mTOR siRNA transfection were co-injected with B16 melanoma cells into allogeneic recipient lal$^{+/+}$ mice intravenously. Two weeks later, mice injected with mTOR siRNA-transfected lal Ly6G$^+$ cells developed less melanoma metastatic lesions in their lungs (FIG. 36A). Sections of the lungs showed less neoplastic cells by H&E staining (FIG. 36B) and less Ki67-positive cells by IHC staining (FIG. 36C). These observations suggest that over-activation of the mTOR signaling pathway in lal/Ly6G$^+$ cells facilitates B16 melanoma cell metastasis.

Figure 37A:
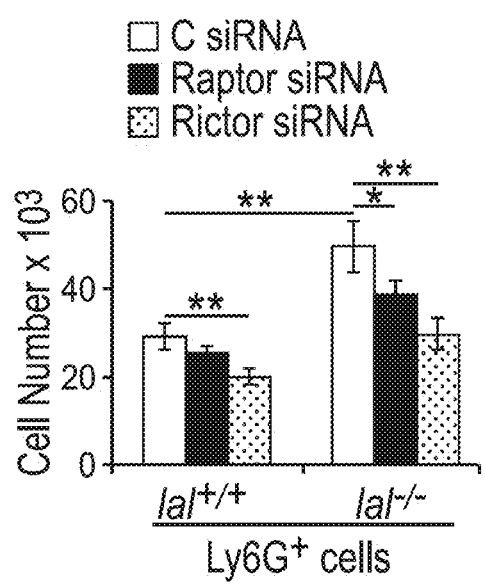
FIGS. 37A-37C show that Raptor or Rictor inhibition impaired the ability of lal$^{-/-}$ Ly6G$^+$ cells to enhance B16 melanoma cell proliferation, growth and metastasis.
Figure 37B:
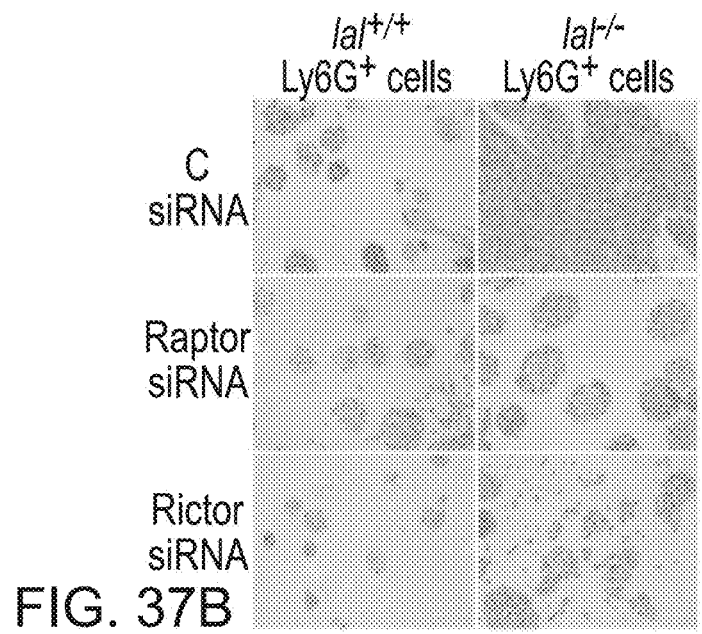
Figure 37C:
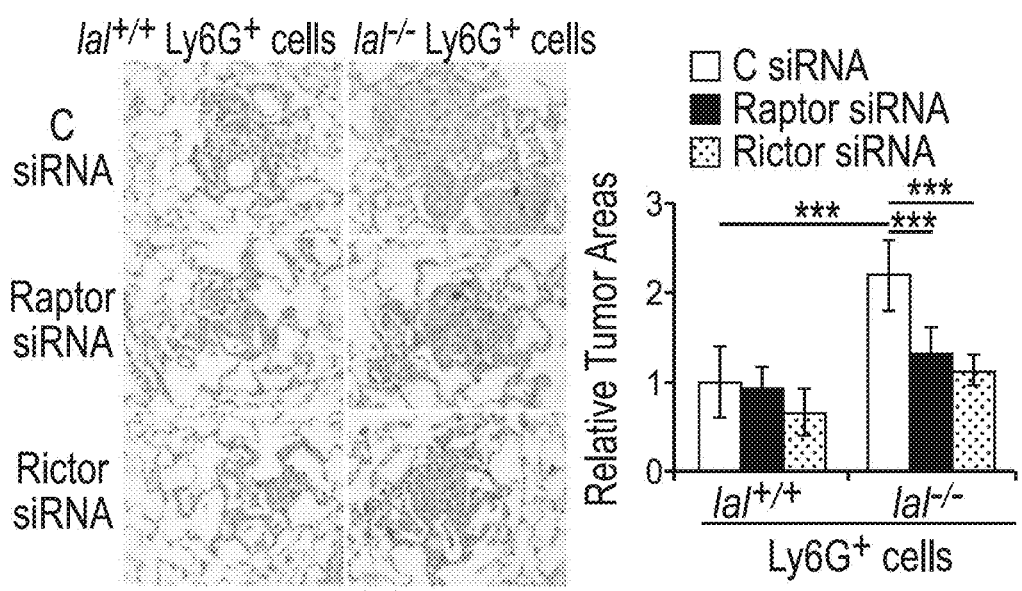

Raptor and Rictor inhibition impaired the ability of lal/Ly6G$^+$ cells to enhance B16 melanoma cell proliferation, growth and metastasis To assess which mTOR complexes (mTORC1 or mTORC2) is involved in lal$^{+/+}$ Ly6G$^+$ cells' stimulatory effects, Ly6G$^+$ cells were transfected with Raptor, Rictor or control siRNAs. The decreased protein expression levels of Raptor and Rictor in Ly6G$^+$ cells after siRNAs transfections have been confirmed previously. For in vitro co-culture study, Raptor and Rictor knockdown significantly reduced lal$^{-/-}$ Ly6G$^+$ cell stimulation of melanoma cell proliferation (FIG. 37A) Similarly, in the in vivo co-culture MATRIGEL® assay, less neoplastic cells were detected in the plugs with Raptor and Rictor knockdown in lal$^{-/-}$ Ly6G$^+$ cells (FIG. 37B). For in vivo metastasis study, less melanoma metastatic lesions developed in the lungs of mice that were co-injected with B16 melanoma cells and Raptor or Rictor siRNA knockdown lal$^{-/-}$ Ly6G$^+$ cells, and H&E staining of lung sections showed significantly less neoplastic cells (FIG. 37C). Taken together, both mTORC1 and mTORC2 are involved in lal$^{-/-}$ Ly6G$^+$ cell stimulation on B16 melanoma cell proliferation, growth and metastasis.

Figure 38A:
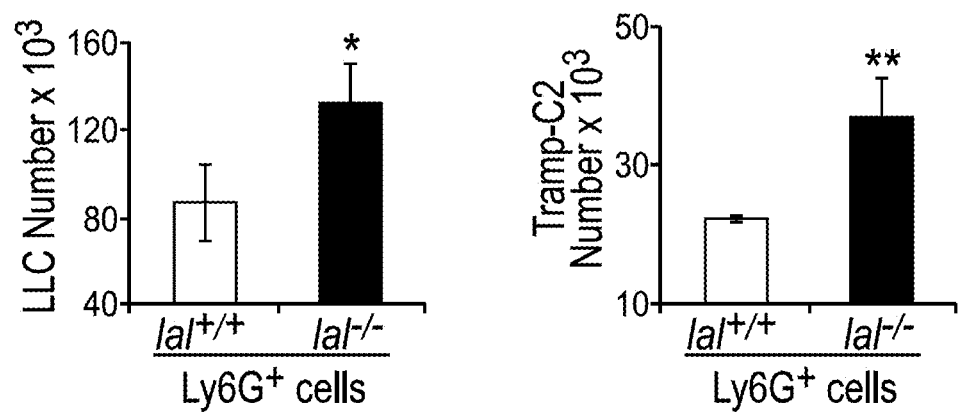
FIGS. 38A-38D show lal$^{-/-}$ Ly6G$^+$ cells stimulated LLC and Tramp-C2 growth through over-activation of mTOR signaling pathway.
Figure 38B:
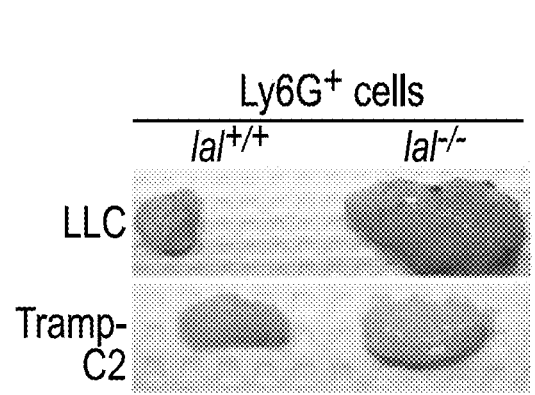
Figure 38C:
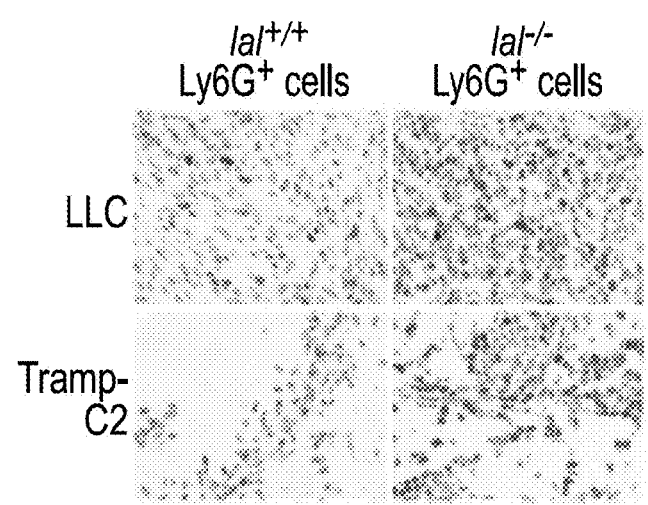
Figure 38D:
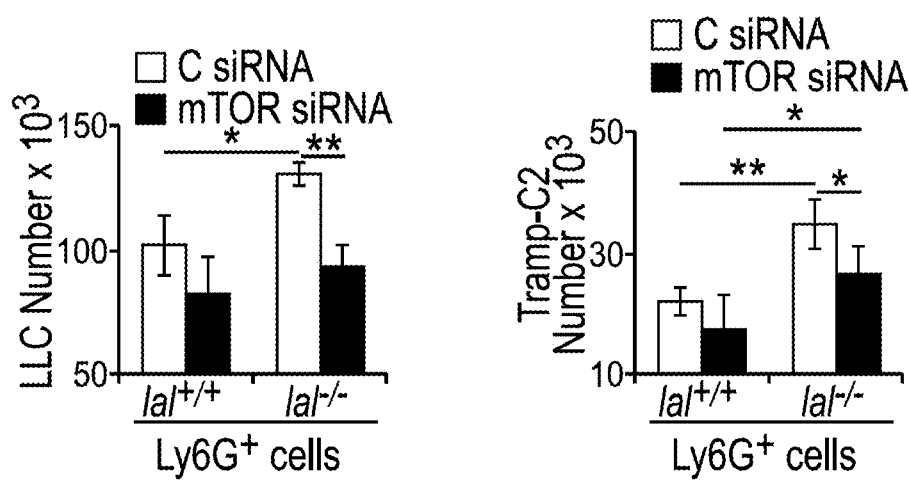

LAL deficiency in Ly6G$^+$ cells stimulated Lewis lung carcinoma (LLC) and transgenic mouse prostate cancer (Tramp)-C2 proliferation and growth, which was reversed by mTOR inhibition To further confirm that lal$^{-/-}$ Ly6G$^+$ cells generally stimulate cancer cell proliferation and growth, the above experiments were repeated in two more cancer cell line models, LLC and Tramp-C2. In in vitro co-culture study, proliferation of LLC or Tramp-C2 was significantly increased after co-cultured with lal$^{-/-}$ Ly6G$^+$ cells (FIG. 38A). As shown in FIGS. 38B & 38C, the MATRIGEL® plugs mixed with lal$^{-/-}$ Ly6G$^+$ cells showed larger size and more Ki67-positive proliferative cells than those mixed with lal$^{+/+}$ Ly6G$^+$ cells. Furthermore, lal$^{-/-}$ Ly6G$^+$ cells with mTOR knockdown significantly reduced their abilities to stimulate cancer cell proliferation in in vitro co-culture experiment (FIG. 38D). Therefore, lal$^{-/-}$ Ly6G$^+$ cells stimulate proliferation of multiple cancer cell models.

Discussion

Given the importance of lal$^{-/-}$ MDSCs in cancer cell metastasis, it is important to identify the molecular mechanisms that mediate lal$^{-/-}$ MDSCs malfunction, especially their stimulation on cancer cell proliferation. Identification of such mechanisms and pathways will help find pharmacological intervention in immune therapy for cancer treatment. To achieve this goal, the intrinsic molecular defects in lal$^{-/-}$ MDSCs were identified by Affymetrix GeneChip microarray analysis. Ingenuity Pathway Analysis of gene transcripts revealed upregulation of multiple genes in the mTOR signaling pathway in lal$^{-/-}$ MDSCs. The mTOR-associated cellular defects, including increased reactive oxygen species production, elevated ATP synthesis and reduced membrane potential, have been observed in lal$^{-/-}$ MDSCs as reported previously.

Figure 35A:
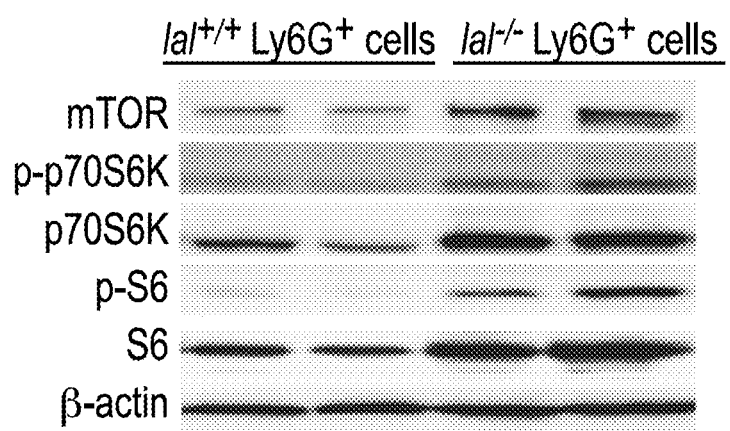
FIGS. 35A-35D show that mTOR inhibition impaired the ability of lal$^{-/-}$ Ly6G$^+$ cells to enhance B16 melanoma cell proliferation and growth.
Figure 35C:
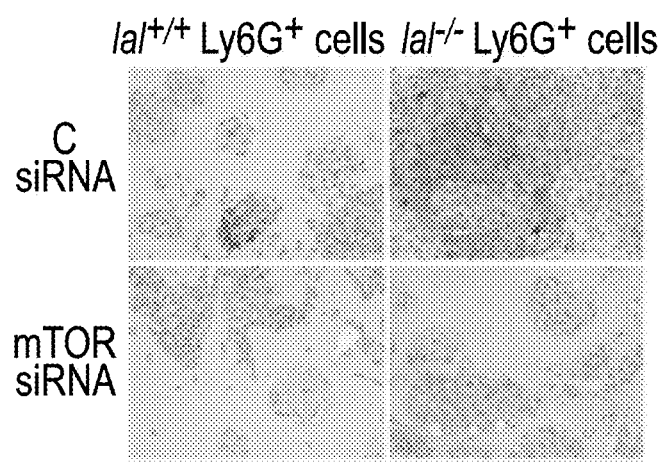
Figure 35B:
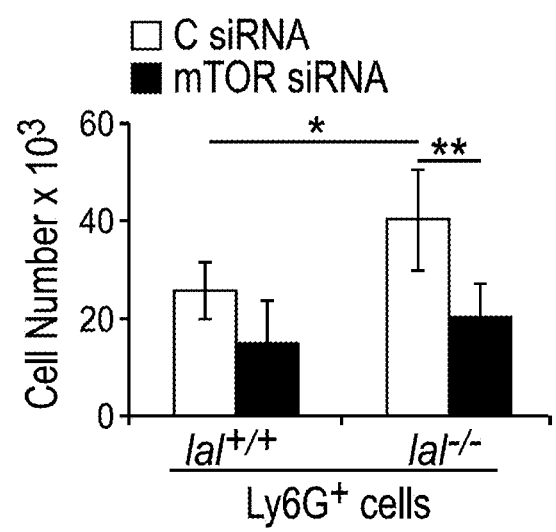
Figure 35D:
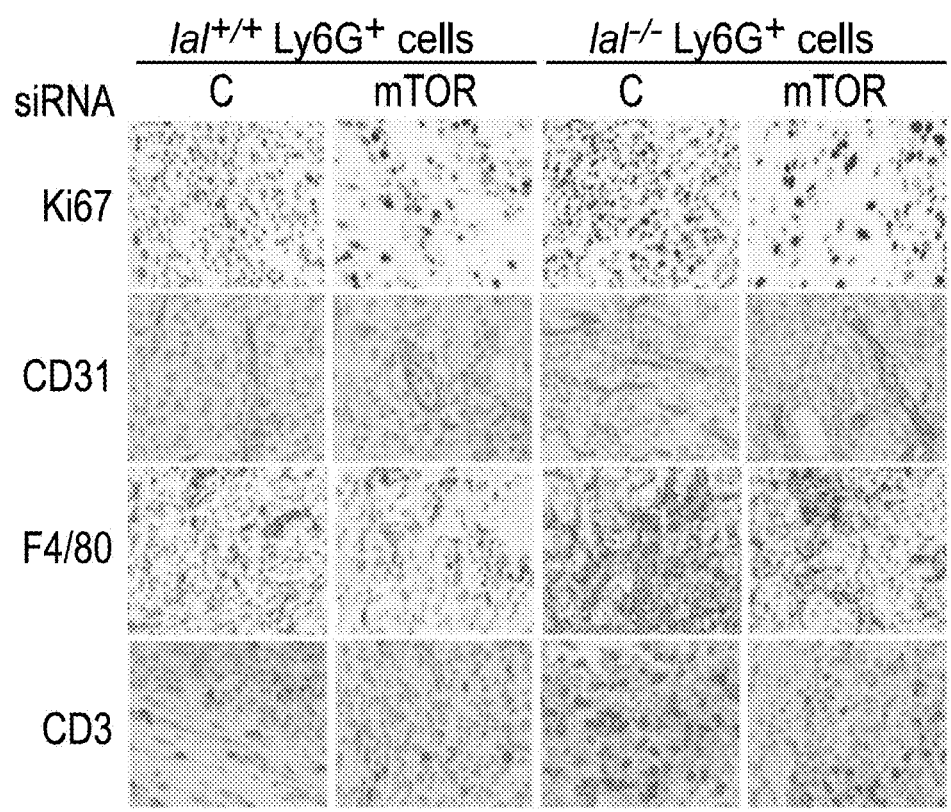

In the present Example, it was found that LAL deficiency induced over-activation of the mTOR pathway in MDSCs by activating the mTOR downstream genes (FIG. 35A). Inhibition of mTOR in lal$^{-/-}$ MDSCs by siRNA transfection not only impaired their stimulatory effects on cancer cell proliferation in in vitro co-culturing assay (FIGS. 35A and 39D) and in vivo MATRIGEL® assay (FIGS. FIGS. 35C and 35D), but also significantly retarded their ability on B16 melanoma cell metastasis (FIGS. 36A-36C). Tumor-associated F4/80$^+$ macrophages, CD3$^+$ T cells and CD31$^+$ endothelial cells in the B16 melanoma cell-injected MATRIGEL® plugs were also reduced after inhibition of mTOR in lal$^{-/-}$ MDSCs by siRNA transfection (FIG. 35D), suggesting that over-activation of the mTOR pathway in lal MDSCs is a major molecular mechanism underlying their stimulatory effects on cancer cell proliferation and metastasis. Furthermore, both mTORC1 and mTORC2 were involved in the lal$^{-/-}$ MDSCs' stimulatory activity on B16 melanoma cell proliferation, growth and metastasis (FIGS. 37A-37C). In addition to lal$^{-/-}$ MDSCs, inhibition of mTOR, Raptor and Rictor also showed effects in lal$^{+/+}$ MDSCs (FIGS. 33A-33D, 37A-37C and 38A-38D). The mTOR signaling pathway is involved in regulating cell growth, proliferation, migration, survival, protein synthesis and transcription in response to growth factors and mitogens. It is conceivable that inhibition of mTOR may also suppress the normal functions of mTOR in wild-type cells. Although it is important to suppress abnormal activities of MDSCs during cancer treatment, it is critical to control dosage use for patient care in the future. Nevertheless, it is still beneficial to treat cancer patients by eliminating MDSCs to decrease tumor growth and metastasis, as mTOR shows over-activation in tumor MDSCs.

Recently, it was shown that inhibition of mTOR in lal$^{-/-}$ mice (1) reduced bone marrow myelopoiesis and systemic MDSC expansion; (2) reversed the increased cell proliferation, decreased apoptosis, increased ATP synthesis and increased cell cycling of bone marrow-derived MDSCs; (3) corrected enhanced lal$^{-/-}$ MDSCs development from lineage-negative progenitor cells; and (4) reversed the immune suppression on T-cell proliferation and function that are associated with decreased reactive oxygen species production and recovery from impairment of mitochondrial membrane potential. These results indicate a critical role of LAL-regulated mTOR signaling in the production and function of lal$^{-/-}$ MDSCs.

In conclusion, neutral lipid metabolism controlled by LAL critically regulates MDSCs' ability to directly stimulate cancer cell proliferation, metastasis and immune suppression through modulation of the mTOR pathway. The mTOR pathway may be served as a novel target to modulate the emergence of MDSCs to reduce the risk of cancer metastasis.

Example 6

In this example, the lysosomal acid lipase (LAL) deficient (lal$^{-/-}$) mouse model mimics human chronic inflammation and serves as a xenotransplantable system to study the relationship between host immunity and human cancers, in which growth of human A549 lung or MDA-MB-231 breast cancer cells was greatly accelerated and tumor rejection was significantly delayed. The lipid metabolic defect led to a lower survival rate, changed morphological shapes and cancer attacking ability of lymph node cells with abnormal functions. The lal$^{-/-}$ lymph node showed increased T regulatory cells (Tregs). Transitional 2-marginal zone precursor (T2-MZP) and marginal zone (MZ) B regulatory cells (Bregs) were also increased that expressed IL-10 and IL-35. The lal$^{-/-}$ lymph node showed increased expression of PD-L1 in Treg, Breg and antigen presenting (APC) cells. These metabolic-induced abnormalities compromised lymph node functions to reject human cancer in lal$^{-/-}$ mice.

Materials & Methods

Animal Care

The scientific protocols related to animal uses were approved by the Institutional Animal Care and Usage Committee (IACUC) of Indiana University School of Medicine. Protocols involving the use of biohazard materials have been approved by the Institutional Biosafety Committee and followed the guideline established by National Institutes of Health. Animals were housed under IACUC-approved conditions in the facility at Indiana University School of Medicine.

Animals and Cells

The FVB/N mice with lysosomal acid lipase (LAL) gene knockout (lal$^{-/-}$) were described in Du, H. et al. (Journal of lipid research 42, 489-500 (2001)). Human lung cancer cells A549 and human breast cancer cells MDA-MB-231 were purchased from American Type Culture Collection (ATCC, Manassas, Va.). A549 cells were grown in F-12K medium supplemented with 10% fetal bovine serum (FBS) in a 37° C. incubator with 5% CO2. MDA-MB-231 cells were grown in Leibovitz's L-15 medium supplemented with 10% FBS in a 37° C. incubator with 5% $CO_2$.

Xenotr Ansplantation of Human Tumor Cells in Mice

The human tumor cells ($1\times10^6$ for A549 or $5\times10^6$ for MDA-MB-231) were subcutaneously injected to the flanking region in mice. The tumor growth was assessed twice a week. The tumor volume (mm$^3$) was estimated by measuring the maximal length (L) and width (W) of a tumor and calculated using the formula of $L \times W^2/2$.

Isolation of Lymph Node Cells

Mouse brachial, axillary and inguinal lymph nodes were harvested from the anesthetized mice in 1×PBS. The lymph nodes were crushed by the frost side of a glass slide and ground gently to release lymph node cells. Collected cells were washed two times with 1×PBS, and passed through a 40 μm cell strainer. The cell suspension was centrifuged at 1500 rpm for 5 minutes to collect pellets of lymph node cells.

Fluorescence Tracking of Lymph Node Cells and A549 Cells

A549 cells were labeled by carboxyfluorescein succinimidyl ester (CFSE) and seeded in a 48-well plate at $2.5\times10^4$ cell/well. Next day, lymph node cells were isolated from wild type and mice that were injected with or without A549 cells ($1.5\times10^6$), and labeled with red fluorescence (CMTPX) dye for 20 minutes at room temperature. The labeled lymph node cells were added to A549 cells at a 2:1 ratio (lymph node cells: A549). Photographs were taken after 4 hours of incubation. The inclusion rate was determined by total red cells and attacking red/green cells in each field of culturing dishes. Statistical analysis was performed by Student's t-test, n=5.

Flow Cytometry Analysis

For immune cell profiling analysis, single cells from lymph nodes from wild type and lal$^{-/-}$ mice that were injected with or without A549 cells ($1.5\times10^6$) were prepared by grind. Cells were labeled with isotype controls or surface marker-specific antibodies at 4° C. for 15 minutes, and washed with PBS. Anti-mouse MHC class II (MHC II)(I-A) FITC, anti-mouse CD4 FITC, anti-mouse CD8 PE, anti-mouse Ly6C PE, anti-mouse CD23 PE, anti-mouse CD69 PE-Cy7, anti-mouse CD11b (M1/70) PE-Cy7, anti-mouse CD8 APC, anti-mouse CD21 APC, anti-mouse CD11c APC, anti-mouse CD25 APC, anti-mouse B220 APC, anti-Ly6G (RB6-8c5) APC-eFluor 780, anti-mouse B220 APC-eFluor 780 antibodies and anti-mouse PD-L1 (10F.9G2) APC were purchased from eBiosciences (San Diego, Calif.). For intracellular staining, single cell suspensions were prepared and stained for surface markers. After wash, the cells were fixed and permeabilized using BD CYTOFIX/CYTOPERM™ Fixation/permeabilization Kit according to the manufacture's instruction (BD Bioscience, San Jose, Calif.). Cells were labeled with antibodies against intracellular molecules, including anti-mouse Foxp3 APC, anti-mouse IL-10 APC, anti-mouse Granzyme B PE (eBiosciences, San Diego, Calif.), antimouse IL-35 APC (R&D Systems) at 4° C. overnight. The cells were analyzed on a LSR II flow cytometer (BD Bioscience). Data were processed using CellQuest software (BD Bioscience).

Measurement of IL-10, IFNγ and TNFα by ELISA

The freshly-isolated lymph node cells from wild type and lal$^{-/-}$ mice that were injected with or without A549 cells ($1.5\times10^6$) were cultured in 96-well flat-bottom plates coated with or without anti-CD3 mAb (2 μg/ml) and anti-CD28 mAb (5 μg/ml) at $2\times10^5$ cells per well. The cells were treated with or without A549 cell lysate (20 μg/well) and cultured for 2 days. The A549 cell lysate was prepared following procedures described in Gatza, E. & Okada, C. Y. (J Immunol 169, 5227-5235 (2002)). The secretion of IL-10, FNγ or TNFα in the supernatant of cultured lymph node cells was measured using OptEIA ELISA kits according to manufacturer's instructions (BD Bioscience).

Histology and Immunohistochemistry (IHC) Staining

The harvested lymph nodes were fixed with 4% paraformaldehyde at 4° C. overnight. The tissues were transferred to 70% ethanol and embedded in paraffin. The tissue blocks were sectioned in 5 μm thickness. Hematoxylin and eosin (HE) stain and IHC staining against mouse CD3, B220, F4/80, and Mac-3 were performed by Immunohistochemistry Core, Department of Pathology and Laboratory Medicine, Indiana University. For PD-L1 staining, the tissue slides were deparaffinized. Antigen retrieval was performed for 30 minutes by heating in citrate buffer (pH 6.0). The tissue sections were incubated with rat-anti-mouse PD-L1 antibody (clone 10F.9G2) (eBiosciences) at 4° C. overnight. The slides were washed, followed by the incubation with secondary antibody and final development with 3,3'-diaminobenzidine (DAB) kit (Vector Laboratories, Burlingame, Calif.) for 2 minutes. The stained slides were examined under Nikon Eclipse 80i light microscope (Nikon Instruments Inc., Melville, N.Y.). Photographs were taken by NIS Elements software (Nikon Instruments Inc.).

Statistical Analysis

The data shown were expressed as average±standard deviation. Student's t-test was used to determine the significance of the difference. *, $p<0.05$. **, $p<0.01$.

Results

Figure 39A:
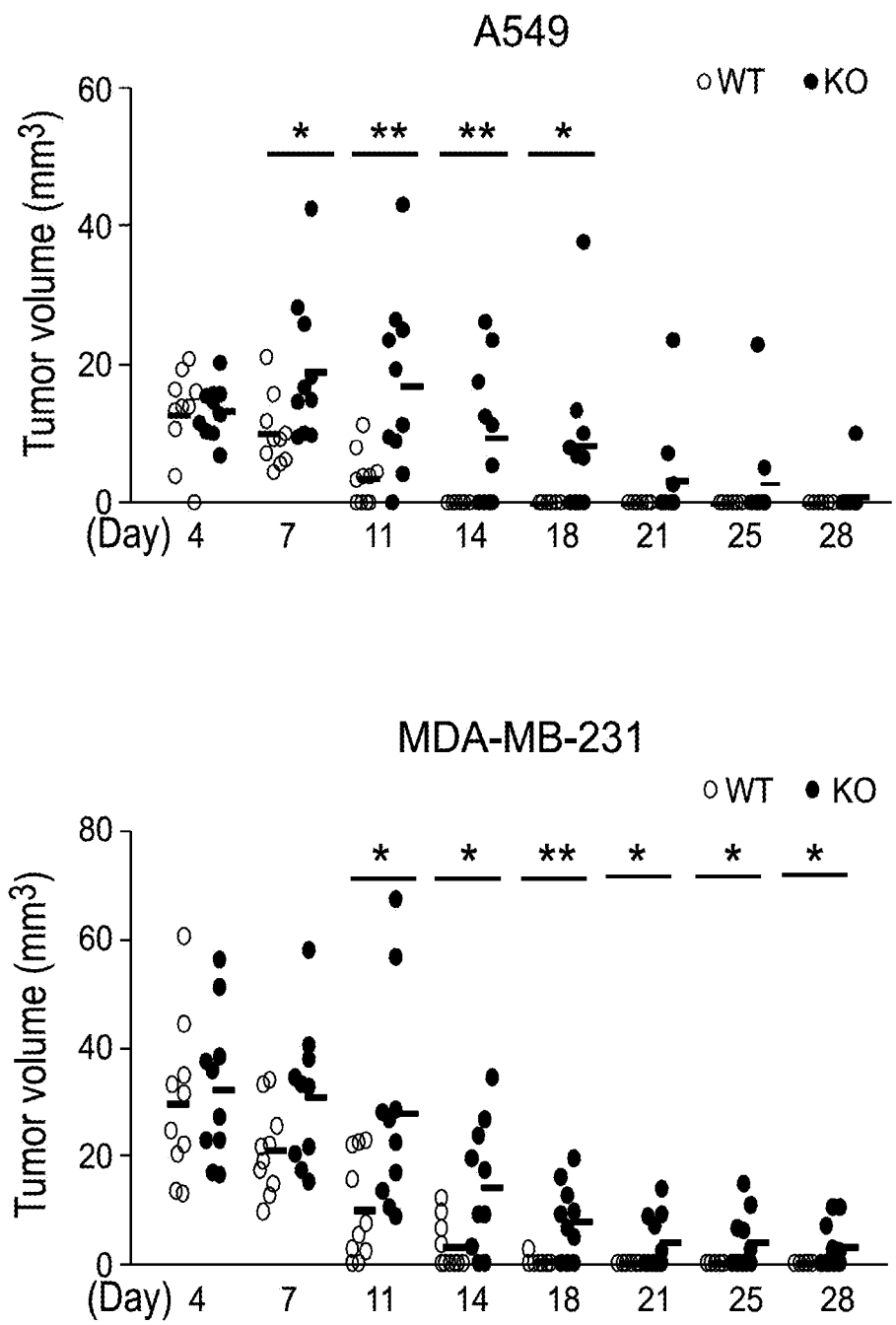
FIGS. 39A-39G depict growth of human cancer cells in lal$^{-/-}$ mice.

To see if xenotransplanted cancer cells grow in a genetic ablated mouse model (lal$^{-/-}$) of lysosomal acid lipase (LAL) further across the species, human lung cancer A549 cells were subcutaneously injected in the flank sides of FVB/N wild type and lal$^{-/-}$ recipient mice. In wild type mice, the tumor growing size was peaked at day 4-7 and completely eradicated at day 14 due to immunorejection. In comparison, the tumor sizes in lal$^{-/-}$ mice were much larger and peaked at day 11-14 (FIG. 39A). Although gradually eradicated, a few lal$^{-/-}$ mice kept tumor growing beyond day 18 to day 28. A similar observation was observed when the human breast cancer MDA-MB-231 cell model was used (FIG. 39A). This delayed tumor rejection implicated a compromised immune surveillance in mice.

Figure 39B:
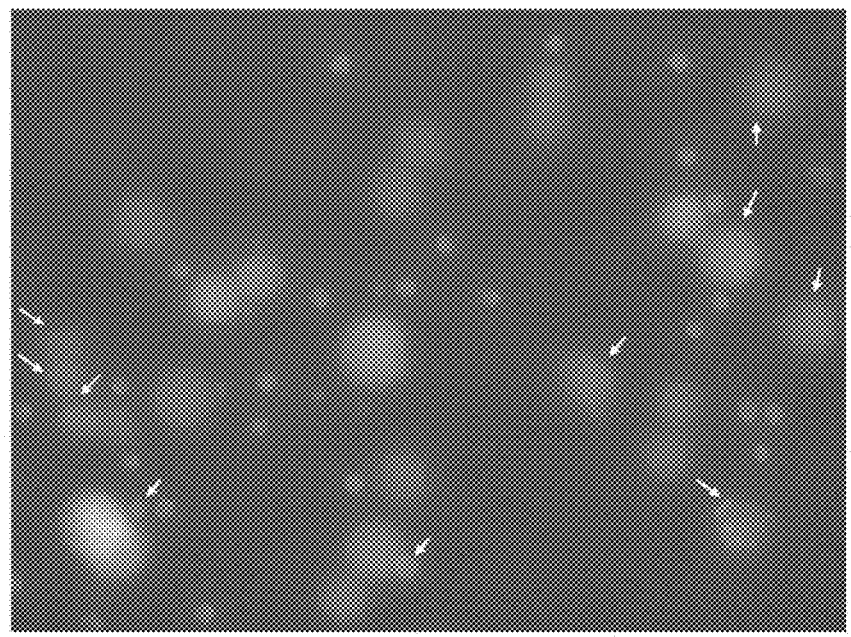
Figure 39B:
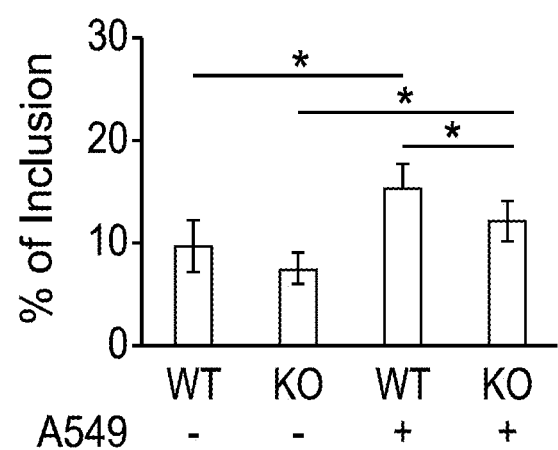
Figure 39C:
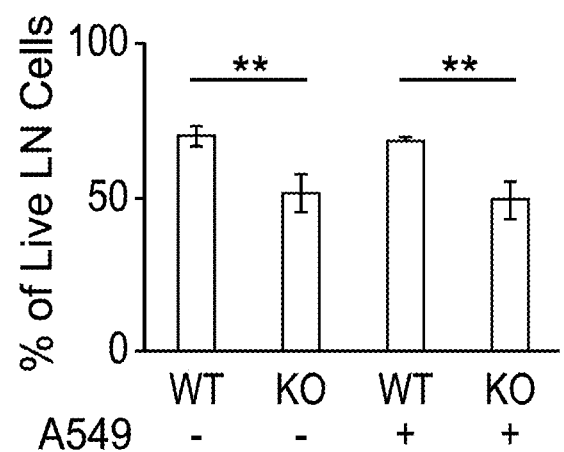
Figure 39D:
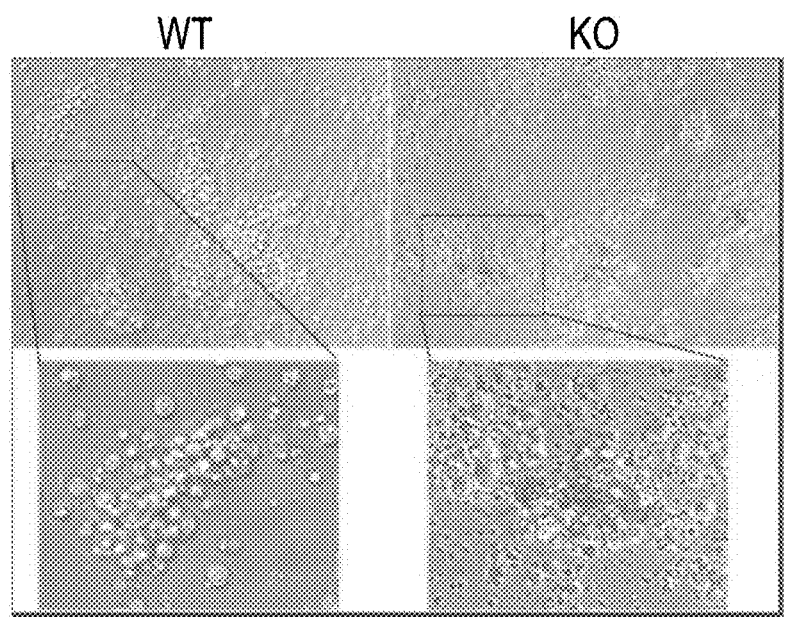
Figure 39E:
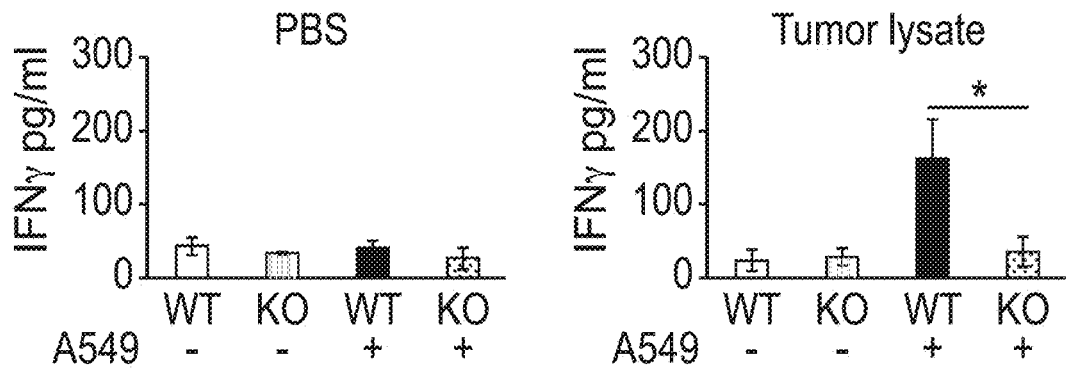
Figure 39F:
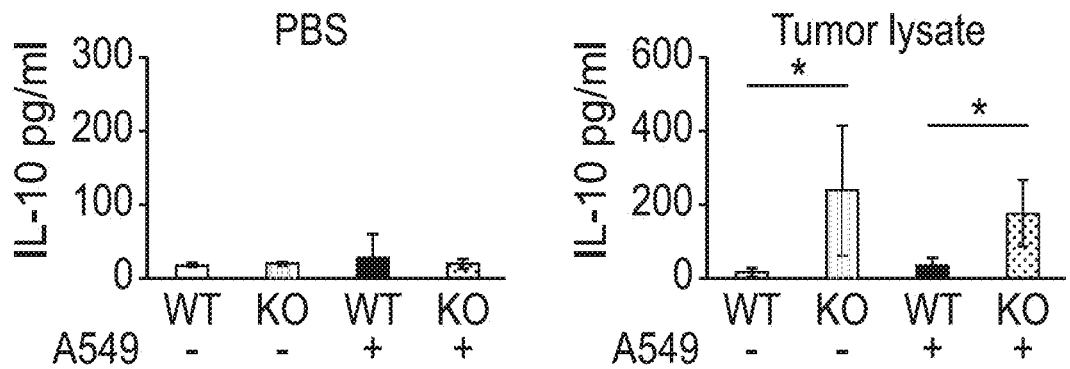
Figure 39G:
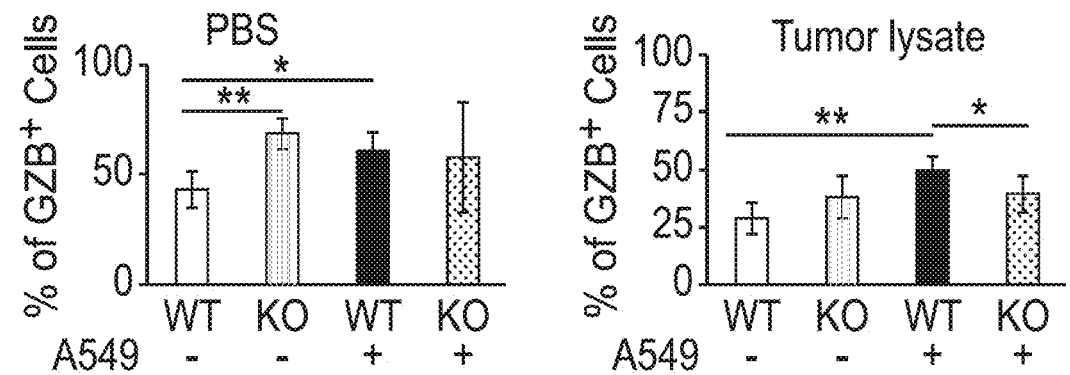

The attacking cytotoxicity of lymph node cells to A549 cancer cells was evaluated first by co-culture experiment of fluorescence tracking. At 4 hours of incubation, lymph node cells attached and penetrated into A549 cancer cells (FIG. 39B, left). There was no difference of the inclusion rate between wild type and lal$^{-/-}$ mice. However, the inclusion rate of A549 cancer cells was statistically lower for lymph node cells from A549-injected lal$^{-/-}$ mice than those from A549-injected wild type mice (FIG. 39B, right). To assess the quality of lymph node cells, the survival rate of lal$^{-/-}$ lymph node cells was statistically lower than wild type lymph node cells after overnight in vitro culture (FIG. 39C). The morphologic growing shape of lal$^{-/-}$ lymph node cells was poorly differentiated compared with that of wild type lymph node cells after stimulation by anti-CD3/anti-CD28 antibodies (FIG. 39D). Functionally, secretion of interferon-γ (IFNγ), interleukin 10 (IL-10) and granzyme B (GZB) was measured. The A549 cancer cell lysate or PBS control was added to wild type or lal$^{-/-}$ lymph node cells from A549-injected or uninjected mice. It has been well documented that lymph node IFNγ promotes anti-tumor immunity. Secretion of IFNγ was strongly stimulated in wild type lymph node cells from A549-injected mice compared with those from A549-uninjected mice upon the treatment of the A549 cancer cell lysate. In contrast, A549-injected lal$^{-/-}$ lymph node cells failed to respond to the same treatment (FIG. 39E). IL-10 suppresses anti-tumor immunity. Even without A549-injection, lal$^{-/-}$ lymph node cells showed a much higher response by secreting a higher level of IL-10 than that from wild type lymph node cells upon the treatment of the A549 cancer cell lysate (FIG. 39F). Wild type and lal$^{-/-}$ lymph node cells did not show IL-10 secretion change in responding to the treatment of the A549 cancer cell lysate (FIG. 39F). GZB is a CD8$^+$ T cell producing killing factor of cancer cells. In the PBS control group, lal$^{-/-}$ lymph node cells showed a slightly higher percentage of GZB positive cells (FIG. 39G, left). In the A549 cancer cell lysate treated group, while wild type lymph node cells from A549-injected mice showed an increased GZB positive cells compared with those from uninjected mice, lal$^{-/-}$ lymph node cells showed no response (FIG. 39G, right). Secretion of TNFα was also determined, which showed no difference between wild type and lal$^{-/-}$ lymph node cells upon the treatment of the A549 cancer cell lysate. Taken together, metabolic defect significantly affected morphological formation and functions of lal$^{-/-}$ lymph node cells in fighting cancer.

Figure 40A:
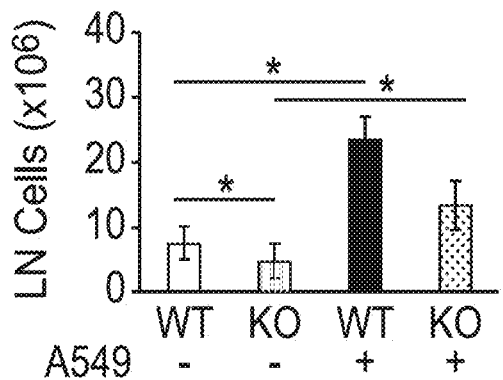
FIGS. 40A-40F depict lymph node cell populations in wild-type and lal$^{-/-}$ mice. Lymph node cells were isolated from wild-type and lal$^{-/-}$ mice with or without A549 cancer cell injection for 14 days, and analyzed by flow cytometry using proper surface antibodies.
Figure 40B:
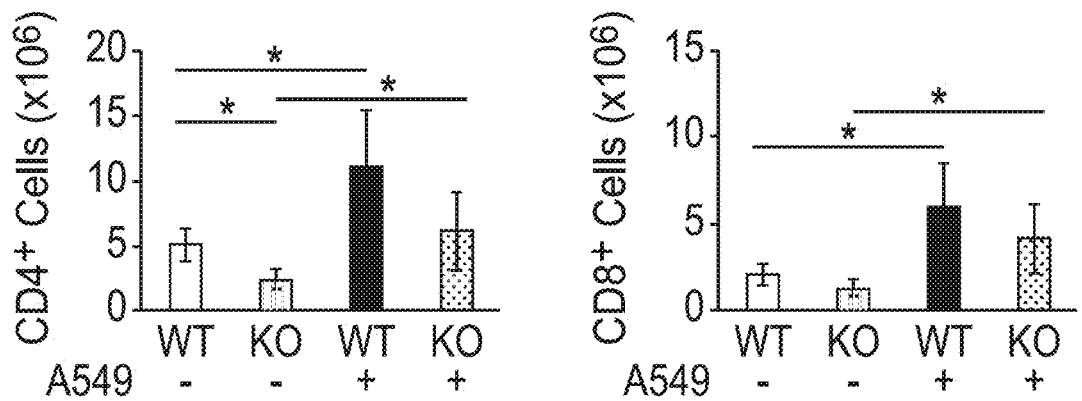
Figure 40B:
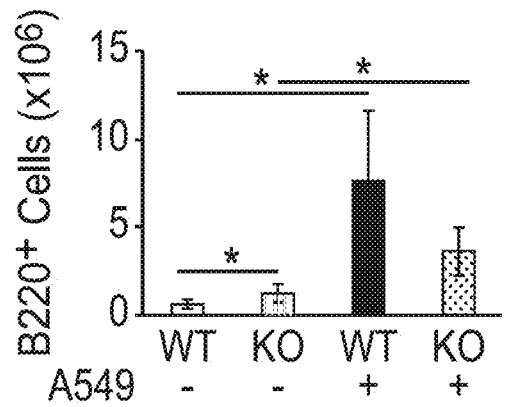
Figure 40C:
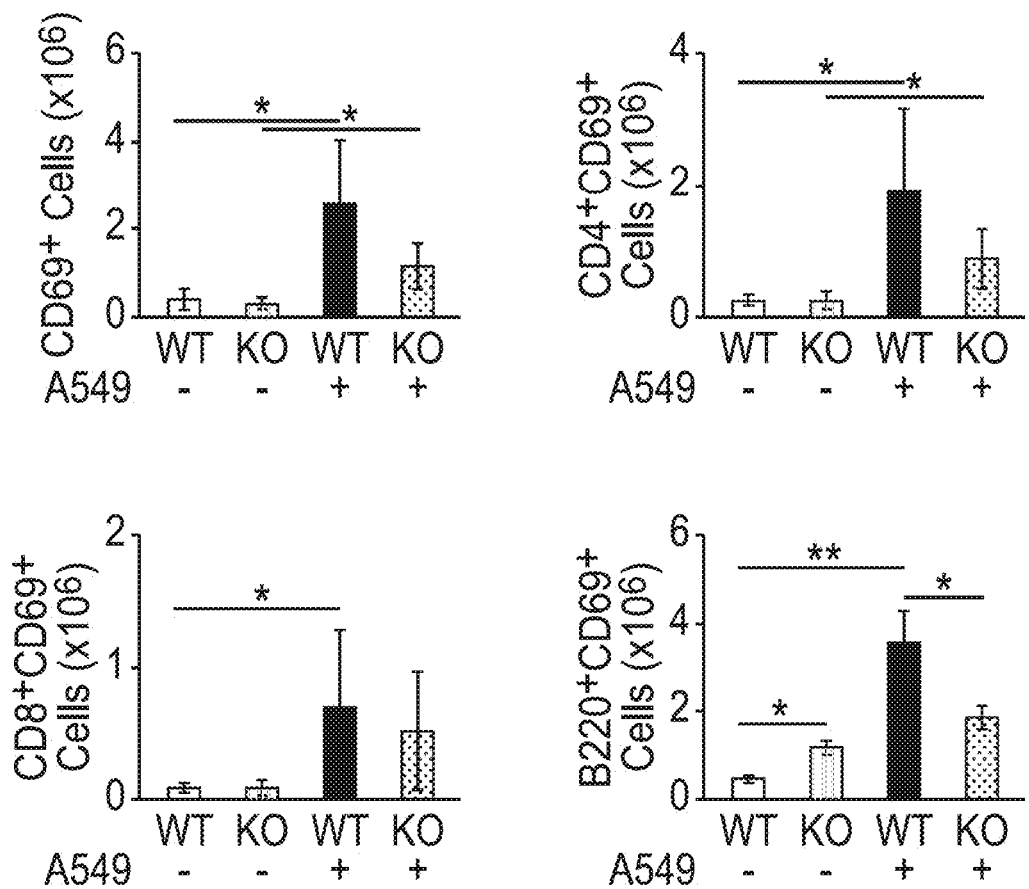
Figure 40D:
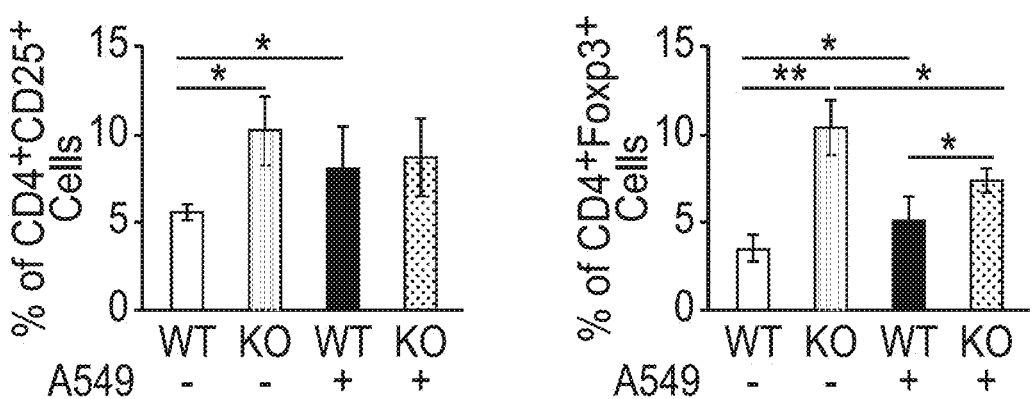

Various cell populations in the lymph node were further determined by flow cytometry. The total number of lymph node cells of lal$^{-/-}$ mice was less than those of wild type mice (FIG. 40A). Upon A549-injection, the total number of lymph node cells was increased significantly in both wild type and lal$^{-/-}$ mice (FIG. 40A) with expansion in lymph node sizes, but lal$^{-/-}$ lymph node cells were increased to a less degree. In the lymphocyte compartment of the lymph node, the total and percentage numbers of CD4$^+$ T cells were lower and B220$^+$ cells were higher in lal$^{-/-}$ mice than those in wild type mice, whereas CD8$^+$ T cells showed no statistic difference (FIG. 40B). With A549-injection, the total numbers of CD4$^+$, CD8$^+$, and B220$^+$ cells were all increased significantly in lal$^{-/-}$ and wild type lymph nodes compared with un-injected control groups (FIG. 40B). In terms of the percentage numbers, only B220$^+$ cells were increased in wild type lymph nodes in response to A549-injection. Activated lymphocytes were measured by the lymphocyte proliferation marker CD69. lal$^{-/-}$ lymph nodes showed higher total number of activated B220$^+$ cells (B220$^+$CD69$^+$) and higher percentage numbers of activated CD4$^+$ (CD4$^+$CD69$^+$) and activated B220$^+$ cells (B220$^+$CD69$^+$) than wild type lymph nodes in A549-uninjected mice (FIG. 40C). A549-injection showed higher total and percentage numbers of activated CD4$^+$, CD8$^+$ and B220$^+$ cells in the wild type lymph nodes, higher total numbers of activated CD4$^+$ and B220$^+$ cells but not percentage numbers in the lal$^{-/-}$ lymph nodes (FIG. 2B, Expanded FIG. 2B). Since T regulatory (Treg) cells critically regulate anti-tumor immunity, the CD4$^+$Foxp3$^+$ T cell population was also investigated. Although lal$^{-/-}$ lymph nodes showed a significantly higher percentage number of CD4$^+$Foxp3$^+$ T regulatory (Treg) cells than those of the wild type lymph node, no total number increases were observed in A549-uninjection mice. However, A549-injection increased percentage numbers of Tregs in wild type lymph nodes, and total number of Tregs increased in wild type and lal$^{-/-}$ lymph nodes (FIG. 40D).

Figure 40E:
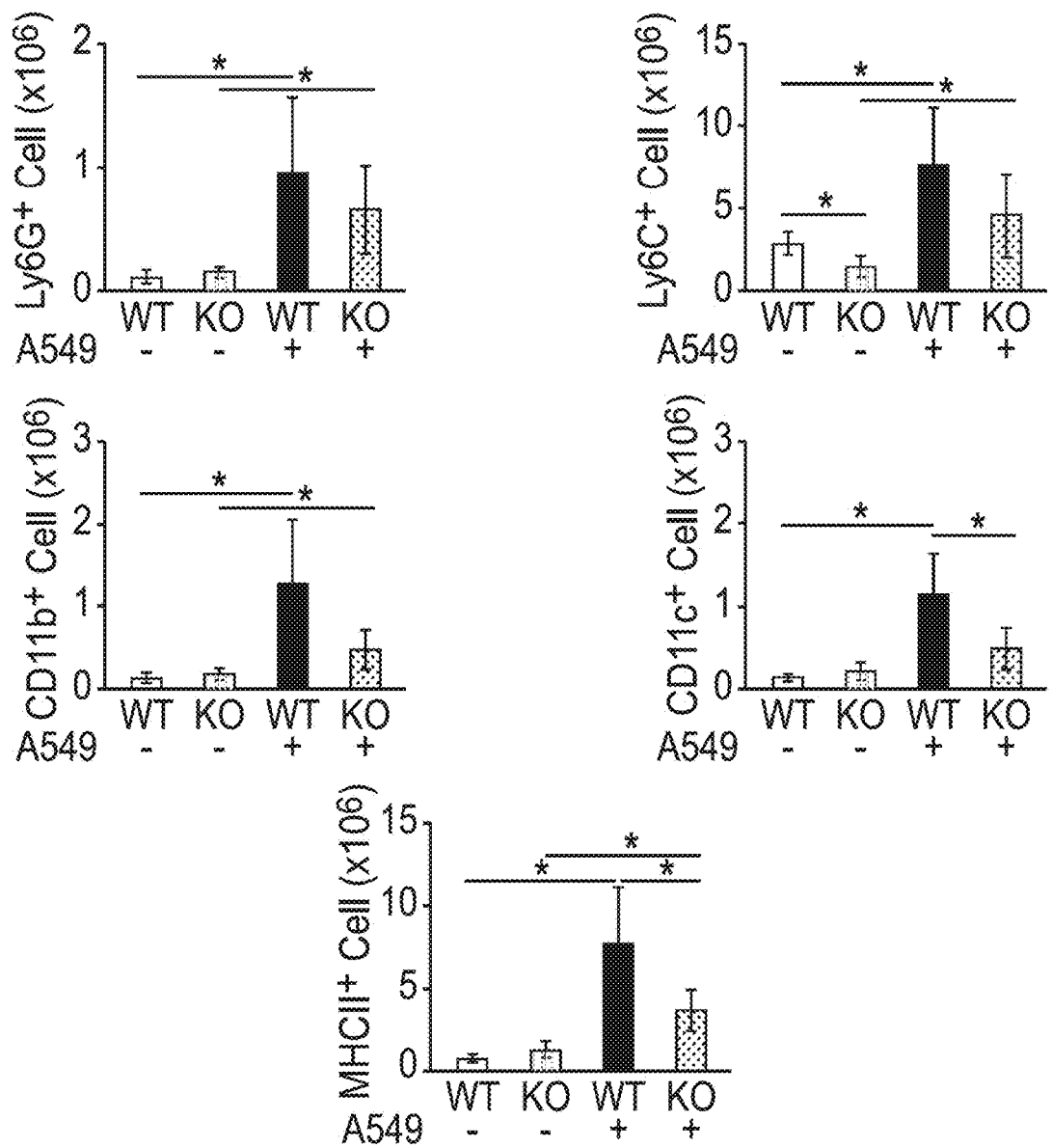
Figure 40F:
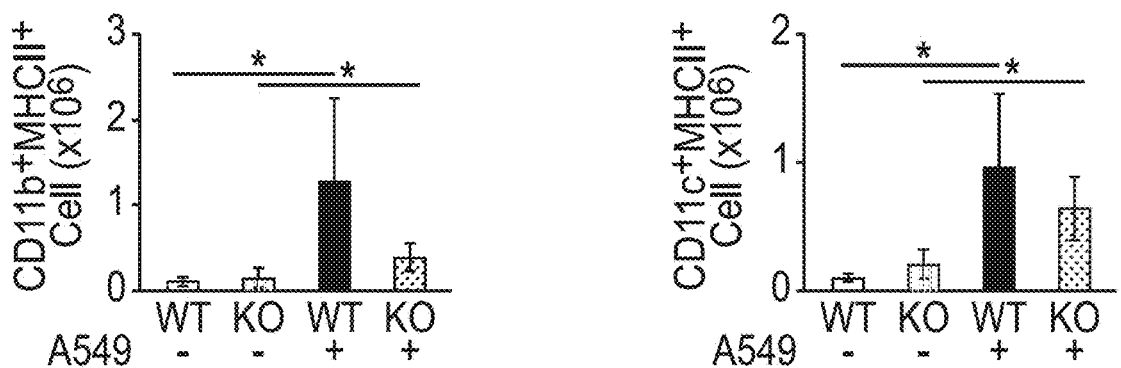

In the myeloid compartment of the lymph node, A549-injection increased total numbers of Ly6G$^+$, Ly6C$^+$, CD11b$^+$, and MHC II$^+$ cells in the wild type and lal$^{-/-}$ lymph nodes compared with the A549-uninjected control groups (FIG. 40E). The total number of CD11c$^+$ cells were only increased in the wild type lymph node in the same setting. In terms of percentages, CD11b$^+$, CD11c$^+$ and MHC II$^+$ cells were significantly increased in lal$^{-/-}$ lymph nodes than those in wild type lymph nodes in A549-uninjected mice. A549-injection significantly increased the percentage of Ly6G$^+$, CD11b$^+$, CD11c$^+$ and MHC II$^+$ cells in wild type lymph nodes, but not in lal$^{-/-}$ lymph nodes. CD11b$^+$, CD11c$^+$ and MHC II$^+$ cells are major antigen presenting cells (APC). While the total numbers of CD11b$^+$MHC II$^+$ cells and CD11c$^+$MHC II$^+$ cells were the same between the wild type and lal$^{-/-}$ lymph nodes, the percentage numbers of these populations were significantly higher in the lal$^{-/-}$ lymph nodes in A549-uninjected mice. A549-injection increased the total numbers of CD11b$^+$MHC II$^+$ cells and CD11c$^+$MHC II$^+$ cells in wild type lymph nodes, and to less extend in lal$^{-/-}$ lymph nodes. A549-injection increased the percentage numbers of CD11b$^+$MHC II$^+$ cells and CD11c$^+$ MHC II$^+$ cells only in wild type lymph nodes (FIG. 40F).

Figure 41A:
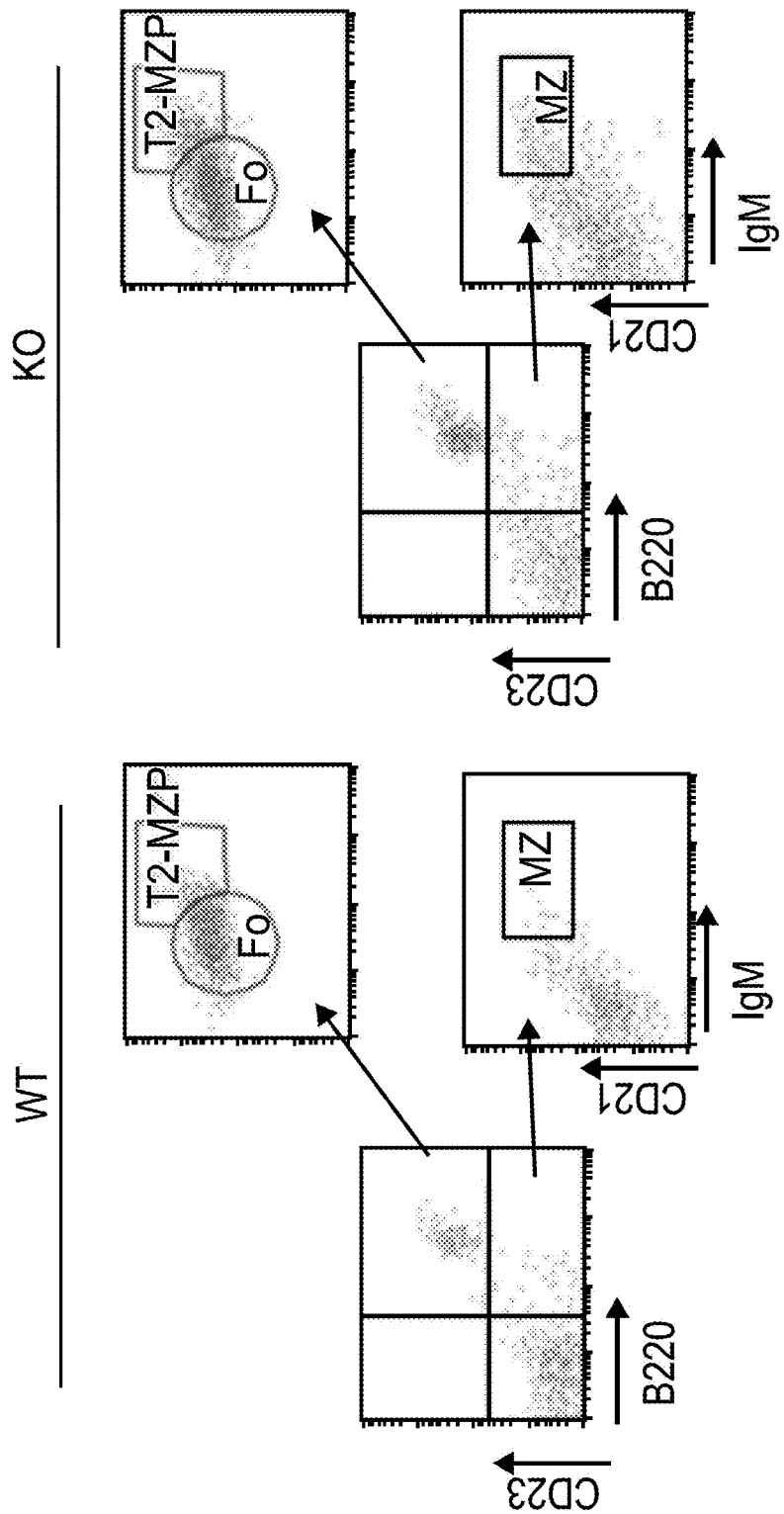
FIGS. 41A-41C depict the increase of Breg cells in the lal$^{-/-}$ lymph node. Lymph node cells were isolated from wild type and lal$^{-/-}$ mice with or without A549 cancer cell injection for 14 days, and analyzed by flow cytometry using CD23, B220, CD21 and IgM surface markers.
Figure 41B:
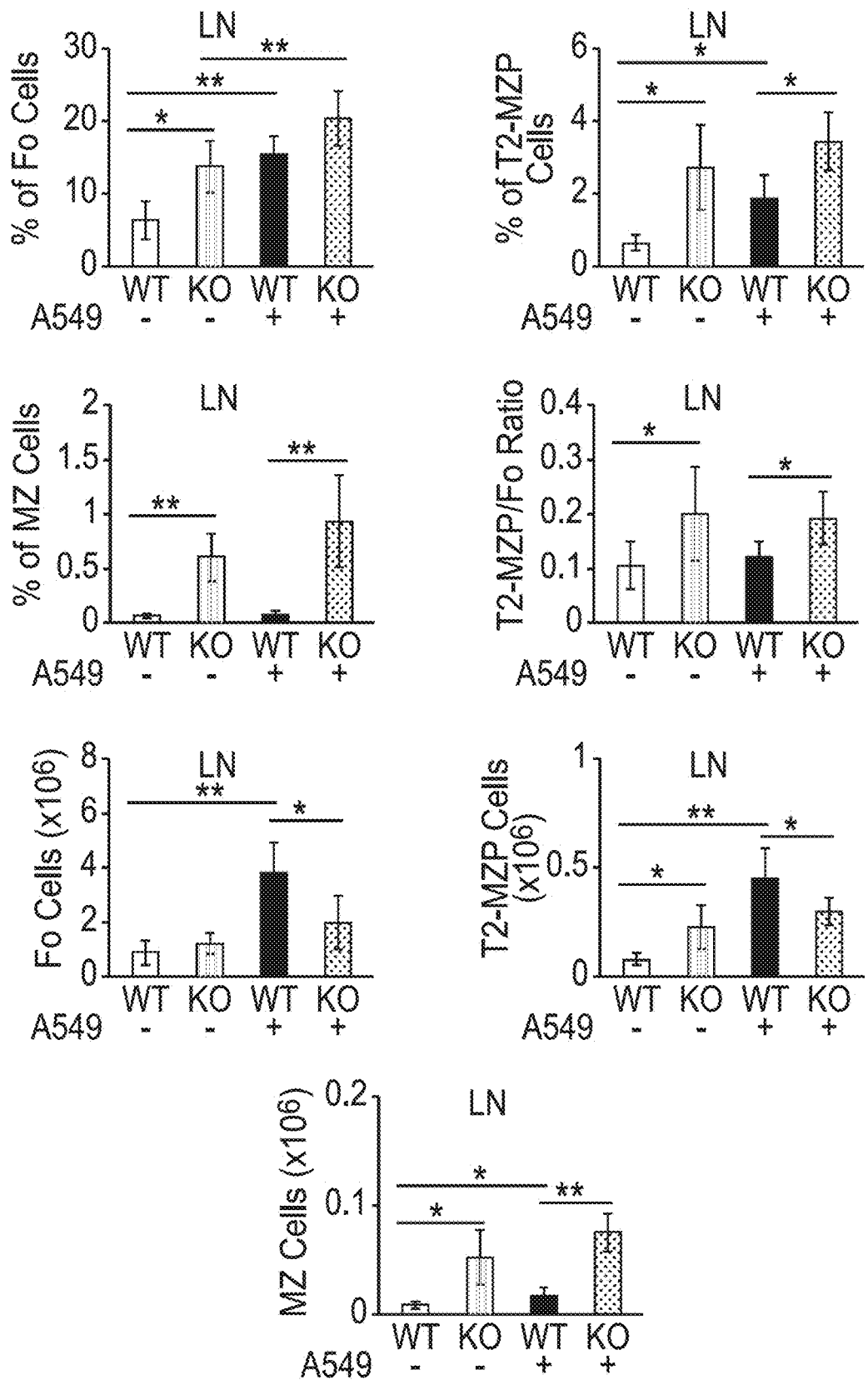
Figure 41C:
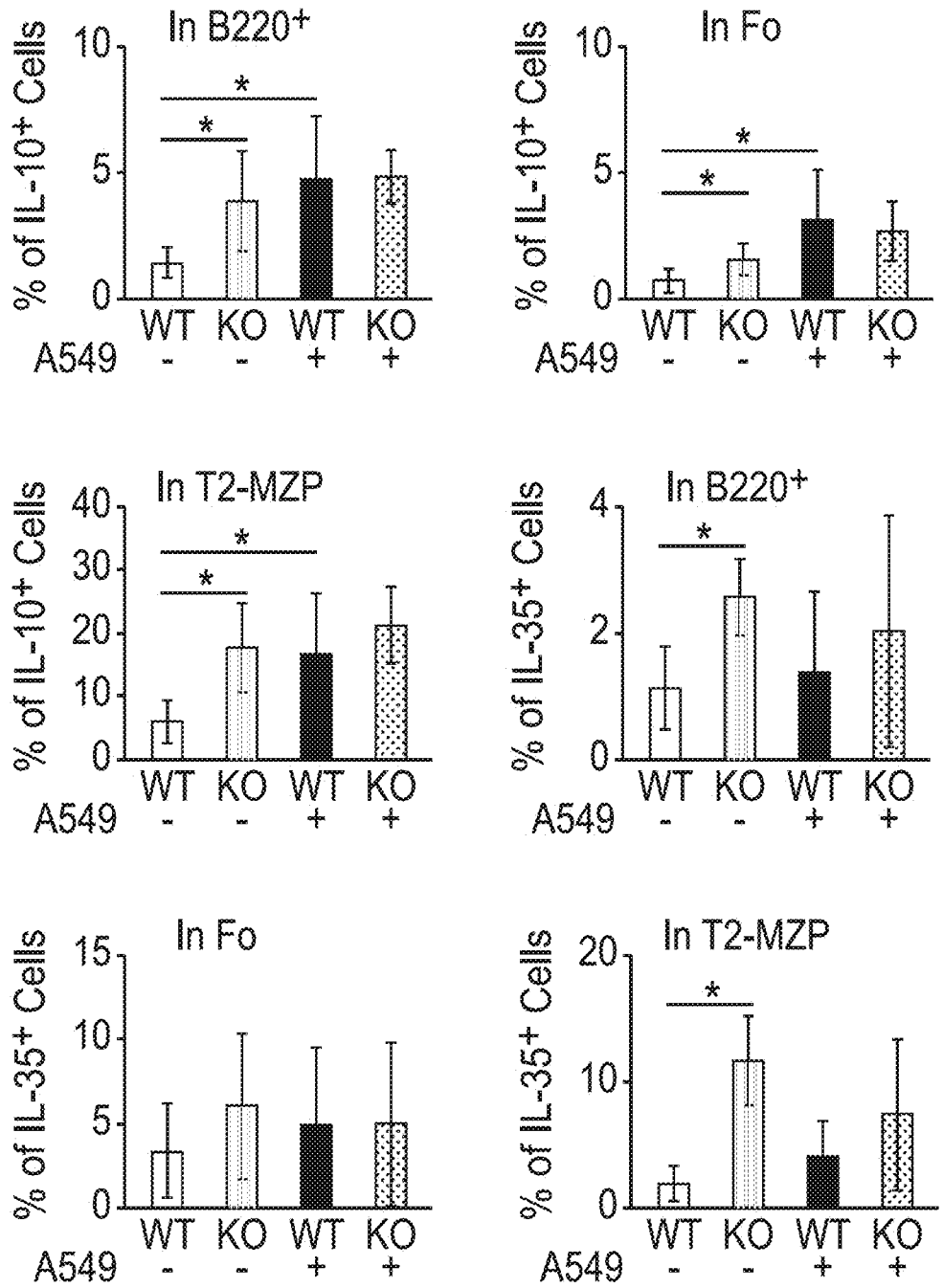
Figure 42A:
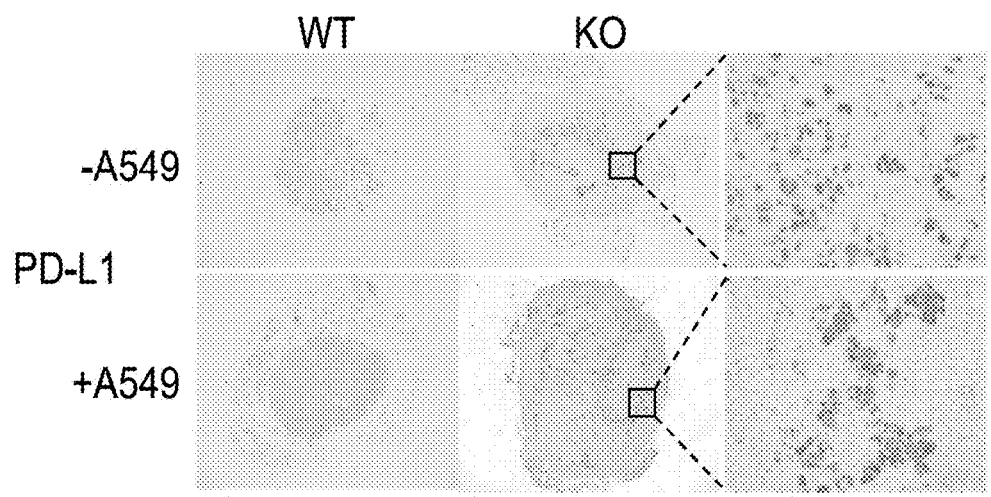
FIGS. 42A-42D depict immunohistochemical staining of lymph nodes. Lymph nodes were harvested from wild type and lal$^{-/-}$ mice with or without A549 cancer cell injection for 14 days, and IHC stained using antibodies against (A) PD-L1, (B) CD3, (C) B220 and (D) F4/80. Original magnification: 40×.
Figure 42B:
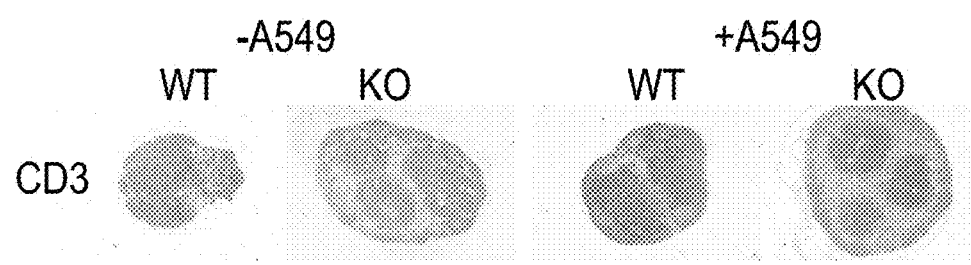
Figure 42C:
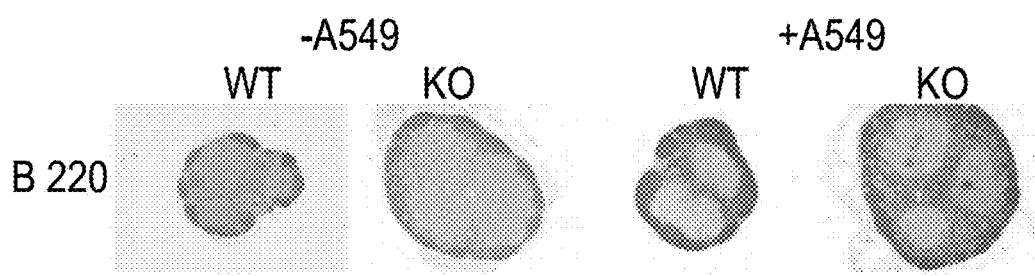
Figure 42D:
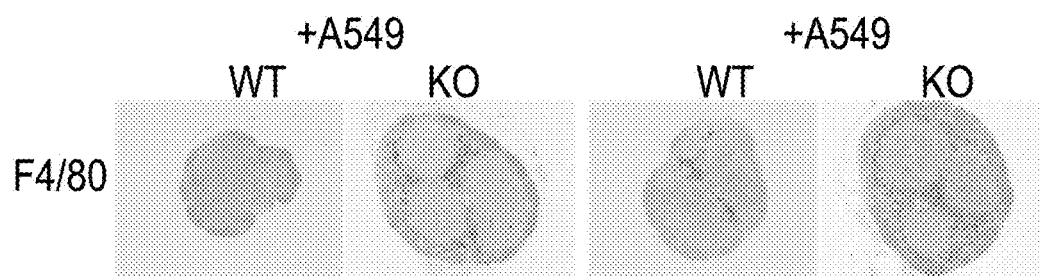

The increased B cell population in the lal$^{-/-}$ lymph node upon A549 challenge indicated that B lymphocytes play a critical role in promotion of tumor growth by suppressing anti-tumor immunity. Specifically, populations of follicle (Fo), transitional 2-marginal zone precursor (T2-MZP) and marginal zone (MZ) cells were defined within the B220 population (FIG. 41A). Collectively, T2-MZP and MZ populations belong to B regulatory cells (Breg), which are well known for their roles in suppressing T cells against tumor growth. The percentage numbers of Fo, T2-MZP and MZ cells in the lal$^{-/-}$ lymph node were all significantly higher than those in the wild type lymph node, while only T2-MZP and MZ cells showed total number increases (FIG. 41B). After A549-injection, the increased percentage number of the T2-MZP subpopulation in the wild type lymph node were still lower than those in the lal$^{-/-}$ lymph node. The overall T2-MZP/Fo ratio is an indicator of Breg activity and was significantly higher in the lal$^{-/-}$ lymph node compared with the wild type lymph node regardless injection of A549 cancer cells (FIG. 41B). IL-10 or IL-35 are two major lymphokines secreted by Breg cells. Much higher percentages of IL-10 and IL-35 positive B220 and Breg cells were observed in the lal$^{-/-}$ lymph node than those in the wild type lymph node of A549-uninjected mice (FIG. 41C). A549-injection increased the percentage numbers of IL-10$^+$ B220 and T2-MZP Breg cells in the wild type lymph node, and remained relatively the same in the lal$^{-/-}$ lymph node without further increase (FIG. 41C). The percentage numbers of IL-35$^+$B220 and T2-MZP Breg cells remained relatively the same in both the wild type and the lal$^{-/-}$ lymph nodes.

T lymphocytes were mostly localized to the deep cortical unit (DCU), while B lymphocytes were mainly present in the follicles. The region between follicles and DCU is the interfollicular cortex where the circulated blood cells located. Programmed death ligand 1 (PD-L1) plays a critical role in blocking T cell development and functions to kill cancer cells. Immunohistochemical staining revealed very little PD-L1$^+$ cells in the wild type lymph node regardless of A549-injection. In contrast, significant amount of PD-L1$^+$ cells were detected in the interfollicular cortex of the lal$^{-/-}$ lymph node (FIG. 42) Immunohistochemical staining with CD3 and B220 surface markers revealed shrunk DCU where T lymphocytes reside and increased follicles where B lymphocytes reside. It was noticeable that F4/80$^+$ myeloid lineage cells in the interfollicular cortex were increased in the lal$^{-/-}$ lymph node, an implication of increased myeloid infiltration. Mac-3 staining showed a similar observation (not shown).

Figure 43A:
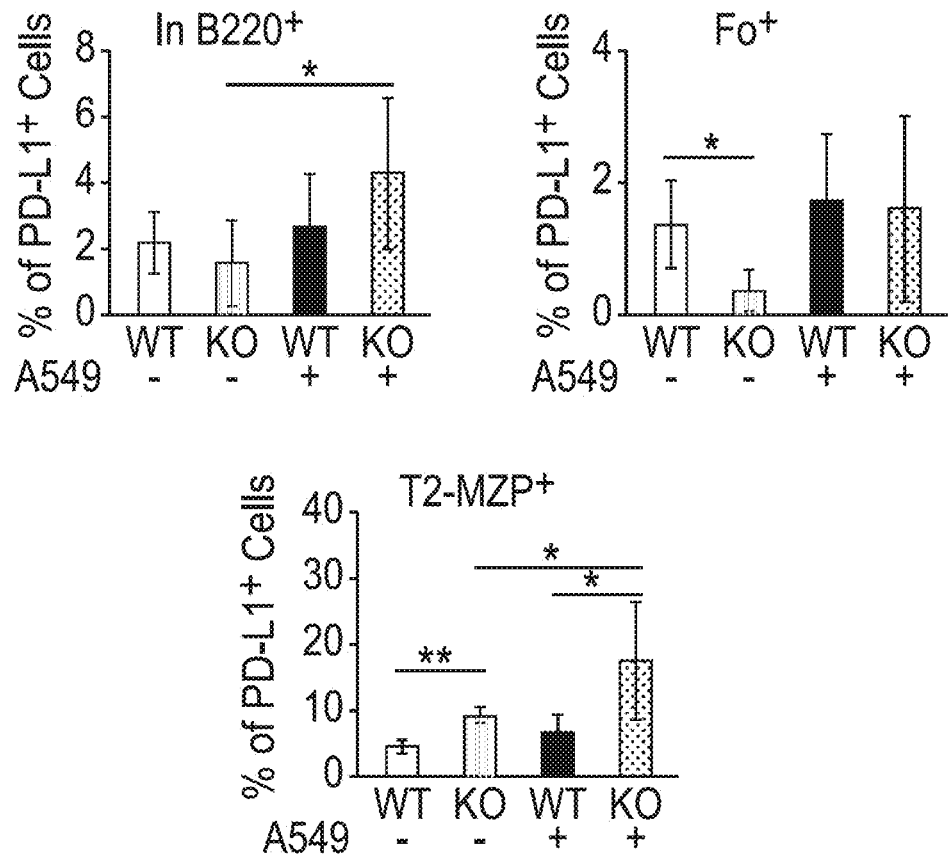
FIGS. 43A-43D depict the increase of PD-L1 in various immune populations of the lal$^{-/-}$ lymph node. Lymph node cells were isolated from wild type and lal$^{-/-}$ mice with or without A549 cancer cell injection for 14 days, and analyzed by flow cytometry using antibody against PD-L1.
Figure 43B:
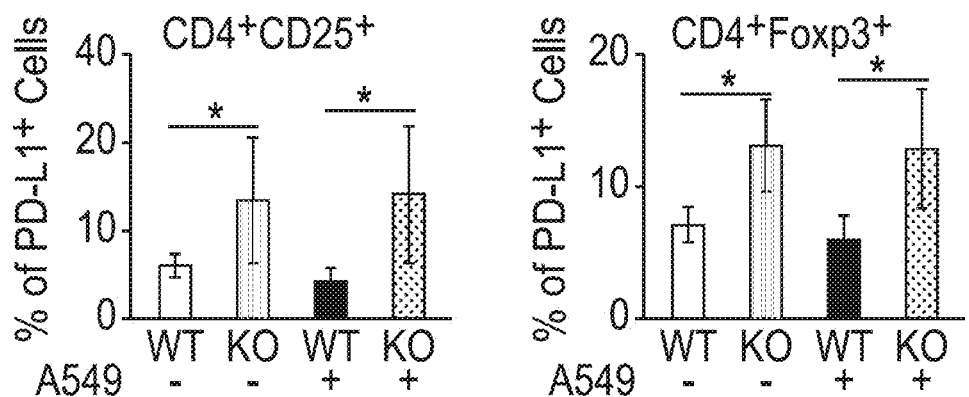
Figure 43C:
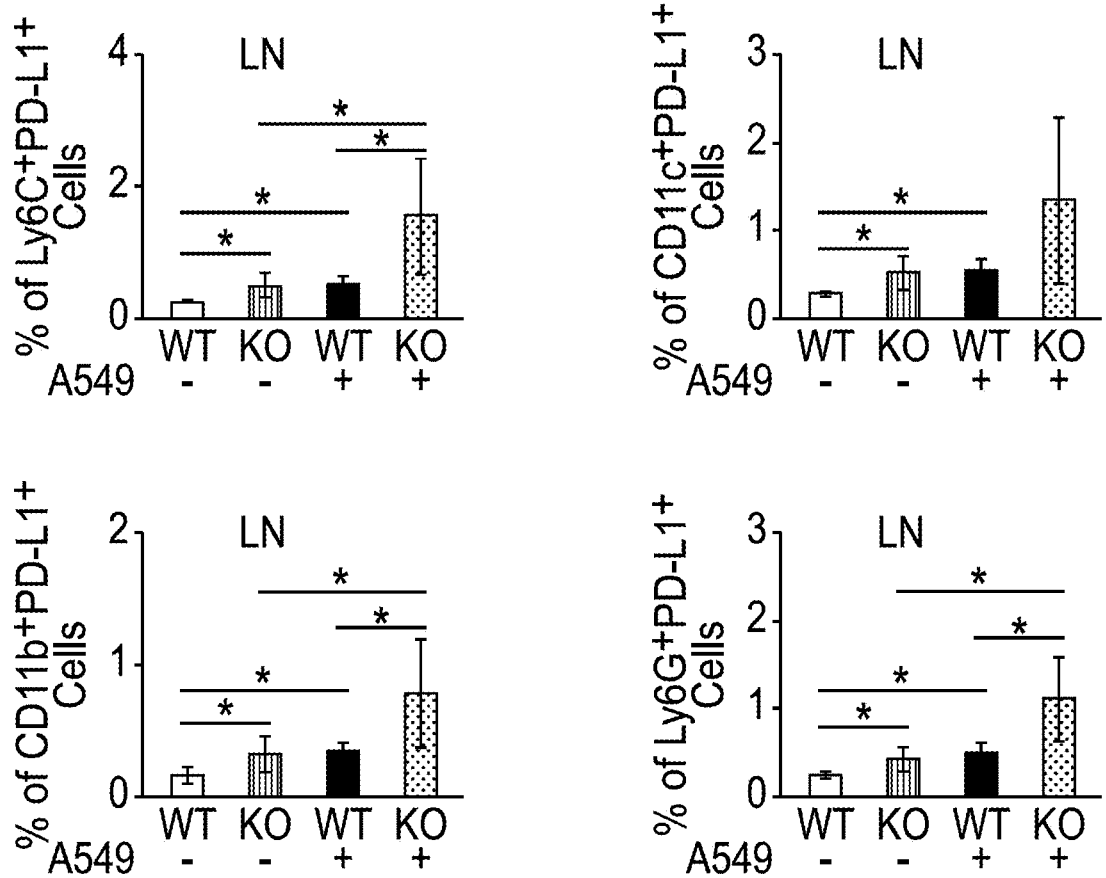
Figure 43D:
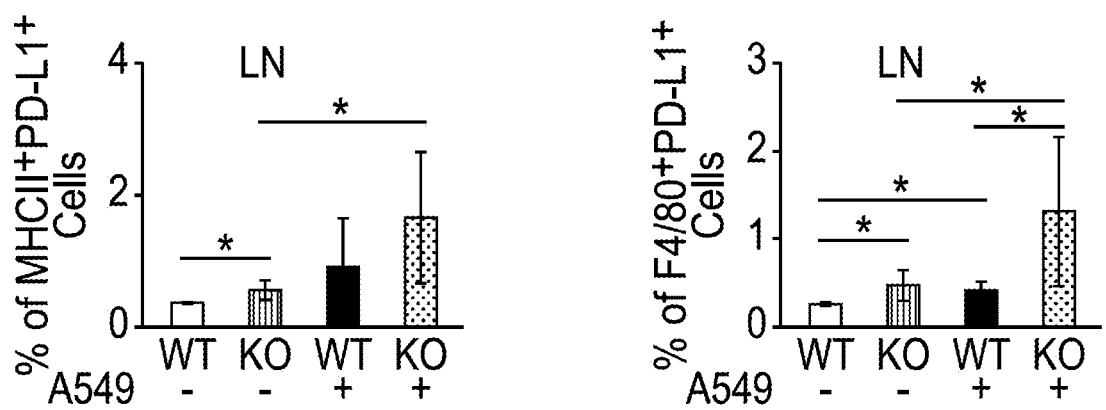

When analyzed further by flow cytometry, the percentages of PD-L1$^+$ T2-MZP Breg and Treg cells were significantly higher in the lal$^{-/-}$ lymph node than those in the wild type lymph node (FIGS. 43A-43B). The percentages of various PD-L1$^+$ myeloid lineage cells were also higher in the lal$^{-/-}$ lymph node, and further increased by A549-injection (FIG. 43C). Especially, the increased percentage number of PD-L1$^+$MHCII$^+$ cells indicated weakened T cell activation by APC in the lal$^{-/-}$ lymph node to fight with cancer (FIG. 43D). Collectively, increased PD-L1 in Breg, Treg and APC cells serves as a mechanism to compromise the anti-tumor immunity and human cancer rejection in lal$^{-/-}$ mice.

Discussion

For many years of cancer research, emphasis has been given to the characterization of malignant cells. Only recently, the interaction between the host immune system and invading cancer cells has been greatly appreciated. One major obstacle to investigate human cancer and its treatment is lack of proper mouse models that recapitulate human conditions. Some commonly used mouse models in human cancer research are more or less deficient in certain parts of immune system. The immunodeficiency allows these mice as ideal recipients of human cancer cells since no immune rejection is present. However, the severely compromised immune system does not mimic clinical settings in humans Human patients are not always immunedeficient and most of them still have the intact immune system. The lal$^{-/-}$ mouse model on the other hand exhibits phenotypes mimicking human chronic inflammatory conditions. Metabolic reprogram happening in cancer patients exists in lal$^{-/-}$ mice, in which the mTOR signaling pathway is highly upregulated in various cells to facilitate tumor initiation, progression and invasion. Therefore, lal$^{-/-}$ mouse model is an ideal inflammatory system for human cancer research. To test this feasibility, human A549 or MDA-MB-231 cancer cells were used for host injection, which formed significantly bigger tumors and their rejection was significantly less and delayed by the host immune system in lal$^{-/-}$ mice (FIG. 39A).

One of the earliest host immune responses to tumor invasion happens in the lymph node. Lymph node draining is an important step in the peripheral lymphoid tissue mediating activation of the immune response. The lymph flow from tumors is increased compared with that from normal tissue and increased lymph drainage is positively correlated with metastasis. The lymph node is structured for T and B lymphocytes to interact with antigen presenting cells (APC) that carry processed tumor antigens.

As demonstrated herein, LAL deficiency led to increased human cancer tolerance in lal$^{-/-}$ mice as a result of poorly differentiated and functioned (lower secretion of IFNγ, reduced production of GZB, and higher secretion of IL-10) lymph node cells. Substantially increased Treg and Breg cell populations in the lymph node serve as major cellular mechanisms for immuno-compromise in lal$^{-/-}$ mice. Both Treg and Breg (T2-MZP and MZ B) cells support immunological tolerance of cancer. These cells suppress the differentiation of lymphocytes, such as Th1, Th17, and cytotoxic CD8$^+$ T cells. Breg cells also induce the differentiation of immunosuppressive T cells, Foxp3$^+$ T cells, and T regulatory 1 (Tr1) cells. Breg cells preferentially accumulate in tumor-draining lymph nodes and promote tumor growth. Breg cells are also involved in autoimmune diseases and allergy. Despite considerable effort, no lineage-specific marker equivalent to Foxp3 has been conclusively identified in Breg cells, suggesting that Breg cells are not lineage specific but rather "react" to the environment, as evidenced in highly inflammatory lal$^{-/-}$ mice.

In lal$^{-/-}$ mice, PD-L1 upregulation appeared to serve a major role in immune tolerance. In the lymphocyte compartment, PD-L1 positive Treg and Breg cells were substantially increased in the lal$^{-/-}$ lymph node (FIGS. 43A and 43B). PD-L1 is a major check point inhibitor to suppress T cell anti-tumor functions. Targeting the interaction between programmed death 1 (PD1) and its ligand PD-L1 shows a great potential for cancer immunotherapy. In the myeloid compartment, PD-L1 positive MHCII APCs were also substantially increased in the lal$^{-/-}$ lymph node (FIG. 43D). In normal conditions, APC process and present tumor antigens to activate specific T cell populations. It is conceivable that the increased PD-L1 expression in APCs blocks the T cell expansion and activity in the lal$^{-/-}$ lymph node. Taken together, increased PD-L1 in Breg cells, Treg cells and APCs serves as an important mechanism to suppress anti-tumor immunity that promotes human cancer growth in lal$^{-/-}$ mice. This observation provides an extra approach and target for immunotherapy in human cancer treatment. The lal$^{-/-}$ mouse model is a great system to depict the relationship between host and invading human cancers, including primary surgical human cancer cells. This will greatly facilitate mechanistic study and drug screen, which cannot be done in humans LAL deficiency increased PD-L1 expression in multiple cells (T, B, myeloid cells) to facilitate tumor growth. Therefore LAL treatment can decrease PD-L1 expression, and PD-L1 mediated T cell suppression can be reversed. As a result, anti-tumor immunity will be enhanced to block tumor growth by LAL treatment. Clinically, LAL can be used alone, or with other check point inhibitors for cancer treatment.

LAL treatment in combination with check point inhibitors (e.g., PD-L1 and PD-1 inhibitor) will enhance the efficacy of cancer treatment by FDA-approved check point inhibitors. LAL deficiency increased PD-L1 expression in multiple cells (T, B, myeloid cells) to facilitate tumor growth. Therefore LAL treatment can decrease PD-L1 expression and PD-L1 mediated immune suppression in cancer therapy.

In view of the above, it will be seen that the several advantages of the disclosure are achieved and other advantageous results attained. As various changes could be made in the above methods without departing from the scope of the disclosure, it is intended that all matter contained in the above description and shown in the accompanying drawings shall be interpreted as illustrative and not in a limiting sense.

When introducing elements of the present disclosure or the various versions, embodiment(s) or aspects thereof, the articles "a", "an", "the" and "said" are intended to mean that there are one or more of the elements. The terms "comprising", "including" and "having" are intended to be inclusive and mean that there may be additional elements other than the listed elements.

What is claimed is:

1. A method for treating lung cancer in an individual in need thereof, the method comprising administering a therapeutically effective amount of lysosomal acid lipase (LAL) to the individual.

2. The method of claim 1 comprising administering LAL via an injection route selected from the group consisting of intramuscular, subcutaneous, intramedullary, intrathecal, intraventricular, intravenous, intravitreal, and combinations thereof.

3. The method of claim 1 wherein the LAL is administered as a pharmaceutical composition, the composition further comprising a pharmaceutically acceptable carrier.

4. The method of claim 1 further comprising administering a peroxisome proliferator-activated receptor gamma (PPARγ) ligand to the individual.

5. The method of claim 4 wherein the PPARγ ligand is selected from the group consisting of 9-hydroxyoctadecadienoic acid (9-HODE), 13-hydroxyoctadecadienoic acid (13-HODE), 15-deoxy-Delta12-14-prostaglandin (J2) (15d-PGD2), prostaglandin A1 (PGA1), prostaglandin A2 (PGA2), rosiglitazone (BRL49653), ciglitazone, pioglitazone, troglitazone, farglitazar, [[4-[2-(6-Benzoyl-2-oxo-3 (2H)-benzothiazolyl)ethoxy]phenyl]methyl]-1,3-propanedioic acid dimethyl ester (S26948), T0903131 (INT131) Besylate, and combinations thereof.

6. The method of claim 4 comprising administering the PPARγ ligand via an injection route selected from the group consisting of intramuscular, subcutaneous, intramedullary, intrathecal, intraventricular, intravenous, intravitreal, and combinations thereof.

7. The method of claim 4 wherein about 20 μmol/L of PPARγ ligand is administered to the individual.

8. The method of claim 1 wherein the administering step inhibits immune suppression in a tumor microenvironment.

9. The method of claim 1 wherein the administering step reduces the number and/or function of myeloid-derived suppressor cells in a tumor microenvironment.

10. A method of inhibiting tumor progression in an individual having lung cancer, the method comprising administering a therapeutically effective amount of lysosomal acid lipase (LAL) to the individual.

11. The method of claim 10 comprising administering LAL via an injection route selected from the group consisting of intramuscular, subcutaneous, intramedullary, intrathecal, intraventricular, intravenous, intravitreal, and combinations thereof.

12. The method of claim 10 wherein the administering step inhibits immune suppression in a tumor microenvironment.

13. The method of claim 10 wherein the administering step reduces the number and/or function of myeloid-derived suppressor cells in a tumor microenvironment.

14. A method for reducing lung cancer, liver cancer or melanoma tumor growth in an individual in need thereof, the method comprising administering a therapeutically effective amount of lysosomal acid lipase (LAL) in combination with a check point inhibitor to the individual.

15. The method of claim 14 wherein the check point inhibitor comprises PD-L1, PD-1 inhibitor, and combinations thereof.

* * * * *

SEQUENCE LISTING

```
<160> NUMBER OF SEQ ID NOS: 6

<210> SEQ ID NO 1
<211> LENGTH: 22
<212> TYPE: DNA
<213> ORGANISM: Artificial Sequence
<220> FEATURE:
<223> OTHER INFORMATION: Synthetic

<400> SEQUENCE: 1
agccaggctg ttaaattcca aa                                              22

<210> SEQ ID NO 2
<211> LENGTH: 22
<212> TYPE: DNA
<213> ORGANISM: Artificial Sequence
<220> FEATURE:
<223> OTHER INFORMATION: Synthetic

<400> SEQUENCE: 2
gaatgctctc atggaacacc aa                                              22

<210> SEQ ID NO 3
<211> LENGTH: 17
<212> TYPE: DNA
<213> ORGANISM: Artificial Sequence
<220> FEATURE:
<223> OTHER INFORMATION: Synthetic

<400> SEQUENCE: 3
tgcagtctgg agcgggg                                                    17

<210> SEQ ID NO 4
<211> LENGTH: 23
<212> TYPE: DNA
<213> ORGANISM: Artificial Sequence
<220> FEATURE:
<223> OTHER INFORMATION: Synthetic

<400> SEQUENCE: 4
tgtcatcgtc gtccttgtag tcc                                             23

<210> SEQ ID NO 5
<211> LENGTH: 22
<212> TYPE: DNA
<213> ORGANISM: Artificial Sequence
<220> FEATURE:
<223> OTHER INFORMATION: Synthetic

<400> SEQUENCE: 5
accgtgaaaa gatgacccag at                                              22

<210> SEQ ID NO 6
<211> LENGTH: 21
<212> TYPE: DNA
<213> ORGANISM: Artificial Sequence
<220> FEATURE:
<223> OTHER INFORMATION: Synthetic
```

```
<400> SEQUENCE: 6
gcctggatgg ctacgtacat g                                           21
```